(12) United States Patent
Hellwege et al.

(10) Patent No.: US 10,433,550 B2
(45) Date of Patent: Oct. 8, 2019

(54) ACTIVE COMPOUNDS COMBINATION CONTAINING FLUOPYRAM BACILLUS AND BIOLOGICALLY CONTROL AGENT

(71) Applicants: BAYER INTELLECTUAL PROPERTY GMBH, Monheim (DE); BAYER CROPSCIENCE AG, Monheim (DE)

(72) Inventors: Elke Hellwege, Langenfeld (DE); Heike Hungenberg, Langenfeld (DE)

(73) Assignees: BAYER INTELLECTUAL PROPERTY GMBH, Monheim am Rhein (DE); BAYER CROPSCIENCE AG, Monheim (DE)

( * ) Notice: Subject to any disclaimer, the term of this patent is extended or adjusted under 35 U.S.C. 154(b) by 0 days.

(21) Appl. No.: 15/175,810

(22) Filed: Jun. 7, 2016

(65) Prior Publication Data

US 2016/0286803 A1 Oct. 6, 2016

Related U.S. Application Data

(62) Division of application No. 14/373,916, filed as application No. PCT/EP2013/051108 on Jan. 22, 2013, now Pat. No. 9,433,214.

(30) Foreign Application Priority Data

Jan. 25, 2012 (EP) .................................... 12152488

(51) Int. Cl.
| | | |
|---|---|---|
| *A01N 43/40* | (2006.01) | |
| *A01N 63/00* | (2006.01) | |
| *A01N 63/02* | (2006.01) | |
| *A01N 63/04* | (2006.01) | |
| *A01N 65/00* | (2009.01) | |

(52) U.S. Cl.
CPC ............. *A01N 43/40* (2013.01); *A01N 63/00* (2013.01); *A01N 63/02* (2013.01); *A01N 63/04* (2013.01); *A01N 65/00* (2013.01)

(58) Field of Classification Search
None
See application file for complete search history.

(56) References Cited

U.S. PATENT DOCUMENTS

| | | | | |
|---|---|---|---|---|
| 5,989,543 A | * | 11/1999 | Davide | ...................... C12R 1/79 424/93.5 |
| 9,089,135 B2 | * | 7/2015 | Andersch | ............... A01N 43/40 |
| 9,433,214 B2 | * | 9/2016 | Hellwege | ............... A01N 43/40 |
| 2005/0234110 A1 | | 10/2005 | Mansfield et al. | |
| 2010/0209410 A1 | | 8/2010 | Schoefl et al. | |
| 2010/0249193 A1 | * | 9/2010 | Andersch | ............... A01N 43/40 514/341 |
| 2011/0110906 A1 | * | 5/2011 | Andersch | ............... A01N 63/00 424/93.46 |
| 2014/0005047 A1 | | 1/2014 | Hungenberg et al. | |
| 2014/0056866 A1 | | 2/2014 | Andersch et al. | |

FOREIGN PATENT DOCUMENTS

| | | |
|---|---|---|
| EP | 2460407 A1 | 6/2012 |
| WO | 199632840 A1 | 10/1996 |
| WO | 9821966 A2 | 5/1998 |
| WO | 2004016088 A2 | 2/2004 |
| WO | 2008/057131 A1 | 5/2008 |
| WO | 2008126922 A1 | 10/2008 |
| WO | 2012016989 A2 | 2/2012 |
| WO | 2012038480 A2 | 3/2012 |

OTHER PUBLICATIONS

International Search Report received in PCT/EP2013/051108, dated May 7, 2013.

* cited by examiner

*Primary Examiner* — Alton N Pryor
(74) *Attorney, Agent, or Firm* — McBee Moore Woodward & Vanik IP, LLC

(57) ABSTRACT

The present invention relates to active compound combinations for reducing the damage of plants and plant parts as well as losses in harvested fruits or vegetables caused by insects, nematodes or phytopathogens and which have fungicidal or nematicidal or insecticidal activity including any combination of the three activities, in particular within a composition, which comprises (A) Fluopyram, (B) a spore-forming bacterium of the genera *Bacillus,* selected from *Bacillus firmus, Bacillus cereus, Bacillus pumilis, Bacillus amyloliquefaciens, Bacillus subtilis* strain GB03, *Bacillus subtilis* strain QST713, and (C) at least one biological control agent, in particular bacteria, fungi or yeasts, protozoa, viruses, entomopathogenic nematodes, inoculants, botanicals and products produced by microorganisms including proteins or secondary metabolites. Moreover, the invention relates to a method for curatively or preventively controlling insects, nematodes or phytopathogens on the plant, plant parts, harvested fruits or vegetables, to the use of a combination according to the invention for the treatment of seed, to a method for protecting a seed and not at least to the treated seed.

12 Claims, No Drawings

ACTIVE COMPOUNDS COMBINATION CONTAINING FLUOPYRAM BACILLUS AND BIOLOGICALLY CONTROL AGENT

CROSS REFERENCE TO RELATED APPLICATIONS

This application is a divisional application of Ser. No. 14/373,916 (filed Jul. 23, 2014), which is a § 371 National Stage Application of PCT/EP2013/051108 (filed Jan. 22, 2013), which claims priority to EP 12152488.8 (filed Jan. 25, 2012), the contents of each of which are incorporated herein by reference in their entirety.

BACKGROUND

Field of the Invention

The present invention relates to active compound combinations and compostions for reducing the damage of plants and plant parts as well as losses in harvested fruits or vegetables caused by insects, nematodes or phytopathogens and which have fungicidal or nematicidal or insecticidal activity including any combination of the three activities, in particular within a composition, which comprises (A) Fluopyram, (B) a spore-forming bacterium of the genera *Bacillus*, selected from *Bacillus firmus, Bacillus cereus, Bacillus pumilis, Bacillus amyloliquefaciens, Bacillus subtilis* strain GB03, *Bacillus subtilis* strain QST713, and (C) at least one biological control agent, in particular bacteria, fungi or yeasts, protozoa, viruses, entomopathogenic nematodes, inoculants, botanicals and products produced by microorganisms including proteins or secondary metabolites. Moreover, the invention relates to a method for curatively or preventively controlling insects, nematodes or phytopathogens on the plant, plant parts, harvested fruits or vegetables, to the use of a combination according to the invention for the treatment of seed, to a method for protecting a seed and not at least to the treated seed.

Description of Related Art

Fluopyram is defined to be the compound of the formula (I)

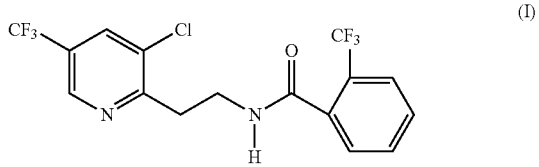 [SMILES: O=C(NCCc1ncc(C(F)(F)F)cc1Cl)c1ccccc1C(F)(F)F]

as well as the N-oxides of the compound thereof.

Fluopyram is a broad spectrum fungicide of the chemical class of pyridylethylbenzamide derivatives with penetrant and translaminar properties for foliar, drip, drench and seed treatment applications on a wide range of different crops against many economically important plant diseases. It is very effective in preventative applications against powdery mildew species, grey mould and white mould species. It has an efficacy against many other plant diseases. Fluopyram has shown activity in spore germination, germ tube elongation and mycelium growth tests. At the biochemical level, fluopyram inhibits mitochondrial respiration by blocking the electron transport in the respiratory chain of Succinate Dehydrogenase (complex II-SDH inhibitor).

Fluopyram and its manufacturing process starting from known and commercially available compounds is described in EP-A 1 531 673 and WO 2004/016088.

A general description of the nematicidal activity of pyridylethylbenzamide derivatives is found in WO-A 2008/126922. A description of nematicidal activity of Bacteria, in particular *Bacillus firmus* is found in WO-A 1996/32840, a description of nematicidal activity of *Bacillus chitinosporus* is found in WO-A 9821966.

The use of bacteria such as *Bacillus* sp. as biological control agent in synergistic compositions with fungicides e.g. Fluopyram for controlling phytopathogenic organisms in agriculture is described e.g. in US 2011/0110906 A, US 2010/0249193 A, US 20100/209410 A, EP 2460407 A and WO 2012/016989. In these documents only binary mixtures of the biological control agent and Fluopyram are disclosed. WO 2012/038480 A discloses seeds of a plant comprising (a) a gene preferably Axmi031, and Axn2 (producing proteins of *Bacillus thuringiensis*), (b) a biological control agent preferably *Bacillus firmus* CNCM I-1582, (c) one or more insecticides (including biological control agents preferably *Pasteuria* and *Verticillum* and (d) one or more fungicides preferably Fluopyram. In this document *Pasteuria* and *Verticillium* are not further specified.

Since the environmental and economic requirements imposed on modern-day crop protection compositions are continually increasing, with regard, for example, to the spectrum of action, toxicity, selectivity, application rate, formation of residues, and favourable preparation ability, and since, furthermore, there may be problems, for example, with resistances, a constant task is to develop new compositions, in particular fungicidal or nematicidal agents, which in some areas at least help to fulfil the abovementioned requirements. The present invention provides active compound combinations/compositions which in some aspects at least achieve the stated objective.

SUMMARY

It has now been found, surprisingly, that the combinations according to the invention not only bring about the additive enhancement of the spectrum of action with respect to the insects, nematodes or phytopathogens to be controlled that was in principle to be expected but achieves a synergistic effect which extends the range of action of the component (A) and of the component (B) and of the component (C) in two ways. Firstly, the rates of application of the component (A) and of the component (B) and of the component (C) are lowered whilst the action remains equally good. Secondly, the combination still achieves a high degree of control of insects, nematodes or phytopathogens even where the two individual compounds have become totally ineffective in such a low application rate range. This allows, on the one hand, a substantial broadening of the spectrum of phytopathogenic fungi and nematodes that can be controlled and, on the other hand, increased safety in use.

In addition to the fungicidal or nematicidal or insecticidal synergistic activity, the active compound combinations according to the invention have further surprising properties which, in a wider sense, may also be called synergistic, such as, for example: broadening of the activity spectrum to other insects, nematodes or phytopathogens, for example to resistant strains of plant diseases; lower application rates of the active compound combination; sufficient control of pests with the aid of the active compound combinations according to the invention even at application rates where the individual compounds show no or virtually no activity; advantageous behaviour during formulation or during use, for example during grinding, sieving, emulsifying, dissolving or dispensing; improved storage stability and light stability; advantageous residue formation; improved toxicological or ecotoxicological behaviour; improved properties of the plant so called plant physiology effects, for example better growth, increased harvest yields, a better developed root system, a larger leaf area, greener leaves, stronger shoots, less seed required, lower phytotoxicity, mobilization of the defence system of the plant, good compatibility with plants. Thus, the use of the active compound combinations or compositions according to the invention contributes considerably to keeping young cereal stands healthy, which increases, for example, the winter survival of the cereal seed treated, and also safeguards quality and yield. Moreover, the active compound combinations according to the invention may contribute to enhanced systemic action. Even if the individual compounds of the combination have no sufficient systemic properties, the active compound combinations according to the invention may still have this property. In a similar manner, the active compound combinations according to the invention may result in higher long term efficacy of the fungicidal or nematicidal or nematicidal action.

DETAILED DESCRIPTION OF A PREFERRED EMBODIMENT

The combinations or compositions according to the present invention are now described in detail:

Accordingly, the present invention provides an active compound combination comprising:
(A) Fluopyram,
(B) a spore-forming bacterium of the genera *Bacillus*, selected from the group consisting of *Bacillus firmus*, *Bacillus cereus*, *Bacillus pumilis*, *Bacillus amyloliquefaciens*, *Bacillus subtilis* strain GB03, *Bacillus subtilis* strain QST713, and
(C) at least one biological control agent selected from the group consisting of
(C1) bacteria,
(C2) fungi or yeasts,
(C3) protozoas,
(C4) viruses,
(C5) entomopathogenic nematodes,
(C6) inoculants,
(C7) botanicals, and
(C8) products produced by microorganisms including proteins or secondary metabolites for reducing overall damage of plants and plant parts as well as losses in harvested fruits or vegetables caused by insects, nematodes or phytopathogens.

The term active compound combination shall refer to the species as well as to individual strains of the respective species Accordingly, the present invention provides particularly an active compound combination comprising
(A) Fluopyram,
(B) a spore-forming bacterium of the genera *Bacillus*, selected from the group consisting of *Bacillus firmus*, *Bacillus firmus* CNCM I-1582, *Bacillus cereus*, *Bacillus pumilis*, *Bacillus amyloliquefaciens*, *Bacillus subtilis* strain GB03, *Bacillus subtilis* strain QST713, and
(C) at least one biological control agent selected from the group consisting of
(C1) bacteria,
(C2) fungi or yeasts,
(C3) protozoas,
(C4) viruses,
(C5) entomopathogenic nematodes,
(C6) inoculants,
(C7) botanicals, and (C8.1) Halpin (produced by *Erwinia amylovora*) for reducing overall damage of plants and plant parts as well as losses in harvested fruits or vegetables caused by insects, nematodes or phytopathogens, with the proviso that the spore-forming bacterium (B) of the genera *Bacillus* and the biological control agent (C) are not identical.

Accordingly, the present invention provides particularly an active compound combination comprising
(A) Fluopyram,
(B) a spore-forming bacterium of the genera *Bacillus*, selected from the group consisting of *Bacillus firmus*, *Bacillus firmus* CNCM I-1582, *Bacillus cereus*, *Bacillus pumilis*, *Bacillus amyloliquefaciens*, *Bacillus subtilis* strain GB03, *Bacillus subtilis* strain QST713, and
(C) one biological control agent selected from the group consisting of
(C1) bacteria,
(C2) fungi or yeasts,
(C3) protozoas,
(C4) viruses,
(C5) entomopathogenic nematodes,
(C6) inoculants,
(C7) botanicals, and (C8.1) Harpin (produced by *Erwinia amylovora*) for reducing overall damage of plants and plant parts as well as losses in harvested fruits or vegetables caused by insects, nematodes or phytopathogens, with the proviso that the spore-forming bacterium (B) of the genera *Bacillus* and the biological control agent (C) are not identical.

The term active compound combination shall refer to the species as well as to individual strains of the respective species.

In particular, the spore-forming bacterium (B) of the genera *Bacillus* is selected from the group consisting of
(B1) *Bacillus firmus* strain CNCM I-1582, in particular the spores (U.S. Pat. No. 6,406,690),
(B2) *Bacillus cereus* strain CNCM I-1562, in particular the spores, (U.S. Pat. No. 6,406,690),
(B3) *Bacillus amyloliquefaciens* strain IN937a,
(B4) *Bacillus amyloliquefaciens* strain FZB42 (product known as RhizoVitar®),
(B5) *Bacillus subtilis* strain GB03 (marketed as Kodiak™ Gustafson LLC),
(B6) *Bacillus subtilis* strain QST713 (marketed as Serenade™ by Agraquest),
(B7) *Bacillus pumilus* strain GB34 (marketed as YieldShield™ by Gustafson LLC),
(B8) *Bacillus pumilus* strain QST2808 (marketed as Sonata™ by Agraquest).

As used herein "biological control" is defined as control of a phytopathogen or insect or an acarid or a nematode by the use of a second organism or by the use of botanicals or products produced by microorganisms including proteins or secondary metabolites, particularly (C8.1) Harpin. Particularly preferred is the control of nematodes. Particularly preferred "biological control" is defined as control of nematodes by the use of a second organism or by the use of botanicals or products produced by microorganisms including proteins or secondary metabolites, particularly (C8.1) Harpin.

In the context of the present invention, "control of a phytopathogen or insect or an acarid or a nematode" means a reduction in infestation by harmful phytopathogens or insect or an acarid or a nematode, compared with the untreated plant measured as fungicidal or insecticidal or nematicidal efficacy, preferably a reduction by 25-50%, compared with the untreated plant (100%), more preferably a reduction by 40-79%, compared with the untreated plant (100%); even more preferably, the infection by harmful phytopathogens or insect or an acarid or a nematode, is entirely suppressed (by 70-100%). The control may be curative, i.e. for treatment of already infected plants, or protective, for protection of plants which have not yet been infected.

Preferably, the compound (A) Fluopyram and the spore-forming bacterium (B) of the genera *Bacillus* is mixed with one biological control agent (C), in particular bacteria, fungi or yeasts, protozoa, viruses, entomopathogenic nematodes, botanicals or products produced by microorganisms including proteins or secondary metabolites, particularly (C8.1) Harpin, for reducing overall damage of plants and plant parts as well as losses in harvested fruits or vegetables caused by insects, nematodes or phytopathogens.

Mutants of the bacterial, fungal, nematodal or protozoan strains having all the identifying characteristics of the respective strain shall be included within the definition of the biological control agent.

The products produced by microorganisms including proteins or secondary metabolites, particularly (C8.1) Harpin are characterized that they exhibit activity against phytopathogenic insects, phytopathogenic nematodes or phytopathogens.

Accordingly, in the present invention the biological control agents (C) comprises bacteria, fungi or yeasts, protozoa, viruses, entomopathogenic nematodes, botanicals and products produced by microorganisms including proteins or secondary metabolites, particularly (C8.1) Harpin.

Accordingly, in the present invention biological control (C) agents consist of bacteria, fungi or yeasts, protozoa, viruses, entomopathogenic nematodes, botanicals and products produced by microorganisms including proteins or secondary metabolites, particularly (C8.1) Halpin.

Accordingly, in the present invention biological control agents are in particular bacteria, fungi or yeasts, protozoa, viruses, entomopathogenic nematodes, botanicals and products produced by microorganisms including proteins or secondary metabolites, particularly (C8.1) Harpin.

In particular, the biological control agent (C) is selected from the group comprising (C1) bacteria including spore-forming, root-colonizing bacteria, or bacteria useful as biofungicide, bioinsecticide or nematicide selected from the group consisting of (C1.1) *Bacillus agri*, (C1.2) *Bacillus aizawai*, (C1.3) *Bacillus albolactis*, (C1.6) *Bacillus coagulans*,(C1.7) *Bacillus endoparasiticus*, (C1.8) *Bacillus endorhythmos*, (C1.9) *Bacillus azotoformans*, (C1.10) *Bacillus kurstaki*, (C1.11) *Bacillus lacticola*, (C1.12) *Bacillus lactimorbus*, (C1.13) *Bacillus lactis*, (C1.14) *Bacillus laterosporus*, (C1.15) *Bacillus lentimorbus*, (C1.16) *Bacillus licheniformis*, (C1.17) *Bacillus medusa*, (C1.18) *Bacillus megaterium*, (C1.19) *Bacillus metiens*, (C1.20) *Bacillus natto*, (C1.21) *Bacillus nigrificans*, (C1.22) *Bacillus popillae* (neu *Paenibacillus popilliae*), (C1.24) *Bacillus siamensis*, (C1.25) *Bacillus sphaericus* (products known as VectoLexs®), (C1.26) *Bacillus subtilis var. amyloliquefaciens* strain FZB24 (products known as Taegro®), (C1.27) *Bacillus thuringiensis*, in particular (C1.27a) *Bacillus thuringiensis* var. israelensis (products known as VectoBac®) or (C1.27b) *Bacillus thuringiensis* subsp. aizawai strain ABTS-1857 (products known as XenTari®), or (C1.27c) *Bacillus thuringiensis* subsp. kurstaki strain HD-1 (products known as Dipel® ES) or (C1.27d) *Bacillus thuringiensis* subsp. tenebrionis strain NB 176 (products known as Novodor® FC) or (C1.27e) *Bacillus thuringiensis* subsp. morrisoni or (C1.27f) Bacillus thuringiensis var son diego, (C1.28) *Bacillus uniflagellatus*, (C1.29) Delftia acidovorans, in particular strain RAY209 (products known as BioBoost®), (C1.30) *Lysobacter antibioticus*, in particular strain 13-1 (cf. Biological Control 2008, 45, 288-296), (C1.31) *Pasteuria penetrans* (synonym *Bacillus penetrans*), (C1.32) *Pseudomonas chlororaphis*, in particular strain MA 342 (products known as Cedomon), (C1.33) *Pseudomonas proradix* (products known as Proradix®), (C1.34) *Streptomyces galbus*, in particular strain K61 (products known as Mycostop®, cf. Crop Protection 2006, 25, 468-475), (C1.35) *Streptomyces griseoviridis* (products known as Mycostop®), (C1.36) *Bacillus lautus*, (C1.37) *Bacillus atrophaeus*, (C1.39) *Bacillus mycoides*, (C1.40) *Bacillus acidoterrestris*, (C1.41) *Bacillus fastidiosus*, (C1.42) *Bacillus megaterium*, (C1.43) *Bacillus psychrosaccharolyticus*, (C1.44) *Bacillus maroccanus*, (C1.45) *Bacillus megaterium* C, (C1.46) *Bacillus pantothenticus*, (C1.47) *Bacillus lentus*, (C1.48) *Bacillus badius*, (C1.49) *Bacillus smithi*, (C1.50) *Acinetobacter* spec, (C1.51) *Acinetobacter lwoffii*, (C1.52) *Bacillus luciferensis*, (C1.53) *Chromobacterium subtsugae* strain PRAA4-1T (product known as Grandevo), (C1.54) *Pasteuria usgae* (product known as Econem™ Biological Nematicide), (C1.55) *Paenibacillus polymyxa*, (C1.56) *Bacillus subtilis var. amyloliquefaciens* strain FZB24 (products known as Taegro®), (C1.57) *Serratia entomophila* (product known as Invade®), (C1.58) *Bacillus chitinosporus* (C1.59) *Pseudomonas cepacia* (ex *Burkholderia cepacia*) strains M54 and J82, (C1.60) *Bacillus nematocida*, in particular strain B-16;

(C2) fungi or yeasts selected from the group consisting of:

(C2.1) *Ampelomyces quisqualis*, in particular strain AQ 10 (product known as AQ 10®), (C2.2) *Aureobasidium pullulans*, in particular blastospores of strain DSM14940 or blastospores of strain DSM 14941 or mixtures thereof (product known as Blossom Protect®), (C2.3) *Beauveria bassiana*, in particular strain ATCC 74040 (products known as Naturalis®, from Intrachem) and strain GHA (products known as Mycotrol, BotaniGard), (C2.4) *Candida oleophila*, in particular strain O (products known as Nexy ®), (C2.5) *Coniothyrium minitans*, in particular strain CON/M/91-8 (products known as Contans ®), (C2.6) *Dilophosphora alopecuri* (products known as Twist Fungus ®), (C2.7) *Gliocladium catenulatum*, in particular strain J1446 (products known as Prestop ®), (C2.8) *Lecanicillium lecanii* (formerly known as *Verticillium lecanii*), in particular conidia of strain KV01 (products known as Mycotal®, Vertalec®), (C2.9) *Metarhizium anisopliae*, in particular strain F52 (products known as BIO 1020), (C2.10) *Metschnikovia fructicola*, in particular the strain NRRL Y-30752 (products known as Shemer ®), (C2.11) *Microsphaeropsis ochracea* (products known as Microx®), (C2.12) *Muscodor albus*, in particular strain QST 20799 (products known as QRD300), (C2.13) *Nomuraea rileyi*, in particular strains SA86101, GU87401, SR86151, CG128 and VA9101, (C2.14) *Paecilomyces lilacinns*, in particular spores of *P. lilacinus* strain 251 (products known as BioAct®, cf. Crop Protection 2008, 27, 352-361), (C2.15) *Paecilomyces fumosorosens* (also known as *Isaria fumosorosae*, products known as PFR-97TM 20% WDG), (C2.16) *Penicillium bilaii*, in particular strain ATCC22348 (products known as JumpStart®, PB-50, Provide), (C2.17) *Pichia anomala*, in particular strain WRL-076, (C2.18) *Psend-*

*ozyma flocculosa,* in particular strain PF-A22 UL (products known as Sporodex®L), (C2.19) *Pythium oligandrum* DV74 (products known as Polyversum), (C2.20) *Trichoderma asperellum,* in particular strain ICC 012 (products known as Bioten®), (C2.21) *Trichoderma harzianum,* in particular *T. harzianum* T39 (products known as Trichodex®), (C2.22) *Beauveria brongniartii* (products known as Beaupro), (C2.23) *Asohersonia aleyrodes,* (C2.24) *Hirsutelia thompsoni* (products known as Mycohit), (C2.25) *Lagenidium giganteum* (products known as LAGINEX®), (C2.26) *Myrothecium verrucaria* strain AARC-0255 (products known as DiTera™), (C2.27) *Pandora delphacis,* (C2.28) *Tsukamurella paurometabola* (products known as HeberNem®), (C2.29) *Verticillium lecanii,* in particular strain DAOM198499 and DAOM216596, (C2.30) ARF 18 (Arkansas Fungus 18), (C2.31) *Trichoderma atroviride* (products known as Esquive®) (C2.32) *Glomus aggregatum,* (C2.33) *Glomus etunicatum,* (C2.34) *Glomus intraradices,* (C2.35) *Glomus mosseae,* (C2.36) *Glomus deserticola,* (C2.37) *Glomus clarum,* (C2.38) *Glomus brasilianum,* (C2.39) *Glomus monosporum,* (C2.40) *Gigaspora margarita,* (C2.41) *Rhizopogon villosullus,* (C2.42) *Rhizopogon. luteolus,* (C2.43) *Rhizopogon. amylopogon,* (C2.44) *Rhizopogon. fulvigleba,* (C2.45) *Pisolithus tinctorius,* (C2.46) *Scleroderma cepa,* (C2.47) *Scleroderma citrinum,* (C2.48) *Suillus granulatus,* (C2.49) *Suillus punctatapies,* (C2.50) *Laccaria laccata,* (C2.51) *Laccaria bicolor;*

(C3) Protozoas selected from the group consisting of
(C3.1) *Nosema locustae,* (C3.2) *Thelohania,* (C3.3) *Vairimorpha;*

(C4) Viruses selected from the group consisting of
(C4.1) Gypsy moth (*Lymantria dispar*) nuclear polyhedrosis virus (NPV), (C4.2) Tussock moth (Lymantriidae) NPV, (C4.3) Heliothis NPV, (C4.4) Pine sawfly (Neodiprion) NPV, and (C4.5) Codling moth (*Cydia pomonella*) granulosis virus (GV);), (C4.6) *Adoxophyes orana* GV (product known as Capex®), (C4.7) *Helicoverpa armigera* NPV (products known as Vivus Max®, Vivus Gold®) or Gemstar®), (C4.8) *Spodoptera exigua* NPV, (C4.9) *Spodoptera littoralis* NPV, (C4.10) *Spodoptera litura* NPV, (C4.11) *Neodiprion abietis* NPV (product known as ABIETIV™), (C4.12) *Neodiprion sertifer* NPV (product known as Neocheck-S™);

(C5) entomopathogenic nematodes selected from the group consisting of
(C5.1) *Steinernema* ssp. (=*Neoaplectana* spp.), (C5.2) *Steinernema scapterisci,* (C5.3) *Steinernema feltiae,* (C5.4) *Steinernema carpocapsae,* (C5.5) *Heterorhabditis* spp., (C5.6) *Heterorhabditis heliothidis,* (C5.7) *Hexamermis* spp., (C5.8) *Amphimermis* spp., (C5.9) *Mermis nigrescens,* (C5.10) *Agamermis decaudata,* (C5.11) *Maupasina weissi,* (C5.12) *Subulura* spp., (C5.13) *Seuratum cadarachense,* (C5.14) *Ptery godermatites* spp., (C5.15) *Abbreviata caucasica,* (C5.16) *Spirura guianensis,* (C5.17) *Diplotriaena* spp., (C5.18) *Tetrameres* spp., (C5.19) *Acuaria* spp., (C5.20) *Gongylonema* spp., (C5.21) *Protrellatus* spp., (C5.22) *Hydromermis* spp., (C5.23) *Cameronia* spp., (C5.24) *Physaloptera* spp., (C5.25) *Chitwoodiella ovofilamenta,* (C5.26) *Gynopoecilia pseudovipara,* (C5.27) *Parasitylenchus* spp., (C5.28) *Neoparasitylenchus rugulosi,* (C5.29) *Sulphuretylenchus elongatus,* (C5.30) *Sphaerulariopsis* spp., (C5.31) *Allantonema* spp., (C5.32) *Contortylenchus* spp., (C5.33) *Bovienema* spp., (C5.34) *Parasitaphelenchus* spp., (C5.35) *Parasitorhabditis* spp., (C5.36) *Phasmarhabditis hermaphrodita,* (C5.37) *Romanomermis* spp., (C5.38) *Octomyomermis* spp., (C5.39) *Strelkovimermis peterseni,* (C5.40) *Perutilimermis culicis,* (C5.41) *Culicimermis* spp., (C5.42) *Empidomermis* spp., (C5.43) *Gastromermis* spp., (C5.44) *Isomermis* spp., (C5.45) *Neomesomermis* spp., (C5.46) *Limnomermis* spp., (C5.47) *Mesomermis* spp., and (C5.48) *Xenorhabdus luminescence* (entomopathogenic bacteria symbiotically associated with nematodes);

(C6) Inoculants selected from the group consisting of
(C6.1) *Rhizobium leguminosarum,* (C6.2) *Rhizobium tropici,* (C6.3) *Rhizobium loti,* (C6.4) *Rhizobium trifolii,* (C6.5) *Rhizobium meliloti,* (C6.6) *Rhizobium fredii,* (C6.7) *Azorhizobium caulinodans,* (C6.8) *Pseudomonas,* (C6.9) *Azospirillum,* (C6.10) *Azotobacter,* (C6.11) *Streptomyces,* (C6.12) *Burkholdia,* (C6.13) *Agrobacterium,* (C6.14) *Endo Mycorhiza,* (C6.15) *Ecto Mycorhiza,* (C6.16) Vesicular Arbuscular (VA) *Mycorhiza,* (6.17) *Bradyrhizobium;*

(C7) Botanicals (or: plant extracts) selected from the group consisting of
(C7.1) Thymus oil, (C7.2) Azadirachtin (Neem), (C7.3) Pyrethrum, (C7.4) *Cassia* nigricans, (C7.5) *Quassia amara,* (C7.6) Rotenon , (C7.7) Garlic, (C7.8) Quillaja, (C7.9) Sabadilla, in particular Veratrin, (C7.10) Ryania, in particular Ryanodine, (C7.11) *Viscum album* (mistel), (C7.12) mugwort or common tansy (*Tanacetum vulgare*), (C7.13) *Artemisia absinthium,* (C7.14) *Urtica dioica,* (C7.15) *Symphytum officinale,* (C7.16) *Tropaeulum majus,* (C7.17) *Quercus,* (C7.18) mustard flour, (C7.19) *Chenopodium anthelminticum,* (C7.20) *Dryopteris filix-mas,* (C7.21) bark of Chinese bittersweet (*Celastrus orbiculatus*), (C7.22) *Equisetum arvense,* (C7.23) bark of Celastus angulatus, (C7.24) Laminarin (Brown Algae), (C7.25) Alginic acid (Brown Algae), (C7.26) Chitin/Chitinosan. (C7.27) *Chenopodium quinoa* (product known as Head-sUp), (C7.28) *Melaleuca alternifolia* (products known as Timorex Gold®), (C7.29) Sesame oil (product known as DragongfireCCPTM);

(C8) Products produced by microorganisms including proteins or secondary metabolites selected from the group consisting of
(C8.1) Harpin (produced by *Erwinia amylovora,* products known as Harp-N-Tek™, Messenger®, Employ™ ProAct™), (C8.2) Thymol.

In particular, the biological control agent (C) is selected from the group comprising
(C1) bacteria including spore-forming, root-colonizing bacteria, or bacteria useful as biofungicide, bioinsecticide or nematicide selected from the group consisting of
(C1.1) *Bacillus agri,* (C1.2) *Bacillus aizawai,* (C1.3) *Bacillus albolactis,* (C1.6) *Bacillus coagulans,* (C1.7) *Bacillus endoparasiticus,* (C1.8) *Bacillus endorhythmos,* (C1.9) *Bacillus azotoformans,* (C1.10) *Bacillus kurstaki,* (C1.11) *Bacillus lacticola,* (C1.12) *Bacillus lactimorbus,* (C1.13) *Bacillus lactis,* (C1.14) *Bacillus laterosporus,* (C1.15) *Bacillus lentimorbus,* (C1.16) *Bacillus licheniformis,* in particular strain SB3086 (product known as EcoGuard™ Biofungicide or Green Releaf from Novozymes Biologicals, US), (C1.17) *Bacillus medusa,* (C1.18) *Bacillus megaterium,* (C1.19) *Bacillus metiens,* (C1.20) *Bacillus natto,* (C1.21) *Bacillus nigrificans,* (C1.22) *Bacillus popillae* (also known as *Paenibacillus popilliae,* product known as Milky spore disease from St. Gabriel Laboratories), (C1.24) *Bacillus siamensis,* (C1.25) *Bacillus sphaericus,* in particular Serotype H5a5b strain 2362, (product known as VectoLex® from Valent BioSciences, US), (C1.26) *Bacillus subtilis var. amyloliquefaciens* strain FZB24 (products known as Taegro®, Rhizopro, FZB24), (C1.27) *Bacillus thuringiensis,* in particular (C1.27a) *Bacillus thuringiensis var. israelensis* (serotype H-14), in particular strain AM65-52 (Accession No. ATCC 1276, products known as VectoBac®, from Valent BioSciences, US) or strain BMP 144, (product known as Aquabac from Becker Microbial Products Ill.), (C1.27b) *Bacillus thuringiensis* subsp. aizawai strain ABTS-1857 (products known as XenTari® from Bayer Crop Science, DE) or strain GC-91 (Accession No. NCTC 11821), or serotype H-7, (products known as Florbac WG from Valent BioSciences, US) or (C1.27c) *Bacillus thuringiensis* subsp. kurstaki strain HD-1, (products known as Dipel® ES from Valent BioSciences, US), or strain BMP 123 from Becker Microbial Products, IL., or strain ABTS 351 (Accession No. ATCC SD-1275), or strain PB 54 (Accession No. CECT 7209), or strain SA 11 (Accession No. NRRL B-30790), or strain SA 12 (Accession No. NRRL B-30791), or strain EG 2348 (Accession No. NRRL B-18208) or (C1.27d) *Bacillus thuringiensis* subsp. tenebrionis strain NB 176 (products known as Novodor® FC from BioFa, Del.) or (C1.27e) *Bacillus thuringiensis* subsp. morrisoni or (C1.27f) *Bacillus thuringiensis* var. san die go (product known as M-One® from Mycogen Corporation, US) or (C1.27g) *Bacillus thuringiensis* subsp. *thuringiensis* (serotype 1) MPPL002, or (C1.27h) *Bacillus thuringiensis* var. aegyptii, or (C1.27k) *Bacillus thuringiensis* var. colmeri, or (C1.27l) *Bacillus thuringiensis* var. darmstadiensis, or (C1.27m) *Bacillus thuringiensis* var. dendrolimus, or (C1.27n) *Bacillus thuringiensis* var. galleriae, or (C1.27o) *Bacillus thuringiensis* var. japonensis, in particular strain Bulbul or (C1.27r) *Bacillus thuringiensis* var. 7216 (products known as Amactic, Pethian), or (C1.27s) *Bacillus thuringiensis* var. T36, or (C1.27t) *Bacillus thuringiensis* strain BD#32 (Accession No. NRRL B-21530) from Agraquest, or (C1.27u) *Bacillus thuringiensis* strain AQ52 (Accession No. NRRL B-21619) from Agraquest, or (C1.27v) *Bacillus thuringiensis* strain CR-371 (Accession No. ATCC 55273), (C1.28) *Bacillus uniflagellatus*, (C1.29) *Delftia acidovorans*, in particular strain RAY209 (products known as BioBoose®), (C1.30) *Lysobacter antibioticus*, in particular strain 13-1 (cf. Biological Control 2008, 45, 288-296), (C1.31) Pasteuria penetrans (synonym *Bacillus penetrans*), (C1.32) *Pseudomonas chlororaphis*, in particular strain MA 342 (products known as Cedomon from Bioagri, S) or strain 63-28 (product known as ATEze from EcoSoil Systems, US), (C1.33) *Pseudomonas proradix* (products known as Proradix®), (C1.34) *Streptomyces galbus*, in particular strain K61 (Accession No. DSM 7206, products known as Mycostop®, cf. Crop Protection 2006, 25, 468-475) or strain NRRL 30232, (C1.35) *Streptomyces griseoviridis* (products known as Mycostop®), (C1.36) *Bacillus lautus*, (C1.37) *Bacillus atrophaeus*, (C1.39) *Bacillus mycoides*, in particular isolate J (product known as BmJ from Certis USA) or strain 683 or strain AQ726 (Accession No. NRRL B21664), (C1.40) *Bacillus acidoterrestris*, (C1.41) *Bacillus fastidiosus*, (C1.42) *Bacillus megaterium* (products known as Bioarc®, from BioArc), or strain YFM3.25, (C1.43) *Bacillus psychrosaccharolyticus*, (C1.44) *Bacillus maroccanus*, (C1.45) *Bacillus megaterium* C, (C1.46) *Bacillus pantothenticus* (also known as *Virgibacillus pantothenticus*), in particular strain ATCC 14576/DSM 491, (C1.47) *Bacillus lentus*, (C1.48) *Bacillus badius*, (C1.49) *Bacillus smithi*, (C1.50) *Acinetobacter* spec, (C1.51) *Acinetobacter lwoffii*, (C1.52) *Bacillus luciferensis*, (C1.53) *Chromobacterium subtsugae*, in particular strain PRAA4-1T (product known as Grandevo, from Marrone Bio Innovations), (C1.54) *Pasteuria usgae* (product known as Econem™ Biological Nematicide), (C1.55) *Paenibacillus polymyxa*, in particular strain AC-1 (product known as Topseed from Green Bio-tech Company Ltd.), (C1.57) *Serratia entomophila* (product known as Invade®), (C1.58) *Bacillus chitinosporus*, in particular strain AQ746 (Accession No. NRRL B-21618), (C1.59) *Pseudomonas cepacia* (ex *Burkholderia cepacia*, product known as Deny from Stine Microbial Products), (C1.60) *Bacillus nematocida*, in particular strain B-16, (C1.61) *Bacillus circulans*, (C1.62) *Brevibacillus laterosporus* (also known as *Bacillus laterosporus*), in particular strain ATCC 64 or strain NRS 1111 or strain NRS 1645 or strain NRS 1647 or strain BPM3 or strain G4 or strain NCIMB 41419, (C1.63) *Corynebacterium paurometabolum*, (C1.64) *Lactobacillus acidophilus* (products known as Fruitsan® from Inagrosa-Industrias Agrobiologicas, S.A), (C1.65) *Paenibacillus alvei*, in particular strain T36 or strain III3DT-1A or strain III2E or strain 46C3 or strain 2771, (C1.66) *Paenibacillus macerans*, (C1.67) *Pasteuria nishizawae*, in particular strain Pn1, (C1.68) *Pasteuria ramosa*, (C1.69) *Pasteuria thornei*, (C1.70) *Pseudomonas aeruginosa*, in particular strains WS-1 or PN1, (C1.71) *Pseudomonas aureofaciens*, in particular strain TX-1 (product known as Spot-Less Biofungicide from Eco Soils Systems, CA), (C1.72) *Pseudomonas fluorescens*, in particular strain A506 (products known as Blightban or BlightBan A506 from NuFarm), (C1.73) *Pseudomonas putida*, (C1.74) *Pseudomonas resinovorans* (products known as Solanacure), (C1.75) *Pseudomonas syringae*, in particular strain MA-4 (products known as Biosave from EcoScience, US), (C1.76) *Serratia marcescens*, in particular strain SRM (MTCC8708) or strain R35, (C1.77) *Streptomyces candidus*, in particular strain Y21007-2, (products known as Bio-bac), (C1.78) *Streptomyces lydicus*, in particular strain WYCD108 (products known as ActinovateSP) or strain WYEC108 (products known as Actino-iron from Natural Industries), (C1.79) *Streptomyces saraceticus*, (C1.80) *Streptomyces venezuelae*, (C1.81) *Xenorhabdus nematophila*, (C1.82) *Agrobacterium radiobacter*, (C1.83) *Bacillus mojavensis*, especially strain CECT-7666, (C1.84) *Pantoea agglomerans*, in particular strain E325 (products known as Bloomtime Biological FD Biopesticide), (C1.85) *Streptomyces colombiensis*, (C1.86) *Streptomyces* sp. WYE 20 (KCTC 0341 BP) and WYE 324 (KCTC 0342BP), (C1.87) *Bacillus brevis* (also known as *Brevibacillus brevis*, product known as Brevisin), in particular strain SS86-3 or strain SS86-4 or strain SS86-5 or strain 2904, (C1.88) *Erwinia carotovora* (also known as *Pectobacterium carotovorum*) carotovora (product known as Biokeeper), (C1.89) *Xanthomonas campestris* pv vesicatoria (product known as Camprico), (C1.90) *Pasteuria reniformis*, in particular strain Pr3, (C1.91) *Burkholderia* spec strain A396 (Accession No. NRRL B-50319, product known as MBI-206 TGAI from Marrone Bio Innovations), (C1.92) *Bacillus firmus* CNCM I-1582, in particular the spores (cf. U.S. Pat. No. 6,406,690, products known as Bionem, VOTIVO), (C1.93) *Bacillus cereus* (synonyms: *Bacillus endorhythmos*, *Bacillus medusa*), in particular spores of *Bacillus cereus* strain CNCM I-1562 (cf. U.S. Pat. No. 6,406,690), or strain BP01 (ATCC 55675, product known as Mepichlor from Arysta, US or Mepplus, Micro-Flo Company LLC, US), (C1.94) *Bacillus amyloliquefaciens* strain IN937a or strain FZB42 (DSM 231179, product known as RhizoVital® from ABiTEP, DE), or strain B3, or strain D747, (products known as Bacstar® from Etec Crop Solutions, NZ, or Double Nickel™ from Certis, US), (C1.95) *Bacillus subtilis,* in particular strain GB03 (Accession No. ATCC SD-1397, product known as Kodiak® from Bayer Crop Science, DE) or strain QST713/AQ713 (Accession No. NRRL B-21661, products known as Serenade QST 713C), Serenade Soil and Serenade Max from AgraQuest, US) or strain AQ 153 (ATCC accession No. 55614) or strain AQ743 (Accession No. NRRL B-21665) or strain DB 101, (products known as Shelter from Dagutat Bio lab, ZA) or strain DB 102, (products known as Artemis from Dagutat Bio lab, ZA) or strain MBI 600, (products known as Subtilex from Becker Underwood, US) or strain QST30002/AQ30002 (Accession No. NRRL B-50421, cf. WO 2012/087980) or strain QST30004/AQ30004 (Accession No. NRRL B-50455, cf. WO 2012/087980), (C1.96) *Bacillus pumilus,* in particular strain GB34 (Accession No. ATCC 700814, products known as Yield Shield® from Bayer Crop Science, DE) or strain QST2808 (Accession No. NRRL B-30087, products known as Sonata QST 2808® from Agra-Quest, US), or strain BU F-33 (product known as Integral F-33 from Becker Underwood, US), or strain AQ717 (Accession No. NRRL B21662, (C1.97) *Pasteuria* sp., in particular strain SD-5832 and (C1.98) *Pasteuria* sp., in particular strain PTA-9643, (C1.98) *Agrobacterium radiobacter,* in particular strain K84 (products known as Galltrol-A from Ag-BioChem) or strain K1026 (products known as Nogall, Becker Underwood), (C1.99) *Agrobacterium vitis,* in particular the non-pathogenic strain VAR03-1, (C1.100) *Azorhizobium caulinodans,* preferably strain ZB-SK-5, (C1.101) *Azospirillum amazonense,* (C1.102) *Azospirillum brasilense,* (C1.103) *Azospirillum halopraeference,* (C1.104) *Azospirillum irakense,* (C1.105) *Azospirillum hpoferum,* (C1.106), *Azotobacter chroococcum,* preferably strain H 23 (CECT 4435), (C1.107) *Azotobacter vinelandii,* preferably strain ATCC 12837, (C1.108) *Bacillus acidocaldarius,* (C1.109) *Bacillus acidoterrestris,* (C1.110) *Bacillus alcalophilus,* (C1.111) *Bacillus alvei,* (C1.112) *Bacillus aminoglucosidicus,* (C1.113) *Bacillus aminovorans,* (C1.114) *Bacillus amylolyticus* (also known as *Paenibacillus amylolyticus*), (C1.115) *Bacillus aneurinolyticus,* (C1.116) *Bacillus subtilis* isolate B246, for example in form of the commercially available product Avogreen from RE at UP), (C1.117) *Bacillus tequilensis,* in particular strain NII-094, (C1.118) *Bacillus* sp. strain AQ175 (ATCC Accession No. 55608), (C1.119) *Bacillus* sp. strain AQ177 (ATCC Accession No. 55609), (C1.120) *Bacillus* sp. strain AQ178 (ATCC Accession No. 53522), (C1.121) *Gluconacetobacter diazotrophicus,* (C1.122) *Herbaspirilum rubrisubalbicans,* (C1.123) *Herbaspirilum seropedicae,* (C1.124) *Lactobacillus* sp. (products known as Lactoplant from LactoPAFI), (C1.125) *Lysobacter enzymogenes,* in particular strain C3 (cf. J Nematol. 2006 June; 38(2): 233-239), (C1.126) *Rhodococcus globerulus* strain AQ719 (Accession No. NRRL B21663, from AgraQuest), (C1.127) *Streptomyces* sp. Strain NRRL B-30145 (from Agraquest), (C1.128) *Streptomyces acidiscabies,* in particular strain RL-110T, (product known as MBI-005EP from Marrone Bioinnovations), (C1.129) *Streptomyces goshikiensis,* (C1.130) *Streptomyces lavendulae,* (C1.131) *Streptomyces prasinus* (cf. "Prasinons A and B: potent insecticides from *Streptomyces* prasinus" Applied microbiology 1973 Nov), (C1.132) *Streptomyces rimosus*;

(C2) fungi or yeasts selected from the group consisting of:

(C2.1) *Ampelomyces quisqualis,* in particular strain AQ 10 (product known as AQ 10®), (C2.2) *Aureobasidium pullulans,* in particular blastospores of strain DSM14940 or blastospores of strain DSM 14941 or mixtures thereof (product known as Blossom Protect®), (C2.3) *Beauveria bassiana,* in particular strain ATCC 74040 (products known as Naturalis®) or strain GHA (products known as Mycotrol, BotaniGard) or strain ATP02 (DSM 24665) or strain CG716 (product known as BoveMax), (C2.4) *Candida oleophila,* in particular strain O (products known as Nexy ®) or strain I-182 (products known as ASPIRE®, Decco I-182), (C2.5) *Coniothyrium minitans,* in particular strain CON/M/91-8 (DSM-9660) (products known as Contans®), (C2.6) *Dilophosphora alopecuri* (products known as Twist Fungus™), (C2.7) *Gliocladium catenulatum,* in particular strain J1446 (products known as Prestop®), (C2.8) *Lecanicillium lecanii* (formerly known as *Verficillium lecanii*), in particular conidia of strain KV01 (products known as Mycotal®, Vertalec®, from Koppert/Alysta) or strain DAOM198499 or DAOM216596, (C2.9) *Metarhizium anisopliae,* in particular strain F52 (DSM 3884, ATCC 90448, products known as BIO 1020, MET52) or var. acridum isolate IMI 330189/ARSEF 7486 (products known as Green Muscle®) (C2.10) *Metschnikovia fruchcola,* in particular the strain NRRL Y-30752 (products known as Shemer®), (C2.11) *Microsphaeropsis ochracea* (products known as Microx®), (C2.12) *Muscodor albus,* in particular strain QST 20799 (products known as QRD300), (C2.13) *Nomuraea rileyi,* in particular strains SA86101, GU87401, SR86151, CG128 and VA9101, (C2.14) *Paecilomyces lilacinus,* in particular spores of *P. lilacinus* strain 251(AGAL 89/030550) (products known as BioAct®, cf. Crop Protection 2008, 27, 352-361), (C2.15) *Paecilomyces fumosoroseus* (also known as *Isaria fumosorosae*), in particular strain apopka 97 (ATCC 20874) (products known as PFR-97TM 20% WDG, PreFeRal® WG,), (C2.16) *Penicillium bilaii,* in particular strain ATCC22348 (products known as JumpStart®, PB-50, Provide), (C2.17) *Pichia anomala,* in particular strain WRL-076, (C2.18) *Pseudozyma flocculosa,* in particular strain PF-A22 UL (products known as Sporodex®L), (C2.19) *Pythium oligandrum,* in particular strain DV74 (products known as Polyversum) or strain M1 (ATCC 38472), (C2.20) *Trichoderma asperellum,* in particular strain ICC 012 (also known as *Trichoderma harzianum* ICC012, products known as Bioten ®) or strain SKT-1 (products known as Triderma® or ECO-HOPE®) or strain T34 (products known as T34 Biocontrol) or strain SF04 or strain TV1 (also known as *Trichoderma viride* TV1) or strain T11 (also known as *Trichoderma viride* T25), (C2.21) *Trichoderma harzianum,* in particular *T. harzianum* T39 (products known as Trichodex®) or strain T-22 (products known as PLANT SHIELD®T-22G, Rootshield, TurfShield), or strain TH 35 (products known as ROOT PRO®) or strain TSTh20/PTA-0317 or strain 1295-22 (products known as Bio-Trek), (C2.22) *Beauveria brongniartii* (products known as Beaupro), (C2.23) *Aschersonia aleyrodes,* (C2.24) *Hirsutella thompsoni* (products known as Mycohit), (C2.25) *Lagenidium giganteum* (products known as LAGINEX®), (C2.26) *Myrothecium verrucaria* strain AARC-0255 (products known as DiTeraTM), (C2.27) *Pandora delphacis,* (C2.28) *Tsukamurella paurometabola,* in particular strain C-924 (products known as HeberNem®), (C2.30) ARF 18 (Arkansas Fungus 18), (C2.31) *Trichoderma atroviride* in particular strain CNCM 1-1237 (products known as Esquive® WP, Sentinel®, Tenet®) or strain NMI No. V08/002387 or strain NMI No. V08/002389 or strain NMI No. V08/002390 or strain NMI No. V08/002388 (patent application US 2011/0009260) or strain ATCC 20476 (IMI 206040) or strain T11 (IM1352941) or strain LC52 (products known as Sentinel®, Agrimm Technologies, (products known as Esquive®) or strain NMI V08/002387, or strain NMI V08/002389 or strain SKT-1/FERM P-1651 or strain SKT-2/FERM P-16511 or strain SKT-3/FERM P-17021 (described in JP3691264) or strain L52 (product known as SENTINEL®) , (C2.32) *Glomus aggregatum,* (C2.33) *Glomus etunicatum,* (C2.34) *Glomus intraradices,* (C2.35) *Glomus mosseae,* (C2.36) *Glomus deserticola,* (C2.37) *Glomus clarum,* (C2.38) *Glomus brasilianum,* (C2.39) *Glomus monosporum,* (C2.40) *Gigaspora margarita,* (C2.41) *Rhizopogon villosullus,* (C2.42) *Rhizopogon. luteolus,* (C2.43) *Rhizopogon. amylopogon,* (C2.44) *Rhizopogon fulvigieba,* (C2.45) *Pisolithus tinctorius,* (C2.46) *Scleroderma cepa,* (C2.47) *Scleroderma citrinum,* (C2.48) *Sullins granulatus,* (C2.49) *Sullins punctatapies,* (C2.50) *Laccaria laccata,* (C2.51) *Laccaria bicolor;* (C2. 52) *Metarhizium flavoviride,* (C2.53) *Arthrobotrys dactyloides,* (C2.54) *Arthrobotrys oligospora,* (C2.55) *Arthrobotrys superba* (C2.56) *Aspergillus flavus* strain NRRL 21882 (product known as Afla-Guard®, from Syngenta) or strain AF36 (product known as AF36), (C2.57) *Candida saitoana,* in particular strain NRRL Y-21022 (products known as BIOCURE® or BIOCOAT®), (C2.58) *Chaetomium cupreum,* (C2.59) *Chaetomium globosum,* (C2.60) *Chondrostereum purpureum,* in particular strain PFC2139 , (C2.61) *Cladosporium cladosporioides* strain H39 (as described in EP2230918 A1), (C2.62) *Conidiobolus obscurus,* (C2.63) *Cryptococcus albidus* (product known as Yield Plus®.), (C2.64) *Cryptococcus flavescens,* in particular strain NRRL Y-50378 and strain NRRL Y-50379, (C2.65) , *Dactylaria candida,* (C2.66) *Entomophthora virulenta,* (C2.67) *Harposporium anguilluilae,* (C2.68) *Hirsutella minnesotensis,* (C2.69) *Hirsutella rhossiliensis,* (C2.70) *Meristacrum asterospermum,* (C2.71) *Microdochium dimerum,* in particular strain L13 (products known as ANTIBOT®, Agrauxine), (C2.72) *Monacrosporium cionopagum,* (C2. 73) *Monacrosporium psychrophilum,* (C2. 74) *Monacrosporium drechsieri,* (C2. 75) *Monacrosporium gephyropagum,* (C2.76) *Ophiostoma piliferum,* in particular strain D97 (products known as Sylvanex), (C2.77) *Paecilomyces variotii,* in particular strain Q-09 (product known as Nemaquim), (C2.78) *Pochonia chiamydosporia (=Vercillium chiamydosporiumi),* (C2.79) *Pseudozyma aphidis* (C2.80) *Stagonospora heteroderae,* (C2.81) *Stagonospora phaseoli,* (C2.82) *Talaromyces flavus,* in particular strain V117b (products known as PROTUS®), (C2.83) *Trichoderma viride* (also known as *Trichoderma gamsii*), in particular strain ICC 080 (products known as REMEDIER® WP, Bioderme®) and strain TV1 (products known as T. viride TV1, Agribiotec), (C2.84) *Trichoderma harmatum,* isolate 382 (C2.85) *Trichoderma koningii,* (C2.86) *Trichoderma lignorum,* (C2.87) *Trichoderma polysporum,* isolate IMI 206039 (ATCC 20475), (C2.88) *Trichoderma stromaticum,* (C2.89) *Trichoderma vixens* (also known as *Gliociadium virens*), in particular strain GL-21 (products known as SOILGARD®) or strain G41 (products known as BW240 WP Biological Fungicide), (C2.90) *Ulociadium oudemansii,* in particular strain HRU3 (products known as BOTRY-ZEN®), (C2.91) *Verticillium albo-atrum* in particular strain WCS850, (C2.92) *Verticillium chiamydosporium,* (C2.93) *Verticillium dahlia* isolate WCS 850 (products known as Dutch Trig), (2.94) *Zoophtora radicans,* (2.95) *Cylindrocarpon heteronema,* (C2.96) *Exophiala jeanselmei,* (C2.97) *Exophilia pisciphila,* (C2.98) *Fusarium aspergilus,* (C2.99) *Fusarium oxysporum,* for example the non pathogenic strain Fo47 (product FUSACLEAN) or the non pathogenic strain 251/2RB (product known as BIOFOX®), (C2.100) *Fusarium solani,* for example strain Fs-K (as described in patent application US20110059048), (C2.101) *Gliocladium roseum,* in particular strain 321U, (C2.102) *Mucor haemelis* (products known as BIO-AVARD), (C2.103) *Nematoctonus geogenius,* (C2.104) *Nematoctonus leiosporus,* (C2.105) *Phlebiopsis gigantea* (products known as ROTSOP®), (C2.106) *Trichoderma album* (products known as Biozeid®), (C2.107) *Trichoderma asperellum* (products known as BIO-TAM™) and, (C2.108) *Trichoderma gamsii* (products known as BIO-TAM™) or in particular strain ICC080 (products known as Bioderma), (C2.109) *Hirsutella citriformis,* (C2.110) *Muscodor roseus* strain A3-5 (Accession No. NRRL 30548), (C2.111) *Neocosmospora vasinfecta,* (C2.112) *Penicillium vermiculatum* (products known as Vermiculen®), (C2.113) *Saccharomyces cerevisae,* in particular strain CNCM No. I-3936, strain CNCM No. I-3937, strain CNCM No. I-3938, strain CNCM No. I-3939 (patent application US 2011/0301030), (C2.114) *Sporothrix insectorum* (products known as Sporothrix®), (C3) Protozoas selected from the group consisting of (C3.1) *Nosema locustae,* (C3.2) *Thelohania,* (C3.3) *Vairimorpha;*

(C4) Viruses selected from the group consisting of (C4.1) Gypsy moth (*Lymantria dispar*) nuclear polyhedrosis virus (NPV), (C4.2) Tussock moth (*Lymantriidae*) NPV, (C4.3) Heliothis NPV, (C4.4) Pine sawfly (*Neodiprion*) NPV, (C4.5) Codling moth (*Cydia pomonella*) granulosis virus (GV), (C4.6) *Adoxophyes orana* GV (product known as Capex®), (C4.7) *Helicoverpa armigera* NPV (products known as Vivus Max®, Vivus Gold®) or Gemstar®), (C4.8) *Spodoptera exigua* NPV, (C4.9) *Spodoptera littoralis* NPV, (C4.10) *Spodoptera litura* NPV, (C4.11) *Neodiprion abietis* NPV (product known as ABIETIV™), (C4.12) *Neodiprion sertifer* NPV (product known as Neocheck-S™), (C4.13) *Agrotis segetum* (turnip moth) nuclear polyhedrosis virus (NPV), (C4.14) *Anticarsia gemmatalis* (Woolly pyrol moth) mNPV (products known as Poly gen), (C4.15) *Autographa califomica* (Alfalfa Looper) mNPV (products known as VPN80 from Agricola El Sol);

(C5) entomopathogenic nematodes selected from the group consisting of (C5.1) *Steinernema* ssp. (=*Neoaplectana* spp.), (C5.2) *Steinernema scapterisci,* (C5.3) *Steinernema feltiae* (=*Neoplectana carpcapsae,* products known as Nemasys®), (C5.4) *Steinernema carpcapsae* (products known as Biocontrol; Nematac® C) , (C5.5) *Heterorhabditis* spp., (C5.6) *Heterorhabditis heliothidis,* (C5.7) *Hexamermis* spp., (C5.8) *Amphimermis* spp., (C5.9) *Mennis nigrescens,* (C5.10) *Agamermis decaudata,* (C5.11) *Maupasina weissi,* (C5.12) *Subulura* spp., (C5.13) *Seuratum cadarachense,* (C5.14) *Pterygodermatites* spp., (C5.15) *Abbreviata caucasica,* (C5.16) *Spirura guianensis,* (C5.17) *Diplotriaena* spp., (C5.18) *Tetrameres* spp., (C5.19) *Acuaria* spp., (C5.20) *Gongylonema* spp., (C5.21) *Protrellatus* spp., (C5.22) *Hydromermis* spp., (C5.23) *Cameronia* spp., (C5.24) *Physaloptera* spp., (C5.25) *Chitwoodiella ovofilamenta,* (C5.26) *Gynopoecilia pseudovipara,* (C5.27) *Parasitylenchus* spp., (C5.28) *Neoparasitylen-chus rugulosi,* (C5.29) *Sulphurety-*

*lenchus elongatus,* (C5.30) *Sphaerulariopsis* spp., (C5.31) *Allantonema* spp., (C5.32) *Contortylenchus* spp., (C5.33) *Bovienema* spp., (C5.34) *Parasitaphelenchus* spp., (C5.35) *Parasitorhabditis* spp., (C5.36) *Phasmarhabditis hermaphrodita,* (C5.37) *Romanomermis* spp., (C5.38) *Octomyomermis* spp., (C5.39) *Strelkovimermis petersen,* (C5.40) *Perutilimermis culicis,* (C5.41) *Culicimermis* spp., (C5.42) *Empidomermis* spp., (C5.43) *Gastromermis* spp., (C5.44) *Isomermis* spp., (C5.45) *Neomesomermis* spp., (C5.46) *Limnomermis* spp., (C5.47) *Mesomermis* spp., (C5.48) *Xenorhabdus luminescence* (entomopathogenic bacteria symbiotically associated with nematodes); (C5.49) *Heterorhabditis bacteriophora* (products known as B-Green, Nemasys® G), (C5.50) *Heterorhabditis baujardi,* (C5.51) *Heterorhabditis indica* (products known as Nematon), (C5.52) *Heterorhabditis marelatus,* (C5.53) *Heterorhabditis megidis,* (C5.54) *Heterorhabditis zealandica,* (C5.55) *Phasmarhabditis hermaphrodita,* (C5.56) *Steinernema bibionis,* (C5.57) *Steinernema glaseri* (products known as Biotopia), (C5.58) *Steinernema kraussei* (products known as Larvesure, Nemasys® L), (C5.59) *Steinernema riobrave* (products known as Biovector), (C5.60) *Steinernema scapterisci* (products known asNematac S), (C5.61) *Steinernema scarabaei,* (C5.62) *Steinernema siamkayai,* (C5.63) *Beddingia (=Deladenus) siridicola,* (C5.64) *Filipjevimermis leipsandra,* (C5.65) *Steinernema thailandse* products known as Nemanox®), (C6) Inoculants selected from the group consisting of (C6.1) *Rhizobium leguminosarum,* in particular bv. viceae strain Z25 (Accession No. CECT 4585), (C6.2) *Rhizobium tropici,* (C6.3) *Rhizobium loti,* (C6.4) *Rhizobium trifolii,* (C6.5) *Rhizobium meliloti,* (C6.6) *Rhizobium fredii,* (C6.7) *Azorhizobium caulinodans,* (C6.8) *Pseudomonas,* (C6.9) *Azospirillum,* (C6.10) *Azotobacter,* (C6.11) *Streptomyces,* (C6.12) *Burkholdia,* (C6.13) *Agrobacterium,* (C6.14) *Endo Mycorhiza,* (C6.15) Ecto Mycorhiza, (C6.16) Vesicular Arbuscular (VA) Mycorhiza, (C6.17) *Bradyrhizobium;*

(C7) Botanicals (or: plant extracts) selected from the group consisting of (C7.1) Thymus oil, (C7.2) Azadirachtin (Neem), (C7.3) Pyrethrum, (C7.4) Cassia nigricans, (C7.5) Quassia amara, (C7.6) Rotenon, (C7.7) Garlic, (C7.8) Quillaja, (C7.9) Sabadilla, in particular Veratrin, (C7.10) Ryania, in particular Ryanodine, (C7.11) Viscum album (mistel), (C7.12) mugwort or common tansy (*Tanacetum vulgare*), (C7.13) *Artemisia absinthium,* (C7.14) *Urtica dioica,* (C7.15) *Symphytum officinale,* (C7.16) *Tropaeulum majus,* (C7.17) *Quercus* (C7.18) mustard flour, (C7.19) *Chenopodium anthelminticum,* (C7.20) *Dryopteris filix-mas,* (C7.21) bark of Chinese bittersweet (Celastrus orbiculatus), (C7.22) *Equisetum arvense,* (C7.23) bark of Celastus angulatus, (C7.24) Laminarin (Brown Algae), (C7.25) Alginic acid (Brown Algae), (C7.26) Chitin/Chitinosan. (C7.27) *Chenopodium quinoa* (product known as HeadsUp), (C7.28) Melaleuca alternifolia (products known as Timorex Gold®), (C7.29) Sesame oil (product known as Dragonfire-CCPTM) and (C7.30) natural extracts or simulated blend of *Chenopodium ambrosioides* (products known as Requiem).

(C8) Products produced by microorganisms including proteins or secondary metabolites selected from the group consisting of (C8.1) Harpin (produced by *Erwinia amylovora,* products known as Harp-N-Tek™, Messenger®, Employ™ ProAct™). *Bacillus subtilis,* for example the strains GBO3 and QST 713, as well as *Bacillus amyloliquefaciens,* strain FZB 24 and 42, are species with phytopathogenic properties. These bacteria are applied to the soil or to the leaves. *Bacillus thuringiensis* with its different subspecies produces endotoxin containing crystals which have high insect pathogenic specifity. *Bacillus thuringiensis* subsp. kurstaki, strain HD-1, is used for control of lepidopteran larvae, but without noctuidae. *Bacillus thuringiensis* subsp. aizawai, for example the strains SAN 401 I, ABG-6305 and ABG-6346, is effective against different lepidopteran species including also noctuidae. *Bacillus thuringiensis* subsp. *tenebrionis,* for example the strains SAN 418 I and ABG-6479, protects plants against leaf beetle larvae. *Bacillus thuringiensis* subsp. *israelensis,* for example the strains SAN 402 I and ABG-6164, is applied against larvae of various dipteran pests, e.g. mosquitoes and nematoceres.

Preference is given to combinations comprising at least (A) Fluopyram and (B1) *Bacillus firmus* strain CNCM I-1582 and (C) the biological control agent, with the proviso that the spore-forming bacterium (B) of the genera *Bacillus* and the biological control agent (C) are not identical.

Preference is given to combinations comprising at least (A) Fluopyram and (B2) *Bacillus cereus* strain CNCM I-1562 and (C) the biological control agent, with the proviso that the spore-forming bacterium (B) of the genera *Bacillus* and the biological control agent (C) are not identical.

Preference is given to combinations comprising at least (A) Fluopyram and (B3) *Bacillus amyloliquefaciens* strain IN937a, and (C) the biological control agent, with the proviso that the spore-forming bacterium (B) of the genera *Bacillus* and the biological control agent (C) are not identical.

Preference is given to combinations comprising at least (A) Fluopyram and (B4) *Bacillus amyloliquefaciens* strain FZB42 and (C) the biological control agent, with the proviso that the spore-forming bacterium (B) of the genera *Bacillus* and the biological control agent (C) are not identical.

Preference is given to combinations comprising at least (A) Fluopyram and (B5) *Bacillus subtilis* strain GB03 and (C) the biological control agent, with the proviso that the spore-forming bacterium (B) of the genera *Bacillus* and the biological control agent (C) are not identical.

Preference is given to combinations comprising at least (A) Fluopyram and (B6) *Bacillus subtilis* strain QST713 and (C) the biological control agent, with the proviso that the spore-forming bacterium (B) of the genera *Bacillus* and the biological control agent (C) are not identical.

Preference is given to combinations comprising at least (A) Fluopyram and (B7) *Bacillus pumilus* strain GB34 and (C) the biological control agent, with the proviso that the spore-forming bacterium (B) of the genera *Bacillus* and the biological control agent (C) are not identical.

Preference is given to combinations comprising at least (A) Fluopyram and (B8) *Bacillus pumilus* strain QST2808 and (C) the biological control agent, with the proviso that the spore-forming bacterium (B) of the genera *Bacillus* and the biological control agent (C) are not identical.

Preference is given to combinations comprising (A) Fluopyram and (B1) *Bacillus firmus* strain CNCM I-1582 and (C) the biological control agent, with the proviso that the spore-forming bacterium (B) of the genera *Bacillus* and the biological control agent (C) are not identical.

Preference is given to combinations comprising (A) Fluopyram and (B2) *Bacillus cereus* strain CNCM I-1562 and (C) the biological control agent, with the proviso that the spore-forming bacterium (B) of the genera *Bacillus* and the biological control agent (C) are not identical.

Preference is given to combinations comprising (A) Fluopyram and (B3) *Bacillus amyloliquefaciens* strain IN937a, and (C) the biological control agent, with the proviso that the spore-forming bacterium (B) of the genera *Bacillus* and the biological control agent (C) are not identical.

Preference is given to combinations comprising (A) Fluopyram and (B4) *Bacillus amyloliquefaciens* strain FZB42 and (C) the biological control agent, with the proviso that the spore-forming bacterium (B) of the genera *Bacillus* and the biological control agent (C) are not identical.

Preference is given to combinations comprising (A) Fluopyram and (B5) *Bacillus subtilis* strain GB03 and (C) the biological control agent, with the proviso that the spore-forming bacterium (B) of the genera *Bacillus* and the biological control agent (C) are not identical.

Preference is given to combinations comprising (A) Fluopyram and (B6) *Bacillus subtilis* strain QST713 and (C) the biological control agent, with the proviso that the spore-forming bacterium (B) of the genera *Bacillus* and the biological control agent (C) are not identical.

Preference is given to combinations comprising (A) Fluopyram and (B7) *Bacillus pumilus* strain GB34 and (C) the biological control agent, with the proviso that the spore-forming bacterium (B) of the genera *Bacillus* and the biological control agent (C) are not identical.

Preference is given to combinations comprising Fluopyram and (B8) *Bacillus pumilus* strain QST2808 and (C) the biological control agent, with the proviso that the spore-forming bacterium (B) of the genera *Bacillus* and the biological control agent (C) are not identical.

Preference is given to combinations comprising (A) Fluopyram and the (B1) *Bacillus firmus* strain CNCM I-1582 and one biological control agent selected from group (C1) bacteria as described above with the proviso that the spore-forming bacterium (B) of the genera *Bacillus* and the biological control agent (C) are not identical.

Preference is given to combinations comprising (A) Fluopyram and the (B2) *Bacillus cereus* strain CNCM I-1562 and one biological control agent selected from (C1) bacteria as described above with the proviso that the spore-forming bacterium (B) of the genera *Bacillus* and the biological control agent (C) are not identical. Preference is given to combinations comprising (A) Fluopyram and the (B3) *Bacillus amyloliquefaciens* strain IN937a, and one biological control agent selected from (C1) bacteria as described above, with the proviso that the spore-forming bacterium (B) of the genera *Bacillus* and the biological control agent (C) are not identical with the proviso that the spore-forming bacterium (B) of the genera *Bacillus* and the biological control agent (C) are not identical.

Preference is given to combinations comprising (A) Fluopyram and the (B4) *Bacillus amyloliquefaciens* strain FZB42 and one biological control agent selected from (C1) bacteria as described above, with the proviso that the spore-forming bacterium (B) of the genera *Bacillus* and the biological control agent (C) are not identical with the proviso that the spore-forming bacterium (B) of the genera *Bacillus* and the biological control agent (C) are not identical.

Preference is given to combinations comprising (A) Fluopyram and the (B5) *Bacillus subtilis* strain GB03 and one biological control agent selected from (C1) bacteria as described above, with the proviso that the spore-forming bacterium (B) of the genera *Bacillus* and the biological control agent (C) are not identical with the proviso that the spore-forming bacterium (B) of the genera *Bacillus* and the biological control agent (C) are not identical. Preference is given to combinations comprising (A) Fluopyram and the (B6) *Bacillus subtilis* strain QST713 and one biological control agent selected from (C1) bacteria as described above, with the proviso that the spore-forming bacterium (B) of the genera *Bacillus* and the biological control agent (C) are not identical. Preference is given to combinations comprising (A) Fluopyram and the (B7) *Bacillus pumilus* strain GB34 and one biological control agent selected from (C1) bacteria as described above, with the proviso that the spore-forming bacterium (B) of the genera *Bacillus* and the biological control agent (C) are not identical. Preference is given to combinations comprising Fluopyram and the (B8) *Bacillus pumilus* strain QST2808 and one biological control agent selected from (C1) bacteria as described above, with the proviso that the spore-forming bacterium (B) of the genera *Bacillus* and the biological control agent (C) are not identical.

Preference is given to combinations comprising at least (A) Fluopyram and the (B1) *Bacillus firmus* strain CNCM I-1582 and one biological control agent selected from (C2) fungi or yeasts as described above.

Preference is given to combinations comprising at least (A) Fluopyram and the (B2) *Bacillus cereus* strain CNCM I-1562 and one biological control agent selected from (C2) fungi or yeasts as described above.

Preference is given to combinations comprising at least (A) Fluopyram and the (B3) *Bacillus amyloliquefaciens* strain IN937a, and one biological control agent selected from (C2) fungi or yeasts as described above.

Preference is given to combinations comprising at least (A) Fluopyram and the (B4) *Bacillus amyloliquefaciens* strain FZB42 and one biological control agent selected from (C2) fungi or yeasts as described above.

Preference is given to combinations comprising at least (A) Fluopyram and the (B5) *Bacillus subtilis* strain GB03 and one biological control agent selected from (C2) fungi or yeasts as described above.

Preference is given to combinations comprising at least (A) Fluopyram and the (B6) *Bacillus subtilis* strain QST713 and one biological control agent selected from (C2) fungi or yeasts as described above.

Preference is given to combinations comprising at least (A) Fluopyram and the (B7) *Bacillus pumilus* strain GB34 and one biological control agent selected from (C2) fungi or yeasts as described above.

Preference is given to combinations comprising at least (A) Fluopyram and the (B8) *Bacillus pumilus* strain QST2808 and one biological control agent selected from (C2) fungi or yeasts as described above.

Preference is given to combinations comprising at least (A) Fluopyram and the (B1) *Bacillus firmus* strain CNCM I-1582 and one biological control agent selected from (C3) protozoas as described above.

Preference is given to combinations comprising at least (A) Fluopyram and the (B2) *Bacillus cereus* strain CNCM I-1562 and one biological control agent selected from (C3) protozoas as described above.

Preference is given to combinations comprising at least (A) Fluopyram and the (B3) *Bacillus amyloliquefaciens* strain 1N937a, and one biological control agent selected from (C3) protozoas as described above.

Preference is given to combinations comprising at least (A) Fluopyram and the (B4) *Bacillus amyloliquefaciens* strain FZB42 and one biological control agent selected from (C3) protozoas as described above.

Preference is given to combinations comprising at least (A) Fluopyram and the (B5) *Bacillus subtilis* strain GB03 and one biological control agent selected from (C3) protozoas as described above.

Preference is given to combinations comprising at least (A) Fluopyram and the (B6) *Bacillus subtilis* strain QST713 and one biological control agent selected from (C3) protozoas as described above.

Preference is given to combinations comprising at least (A) Fluopyram and the (B7) *Bacillus pumilus* strain GB34 and one biological control agent selected from (C3) protozoas as described above.

Preference is given to combinations comprising at least (A) Fluopyram and the (B8) *Bacillus pumilus* strain QST2808 and one biological control agent selected from (C3) protozoas as described above.

Preference is given to combinations comprising at least (A) Fluopyram and the (B1) *Bacillus firmus* strain CNCM I-1582 and one biological control agent selected from (C4) viruses as described above.

Preference is given to combinations comprising at least (A) Fluopyram and the (B2) *Bacillus cereus* strain CNCM I-1562 and one biological control agent selected from (C4) viruses as described above.

Preference is given to combinations comprising at least (A) Fluopyram and the (B3) *Bacillus amyloliquefaciens* strain IN937a, and one biological control agent selected from (C4) viruses as described above.

Preference is given to combinations comprising at least (A) Fluopyram and the (B4) *Bacillus amyloliquefaciens* strain FZB42 and one biological control agent selected from (C4) viruses as described above.

Preference is given to combinations comprising at least (A) Fluopyram and the (B5) *Bacillus subtilis* strain GB03 and one biological control agent selected from (C4) viruses as described above.

Preference is given to combinations comprising at least (A) Fluopyram and the (B6) *Bacillus subtilis* strain QST713 and one biological control agent selected from (C4) viruses as described above.

Preference is given to combinations comprising at least (A) Fluopyram and the (B7) *Bacillus pumilus* strain GB34 and one biological control agent selected from (C4) viruses as described above.

Preference is given to combinations comprising at least (A) Fluopyram and the (B8) *Bacillus pumilus* strain QST2808 and one biological control agent selected from (C4) viruses as described above.

Preference is given to combinations comprising at least (A) Fluopyram and the (B1) *Bacillus firmus* strain CNCM I-1582 and one biological control agent selected from (C5) entomopathogenic nematodes as described above.

Preference is given to combinations comprising at least (A) Fluopyram and the (B2) *Bacillus cereus* strain CNCM I-1562 and one biological control agent selected from (C5) entomopathogenic nematodes as described above.

Preference is given to combinations comprising at least (A) Fluopyram and the (B3) *Bacillus amyloliquefaciens* strain IN937a, and one biological control agent selected from (C5) entomopathogenic nematodes as described above.

Preference is given to combinations comprising at least (A) Fluopyram and the (B4) *Bacillus amyloliquefaciens* strain FZB42 and one biological control agent selected from (C5) entomopathogenic nematodes as described above.

Preference is given to combinations comprising at least (A) Fluopyram and the (B5) *Bacillus subtilis* strain GB03 and one biological control agent selected from (C5) entomopathogenic nematodes as described above.

Preference is given to combinations comprising at least (A) Fluopyram and the (B6) *Bacillus subtilis* strain QST713 and one biological control agent selected from (C5) entomopathogenic nematodes as described above.

Preference is given to combinations comprising at least (A) Fluopyram and the (B7) *Bacillus pumilus* strain GB34 and one biological control agent selected from (C5) entomopathogenic nematodes as described above.

Preference is given to combinations comprising at least (A) Fluopyram and the (B8) *Bacillus pumilus* strain QST2808 and one biological control agent selected from (C5) entomopathogenic nematodes as described above.

Preference is given to combinations comprising at least (A) Fluopyram and the (B1) *Bacillus firmus* strain CNCM I-1582 and one biological control agent selected from (C6) inoculants as described above.

Preference is given to combinations comprising at least (A) Fluopyram and the (B2) *Bacillus cereus* strain CNCM I-1562 and one biological control agent selected from (C6) inoculants as described above.

Preference is given to combinations comprising at least (A) Fluopyram and the (B3) *Bacillus amyloliquefaciens* strain IN937a, and one biological control agent selected from (C6) inoculants as described above.

Preference is given to combinations comprising at least (A) Fluopyram and the (B4) *Bacillus amyloliquefaciens* strain FZB42 and one biological control agent selected from (C6) inoculants as described above.

Preference is given to combinations comprising at least (A) Fluopyram and the (B5) *Bacillus subtilis* strain GB03 and one biological control agent selected from (C6) inoculants as described above.

Preference is given to combinations comprising at least (A) Fluopyram and the (B6) *Bacillus subtilis* strain QST713 and one biological control agent selected from (C6) inoculants as described above.

Preference is given to combinations comprising at least (A) Fluopyram and the (B7) *Bacillus pumilus* strain GB34 and one biological control agent selected from (C6) inoculants as described above.

Preference is given to combinations comprising at least (A) Fluopyram and the (B8) *Bacillus pumilus* strain QST2808 and one biological control agent selected from (C6) inoculants as described above.

Preference is given to combinations comprising at least (A) Fluopyram and the (B1) *Bacillus firmus* strain CNCM I-1582 and one biological control agent selected from (C7) botanicals as described above.

Preference is given to combinations comprising at least (A) Fluopyram and the (B2) *Bacillus cereus* strain CNCM I-1562 and one biological control agent selected from (C7) botanicals as described above.

Preference is given to combinations comprising at least (A) Fluopyram and the (B3) *Bacillus amyloliquefaciens* strain IN937a, and one biological control agent selected from (C7) botanicals as described above.

Preference is given to combinations comprising at least (A) Fluopyram and the (B4) *Bacillus amyloliquefaciens* strain FZB42 and one biological control agent selected from (C7) botanicals as described above.

Preference is given to combinations comprising at least
(A) Fluopyram and the (B5) *Bacillus subtilis* strain GB03 and one biological control agent selected from (C7) botanicals as described above.

Preference is given to combinations comprising at least
(A) Fluopyram and the (B6) *Bacillus subtilis* strain QST713 and one biological control agent selected from (C7) botanicals as described above.

Preference is given to combinations comprising at least
(A) Fluopyram and the (B7) *Bacillus pumilus* strain GB34 and one biological control agent selected from (C7) botanicals as described above.

Preference is given to combinations comprising at least
(A) Fluopyram and the (B8) *Bacillus pumilus* strain QST2808 and one biological control agent selected from (C7) botanicals as described above.

Preference is given to combinations comprising at least
(A) Fluopyram and the (B1) *Bacillus firmus* strain CNCM I-1582 and one biological control agent selected from (C8.1) Harpin (produced by *Erwinia amylovora*) as described above.

Preference is given to combinations comprising at least
(A) Fluopyram and the (B2) *Bacillus cereus* strain CNCM I-1562 and one biological control agent selected from (C8.1) Harpin (produced by *Erwinia amylovora*) as described above.

Preference is given to combinations comprising at least
(A) Fluopyram and the (B3) *Bacillus amyloliquefaciens* strain IN937a, and one biological control agent selected from (C8.1) Harpin (produced by *Erwinia amylovora*) as described above.

Preference is given to combinations comprising at least
(A) Fluopyram and the (B4) *Bacillus amyloliquefaciens* strain FZB42 and one biological control agent selected from (C8.1) Harpin (produced by *Erwinia amylovora*) as described above.

Preference is given to combinations comprising at least
(A) Fluopyram and the (B5) *Bacillus subtilis* strain GB03 and one biological control agent selected from (C8.1) Harpin (produced by *Erwinia amylovora*) as described above.

Preference is given to combinations comprising at least
(A) Fluopyram and the (B6) *Bacillus subtilis* strain QST713 and one biological control agent selected from (C8.1) Harpin (produced by *Erwinia amylovora*) as described above.

Preference is given to combinations comprising at least
(A) Fluopyram and the (B7) *Bacillus pumilus* strain GB34 and one biological control agent selected from (C8.1) Harpin (produced by *Erwinia amylovora*) as described above.

Preference is given to combinations comprising at least
(A) Fluopyram and the (B8) *Bacillus pumilus* strain QST2808 and one biological control agent selected from (C8.1) Harpin (produced by *Erwinia amylovora*) as described above.

(C5) entomopathogenic nematodes,
(C6) inoculants,
(C7) botanicals, and (C8.1) Harpin (produced by *Erwinia amylovora*)

Preference is also given to the following ternary active compound combinations selected from the group (G1) consisting of (A)+(B1)+(C1.1), (A)+(B1)+(C1.2), (A)+(B1)+(C1.3), (A)+(B1)+(C1.4), (A)+(B1)+(C1.5), (A)+(B1)+(C1.6), (A)+(B1)+(C1.7), (A)+(B1)+(C1.8), (A)+(B1)+(C1.9), (A)+(B1)+(C1.10), (A)+(B1)+(C1.11), (A)+(B1)+(C1.12), (A)+(B1)+(C1.13), (A)+(B1)+(C1.14), (A)+(B1)+(C1.15), (A)+(B1)+(C1.16), (A)+(B1)+(C1.17), (A)+(B1)+(C1.18), (A)+(B1)+(C1.19), (A)+(B1)+(C1.20), (A)+(B1)+(C1.21), (A)+(B1)+(C1.22), (A)+(B1)+(C1.23), (A)+(B1)+(C1.24), (A)+(B1)+(C1.25), (A)+(B1)+(C1.26), (A)+(B1)+(C1.27), (A)+(B1)+(C1.27a), (A)+(B1)+(C1.27b), (A)+(B1)+(C1.27c), (A)+(B1)+(C1.27d), (A)+(B1)+(C1.27e), (A)+(B1)+(C1.27f), (A)+(B1)+(C1.27g), (A)+(B1)+(C1.27h), (A)+(B1)+(C1.27i), (A)+(B1)+(C1.27l), (A)+(B1)+(C1.27m), (A)+(B1)+(C1.27n), (A)+(B1)+(C1.27o), (A)+(B1)+(C1.27r), (A)+(B1)+(C1.27s), (A)+(B1)+(C1.27t), (A)+(B1)+(C1.27u), (A)+(B1)+(C1.27v), (A)+(B1)+(C1.28), (A)+(B1)+(C1.29), (A)+(B1)+(C1.30), (A)+(B1)+(C1.31), (A)+(B1)+(C1.32), (A)+(B1)+(C1.33), (A)+(B1)+(C1.34), (A)+(B1)+(C1.35), (A)+(B1)+(C1.36), (A)+(B1)+(C1.37), (A)+(B1)+(C1.38), (A)+(B1)+(C1.39), (A)+(B1)+(C1.40), (A)+(B1)+(C1.41), (A)+(B1)+(C1.42), (A)+(B1)+(C1.43), (A)+(B1)+(C1.44), (A)+(B1)+(C1.45), (A)+(B1)+(C1.46), (A)+(B1)+(C1.47), (A)+(B1)+(C1.48), (A)+(B1)+(C1.49), (A)+(B1)+(C1.50), (A)+(B1)+(C1.51), (A)+(B1)+(C1.52), (A)+(B1)+(C1.53), (A)+(B1)+(C1.54), (A)+(B1)+(C1.55), (A)+(B1)+(C1.56), (A)+(B1)+(C1.57), (A)+(B1)+(C1.58), (A)+(B1)+(C1.59), (A)+(B1)+(C1.60), (A)+(B1)+(C1.61), (A)+(B1)+(C1.62), (A)+(B1)+(C1.63), (A)+(B1)+(C1.64), (A)+(B1)+(C1.65), (A)+(B1)+(C1.66), (A)+(B1)+(C1.67), (A)+(B1)+(C1.68), (A)+(B1)+(C1.69), (A)+(B1)+(C1.70), (A)+(B1)+(C1.71), (A)+(B1)+(C1.72), (A)+(B1)+(C1.73), (A)+(B1)+(C1.74), (A)+(B1)+(C1.75), (A)+(B1)+(C1.76), (A)+(B1)+(C1.77), (A)+(B1)+(C1.78), (A)+(B1)+(C1.79), (A)+(B1)+(C1.80), (A)+(B1)+(C1.81), (A)+(B1)+(C1.82), (A)+(B1)+(C1.83), (A)+(B1)+(C1.84), (A)+(B1)+(C1.85), (A)+(B1)+(C1.86), (A)+(B1)+(C1.87), (A)+(B1)+(C1.88), (A)+(B1)+(C1.89), (A)+(B1)+(C1.90), (A)+(B1)+(C1.91), (A)+(B1)+(C1.92), (A)+(B1)+(C1.93), (A)+(B1)+(C1.94), (A)+(B1)+(C1.95), (A)+(B1)+(C1.96), (A)+(B1)+(C1.97), (A)+(B1)+(C1.98), (A)+(B1)+(C1.99), (A)+(B1)+(C1.00), (A)+(B1)+(C1.101), (A)+(B1)+(C1.102), (A)+(B1)+(C1.103), (A)+(B1)+(C1.104), (A)+(B1)+(C1.105), (A)+(B1)+(C1.106), (A)+(B1)+(C1.107), (A)+(B1)+(C1.108), (A)+(B1)+(C1.109), (A)+(B1)+(C1.110), (A)+(B1)+(C1.111), (A)+(B1)+(C1.112), (A)+(B1)+(C1.113), (A)+(B1)+(C1.114), (A)+(B1)+(C1.115), (A)+(B1)+(C1.116), (A)+(B1)+(C1.117), (A)+(B1)+(C1.118), (A)+(B1)+(C1.119), (A)+(B1)+(C1.120), (A)+(B1)+(C1.121), (A)+(B1)+(C1.122), (A)+(B1)+(C1.123), (A)+(B1)+(C1.124), (A)+(B1)+(C1.125), (A)+(B1)+(C1.126), (A)+(B1)+(C1.127), (A)+(B1)+(C1.128), (A)+(B1)+(C1.129), (A)+(B1)+(C1.130), (A)+(B1)+(C1.131), (A)+(B1)+(C1.132), (A)+(B1)+(C2.1), (A)+(B1)+(C2.2), (A)+(B1)+(C2.3), (A)+(B1)+(C2.4), (A)+(B1)+(C2.5), (A)+(B1)+(C2.6), (A)+(B1)+(C2.7), (A)+(B1)+(C2.8), (A)+(B1)+(C2.9), (A)+(B1)+(C2.10), (A)+(B1)+(C2.11), (A)+(B1)+(C2.12), (A)+(B1)+(C2.13), (A)+(B1)+(C2.14), (A)+(B1)+(C2.15), (A)+(B1)+(C2.16), (A)+(B1)+(C2.17), (A)+(B1)+(C2.18), (A)+(B1)+(C2.19), (A)+(B1)+(C2.20), (A)+(B1)+(C2.21), (A)+(B1)+(C2.22), (A)+(B1)+(C2.23), (A)+(B1)+(C2.24), (A)+(B1)+(C2.25), (A)+(B1)+(C2.26), (A)+(B1)+(C2.27), (A)+(B1)+(C2.28), (A)+(B1)+(C2.29), (A)+(B1)+(C2.30), (A)+(B1)+(C2.31), (A)+(B1)+(C2.32), (A)+(B1)+(C2.33), (A)+(B1)+(C2.34), (A)+(B1)+(C2.35), (A)+(B1)+(C2.36), (A)+(B1)+(C2.37), (A)+(B1)+(C2.38), (A)+(B1)+(C2.39), (A)+(B1)+(C2.40), (A)+(B1)+(C2.41), (A)+(B1)+(C2.42), (A)+(B1)+(C2.43), (A)+(B1)+(C2.44), (A)+(B1)+(C2.45), (A)+(B1)+(C2.46), (A)+(B1)+(C2.47), (A)+(B1)+(C2.48), (A)+(B1)+(C2.49), (A)+(B1)+(C2.50), (A)+(B1)+(C2.51), (A)+(B1)+(C2.52), (A)+(B1)+(C2.53), (A)+(B1)+(C2.54), (A)+(B1)+(C2.55), (A)+(B1)+(C2.56), (A)+(B1)+(C2.57), (A)+(B1)+(C2.58), (A)+(B1)+(C2.59), (A)+(B1)+(C2.60), (A)+(B1)+(C2.61), (A)+(B1)+(C2.62), (A)+(B1)+(C2.63), (A)+

(B1)+(C2.64), (A)+(B1)+(C2.65), (A)+(B1)+(C2.66), (A)+(B1)+(C2.67), (A)+(B1)+(C2.68), (A)+(B1)+(C2.69), (A)+(B1)+(C2.70), (A)+(B1)+(C2.71), (A)+(B1)+(C2.72), (A)+(B1)+(C2.73), (A)+(B1)+(C2.74), (A)+(B1)+(C2.75), (A)+(B1)+(C2.76), (A)+(B1)+(C2.77), (A)+(B1)+(C2.78), (A)+(B1)+(C2.79), (A)+(B1)+(C2.80), (A)+(B1)+(C2.81), (A)+(B1)+(C2.82), (A)+(B1)+(C2.83), (A)+(B1)+(C2.84), (A)+(B1)+(C2.85), (A)+(B1)+(C2.86), (A)+(B1)+(C2.87), (A)+(B1)+(C2.88), (A)+(B1)+(C2.89), (A)+(B1)+(C2.90), (A)+(B1)+(C2.91), (A)+(B1)+(C2.92), (A)+(B1)+(C2.93), (A)+(B1)+(C2.94), (A)+(B1)+(C2.95), (A)+(B1)+(C2.96), (A)+(B1)+(C2.97), (A)+(B1)+(C2.98), (A)+(B1)+(C2.99), (A)+(B1)+(C2.100), (A)+(B1)+(C2.101), (A)+(B1)+(C2.102), (A)+(B1)+(C103), (A)+(B1)+(C2.104), (A)+(B1)+(C2.105), (A)+(B1)+(C2.106), (A)+(B1)+(C2.107), (A)+(B1)+(C2.108), (A)+(B1), (C2.109), (A)+(B1)+(C2.110), (A)+(B1)+(C2.111), (A)+(B1)+(C2.112), (A)+(B1)+(C2.113), (A)+(B1)+(C2.114), (A)+(B1)+(C3.1), (A)+(B1)+(C3.2), (A)+(B1)+(C3.3), (A)+(B1)+(C4.1), (A)+(B1)+(C4.2), (A)+(B1)+(C4.3), (A)+(B1)+(C4.4), (A)+(B1)+(C4.5), (A)+(B1)+(C4.6), (A)+(B1)+(C4.7), (A)+(B1)+(C4.8), (A)+(B1)+(C4.9) (A)+(B1)+(C4.10), (A)+(B1)+(C4.11), (A)+(B1)+(C4.12), (A)+(B1)+(C4.13), (A)+(B1)+(C4.14), (A)+(B1)+(C4.15), (A)+(B1)+(C5.1), (A)+(B1)+(C5.2), (A)+(B1)+(C5.3), (A)+(B1)+(C5.4), (A)+(B1)+(C5.5), (A)+(B1)+(C5.6), (A)+(B1)+(C5.7), (A)+(B1)+(C5.8), (A)+(B1)+(C5.9), (A)+(B1)+(C5.10), (A)+(B1)+(C5.11), (A)+(B1)+(C5.12), (A)+(B1)+(C5.13), (A)+(B1)+(C5.14), (A)+(B1)+(C5.15), (A)+(B1)+(C5.16), (A)+(B1)+(C5.17), (A)+(B1)+(C5.18), (A)+(B1)+(C5.19), (A)+(B1)+(C5.20), (A)+(B1)+(C5.21), (A)+(B1)+(C5.22), (A)+(B1)+(C5.23), (A)+(B1)+(C5.24), (A)+(B1)+(C5.25), (A)+(B1)+(C5.26), (A)+(B1)+(C5.27), (A)+(B1)+(C5.28), (A)+(B1)+(C5.29), (A)+(B1)+(C5.30), (A)+(B1)+(C5.31), (A)+(B1)+(C5.32), (A)+(B1)+(C5.33), (A)+(B1)+(C5.34), (A)+(B1)+(C5.35), (A)+(B1)+(C5.36), (A)+(B1)+(C5.37), (A)+(B1)+(C5.38), (A)+(B1)+(C5.39), (A)+(B1)+(C5.40), (A)+(B1)+(C5.41), (A)+(B1)+(C5.42), (A)+(B1)+(C5.43), (A)+(B1)+(C5.44), (A)+(B1)+(C5.45), (A)+(B1)+(C5.46), (A)+(B1)+(C5.47), (A)+(B1)+(C5.48), (A)+(B1)+(C5.49), (A)+(B1)+(C5.50), (A)+(B1)+(C5.51), (A)+(B1)+(C5.52), (A)+(B1)+(C5.53), (A)+(B1)+(C5.54), (A)+(B1)+(C5.55), (A)+(B1)+(C5.56), (A)+(B1)+(C5.57), (A)+(B1)+(C5.58), (A)+(B1)+(C5.59), (A)+(B1)+(C5.60), (A)+(B1)+(C5.61), (A)+(B1)+(C5.62), (A)+(B1)+(C5.63), (A)+(B1)+(C5.64), (A)+(B1)+(C5.65), (A)+(B1)+(C6.1), (A)+(B1)+(C6.2), (A)+(B1)+(C6.3), (A)+(B1)+(C6.4), (A)+(B1)+(C6.5), (A)+(B1)+(C6.6), (A)+(B1)+(C6.7), (A)+(B1)+(C6.8), (A)+(B1)+(C6.9), (A)+(B1)+(C6.10), (A)+(B1)+(C6.11), (A)+(B1)+(C6.12), (A)+(B1)+(C6.13), (A)+(B1)+(C6.14), (A)+(B1)+(C6.15), (A)+(B1)+(C6.16), (A)+(B1)+(C6.17), (A)+(B1)+(C7.1), (A)+(B1)+(C7.2), (A)+(B1)+(C7.3), (A)+(B1), (C7.4), (A)+(B1)+(C7.5), (A)+(B1)+(C7.6), (A)+(B1)+(C7.7), (A)+(B1)+(C7.8), (A)+(B1)+(C7.9), (A)+(B1)+(C7.10), (A)+(B1)+(C7.11), (A)+(B1)+(C7.12), (A)+(B1)+(C7.13), (A)+(B1)+(C7.14), (A)+(B1)+(C7.15), (A)+(B1)+(C7.16), (A)+(B1)+(C7.17), (A)+(B1)+(C7.18), (A)+(B1)+(C7.19), (A)+(B1)+(C7.20), (A)+(B1)+(C7.21), (A)+(B1)+(C7.22), (A)+(B1)+(C7.23), (A)+(B1)+(C7.24), (A)+(B1)+(C7.25), (A)+(B1)+(C7.26), (A)+(B1)+(C7.27), (A)+(B1)+(C7.28), (A)+(B1)+(C7.29), (A)+(B1)+(C7.30), (A)+(B1)+(C8.1),
(A)+(B2)+(C1.1), (A)+(B2)+(C1.2), (A)+(B2)+(C1.3), (A)+(B2)+(C1.4), (A)+(B2)+(C1.5), (A)+(B2)+(C1.6), (A)+(B2)+(C1.7), (A)+(B2)+(C1.8), (A)+(B2)+(C1.9), (A)+(B2)+(C1.10), (A)+(B2)+(C1.11), (A)+(B2)+(C1.12), (A)+(B2)+(C1.13), (A)+(B2)+(C1.14), (A)+(B2)+(C1.15), (A)+(B2)+(C1.16), (A)+(B2)+(C1.17), (A)+(B2)+(C1.18), (A)+(B2)+(C1.19), (A)+(B2)+(C1.20), (A)+(B2)+(C1.21), (A)+(B2)+(C1.22), (A)+(B2)+(C1.23), (A)+(B2)+(C1.24), (A)+(B2)+(C1.25), (A)+(B2)+(C1.26), (A)+(B2)+(C1.27), (A)+(B2)+(C1.27a), (A)+(B2)+(C1.27b), (A)+(B2)+(C1.27c), (A)+(B2)+(C1.27d), (A)+(B2)+(C1.27e), (A)+(B2)+(C1.27f), (A)+(B2)+(C1.27g), (A)+(B2)+(C1.27h), (A)+(B2)+(C1.27), (A)+(B2)+(C1.27l), (A)+(B2)+(C1.27m), (A)+(B2)+(C1.27n), (A)+(B2)+(C1.27o), (A)+(B2)+(C1.27r), (A)+(B2)+(C1.27s), (A)+(B2)+(C1.27t), (A)+(B2)+(C1.27u), (A)+(B2)+(C1.27v), (A)+(B2)+(C1.28), (A)+(B2)+(C1.29), (A)+(B2)+(C1.30), (A)+(B2)+(C1.31), (A)+(B2)+(C1.32), (A)+(B2)+(C1.33), (A)+(B2)+(C1.34), (A)+(B2)+(C1.35), (A)+(B2)+(C1.36), (A)+(B2)+(C1.37), (A)+(B2)+(C1.38), (A)+(B2)+(C1.39), (A)+(B2)+(C1.40), (A)+(B2)+(C1.41), (A)+(B2)+(C1.42), (A)+(B2)+(C1.43), (A)+(B2)+(C1.44), (A)+(B2)+(C1.45), (A)+(B2)+(C1.46), (A)+(B2)+(C1.47), (A)+(B2)+(C1.48), (A)+(B2)+(C1.49), (A)+(B2)+(C1.50), (A)+(B2)+(C1.51), (A)+(B2)+(C1.52), (A)+(B2)+(C1.53), (A)+(B2)+(C1.54), (A)+(B2)+(C1.55), (A)+(B2)+(C1.56), (A)+(B2)+(C1.57), (A)+(B2)+(C1.58), (A)+(B2)+(C1.59), (A)+(B2)+(C1.60), (A)+(B2)+(C1.61), (A)+(B2)+(C1.62), (A)+(B2)+(C1.63), (A)+(B2)+(C1.64), (A)+(B2)+(C1.65), (A)+(B2)+(C1.66), (A)+(B2)+(C1.67), (A)+(B2)+(C1.68), (A)+(B2)+(C1.69), (A)+(B2)+(C1.70), (A)+(B2)+(C1.71), (A)+(B2)+(C1.72), (A)+(B2)+(C1.73), (A)+(B2)+(C1.74), (A)+(B2)+(C1.75), (A)+(B2)+(C1.76), (A)+(B2)+(C1.77), (A)+(B2)+(C1.78), (A)+(B2)+(C1.79), (A)+(B2)+(C1.80), (A)+(B2)+(C1.81), (A)+(B2)+(C1.82), (A)+(B2)+(C1.83), (A)+(B2)+(C1.84), (A)+(B2)+(C1.85), (A)+(B2)+(C1.86), (A)+(B2)+(C1.87), (A)+(B2)+(C1.88), (A)+(B2)+(C1.89), (A)+(B2)+(C1.90), (A)+(B2)+(C1.91), (A)+(B2)+(C1.92), (A)+(B2)+(C1.93), (A)+(B2)+(C1.94), (A)+(B2)+(C1.95), (A)+(B2)+(C1.96), (A)+(B2)+(C1.97), (A)+(B2)+(C1.98), (A)+(B2)+(C1.99), (A)+(B2)+(C1.100), (A)+(B2)+(C1.101), (A)+(B2)+(C1.102), (A)+(B2)+(C1.103), (A)+(B2)+(C1.104), (A)+(B2)+(C1.105), (A)+(B2)+(C1.106), (A)+(B2)+(C1.107), (A)+(B2)+(C1.108), (A)+(B2)+(C1.109), (A)+(B2)+(C1.110), (A)+(B2)+(C1.111), (A)+(B2)+(C1.112), (A)+(B2)+(C1.113), (A)+(B2)+(C1.114), (A)+(B2)+(C1.115), (A)+(B2)+(C1.116), (A)+(B2)+(C1.117), (A)+(B2)+(C1.118), (A)+(B2)+(C1.119), (A)+(B2)+(C1.120), (A)+(B2)+(C1.121), (A)+(B2)+(C1.122), (A)+(B2)+(C1.123), (A)+(B2)+(C1.124), (A)+(B2)+(C1.125), (A)+(B2)+(C1.126), (A)+(B2)+(C1.127), (A)+(B2)+(C1.128), (A)+(B2)+(C1.129), (A)+(B2)+(C1.130), (A)+(B2)+(C1.131), (A)+(B2)+(C1.132), (A)+(B2)+(C2.1), (A)+(B2)+(C2.2), (A)+(B2)+(C2.3), (A)+(B2)+(C2.4), (A)+(B2)+(C2.5), (A)+(B2)+(C2.6), (A)+(B2)+(C2.7), (A)+(B2)+(C2.8), (A)+(B2)+(C2.9), (A)+(B2)+(C2.10), (A)+(B2)+(C2.11), (A)+(B2)+(C2.12), (A)+(B2)+(C2.13), (A)+(B2)+(C2.14), (A)+(B2)+(C2.15), (A)+(B2)+(C2.16), (A)+(B2)+(C2.17), (A)+(B2)+(C2.18), (A)+(B2)+(C2.19), (A)+(B2)+(C2.20), (A)+(B2)+(C2.21), (A)+(B2)+(C2.22), (A)+(B2)+(C2.23), (A)+(B2)+(C2.24), (A)+(B2)+(C2.25), (A)+(B2)+(C2.26), (A)+(B2)+(C2.27), (A)+(B2)+(C2.28), (A)+(B2)+(C2.29), (A)+(B2)+(C2.30), (A)+(B2)+(C2.31), (A)+(B2)+(C2.32), (A)+(B2)+(C2.33), (A)+(B2)+(C2.34), (A)+(B2)+(C2.35), (A)+(B2)+(C2.36), (A)+(B2)+(C2.37), (A)+(B2)+(C2.38), (A)+(B2)+(C2.39), (A)+(B2)+(C2.40), (A)+(B2)+(C2.41), (A)+(B2)+(C2.42), (A)+(B2)+(C2.43), (A)+(B2)+(C2.44), (A)+(B2)+(C2.45), (A)+(B2)+(C2.46), (A)+(B2)+(C2.47), (A)+(B2)+(C2.48), (A)+(B2)+(C2.49), (A)+(B2)+(C2.50), (A)+(B2)+(C2.51), (A)+(B2)+(C2.52), (A)+(B2)+(C2.53), (A)+(B2)+(C2.54), (A)+(B2)+(C2.55), (A)+(B2)+(C2.56), (A)+(B2)+(C2.57), (A)+(B2)+(C2.58), (A)+(B2)+(C2.59), (A)+(B2)+(C2.60), (A)+

(B2)+(C2.61), (A)+(B2)+(C2.62), (A)+(B2)+(C2.63), (A)+(B2)+(C2.64), (A)+(B2)+(C2.65), (A)+(B2)+(C2.66), (A)+(B2)+(C2.67), (A)+(B2)+(C2.68), (A)+(B2)+(C2.69), (A)+(B2)+(C2.70), (A)+(B2)+(C2.71), (A)+(B2)+(C2.72), (A)+(B2)+(C2.73), (A)+(B2)+(C2.74), (A)+(B2)+(C2.75), (A)+(B2)+(C2.76), (A)+(B2)+(C2.77), (A)+(B2)+(C2.78), (A)+(B2)+(C2.79), (A)+(B2)+(C2.80), (A)+(B2)+(C2.81), (A)+(B2)+(C2.82), (A)+(B2)+(C2.83), (A)+(B2)+(C2.84), (A)+(B2)+(C2.85), (A)+(B2)+(C2.86), (A)+(B2)+(C2.87), (A)+(B2)+(C2.88), (A)+(B2)+(C2.89), (A)+(B2)+(C2.90), (A)+(B2)+(C2.91), (A)+(B2)+(C2.92), (A)+(B2)+(C2.93), (A)+(B2)+(C2.94), (A)+(B2)+(C2.95), (A)+(B2)+(C2.96), (A)+(B2)+(C2.97), (A)+(B2)+(C2.98), (A)+(B2)+(C2.99), (A)+(B2)+(C2.100), (A)+(B2)+(C2.101), (A)+(B2)+(C2.102), (A)+(B2)+(C2.103), (A)+(B2)+(C2.104), (A)+(B2)+(C2.105), (A)+(B2)+(C2.106), (A)+(B2)+(C2.107), (A)+(B2)+(C2.108), (A)+(B2)+(C2.109), (A)+(B2)+(C2.110), (A)+(B2)+(C2.111), (A)+(B2)+(C2.112), (A)+(B2)+(C2.113), (A)+(B2)+(C2.114), (A)+(B2)+(C3.1), (A)+(B2)+(C3.2), (A)+(B2)+(C3.3), (A)+(B2)+(C4.1), (A)+(B2)+(C4.2), (A)+(B2)+(C4.3), (A)+(B2)+(C4.4), (A)+(B2)+(C4.5), (A)+(B2)+(C4.6), (A)+(B2)+(C4.7), (A)+(B2)+(C4.8), (A)+(B2)+(C4.9), (A)+(B2)+(C4.10), (A)+(B2)+(C4.11), (A)+(B2)+(C4.12), (A)+(B2)+(C4.13), (A)+(B2)+(C4.14), (A)+(B2)+(C4.15), (A)+(B2)+(C5.1), (A)+(B2)+(C5.2), (A)+(B2)+(C5.3), (A)+(B2)+(C5.4), (A)+(B2)+(C5.5), (A)+(B2)+(C5.6), (A)+(B2)+(C5.7), (A)+(B2)+(C5.8), (A)+(B2)+(C5.9), (A)+(B2)+(C5.10), (A)+(B2)+(C5.11), (A)+(B2)+(C5.12), (A)+(B2)+(C5.13), (A)+(B2)+(C5.14), (A)+(B2)+(C5.15), (A)+(B2)+(C5.16), (A)+(B2)+(C5.17), (A)+(B2)+(C5.18), (A)+(B2)+(C5.19), (A)+(B2)+(C5.20), (A)+(B2)+(C5.21), (A)+(B2)+(C5.22), (A)+(B2)+(C5.23), (A)+(B2)+(C5.24), (A)+(B2)+(C5.25), (A)+(B2)+(C5.26), (A)+(B2)+(C5.27), (A)+(B2)+(C5.28), (A)+(B2)+(C5.29), (A)+(B2)+(C5.30), (A)+(B2)+(C5.31), (A)+(B2)+(C5.32), (A)+(B2)+(C5.33), (A)+(B2)+(C5.34), (A)+(B2)+(C5.35), (A)+(B2)+(C5.36), (A)+(B2)+(C5.37), (A)+(B2)+(C5.38), (A)+(B2)+(C5.39), (A)+(B2)+(C5.40), (A)+(B2)+(C5.41), (A)+(B2)+(C5.42), (A)+(B2)+(C5.43), (A)+(B2)+(C5.44), (A)+(B2)+(C5.45), (A)+(B2)+(C5.46), (A)+(B2)+(C5.47), (A)+(B2)+(C5.48), (A)+(B2)+(C5.49), (A)+(B2)+(C5.50), (A)+(B2)+(C5.51), (A)+(B2)+(C5.52), (A)+(B2)+(C5.53), (A)+(B2)+(C5.54), (A)+(B2)+(C5.55), (A)+(B2)+(C5.56), (A)+(B2)+(C5.57), (A)+(B2)+(C5.58), (A)+(B2)+(C5.59), (A)+(B2)+(C5.60), (A)+(B2)+(C5.61), (A)+(B2)+(C5.62), (A)+(B2)+(C5.63), (A)+(B2)+(C5.64), (A)+(B2)+(C5.65), (A)+(B2)+(C6.1), (A)+(B2)+(C6.2), (A)+(B2)+(C6.3), (A)+(B2)+(C6.4), (A)+(B2)+(C6.5), (A)+(B2)+(C6.6), (A)+(B2)+(C6.7), (A)+(B2)+(C6.8), (A)+(B2)+(C6.9), (A)+(B2)+(C6.10), (A)+(B2)+(C6.11), (A)+(B2)+(C6.12), (A)+(B2)+(C6.13), (A)+(B2)+(C6.14), (A)+(B2)+(C6.15), (A)+(B2)+(C6.16), (A)+(B2)+(C6.17), (A)+(B2)+(C7.1), (A)+(B2)+(C7.2), (A)+(B2)+(C7.3), (A)+(B2)+(C7.4), (A)+(B2)+(C7.5), (A)+(B2)+(C7.6), (A)+(B2)+(C7.7), (A)+(B2)+(C7.8), (A)+(B2)+(C7.9), (A)+(B2)+(C7.10), (A)+(B2)+(C7.11), (A)+(B2)+(C7.12), (A)+(B2)+(C7.13), (A)+(B2)+(C7.14), (A)+(B2)+(C7.15), (A)+(B2)+(C7.16), (A)+(B2)+(C7.17), (A)+(B2)+(C7.18), (A)+(B2)+(C7.19), (A)+(B2)+(C7.20), (A)+(B2)+(C7.21), (A)+(B2)+(C7.22), (A)+(B2)+(C7.23), (A)+(B2)+(C7.24), (A)+(B2)+(C7.25), (A)+(B2)+(C7.26), (A)+(B2)+(C7.27), (A)+(B2)+(C7.28), (A)+(B2)+(C7.29), (A)+(B2)+(C7.30), (A)+(B2)+(C8.1), (A)+(B3)+(C1.1), (A)+(B3)+(C1.2), (A)+(B3)+(C1.3), (A)+(B3)+(C1.4), (A)+(B3)+(C1.5), (A)+(B3)+(C1.6), (A)+(B3)+(C1.7), (A)+(B3)+(C1.8), (A)+(B3)+(C1.9), (A)+(B3)+(C1.10), (A)+(B3)+(C1.11), (A)+(B3)+(C1.12), (A)+(B3)+(C1.13), (A)+(B3)+(C1.14), (A)+(B3)+(C1.15), (A)+(B3)+(C1.16), (A)+(B3)+(C1.17), (A)+(B3)+(C1.18), (A)+(B3)+(C1.19), (A)+(B3)+(C1.20), (A)+(B3)+(C1.21), (A)+(B3)+(C1.22), (A)+(B3)+(C1.23), (A)+(B3)+(C1.24), (A)+(B3)+(C1.25), (A)+(B3)+(C1.26), (A)+(B3)+(C1.27), (A)+(B3)+(C1.27a), (A)+(B3)+(C1.27b), (A)+(B3)+(C1.27c), (A)+(B3)+(C1.27d), (A)+(B3)+(C1.27e), (A)+(B3)+(C1.27f), (A)+(B3)+(C1.27g), (A)+(B3)+(C1.27h), (A)+(B3)+(C1.27), (A)+(B3)+(C1.27l), (A)+(B3)+(C1.27m), (A)+(B3)+(C1.27n), (A)+(B3)+(C1.27o), (A)+(B3)+(C1.27r), (A)+(B3)+(C1.27s), (A)+(B3)+(C1.27t), (A)+(B3)+(C1.27u), (A)+(B3)+(C1.27v), (A)+(B3)+(C1.28), (A)+(B3)+(C1.29), (A)+(B3)+(C1.30), (A)+(B3)+(C1.31), (A)+(B3)+(C1.32), (A)+(B3)+(C1.33), (A)+(B3)+(C1.34), (A)+(B3)+(C1.35), (A)+(B3)+(C1.36), (A)+(B3)+(C1.37), (A)+(B3)+(C1.38), (A)+(B3)+(C1.39), (A)+(B3)+(C1.40), (A)+(B3)+(C1.41), (A)+(B3)+(C1.42), (A)+(B3)+(C1.43), (A)+(B3)+(C1.44), (A)+(B3)+(C1.45), (A)+(B3)+(C1.46), (A)+(B3)+(C1.47), (A)+(B3)+(C1.48), (A)+(B3)+(C1.49), (A)+(B3)+(C1.50), (A)+(B3)+(C1.51), (A)+(B3)+(C1.52), (A)+(B3)+(C1.53), (A)+(B3)+(C1.54), (A)+(B3)+(C1.55), (A)+(B3)+(C1.56), (A)+(B3)+(C1.57), (A)+(B3)+(C1.58), (A)+(B3)+(C1.59), (A)+(B3)+(C1.60), (A)+(B3)+(C1.61), (A)+(B3)+(C1.62), (A)+(B3)+(C1.63), (A)+(B3)+(C1.64), (A)+(B3)+(C1.65), (A)+(B3)+(C1.66), (A)+(B3)+(C1.67), (A)+(B3)+(C1.68), (A)+(B3)+(C1.69), (A)+(B3)+(C1.70), (A)+(B3)+(C1.71), (A)+(B3)+(C1.72), (A)+(B3)+(C1.73), (A)+(B3)+(C1.74), (A)+(B3)+(C1.75), (A)+(B3)+(C1.76), (A)+(B3)+(C1.77), (A)+(B3)+(C1.78), (A)+(B3)+(C1.79), (A)+(B3)+(C1.80), (A)+(B3)+(C1.81), (A)+(B3)+(C1.82), (A)+(B3)+(C1.83), (A)+(B3)+(C1.84), (A)+(B3)+(C1.85), (A)+(B3)+(C1.86), (A)+(B3)+(C1.87), (A)+(B3)+(C1.88), (A)+(B3)+(C1.89), (A)+(B3)+(C1.90), (A)+(B3)+(C1.91), (A)+(B3)+(C1.92), (A)+(B3)+(C1.93), (A)+(B3)+(C1.94), (A)+(B3)+(C1.95), (A)+(B3)+(C1.96), (A)+(B3)+(C1.97), (A)+(B3)+(C1.98), (A)+(B3)+(C1.99), (A)+(B3)+(C1.100), (A)+(B3)+(C1.101), (A)+(B3)+(C1.102), (A)+(B3)+(C1.103), (A)+(B3)+(C1.104), (A)+(B3)+(C1.105), (A)+(B3)+(C1.106), (A)+(B3)+(C1.107), (A)+(B3)+(C1.108), (A)+(B3)+(C1.109), (A)+(B3)+(C1.110), (A)+(B3)+(C1.111), (A)+(B3)+(C1.112), (A)+(B3)+(C1.113), (A)+(B3)+(C1.114), (A)+(B3)+(C1.115), (A)+(B3)+(C1.116), (A)+(B3)+(C1.117), (A)+(B3)+(C1.118), (A)+(B3)+(C1.119), (A)+(B3)+(C1.120), (A)+(B3)+(C1.121), (A)+(B3)+(C1.122), (A)+(B3)+(C1.123), (A)+(B3)+(C1.124), (A)+(B3)+(C1.125), (A)+(B3)+(C1.126), (A)+(B3)+(C1.127), (A)+(B3)+(C1.128), (A)+(B3)+(C1.129), (A)+(B3)+(C1.130), (A)+(B3)+(C1.131), (A)+(B3)+(C1.132), (A)+(B3)+(C2.1), (A)+(B3)+(C2.2), (A)+(B3)+(C2.3), (A)+(B3)+(C2.4), (A)+(B3)+(C2.5), (A)+(B3)+(C2.6), (A)+(B3)+(C2.7), (A)+(B3)+(C2.8), (A)+(B3)+(C2.9), (A)+(B3)+(C2.10), (A)+(B3)+(C2.11), (A)+(B3)+(C2.12), (A)+(B3)+(C2.13), (A)+(B3)+(C2.14), (A)+(B3)+(C2.15), (A)+(B3)+(C2.16), (A)+(B3)+(C2.17), (A)+(B3)+(C2.18), (A)+(B3)+(C2.19), (A)+(B3)+(C2.20), (A)+(B3)+(C2.21), (A)+(B3)+(C2.22), (A)+(B3)+(C2.23), (A)+(B3)+(C2.24), (A)+(B3)+(C2.25), (A)+(B3)+(C2.26), (A)+(B3)+(C2.27), (A)+(B3)+(C2.28), (A)+(B3)+(C2.29), (A)+(B3)+(C2.30), (A)+(B3)+(C2.31), (A)+(B3)+(C2.32), (A)+(B3)+(C2.33), (A)+(B3)+(C2.34), (A)+(B3)+(C2.35), (A)+(B3)+(C2.36), (A)+(B3)+(C2.37), (A)+(B3)+(C2.38), (A)+(B3)+(C2.39), (A)+(B3)+(C2.40), (A)+(B3)+(C2.41), (A)+(B3)+(C2.42), (A)+(B3)+(C2.43), (A)+(B3)+(C2.44), (A)+(B3)+(C2.45), (A)+(B3)+(C2.46), (A)+(B3)+(C2.47), (A)+(B3)+(C2.48), (A)+(B3)+(C2.49), (A)+(B3)+(C2.50), (A)+(B3)+(C2.51), (A)+(B3)+(C2.52), (A)+(B3)+(C2.53), (A)+(B3)+(C2.54), (A)+(B3)+(C2.55), (A)+(B3)+(C2.56), (A)+(B3)+(C2.57), (A)+

(B3)+(C2.58), (A)+(B3)+(C2.59), (A)+(B3)+(C2.60), (A)+(B3)+(C2.61), (A)+(B3)+(C2.62), (A)+(B3)+(C2.63), (A)+(B3)+(C2.64), (A)+(B3)+(C2.65), (A)+(B3)+(C2.66), (A)+(B3)+(C2.67), (A)+(B3)+(C2.68), (A)+(B3)+(C2.69), (A)+(B3)+(C2.70), (A)+(B3)+(C2.71), (A)+(B3)+(C2.72), (A)+(B3)+(C2.73), (A)+(B3)+(C2.74), (A)+(B3)+(C2.75), (A)+(B3)+(C2.76), (A)+(B3)+(C2.77), (A)+(B3)+(C2.78), (A)+(B3)+(C2.79), (A)+(B3)+(C2.80), (A)+(B3)+(C2.81), (A)+(B3)+(C2.82), (A)+(B3)+(C2.83), (A)+(B3)+(C2.84), (A)+(B3)+(C2.85), (A)+(B3)+(C2.86), (A)+(B3)+(C2.87), (A)+(B3)+(C2.88), (A)+(B3)+(C2.89), (A)+(B3)+(C2.90), (A)+(B3)+(C2.91), (A)+(B3)+(C2.92), (A)+(B3)+(C2.93), (A)+(B3)+(C2.94), (A)+(B3)+(C2.95), (A)+(B3)+(C2.96), (A)+(B3)+(C2.97), (A)+(B3)+(C2.98), (A)+(B3)+(C2.99), (A)+(B3)+(C2.100), (A)+(B3)+(C2.101), (A)+(B3)+(C2.102), (A)+(B3)+(C2.103), (A)+(B3)+(C2.104), (A)+(B3)+(C2.105), (A)+(B3)+(C2.106), (A)+(B3)+(C2.107), (A)+(B3)+(C2.108), (A)+(B3)+(C2.109), (A)+(B3)+(C2.110), (A)+(B3)+(C2.111), (A)+(B3)+(C2.112), (A)+(B3)+(C2.113), (A)+(B3)+(C2.114), (A)+(B3)+(C3.1), (A)+(B3)+(C3.2), (A)+(B3)+(C3.3), (A)+(B3)+(C4.1), (A)+(B3)+(C4.2), (A)+(B3)+(C4.3), (A)+(B3)+(C4.4), (A)+(B3)+(C4.5), (A)+(B3)+(C4.6), (A)+(B3)+(C4.7), (A)+(B3)+(C4.8), (A)+(B3)+(C4.9), (A)+(B3)+(C4.10), (A)+(B3)+(C4.11), (A)+(B3)+(C4.12), (A)+(B3)+(C4.13), (A)+(B3)+(C4.14), (A)+(B3)+(C4.15), (A)+(B3)+(C5.1), (A)+(B3)+(C5.2), (A)+(B3)+(C5.3), (A)+(B3)+(C5.4), (A)+(B3)+(C5.5), (A)+(B3)+(C5.6), (A)+(B3)+(C5.7), (A)+(B3)+(C5.8), (A)+(B3)+(C5.9), (A)+(B3)+(C5.10), (A)+(B3)+(C5.11), (A)+(B3)+(C5.12), (A)+(B3)+(C5.13), (A)+(B3)+(C5.14), (A)+(B3)+(C5.15), (A)+(B3)+(C5.16), (A)+(B3)+(C5.17), (A)+(B3)+(C5.18), (A)+(B3)+(C5.19), (A)+(B3)+(C5.20), (A)+(B3)+(C5.21), (A)+(B3)+(C5.22), (A)+(B3)+(C5.23), (A)+(B3)+(C5.24), (A)+(B3)+(C5.25), (A)+(B3)+(C5.26), (A)+(B3)+(C5.27), (A)+(B3)+(C5.28), (A)+(B3)+(C5.29), (A)+(B3)+(C5.30), (A)+(B3)+(C5.31), (A)+(B3)+(C5.32), (A)+(B3)+(C5.33), (A)+(B3)+(C5.34), (A)+(B3)+(C5.35), (A)+(B3)+(C5.36), (A)+(B3)+(C5.37), (A)+(B3)+(C5.38), (A)+(B3)+(C5.39), (A)+(B3)+(C5.40), (A)+(B3)+(C5.41), (A)+(B3)+(C5.42), (A)+(B3)+(C5.43), (A)+(B3)+(C5.44), (A)+(B3)+(C5.45), (A)+(B3)+(C5.46), (A)+(B3)+(C5.47), (A)+(B3)+(C5.48), (A)+(B3)+(C5.49), (A)+(B3)+(C5.50), (A)+(B3)+(C5.51), (A)+(B3)+(C5.52), (A)+(B3)+(C5.53), (A)+(B3)+(C5.54), (A)+(B3)+(C5.55), (A)+(B3)+(C5.56), (A)+(B3)+(C5.57), (A)+(B3)+(C5.58), (A)+(B3)+(C5.59), (A)+(B3)+(C5.60), (A)+(B3)+(C5.61), (A)+(B3)+(C5.62), (A)+(B3)+(C5.63), (A)+(B3)+(C5.64), (A)+(B3)+(C5.65), (A)+(B3)+(C6.1), (A)+(B3)+(C6.2), (A)+(B3)+(C6.3), (A)+(B3)+(C6.4), (A)+(B3)+(C6.5), (A)+(B3)+(C6.6), (A)+(B3)+(C6.7), (A)+(B3)+(C6.8), (A)+(B3)+(C6.9), (A)+(B3)+(C6.10), (A)+(B3)+(C6.11), (A)+(B3)+(C6.12), (A)+(B3)+(C6.13), (A)+(B3)+(C6.14), (A)+(B3)+(C6.15), (A)+(B3)+(C6.16), (A)+(B3)+(C6.17), (A)+(B3)+(C7.1), (A)+(B3)+(C7.2), (A)+(B3)+(C7.3), (A)+(B3)+(C7.4), (A)+(B3)+(C7.5), (A)+(B3)+(C7.6), (A)+(B3)+(C7.7), (A)+(B3)+(C7.8), (A)+(B3)+(C7.9), (A)+(B3)+(C7.10), (A)+(B3)+(C7.11), (A)+(B3)+(C7.12), (A)+(B3)+(C7.13), (A)+(B3)+(C7.14), (A)+(B3)+(C7.15), (A)+(B3)+(C7.16), (A)+(B3)+(C7.17), (A)+(B3)+(C7.18), (A)+(B3)+(C7.19), (A)+(B3)+(C7.20), (A)+(B3)+(C7.21), (A)+(B3)+(C7.22), (A)+(B3)+(C7.23), (A)+(B3)+(C7.24), (A)+(B3)+(C7.25), (A)+(B3)+(C7.26), (A)+(B3)+(C7.27), (A)+(B3)+(C7.28), (A)+(B3)+(C7.29), (A)+(B3)+(C7.30), (A)+(B3)+(C8.1), (A)+(B4)+(C1.1), (A)+(B4)+(C1.2), (A)+(B4)+(C1.3), (A)+(B4)+(C1.4), (A)+(B4)+(C1.5), (A)+(B4)+(C1.6), (A)+(B4)+(C1.7), (A)+(B4)+(C1.8), (A)+(B4)+(C1.9), (A)+(B4)+(C1.10), (A)+(B4)+(C1.11), (A)+(B4)+(C1.12), (A)+(B4)+(C1.13), (A)+(B4)+(C1.14), (A)+(B4)+(C1.15), (A)+(B4)+(C1.16), (A)+(B4)+(C1.17), (A)+(B4)+(C1.18), (A)+(B4)+(C1.19), (A)+(B4)+(C1.20), (A)+(B4)+(C1.21), (A)+(B4)+(C1.22), (A)+(B4)+(C1.23), (A)+(B4)+(C1.24), (A)+(B4)+(C1.25), (A)+(B4)+(C1.26), (A)+(B4)+(C1.27), (A)+(B4)+(C1.27a), (A)+(B4)+(C1.27b), (A)+(B4)+(C1.27c), (A)+(B4)+(C1.27d), (A)+(B4)+(C1.27e), (A)+(B4)+(C1.27f), (A)+(B4)+(C1.27g), (A)+(B4)+(C1.27h), (A)+(B4)+(C1.27), (A)+(B4)+(C1.27l), (A)+(B4)+(C1.27m), (A)+(B4)+(C1.27n), (A)+(B4)+(C1.27o), (A)+(B4)+(C1.27r), (A)+(B4)+(C1.27s), (A)+(B4)+(C1.27t), (A)+(B4)+(C1.27u), (A)+(B4)+(C1.27v), (A)+(B4)+(C1.28), (A)+(B4)+(C1.29), (A)+(B4)+(C1.30), (A)+(B4)+(C1.31), (A)+(B4)+(C1.32), (A)+(B4)+(C1.33), (A)+(B4)+(C1.34), (A)+(B4)+(C1.35), (A)+(B4)+(C1.36), (A)+(B4)+(C1.37), (A)+(B4)+(C1.38), (A)+(B4)+(C1.39), (A)+(B4)+(C1.40), (A)+(B4)+(C1.41), (A)+(B4)+(C1.42), (A)+(B4)+(C1.43), (A)+(B4)+(C1.44), (A)+(B4)+(C1.45), (A)+(B4)+(C1.46), (A)+(B4)+(C1.47), (A)+(B4)+(C1.48), (A)+(B4)+(C1.49), (A)+(B4)+(C1.50), (A)+(B4)+(C1.51), (A)+(B4)+(C1.52), (A)+(B4)+(C1.53), (A)+(B4)+(C1.54), (A)+(B4)+(C1.55), (A)+(B4)+(C1.56), (A)+(B4)+(C1.57), (A)+(B4)+(C1.58), (A)+(B4)+(C1.59), (A)+(B4)+(C1.60), (A)+(B4)+(C1.61), (A)+(B4)+(C1.62), (A)+(B4)+(C1.63), (A)+(B4)+(C1.64), (A)+(B4)+(C1.65), (A)+(B4)+(C1.66), (A)+(B4)+(C1.67), (A)+(B4)+(C1.68), (A)+(B4)+(C1.69), (A)+(B4)+(C1.70), (A)+(B4)+(C1.71), (A)+(B4)+(C1.72), (A)+(B4)+(C1.73), (A)+(B4)+(C1.74), (A)+(B4)+(C1.75), (A)+(B4)+(C1.76), (A)+(B4)+(C1.77), (A)+(B4)+(C1.78), (A)+(B4)+(C1.79), (A)+(B4)+(C1.80), (A)+(B4)+(C1.81), (A)+(B4)+(C1.82), (A)+(B4)+(C1.83), (A)+(B4)+(C1.84), (A)+(B4)+(C1.85), (A)+(B4)+(C1.86), (A)+(B4)+(C1.87), (A)+(B4)+(C1.88), (A)+(B4)+(C1.89), (A)+(B4)+(C1.90), (A)+(B4)+(C1.91), (A)+(B4)+(C1.92), (A)+(B4)+(C1.93), (A)+(B4)+(C1.94), (A)+(B4)+(C1.95), (A)+(B4)+(C1.96), (A)+(B4)+(C1.97), (A)+(B4)+(C1.98), (A)+(B4)+(C1.99), (A)+(B4)+(C1.100), (A)+(B4)+(C1.101), (A)+(B4)+(C1.102), (A)+(B4)+(C1.103), (A)+(B4)+(C1.104), (A)+(B4)+(C1.105), (A)+(B4)+(C1.106), (A)+(B4)+(C1.107), (A)+(B4)+(C1.108), (A)+(B4)+(C1.109), (A)+(B4)+(C1.110), (A)+(B4)+(C1.111), (A)+(B4)+(C1.112), (A)+(B4)+(C1.113), (A)+(B4)+(C1.114), (A)+(B4)+(C1.115), (A)+(B4)+(C1.116), (A)+(B4)+(C1.117), (A)+(B4)+(C1.118), (A)+(B4)+(C1.119), (A)+(B4)+(C1.120), (A)+(B4)+(C1.121), (A)+(B4)+(C1.122), (A)+(B4)+(C1.123), (A)+(B4)+(C1.124), (A)+(B4)+(C1.125), (A)+(B4)+(C1.126), (A)+(B4)+(C1.127), (A)+(B4)+(C1.128), (A)+(B4)+(C1.129), (A)+(B4)+(C1.130), (A)+(B4)+(C1.131), (A)+(B4)+(C1.132), (A)+(B4)+(C2.1), (A)+(B4)+(C2.2), (A)+(B4)+(C2.3), (A)+(B4)+(C2.4), (A)+(B4)+(C2.5), (A)+(B4)+(C2.6), (A)+(B4)+(C2.7), (A)+(B4)+(C2.8), (A)+(B4)+(C2.9), (A)+(B4)+(C2.10), (A)+(B4)+(C2.11), (A)+(B4)+(C2.12), (A)+(B4)+(C2.13), (A)+(B4)+(C2.14), (A)+(B4)+(C2.15), (A)+(B4)+(C2.16), (A)+(B4)+(C2.17), (A)+(B4)+(C2.18), (A)+(B4)+(C2.19), (A)+(B4)+(C2.20), (A)+(B4)+(C2.21), (A)+(B4)+(C2.22), (A)+(B4)+(C2.23), (A)+(B4)+(C2.24), (A)+(B4)+(C2.25), (A)+(B4)+(C2.26), (A)+(B4)+(C2.27), (A)+(B4)+(C2.28), (A)+(B4)+(C2.29), (A)+(B4)+(C2.30), (A)+(B4)+(C2.31), (A)+(B4)+(C2.32), (A)+(B4)+(C2.33), (A)+(B4)+(C2.34), (A)+(B4)+(C2.35), (A)+(B4)+(C2.36), (A)+(B4)+(C2.37), (A)+(B4)+(C2.38), (A)+(B4)+(C2.39), (A)+(B4)+(C2.40), (A)+(B4)+(C2.41), (A)+(B4)+(C2.42), (A)+(B4)+(C2.43), (A)+(B4)+(C2.44), (A)+(B4)+(C2.45), (A)+(B4)+(C2.46), (A)+(B4)+(C2.47), (A)+(B4)+(C2.48), (A)+(B4)+(C2.49), (A)+(B4)+(C2.50), (A)+(B4)+(C2.51), (A)+(B4)+(C2.52), (A)+(B4)+(C2.53), (A)+(B4)+(C2.54), (A)+

(B4)+(C2.55), (A)+(B4)+(C2.56), (A)+(B4)+(C2.57), (A)+
(B4)+(C2.58), (A)+(B4)+(C2.59), (A)+(B4)+(C2.60), (A)+
(B4)+(C2.61), (A)+(B4)+(C2.62), (A)+(B4)+(C2.63), (A)+
(B4)+(C2.64), (A)+(B4)+(C2.65), (A)+(B4)+(C2.66), (A)+
(B4)+(C2.67), (A)+(B4)+(C2.68), (A)+(B4)+(C2.69), (A)+
(B4)+(C2.70), (A)+(B4)+(C2.71), (A)+(B4)+(C2.72), (A)+
(B4)+(C2.73), (A)+(B4)+(C2.74), (A)+(B4)+(C2.75), (A)+
(B4)+(C2.76), (A)+(B4)+(C2.77), (A)+(B4)+(C2.78), (A)+
(B4)+(C2.79), (A)+(B4)+(C2.80), (A)+(B4)+(C2.81), (A)+
(B4)+(C2.82), (A)+(B4)+(C2.83), (A)+(B4)+(C2.84), (A)+
(B4)+(C2.85), (A)+(B4)+(C2.86), (A)+(B4)+(C2.87), (A)+
(B4)+(C2.88), (A)+(B4)+(C2.89), (A)+(B4)+(C2.90), (A)+
(B4)+(C2.91), (A)+(B4)+(C2.92), (A)+(B4)+(C2.93), (A)+
(B4)+(C2.94), (A)+(B4)+(C2.95), (A)+(B4)+(C2.96), (A)+
(B4)+(C2.97), (A)+(B4)+(C2.98), (A)+(B4)+(C2.99), (A)+
(B4)+(C2.100), (A)+(B4)+(C2.101), (A)+(B4)+(C2.102),
(A)+(B4)+(C2.103), (A)+(B4)+(C2.104), (A)+(B4)+
(C2.105), (A)+(B4)+(C2.106), (A)+(B4)+(C2.107), (A)+
(B4)+(C2.108), (A)+(B4)+(C2.109), (A)+(B4)+(C2.110),
(A)+(B4)+(C2.111), (A)+(B4)+(C2.112), (A)+(B4)+
(C2.113), (A)+(B4)+(C2.114), (A)+(B4)+(C3.1), (A)+(B4)+
(C3.2), (A)+(B4)+(C3.3), (A)+(B4)+(C4.1), (A)+(B4)+
(C4.2), (A)+(B4)+(C4.3), (A)+(B4)+(C4.4), (A)+(B4)+
(C4.5), (A)+(B4)+(C4.6), (A)+(B4)+(C4.7), (A)+(B4)+
(C4.8), (A)+(B4)+(C4.9), (A)+(B4)+(C4.10), (A)+(B4)+
(C4.11), (A)+(B4)+(C4.12), (A)+(B4)+(C4.13), (A)+(B4)+
(C4.14), (A)+(B4)+(C4.15), (A)+(B4)+(C5.1), (A)+(B4)+
(C5.2), (A)+(B4)+(C5.3), (A)+(B4)+(C5.4), (A)+(B4)+
(C5.5), (A)+(B4)+(C5.6), (A)+(B4)+(C5.7)+(A)+(B4)+
(C5.8), (A)+(B4)+(C5.9), (A)+(B4)+(C5.10), (A)+(B4)+
(C5.11), (A)+(B4)+(C5.12), (A)+(B4)+(C5.13), (A)+(B4)+
(C5.14), (A)+(B4)+(C5.15), (A)+(B4)+(C5.16), (A)+(B4)+
(C5.17), (A)+(B4)+(C5.18), (A)+(B4)+(C5.19), (A)+(B4)+
(C5.20), (A)+(B4)+(C5.21), (A)+(B4)+(C5.22), (A)+(B4)+
(C5.23), (A)+(B4)+(C5.24), (A)+(B4)+(C5.25), (A)+(B4)+
(C5.26), (A)+(B4)+(C5.27), (A)+(B4)+(C5.28), (A)+(B4)+
(C5.29), (A)+(B4)+(C5.30), (A)+(B4)+(C5.31), (A)+(B4)+
(C5.32), (A)+(B4)+(C5.33), (A)+(B4)+(C5.34), (A)+(B4)+
(C5.35), (A)+(B4)+(C5.36), (A)+(B4)+(C5.37), (A)+(B4)+
(C5.38), (A)+(B4)+(C5.39), (A)+(B4)+(C5.40), (A)+(B4)+
(C5.41), (A)+(B4)+(C5.42), (A)+(B4)+(C5.43), (A)+(B4)+
(C5.44), (A)+(B4)+(C5.45), (A)+(B4)+(C5.46), (A)+(B4)+
(C5.47), (A)+(B4)+(C5.48), (A)+(B4)+(C5.49), (A)+(B4)+
(C5.50), (A)+(B4)+(C5.51), (A)+(B4)+(C5.52), (A)+(B4)+
(C5.53), (A)+(B4)+(C5.54), (A)+(B4)+(C5.55), (A)+(B4)+
(C5.56), (A)+(B4)+(C5.57), (A)+(B4)+(C5.58), (A)+(B4)+
(C5.59), (A)+(B4)+(C5.60), (A)+(B4)+(C5.61), (A)+(B4)+
(C5.62), (A)+(B4)+(C5.63), (A)+(B4)+(C5.64), (A)+(B4)+
(C5.65), (A)+(B4)+(C6.1), (A)+(B4)+(C6.2), (A)+(B4)+
(C6.3), (A)+(B4)+(C6.4), (A)+(B4)+(C6.5), (A)+(B4)+
(C6.6), (A)+(B4)+(C6.7), (A)+(B6.8)+(A)+(B4)+(C6.9),
(A)+(B4)+(C6.10), (A)+(B4)+(C6.11), (A)+(B4)+(C6.12),
(A)+(B4)+(C6.13), (A)+(B4)+(C6.14), (A)+(B4)+(C6.15),
(A)+(B4)+(C6.16), (A)+(B4)+(C6.17), (A)+(B4)+(C7.1),
(A)+(B4)+(C7.2), (A)+(B4)+(C7.3), (A)+(B4)+(C7.4), (A)+
(B4)+(C7.5), (A)+(B4)+(C7.6), (A)+(B4)+(C7.7), (A)+
(B4)+(C7.8), (A)+(B4)+(C7.9), (A)+(B4)+(C7.10), (A)+
(B4)+(C7.11), (A)+(B4)+(C7.12), (A)+(B4)+(C7.13), (A)+
(B4)+(C7.14), (A)+(B4)+(C7.15), (A)+(B4)+(C7.16), (A)+
(B4)+(C7.17), (A)+(B4)+(C7.18), (A)+(B4)+(C7.19), (A)+
(B4)+(C7.20), (A)+(B4)+(C7.21), (A)+(B4)+(C7.22), (A)+
(B4)+(C7.23), (A)+(B4)+(C7.24), (A)+(B4)+(C7.25), (A)+
(B4)+(C7.26), (A)+(B4)+(C7.27), (A)+(B4)+(C7.28), (A)+
(B4)+(C7.29), (A)+(B4)+(C7.30), (A)+(B4)+(C8.1),
(A)+(B5)+(C1.1), (A)+(B5)+(C1.2), (A)+(B4)+(C1.3),
(A)+(B4)+(C1.4), (A)+(B5)+(C1.5), (A)+(B5)+(C1.6), (A)+
(B5)+(C1.7), (A)+(B5)+(C1.8), (A)+(B5)+(C1.9), (A)+
(B5)+(C1.10), (A)+(B5)+(C1.11), (A)+(B5)+(C1.12), (A)+
(B5)+(C1.13), (A)+(B5)+(C1.14), (A)+(B5)+(C1.15), (A)+
(B5)+(C1.16), (A)+(B5)+(C1.17), (A)+(B5)+(C1.18), (A)+
(B5)+(C1.19), (A)+(B5)+(C1.20), (A)+(B5)+(C1.21), (A)+
(B5)+(C1.22), (A)+(B5)+(C1.23), (A)+(B5)+(C1.24), (A)+
(B5)+(C1.25), (A)+(B5)+(C1.26), (A)+(B5)+(C1.27), (A)+
(B5)+(C1.27a), (A)+(B5)+(C1.27b), (A)+(B5)+(C1.27c),
(A)+(B5)+(B5)+(C1.27), (A)+(B5)+(C1.27l), (A)+(B5)+
(1.27m), (A)+(B5)+(1.27n), (A)+(B5)+(C1.27o), (A)+(B5)+
(C1.27r), (A)+(B5)+(C1.27s), (A)+(B5)+(C1.27t), (A)+
(B5)+(C1.27u), (A)+(B5)+(C127v), (A)+(B5)+(C1.28),
(A)+(B5)+(C1.29), (A)+(B5)+(C1.30), (A)+(B5)+(C1.31),
(A)+(B5)+(C1.32), (A)+(B5)+(C1.33), (A)+(B5)+(C1.34),
(A)+(B5)+(C1.35), (A)+(B5)+(C1.36), (A)+(B5)+(C1.37),
(A)+(B5)+(C1.38), (A)+(B5)+(C1.39), (A)+(B5)+(C1.40),
(A)+(B5)+(C1.41), (A)+(B5)+(C1.42), (A)+(B5)+(C1.43),
(A)+(B5)+(C1.44), (A)+(B5)+(C1.45), (A)+(B5)+(C1.46),
(A)+(B5)+(C1.47), (A)+(B5)+(C1.48), (A)+(B5)+(C1.49),
(A)+(B5)+(C1.50), (A)+(B5)+(C1.51), (A)+(B5)+(C1.52),
(A)+(B5)+(C1.53), (A)+(B5)+(C1.54), (A)+(B5)+(C1.55),
(A)+(B5)+(C1.56), (A)+(B5)+(C1.57), (A)+(B5)+(C1.58),
(A)+(B5)+(C1.59), (A)+(B5)+(C1.60), (A)+(B5)+(C1.61),
(A)+(B5)+(C1.62), (A)+(B5)+(C1.63), (A)+(B5)+(C1.64),
(A)+(B5)+(C1.65), (A)+(B5)+(C1.66), (A)+(B5)+(C1.67),
(A)+(B5)+(C1.68), (A)+(B5)+(C1.69), (A)+(B5)+(C1.70),
(A)+(B5)+(C1.71), (A)+(B5)+(C1.72), (A)+(B5)+(C1.73),
(A)+(B5)+(C1.74), (A)+(B5)+(C1.75), (A)+(B5)+(C1.76),
(A)+(B5)+(C1.77), (A)+(B5)+(C1.78), (A)+(B5)+(C1.79),
(A)+(B5)+(C1.80), (A)+(B5)+(C1.81), (A)+(B5)+(C1.82),
(A)+(B5)+(C1.83), (A)+(B5)+(C1.84), (A)+(B5)+(C1.85),
(A)+(B5)+(C1.86), (A)+(B5)+(C1.87), (A)+(B5)+(C1.88),
(A)+(B5)+(C1.89), (A)+(B5)+(C1.90), (A)+(B5)+(C1.91),
(A)+(B5)+(C1.92), (A)+(B5)+(C1.93), (A)+(B5)+(C1.94),
(A)+(B5)+(C1.95), (A)+(B5)+(C1.96), (A)+(B5)+(C1.97),
(A)+(B5)+(C1.98), (A)+(B5)+(C1.99), (A)+(B5)+(C1.100),
(A)+(B5)+(C1.101), (A)+(B5)+(C1.102), (A)+(B5)+
(C1.103), (A)+(B5)+(C1.104), (A)+(B5)+(C1.105), (A)+
(B5)+(C1.106), (A)+(B5)+(C1.107), (A)+(B5)+(C1.108),
(A)+(B5)+(C1.109), (A)+(B5)+(C1.110), (A)+(B5)+
(C1.111), (A)+(B5)+(C1.112), (A)+(B5)+(C1.113), (A)+
(B5)+(C1.114), (A)+(B5)+(C1.115), (A)+(B5)+(C1.116),
(A)+(B5)+(C1.117), (A)+(B5)+(C1.118), (A)+(B5)+
(C1.119), (A)+(B5)+(C1.120), (A)+(B5)+(C1.121), (A)+
(B5)+(C1.122), (A)+(B5)+(C1.123), (A)+(B5)+(C1.124),
(A)+(B5)+(C1.125), (A)+(B5)+(C1.126), (A)+(B5)+
(C1.127), (A)+(B5)+(C1.128), (A)+(B5)+(C1.129), (A)+
(B5)+(C1.130), (A)+(B5)+(C1.131), (A)+(B5)+(C1.132),
(A)+(B5)+(C2.1), (A)+(B5)+(C2.2), (A)+(B5)+(C2.3), (A)+
(B5)+(C2.4), (A)+(B5)+(C2.5), (A)+(B5)+(C2.6), (A)+
(B5)+(C2.7), (A)+(B5)+(C2.8), (A)+(B5)+(C2.9), (A)+
(B5)+(C2.10), (A)+(B5)+(C2.11), (A)+(B5)+(C2.12), (A)+
(B5)+(C2.13), (A)+(B5)+(C2.14), (A)+(B5)+(C2.15), (A)+
(B5)+(C2.16), (A)+(B5)+(C2.17), (A)+(B5)+(C2.18), (A)+
(B5)+(C2.19), (A)+(B5)+(C2.20), (A)+(B5)+(C2.21), (A)+
(B5)+(C2.22), (A)+(B5)+(C2.23), (A)+(B5)+(C2.24), (A)+
(B5)+(C2.25), (A)+(B5)+(C2.26), (A)+(B5)+(C2.27), (A)+
(B5)+(C2.28), (A)+(B5)+(C2.29), (A)+(B5)+(C2.30), (A)+
(B5)+(C2.31), (A)+(B5)+(C2.32), (A)+(B5)+(C2.33), (A)+
(B5)+(C2.34), (A)+(B5)+(C2.35), (A)+(B5)+(C2.36), (A)+
(B5)+(C2.37), (A)+(B5)+(C2.38), (A)+(B5)+(C2.39), (A)+
(B5)+(C2.40), (A)+(B5)+(C2.41), (A)+(B5)+(C2.42), (A)+
(B5)+(C2.43), (A)+(B5)+(C2.44), (A)+(B5)+(C2.45), (A)+
(B5)+(C2.46), (A)+(B5)+(C2.47), (A)+(B5)+(C2.48), (A)+
(B5)+(C2.49), (A)+(B5)+(C2.50), (A)+(B5)+(C2.51), (A)+
(B5)+(C2.52), (A)+(B5)+(C2.53), (A)+(B5)+(C2.54), (A)+
(B5)+(C2.55), (A)+(B5)+(C2.56), (A)+(B5)+(C2.57), (A)+
(B5)+(C2.58), (A)+(B5)+(C2.59), (A)+(B5)+(C2.60), (A)+

(B5)+(C2.61), (A)+(B5)+(C2.62), (A)+(B5)+(C2.63), (A)+(B5)+(C2.64), (A)+(B5)+(C2.65), (A)+(B5)+(C2.66), (A)+(B5)+(C2.67), (A)+(B5)+(C2.68), (A)+(B5)+(C2.69), (A)+(B5)+(C2.70), (A)+(B5)+(C2.71), (A)+(B5)+(C2.72), (A)+(B5)+(C2.73), (A)+(B5)+(C2.74), (A)+(B5)+(C2.75), (A)+(B5)+(C2.76), (A)+(B5)+(C2.77), (A)+(B5)+(C2.78), (A)+(B5)+(C2.79), (A)+(B5)+(C2.80), (A)+(B5)+(C2.81), (A)+(B5)+(C2.82), (A)+(B5)+(C2.83), (A)+(B5)+(C2.84), (A)+(B5)+(C2.85), (A)+(B5)+(C2.86), (A)+(B5)+(C2.87), (A)+(B5)+(C2.88), (A)+(B5)+(C2.89), (A)+(B5)+(C2.90), (A)+(B5)+(C2.91), (A)+(B5)+(C2.92), (A)+(B5)+(C2.93), (A)+(B5)+(C2.94), (A)+(B5)+(C2.95), (A)+(B5)+(C2.96), (A)+(B5)+(C2.97), (A)+(B5)+(C2.98), (A)+(B5)+(C2.99), (A)+(B5)+(C2.100), (A)+(B5)+(C2.101), (A)+(B5)+(C2.102), (A)+(B5)+(C2.103), (A)+(B5)+(C2.104), (A)+(B5)+(C2.105), (A)+(B5)+(C2.106), (A)+(B5)+(C2.107), (A)+(B5)+(C2.108), (A)+(B5)+(C2.109), (A)+(B5)+(C2.110), (A)+(B5)+(C2.111), (A)+(B5)+(C2.112), (A)+(B5)+(C2.113), (A)+(B5)+(C2.114), (A)+(B5)+(C3.1), (A)+(B5)+(C3.2), (A)+(B5)+(C3.3), (A)+(B5)+(C4.1), (A)+(B5)+(C4.2), (A)+(B5)+(C4.3), (A)+(B5)+(C4.4), (A)+(B5)+(C4.5), (A)+(B5)+(C4.6), (A)+(B5)+(C4.7), (A)+(B5)+(C4.8), (A)+(B5)+(C4.9), (A)+(B5)+(C4.10), (A)+(B5)+(C4.11), (A)+(B5)+(C4.12), (A)+(B5)+(C4.13), (A)+(B5)+(C4.14), (A)+(B5)+(C4.15), (A)+(B5)+(C5.1), (A)+(B5)+(C5.2), (A)+(B5)+(C5.3), (A)+(B5)+(C5.4), (A)+(B5)+(C5.5), (A)+(B5)+(C5.6), (A)+(B5)+(C5.7), (A)+(B5)+(C5.8), (A)+(B5)+(C5.9), (A)+(B5)+(C5.10), (A)+(B5)+(C5.11), (A)+(B5)+(C5.12), (A)+(B5)+(C5.13), (A)+(B5)+(C5.14), (A)+(B5)+(C5.15), (A)+(B5)+(C5.16), (A)+(B5)+(C5.17), (A)+(B5)+(C5.18), (A)+(B5)+(C5.19), (A)+(B5)+(C5.20), (A)+(B5)+(C5.21), (A)+(B5)+(C5.22), (A)+(B5)+(C5.23), (A)+(B5)+(C5.24), (A)+(B5)+(C5.25), (A)+(B5)+(C5.26), (A)+(B5)+(C5.27), (A)+(B5)+(C5.28), (A)+(B5)+(C5.29), (A)+(B5)+(C5.30), (A)+(B5)+(C5.31), (A)+(B5)+(C5.32), (A)+(B5)+(C5.33), (A)+(B5)+(C5.34), (A)+(B5)+(C5.35), (A)+(B5)+(C5.36), (A)+(B5)+(C5.37), (A)+(B5)+(C5.38), (A)+(B5)+(C5.39), (A)+(B5)+(C5.40), (A)+(B5)+(C5.41), (A)+(B5)+(C5.42), (A)+(B5)+(C5.43), (A)+(B5)+(C5.44), (A)+(B5)+(C5.45), (A)+(B5)+(C5.46), (A)+(B5)+(C5.47), (A)+(B5)+(C5.48), (A)+(B5)+(C5.49), (A)+(B5)+(C5.50), (A)+(B5)+(C5.51), (A)+(B5)+(C5.52), (A)+(B5)+(C5.53), (A)+(B5)+(C5.54), (A)+(B5)+(C5.55), (A)+(B5)+(C5.56), (A)+(B5)+(C5.57), (A)+(B5)+(C5.58), (A)+(B5)+(C5.59), (A)+(B5)+(C5.60), (A)+(B5)+(C5.61), (A)+(B5)+(C5.62), (A)+(B5)+(C5.63), (A)+(B5)+(C5.64), (A)+(B5)+(C5.65), (A)+(B5)+(C6.1), (A)+(B5)+(C6.2), (A)+(B5)+(C6.3), (A)+(B5)+(C6.4), (A)+(B5)+(C6.5), (A)+(B5)+(C6.6), (A)+(B5)+(C6.7), (A)+(B5)+(C6.8), (A)+(B5)+(C6.9), (A)+(B5)+(C6.10), (A)+(B5)+(C6.11), (A)+(B5)+(C6.12), (A)+(B5)+(C6.13), (A)+(B5)+(C6.14), (A)+(B5)+(C6.15), (A)+(B5)+(C6.16), (A)+(B5)+(C6.17), (A)+(B5)+(C7.1), (A)+(B5)+(C7.2), (A)+(B5)+(C7.3), (A)+(B5)+(C7.4), (A)+(B5)+(C7.5), (A)+(B5)+(C7.6), (A)+(B5)+(C7.7), (A)+(B5)+(C7.8), (A)+(B5)+(C7.9), (A)+(B5)+(C7.10), (A)+(B5)+(C7.11), (A)+(B5)+(C7.12), (A)+(B5)+(C7.13), (A)+(B5)+(C7.14), (A)+(B5)+(C7.15), (A)+(B5)+(C7.16), (A)+(B5)+(C7.17), (A)+(B5)+(C7.18), (A)+(B5)+(C7.19), (A)+(B5)+(C7.20), (A)+(B5)+(C7.21), (A)+(B5)+(C7.22), (A)+(B5)+(C7.23), (A)+(B5)+(C7.24), (A)+(B5)+(C7.25), (A)+(B5)+(C7.26), (A)+(B5)+(C7.27), (A)+(B5)+(C7.28), (A)+(B5)+(C7.29), (A)+(B5)+(C7.30), (A)+(B5)+(C8.1),
(A)+(B6)+(C1.1), (A)+(B6)+(C1.2), (A)+(B6)+(C1.3), (A)+(B6)+(C1.4), (A)+(B6)+(C1.5), (A)+(B6)+(C1.6), (A)+(B6)+(C1.7), (A)+(B6)+(C1.8), (A)+(B6)+(C1.9), (A)+(B6)+(C1.10), (A)+(B6)+(C1.11), (A)+(B6)+(C1.12), (A)+(B6)+(C1.13), (A)+(B6)+(C1.14), (A)+(B6)+(C1.15), (A)+(B6)+(C1.16), (A)+(B6)+(C1.17), (A)+(B6)+(C1.18), (A)+(B6)+(C1.19), (A)+(B6)+(C1.20), (A)+(B6)+(C1.21), (A)+(B6)+(C1.22), (A)+(B6)+(C1.23), (A)+(B6)+(C1.24), (A)+(B6)+(C1.25), (A)+(B6)+(C1.26), (A)+(B6)+(C1.27), (A)+(B6)+(C1.27a), (A)+(B6)+(C1.27b), (A)+(B6)+(C1.27c), (A)+(B6)+(C1.27d), (A)+(B6)+(C1.27e), (A)+(B6)+(C1.27f), (A)+(B6)+(C1.27g), (A)+(B6)+(C1.27h), (A)+(B6)+(C1.27i), (A)+(B6)+(C1.27l ), (A)+(B6)+(C1.27m), (A)+(B6)+(C1.27n), (A)+(B6)+(C1.27o), (A)+(B6)+(C1.27r), (A)+(B6)+(C1.27s), (A)+(B6)+(C1.27t), (A)+(B6)+(C1.27u), (A)+(B6)+(C1.27v), (A)+(B6)+(C1.28), (A)+(B6)+(C1.29), (A)+(B6)+(C1.30), (A)+(B6)+(C1.31), (A)+(B6)+(C1.32), (A)+(B6)+(C1.33), (A)+(B6)+(C1.34), (A)+(B6)+(C1.35), (A)+(B6)+(C1.36), (A)+(B6)+(C1.37), (A)+(B6)+(C1.38), (A)+(B6)+(C1.39), (A)+(B6)+(C1.40), (A)+(B6)+(C1.41), (A)+(B6)+(C1.42), (A)+(B6)+(C1.43), (A)+(B6)+(C1.44), (A)+(B6)+(C1.45), (A)+(B6)+(C1.46), (A)+(B6)+(C1.47), (A)+(B6)+(C1.48), (A)+(B6)+(C1.49), (A)+(B6)+(C1.50), (A)+(B6)+(C1.51), (A)+(B6)+(C1.52), (A)+(B6)+(C1.53), (A)+(B6)+(C1.54), (A)+(B6)+(C1.55), (A)+(B6)+(C1.56), (A)+(B6)+(C1.57), (A)+(B6)+(C1.58), (A)+(B6)+(C1.59), (A)+(B6)+(C1.60), (A)+(B6)+(C1.61), (A)+(B6)+(C1.62), (A)+(B6)+(C1.63), (A)+(B6)+(C1.64), (A)+(B6)+(C1.65), (A)+(B6)+(C1.66), (A)+(B6)+(C1.67), (A)+(B6)+(C1.68), (A)+(B6)+(C1.69), (A)+(B6)+(C1.70), (A)+(B6)+(C1.71), (A)+(B6)+(C1.72), (A)+(B6)+(C1.73), (A)+(B6)+(C1.74), (A)+(B6)+(C1.75), (A)+(B6)+(C1.76), (A)+(B6)+(C1.77), (A)+(B6)+(C1.78), (A)+(B6)+(C1.79), (A)+(B6)+(C1.80), (A)+(B6)+(C1.81), (A)+(B6)+(C1.82), (A)+(B6)+(C1.83), (A)+(B6)+(C1.84), (A)+(B6)+(C1.85), (A)+(B6)+(C1.86), (A)+(B6)+(C1.87), (A)+(B6)+(C1.88), (A)+(B6)+(C1.89), (A)+(B6)+(C1.90), (A)+(B6)+(C1.91), (A)+(B6)+(C1.92), (A)+(B6)+(C1.93), (A)+(B6)+(C1.94), (A)+(B6)+(C1.95), (A)+(B6)+(C1.96), (A)+(B6)+(C1.97), (A)+(B6)+(C1.98), (A)+(B6)+(C1.99), (A)+(B6)+(C1.100), (A)+(B6)+(C1.101), (A)+(B6)+(C1.102), (A)+(B6)+(C1.103), (A)+(B6)+(C1.104), (A)+(B6)+(C1.105), (A)+(B6)+(C1.106), (A)+(B6)+(C1.107), (A)+(B6)+(C1.108), (A)+(B6)+(C1.109), (A)+(B6)+(C1.110), (A)+(B6)+(C1.111), (A)+(B6)+(C1.112), (A)+(B6)+(C1.113), (A)+(B6)+(C1.114), (A)+(B6)+(C1.115), (A)+(B6)+(C1.116), (A)+(B6)+(C1.117), (A)+(B6)+(C1.118), (A)+(B6)+(C1.119), (A)+(B6)+(C1.120), (A)+(B6)+(C1.121), (A)+(B6)+(C1.122), (A)+(B6)+(C1.123), (A)+(B6)+(C1.124), (A)+(B6)+(C1.125), (A)+(B6)+(C1.126), (A)+(B6)+(C1.127), (A)+(B6)+(C1.128), (A)+(B6)+(C1.129), (A)+(B6)+(C1.130), (A)+(B6)+(C1.131), (A)+(B6)+(C1.132), (A)+(B6)+(C2.1), (A)+(B6)+(C2.2), (A)+(B6)+(C2.3), (A)+(B6)+(C2.4), (A)+(B6)+(C2.5), (A)+(B6)+(C2.6), (A)+(B6)+(C2.7), (A)+(B6)+(C2.8), (A)+(B6)+(C2.9), (A)+(B6)+(C2.10), (A)+(B6)+(C2.11), (A)+(B6)+(C2.12), (A)+(B6)+(C2.13), (A)+(B6)+(C2.14), (A)+(B6)+(C2.15), (A)+(B6)+(C2.16), (A)+(B6)+(C2.17), (A)+(B6)+(C2.18), (A)+(B6)+(C2.19), (A)+(B6)+(C2.20), (A)+(B6)+(C2.21), (A)+(B6)+(C2.22), (A)+(B6)+(C2.23), (A)+(B6)+(C2.24), (A)+(B6)+(C2.25), (A)+(B6)+(C2.26), (A)+(B6)+(C2.27), (A)+(B6)+(C2.28), (A)+(B6)+(C2.29), (A)+(B6)+(C2.30), (A)+(B6)+(C2.31), (A)+(B6)+(C2.32), (A)+(B6)+(C2.33), (A)+(B6)+(C2.34), (A)+(B6)+(C2.35), (A)+(B6)+(C2.36), (A)+(B6)+(C2.37), (A)+(B6)+(C2.38), (A)+(B6)+(C2.39), (A)+(B6)+(C2.40), (A)+(B6)+(C2.41), (A)+(B6)+(C2.42), (A)+(B6)+(C2.43), (A)+(B6)+(C2.44), (A)+(B6)+(C2.45), (A)+(B6)+(C2.46), (A)+(B6)+(C2.47), (A)+(B6)+(C2.48), (A)+(B6)+(C2.49), (A)+(B6)+(C2.50), (A)+(B6)+(C2.51), (A)+(B6)+(C2.52), (A)+(B6)+(C2.53), (A)+(B6)+(C2.54), (A)+(B6)+(C2.55), (A)+(B6)+(C2.56), (A)+(B6)+(C2.57), (A)+

(B6)+(C2.58), (A)+(B6)+(C2.59), (A)+(B6)+(C2.60), (A)+(B6)+(C2.61), (A)+(B6)+(C2.62), (A)+(B6)+(C2.63), (A)+(B6)+(C2.64), (A)+(B6)+(C2.65), (A)+(B6)+(C2.66), (A)+(B6)+(C2.67), (A)+(B6)+(C2.68), (A)+(B6)+(C2.69), (A)+(B6)+(C2.70), (A)+(B6)+(C2.71), (A)+(B6)+(C2.72), (A)+(B6)+(C2.73), (A)+(B6)+(C2.74), (A)+(B6)+(C2.75), (A)+(B6)+(C2.76), (A)+(B6)+(C2.77), (A)+(B6)+(C2.78), (A)+(B6)+(C2.79), (A)+(B6)+(C2.80), (A)+(B6)+(C2.81), (A)+(B6)+(C2.82), (A)+(B6)+(C2.83), (A)+(B6)+(C2.84), (A)+(B6)+(C2.85), (A)+(B6)+(C2.86), (A)+(B6)+(C2.87), (A)+(B6)+(C2.88), (A)+(B6)+(C2.89), (A)+(B6)+(C2.90), (A)+(B6)+(C2.91), (A)+(B6)+(C2.92), (A)+(B6)+(C2.93), (A)+(B6)+(C2.94), (A)+(B6)+(C2.95), (A)+(B6)+(C2.96), (A)+(B6)+(C2.97), (A)+(B6)+(C2.98), (A)+(B6)+(C2.99), (A)+(B6)+(C2.100), (A)+(B6)+(C2.101), (A)+(B6)+(C2.102), (A)+(B6)+(C2.103), (A)+(B6)+(C2.104), (A)+(B6)+(C2.105), (A)+(B6)+(C2.106), (A)+(B6)+(C2.107), (A)+(B6)+(C2.108), (A)+(B6)+(C2.109), (A)+(B6)+(C2.110), (A)+(B6)+(C2.111), (A)+(B6)+(C2.112), (A)+(B6)+(C2.113), (A)+(B6)+(C2.114), (A)+(B6)+(C3.1), (A)+(B6)+(C3.2), (A)+(B6)+(C3.3), (A)+(C4.1), (A)+(B6)+(C4.2), (A)+(B6)+(C4.3), (A)+(B6)+(C4.4), (A)+(B6)+(C4.5), (A)+(B6)+(C4.6), (A)+(B6)+(C4.7), (A)+(B6)+(C4.8), (A)+(B6)+(C4.9), (A)+(B6)+(C4.10), (A)+(B6)+(C4.11), (A)+(B6)+(C4.12), (A)+(B6)+(C4.13), (A)+(B6)+(C4.14), (A)+(B6)+(C4.15), (A)+(B6)+(C5.1), (A)+(B6)+(C5.2), (A)+(B6)+(C5.3), (A)+(B6)+(C5.4), (A)+(B6)+(C5.5), (A)+(B6)+(C5.6), (A)+(B6)+(C5.7), (A)+(B6)+(C5.8), (A)+(B6)+(C5.9), (A)+(B6)+(C5.10), (A)+(B6)+(C5.11), (A)+(B6)+(C5.12), (A)+(B6)+(C5.13), (A)+(B6)+(C5.14), (A)+(B6)+(C5.15), (A)+(B6)+(C5.16), (A)+(B6)+(C5.17), (A)+(B6)+(C5.18), (A)+(B6)+(C5.19), (A)+(B6)+(C5.20), (A)+(B6)+(C5.21), (A)+(B6)+(C5.22), (A)+(B6)+(C5.23), (A)+(B6)+(C5.24), (A)+(B6)+(C5.25), (A)+(B6)+(C5.26), (A)+(B6)+(C5.27), (A)+(B6)+(C5.28), (A)+(B6)+(C5.29), (A)+(B6)+(C5.30), (A)+(B6)+(C5.31), (A)+(B6)+(C5.32), (A)+(B6)+(C5.33), (A)+(B6)+(C5.34), (A)+(B6)+(C5.35), (A)+(B6)+(C5.36), (A)+(B6)+(C5.37), (A)+(B6)+(C5.38), (A)+(B6)+(C5.39), (A)+(B6)+(C5.40), (A)+(B6)+(C5.41), (A)+(B6)+(C5.42), (A)+(B6)+(C5.43), (A)+(B6)+(C5.44), (A)+(B6)+(C5.45), (A)+(B6)+(C5.46), (A)+(B6)+(C5.47), (A)+(B6)+(C5.48), (A)+(B6)+(C5.49), (A)+(B6)+(C5.50), (A)+(B6)+(C5.51), (A)+(B6)+(C5.52), (A)+(B6)+(C5.53), (A)+(B6)+(C5.54), (A)+(B6)+(C5.55), (A)+(B6)+(C5.56), (A)+(B6)+(C5.57), (A)+(B6)+(C5.58), (A)+(B6)+(C5.59), (A)+(B6)+(C5.60), (A)+(B6)+(C5.61), (A)+(B6)+(C5.62), (A)+(B6)+(C5.63), (A)+(B6)+(C5.64), (A)+(B6)+(C5.65), (A)+(B6)+(C6.1), (A)+(B6)+(C6.2), (A)+(B6)+(C6.3), (A)+(B6)+(C6.4), (A)+(B6)+(C6.5), (A)+(B6)+(C6.6), (A)+(B6)+(C6.7), (A)+(B6)+(C6.8), (A)+(B6)+(C6.9), (A)+(B6)+(C6.10), (A)+(B6)+(C6.11), (A)+(B6)+(C6.12), (A)+(B6)+(C6.13), (A)+(B6)+(C6.14), (A)+(B6)+(C6.15), (A)+(B6)+(C6.16), (A)+(B6)+(C6.17), (A)+(B6)+(C7.1), (A)+(B6)+(C7.2), (A)+(B6)+(C7.3), (A)+(B6)+(C7.4), (A)+(B6)+(C7.5), (A)+(B6)+(C7.6), (A)+(B6)+(C7.7), (A)+(B6)+(C7.8), (A)+(B6)+(C7.9), (A)+(B6)+(C7.10), (A)+(B6)+(C7.11), (A)+(B6)+(C7.12), (A)+(B6)+(C7.13), (A)+(B6)+(C7.14), (A)+(B6)+(C7.15), (A)+(B6)+(C7.16), (A)+(B6)+(C7.17), (A)+(B6)+(C7.18), (A)+(B6)+(C7.19), (A)+(B6)+(C7.20), (A)+(B6)+(C7.21), (A)+(B6)+(C7.22), (A)+(B6)+(C7.23), (A)+(B6)+(C7.24), (A)+(B6)+(C7.25), (A)+(B6)+(C7.26), (A)+(B6)+(C7.27), (A)+(B6)+(C7.28), (A)+(B6)+(C7.29), (A)+(B6)+(C7.30), (A)+(B6)+(C8.1), (A)+(B7)+(C1.1), (A)+(B7)+(C1.2), (A)+(B7)+(C1.3), (A)+(B7)+(C1.4), (A)+(B7)+(C1.5), (A)+(B7)+(C1.6), (A)+(B7)+(C1.7), (A)+(B7)+(C1.8), (A)+(B7)+(C1.9), (A)+(B7)+(C1.10), (A)+(B7)+(C1.11), (A)+(B7)+(C1.12), (A)+(B7)+(C1.13), (A)+(B7)+(C1.14), (A)+(B7)+(C1.15), (A)+(B7)+(C1.16), (A)+(B7)+(C1.17), (A)+(B7)+(C1.18), (A)+(B7)+(C1.19), (A)+(B7)+(C1.20), (A)+(B7)+(C1.21), (A)+(B7)+(C1.22), (A)+(B7)+(C1.23), (A)+(B7)+(C1.24), (A)+(B7)+(C1.25), (A)+(B7)+(C1.26), (A)+(B7)+(C1.27), (A)+(B7)+(C1.27a), (A)+(B7)+(C1.27b), (A)+(B7)+(C1.27c), (A)+(B7)+(C1.27d), (A)+(B7)+(C1.27e), (A)+(B7)+(C1.27f), (A)+(B7)+(C1.27g), (A)+(B7)+(C1.27h), (A)+(B7)+(C1.27), (A)+(B7)+(C1.27l), (A)+(B7)+(C1.27m), (A)+(B7)+(C1.27n), (A)+(B7)+(C1.27o), (A)+(B7)+(C1.27r), (A)+(B7)+(C1.27s), (A)+(B7)+(C1.27t), (A)+(B7)+(C1.27u), (A)+(B7)+(C1.27v), (A)+(B7)+(C1.28), (A)+(B7)+(C1.29), (A)+(B7)+(C1.30), (A)+(B7)+(C1.31), (A)+(B7)+(C1.32), (A)+(B7)+(C1.38), (A)+(B7)+(C1.39), (A)+(B7)+(C1.40), (A)+(B7)+(C1.41), (A)+(B7)+(C1.42), (A)+(B7)+(C1.43), (A)+(B7)+(C1.44), (A)+(B7)+(C1.45), (A)+(B7)+(C1.46), (A)+(B7)+(C1.47), (A)+(B7)+(C1.48), (A)+(B7)+(C1.49), (A)+(B7)+(C1.50), (A)+(B7)+(C1.51), (A)+(B7)+(C1.52), (A)+(B7)+(C1.53), (A)+(B7)+(C1.54), (A)+(B7)+(C1.55), (A)+(B7)+(C1.56), (A)+(B7)+(C1.57), (A)+(B7)+(C1.58), (A)+(B7)+(C1.59), (A)+(B7)+(C1.60), (A)+(B7)+(C1.61), (A)+(B7)+(C1.62), (A)+(B7)+(C1.63), (A)+(B7)+(C1.64), (A)+(B7)+(C1.65), (A)+(B7)+(C1.66), (A)+(B7)+(C1.67), (A)+(B7)+(C1.68), (A)+(B7)+(C1.69), (A)+(B7)+(C1.70), (A)+(B7)+(C1.71), (A)+(B7)+(C1.72), (A)+(B7)+(C1.73), (A)+(B7)+(C1.74), (A)+(B7)+(C1.75), (A)+(B7)+(C1.76), (A)+(B7)+(C1.77), (A)+(B7)+(C1.78), (A)+(B7)+(C1.79), (A)+(B7)+(C1.80), (A)+(B7)+(C1.81), (A)+(B7)+(C1.82), (A)+(B7)+(C1.83), (A)+(B7)+(C1.84), (A)+(B7)+(C1.85), (A)+(B7)+(C1.86), (A)+(B7)+(C1.87), (A)+(B7)+(C1.88), (A)+(B7)+(C1.89), (A)+(B7)+(C1.90), (A)+(B7)+(C1.91), (A)+(B7)+(C1.92), (A)+(B7)+(C1.93), (A)+(B7)+(C1.94), (A)+(B7)+(C1.95), (A)+(B7)+(C1.96), (A)+(B7)+(C1.97), (A)+(B7)+(C1.98), (A)+(B7)+(C1.99), (A)+(B7)+(C1.100), (A)+(B7)+(C1.101), (A)+(B7)+(C1.102), (A)+(B7)+(C1.103), (A)+(B7)+(C1.104), (A)+(B7)+(C1.105), (A)+(B7)+(C1.106), (A)+(B7)+(C1.107), (A)+(B7)+(C1.108), (A)+(B7)+(C1.109), (A)+(B7)+(C1.110), (A)+(B7)+(C1.111), (A)+(B7)+(C1.112), (A)+(B7)+(C1.113), (A)+(B7)+(C1.114), (A)+(B7)+(C1.115), (A)+(B7)+(C1.116), (A)+(B7)+(C1.117), (A)+(B7)+(C1.118), (A)+(B7)+(C1.119), (A)+(B7)+(C1.120), (A)+(B7)+(C1.121), (A)+(B7)+(C1.122), (A)+(B7)+(C1.123), (A)+(B7)+(C1.124), (A)+(B7)+(C1.25), (A)+(B7)+(C1.126), (A)+(B7)+(C1.127), (A)+(B7)+(C1.128), (A)+(B7)+(C1.129), (A)+(B7)+(C1.130), (A)+(B7)+(C1.131), (A)+(B7)+(C1.132), (A)+(B7)+(C2.1), (A)+(B7)+(C2.2), (A)+(B7)+(C2.3), (A)+(B7)+(C2.4), (A)+(B7)+(C2.5), (A)+(B7)+(C2.6), (A)+(B7)+(C2.7), (A)+(B7)+(C2.8), (A)+(B7)+(C2.9), (A)+(B7)+(C2.10), (A)+(B7)+(C2.11), (A)+(B7)+(C2.12), (A)+(B7)+(C2.13), (A)+(B7)+(C2.14), (A)+(B7)+(C2.15), (A)+(B7)+(C2.16), (A)+(B7)+(C2.17), (A)+(B7)+(C2.18), (A)+(B7)+(C2.19), (A)+(B7)+(C2.20), (A)+(B7)+(C2.21), (A)+(B7)+(C2.22), (A)+(B7)+(C2.23), (A)+(B7)+(C2.24), (A)+(B7)+(C2.25), (A)+(B7)+(C2.26), (A)+(B7)+(C2.27), (A)+(B7)+(C2.28), (A)+(B7)+(C2.29), (A)+(B7)+(C2.30), (A)+(B7)+(C2.31), (A)+(B7)+(C2.32), (A)+(B7)+(C2.33), (A)+(B7)+(C2.34), (A)+(B7)+(C2.35), (A)+(B7)+(C2.36), (A)+(B7)+(C2.37), (A)+(B7)+(C2.38), (A)+(B7)+(C2.39), (A)+(B7)+(C2.40), (A)+(B7)+(C2.41), (A)+(B7)+(C2.42), (A)+(B7)+(C2.43), (A)+(B7)+(C2.44), (A)+(B7)+(C2.45), (A)+(B7)+(C2.46), (A)+(B7)+(C2.47), (A)+(B7)+(C2.48), (A)+(B7)+(C2.49), (A)+(B7)+(C2.50), (A)+(B7)+(C2.51), (A)+(B7)+(C2.52), (A)+(B7)+(C2.53), (A)+(B7)+(C2.54), (A)+(B7)+(C2.55), (A)+(B7)+(C2.56), (A)+(B7)+(C2.57), (A)+(B7)+(C2.58), (A)+(B7)+(C2.59), (A)+(B7)+(C2.60), (A)+(B7)+(C2.61), (A)+(B7)+(C2.62), (A)+

(B7)+(C2.63), (A)+(B7)+(C2.64), (A)+(B7)+(C2.65), (A)+(B7)+(C2.66), (A)+(B7)+(C2.67), (A)+(B7)+(C2.68), (A)+(B7)+(C2.69), (A)+(B7)+(C2.70), (A)+(B7)+(C2.71), (A)+(B7)+(C2.72), (A)+(B7)+(C2.73), (A)+(B7)+(C2.74), (A)+(B7)+(C2.75), (A)+(B7)+(C2.65), (A)+(B7)+(C2.66), (A)+(B7)+(C2.67), (A)+(B7)+(C2.79), (A)+(B7)+(C2.80), (A)+(B7)+(C2.81), (A)+(B7)+(C2.82), (A)+(B7)+(C2.83), (A)+(B7)+(C2.84), (A)+(B7)+(C2.85), (A)+(B7)+(C2.86), (A)+(B7)+(C2.87), (A)+(B7)+(C2.88), (A)+(B7)+(C2.89), (A)+(B7)+(C2.90), (A)+(B7)+(C2.91), (A)+(B7)+(C2.92), (A)+(B7)+(C2.93), (A)+(B7)+(C2.94), (A)+(B7)+(C2.95), (A)+(B7)+(C2.96), (A)+(B7)+(C2.97), (A)+(B7)+(C2.98), (A)+(B7)+(C2.99), (A)+(B7)+(C2.100), (A)+(B7)+(C2.101), (A)+(B7)+(C2.102), (A)+(B7)+(C2.103), (A)+(B7)+(C2.104), (A)+(B7)+(C2.105), (A)+(B7)+(C2.106), (A)+(B7)+(C2.107), (A)+(B7)+(C2.108), (A)+(B7)+(B7)+(C2.109), (A)+(B7)+(C2.110), (A)+(B7)+(C2.111), (A)+(B7)+(C2.112), (A)+(B7)+(C2.113), (A)+(B7)+(C2.114), (A)+(B7)+(C3.1), (A)+(B7)+(C3.2), (A)+(B7)+(C3.3), (A)+(B7)+(C4.1), (A)+(B7)+(C4.2), (A)+(B7)+(C4.3), (A)+(B7)+(C4.4), (A)+(B7)+(C4.5), (A)+(B7)+(C4.6), (A)+(B7)+(C4.7), (A)+(B7)+(C4.8), (A)+(B7)+(C4.9), (A)+(B7)+(C4.10), (A)+(B7)+(C4.11), (A)+(B7)+(C4.12), (A)+(B7)+(C4.13), (A)+(B7)+(C4.14), (A)+(B7)+(C4.15), (A)+(B7)+(C5.1), (A)+(B7)+(C5.2), (A)+(B7)+(C5.3), (A)+(B7)+(C5.4), (A)+(B7)+(C5.5), (A)+(B7)+(C5.6), (A)+(B7)+(C5.7), (A)+(B7)+(C5.8), (A)+(B7)+(C5.9), (A)+(B7)+(C5.10), (A)+(B7)+(C5.11), (A)+(B7)+(C5.12), (A)+(B7)+(C5.13), (A)+(B7)+(C5.14), (A)+(B7)+(C5.15), (A)+(B7)+(C5.16), (A)+(B7)+(C5.17), (A)+(B7)+(C5.18), (A)+(B7)+(C5.19), (A)+(B7)+(C5.20), (A)+(B7)+(C5.21), (A)+(B7)+(C5.22), (A)+(B7)+(C5.23), (A)+(B7)+(C5.24), (A)+(B7)+(C5.25), (A)+(B7)+(C5.26), (A)+(B7)+(C5.27), (A)+(B7)+(C5.28), (A)+(B7)+(C5.29), (A)+(B7)+(C5.30), (A)+(B7)⇌(C5.31), (A)+(B7)+(C5.32), (A)+(B7)+(C5.33), (A)+(B7)+(C5.34), (A)+(B7)+(C5.35), (A)+(B7)+(C5.36), (A)+(B7)+(C5.37), (A)+(B7)+(C5.38), (A)+(B7)+(C5.39), (A)+(B7)+(C5.40), (A)+(B7)+(C5.41), (A)+(B7)+(C5.42), (A)+(B7)+(C5.43), (A)+(B7)+(C5.44), (A)+(B7)+(C5.45), (A)+(B7)+(C5.46), (A)+(B7)+(C5.47), (A)+(B7)+(C5.48), (A)+(B7)+(C5.49), (A)+(B7)+(C5.50), (A)+(B7)+(C5.51), (A)+(B7)+(C5.52), (A)+(B7)+(C5.53), (A)+(B7)+(C5.54), (A)+(B7)+(C5.55), (A)+(B7)+(C5.56), (A)+(B7)+(C5.57), (A)+(B7)+(C5.58), (A)+(B7)+(C5.59), (A)+(B7)+(C5.60), (A)+(B7)+(C5.61), (A)+(B7)+(C5.62), (A)+(B7)+(C5.63), (A)+(B7)+(C5.64), (A)+(B7)+(C5.65), (A)+(B7)+(C6.1), (A)+(B7)+(C6.2), (A)+(B7)+(C6.3), (A)+(B7)+(C6.4), (A)+(B7)+(C6.5), (A)+(B7)+(C6.6), (A)+(B7)+(C6.7), (A)+(B7)+(C6.8), (A)+(B7)+(C6.9), (A)+(B7)+(C6.10), (A)+(B7)+(C6.11), (A)+(B7)+(C6.12), (A)+(B7)+(C6.13), (A)+(B7)+(C6.14), (A)+(B7)+(C6.15), (A)+(B7)+(C6.16), (A)+(B7)+(C6.17), (A)+(B7)+(C7.1), (A)+(B7)+(C7.2), (A)+(B7)+(C7.3), (A)+(B7)+(C7.4), (A)+(B7)+(C7.5), (A)+(B7)+(C7.60, (A)+(B7)+(C7.7), (A)+(B7)+(C7.8), (A)+(B7)+(C7.9), (A)+(B7)+(C7.10), (A)+(B7)+(C7.11), (A)+(B7)+(C7.12), (A)+(B7)+(C7.13), (A)+(B7)+(C7.14), (A)+(B7)+(C7.15), (A)+(B7)+(C7.16), (A)+(B7)+(C7.17), (A)+(B7)+(C7.18), (A)+(B7)+(C7.19), (A)+(B7)+(C7.20), (A)+(B7)+(C7.21), (A)+(B7)+(C7.22), (A)+(B7)+(C7.23), (A)+(B7)+(C7.24), (A)+(B7)+(C7.25), (A)+(B7)+(C7.26), (A)+(B7)+(C7.27), (A)+(B7)+(C7.28), (A)+(B7)+(C7.29), (A)+(B7)+(C7.30), (A)+(B7)+(C8.1), (A)+(B8)+(C1.1), (A)+(B8)+(C1.2), (A)+(B8)+(C1.3), (A)+(B8)+(C1.4), (A)+(B8)+(C1.5), (A)+(B8)+(C1.6), (A)+(B8)+(C1.7), (A)+(B8)+(C1.8), (A)+(B8)+(C1.9), (A)+(B8)+(C1.10), (A)+(B8)+(C1.11), (A)+(B8)+(C1.12), (A)+(B8)+(C1.13), (A)+(B8)+(C1.14), (A)+(B8)+(C1.15), (A)+(B8)+(C1.16), (A)+(B8)+(C1.17), (A)+(B8)+(C1.18), (A)+(B8)+(C1.19), (A)+(B8)+(C1.20), (A)+(B8)+(C1.21), (A)+(B8)+(C1.22), (A)+(B8)+(C1.23), (A)+(B8)+(C1.24), (A)+(B8)+(C1.25), (A)+(B8)+(C1.26), (A)+(B8)+(C1.27), (A)+(B8)+(C1.27a), (A)+(B8)+(C1.27b), (A)+(B8)+(C1.27c), (A)+(B8)+(C1.27d), (A)+(B8)+(C1.27e ), (A)+(B8)+(C1.27f), (A)+(B8)+(C1.27g), (A)+(B8)+(C1.27h), (A)+(B8)+(C1.27), (A)+(B8)+(C1.27l), (A)+(B8)+(C1.27m), (A)+(B8)+(C1.27n), (A)+(B8)+(C1.27o), (A)+(B8)+(C1.27r), (A)+(B8)+(C1.27s), (A)+(B8)+(C1.27t), (A)+(B8)+(C1.27u), (A)+(B8)+(C1.27v), (A)+(B8)+(C1.28), (A)+(B8)+(C1.29), (A)+(B8)+(C1.30), (A)+(B8)+(C1.31), (A)+(B8)+(C1.32), (A)+(B8)+(C1.33), (A)+(B8)+(C1.34), (A)+(B8)+(C1.35), (A)+(B8)+(C1.36), (A)+(B8)+(C1.37), (A)+(B8)+(C1.38), (A)+(B8)+(C1.39), (A)+(B8)+(C1.40), (A)+(B8)+(C1.41), (A)+(B8)+(C1.42), (A)+(B8)+(C1.43), (A)+(B8)+(C1.44), (A)+(B8)+(C1.45), (A)+(B8)+(C1.46), (A)+(B8)+(C1.47), (A)+(B8)+(C1.48), (A)+(B8)+(C1.49), (A)+(B8)+(C1.50), (A)+(B8)+(C1.51), (A)+(B8)+(C1.52), (A)+(B8)+(C1.53), (A)+(B8)+(C1.54), (A)+(B8)+(C1.55), (A)+(B8)+(C1.56), (A)+(B8)+(C1.57), (A)+(B8)+(C1.58), (A)+(B8)+(C1.59), (A)+(B8)+(C1.60), (A)+(B8)+(C1.61), (A)+(B8)+(C1.62), (A)+(B8)+(C1.63), (A)+(B8)+(C1.64), (A)+(B8)+(C1.65), (A)+(B8)+(C1.66), (A)+(B8)+(C1.67), (A)+(B8)+(C1.68), (A)+(B8)+(C1.69), (A)+(B8)+(C1.70), (A)+(B8)+(C1.71), (A)+(B8)+(C1.72), (A)+(B8)+(C1.73), (A)+(B8)+(C1.74), (A)+(B8)+(C1.75), (A)+(B8)+(C1.76), (A)+(B8)+(C1.77), (A)+(B8)+(C1.78), (A)+(B8)+(C1.79), (A)+(B8)+(C1.80), (A)+(B8)+(C1.81), (A)+(B8)+(C1.82), (A)+(B8)+(C1.83), (A)+(B8)+(C1.84), (A)+(B8)+(C1.85), (A)+(B8)+(C1.86), (A)+(B8)+(C1.87), (A)+(B8)+(C1.88), (A)+(B8)+(C1.89), (A)+(B8)+(C1.90), (A)+(B8)+(C1.91), (A)+(B8)+(C1.92), (A)+(B8)+(C1.93), (A)+(B8)+(C1.94), (A)+(B8)+(C1.95), (A)+(B8)+(C1.96), (A)+(B8)+(C1.97), (A)+(B8)+(C1.98), (A)+(B8)+(C1.99), (A)+(B8)+(C1.100), (A)+(B8)+(C1.101), (A)+(B8)+(C1.102), (A)+(B8)+(C1.103), (A)+(B8)+(C1.104), (A)+(B8)+(C1.105), (A)+(B8)+(C1.106), (A)+(B8)+(C1.107), (A)+(B8)+(C1.108), (A)+(B8)+(C1.109), (A)+(B8)+(C1.110), (A)+(B8)+(C1.111), (A)+(B8)+(C1.112), (A)+(B8)+(C1.113), (A)+(B8)+(C1.114), (A)+(B8)+(C1.115), (A)+(B8)+(C1.116), (A)+(B8)+(C1.117), (A)+(B8)+(C1.118), (A)+(B8)+(C1.119), (A)+(B8)+(C1.120), (A)+(B8)+(C1.121), (A)+(B8)+(C1.122), (A)+(B8)+(C1.123), (A)+(B8)+(C1.124), (A)+(B8)+(C1.125), (A)+(B8)+(C1.126), (A)+(B8)+(C1.127), (A)+(B8)+(C1.128), (A)+(B8)+(C1.129), (A)+(B8)+(C1.130), (A)+(B8)+(C1.131), (A)+(B8)+(C1.132), (A)+(B8)+(C2.1), (A)+(B8)+(C2.2), (A)+(B8)+(C2.3), (A)+(B8)+(C2.4), (A)+(B8)+(C2.5), (A)+(B8)+(C2.6), (A)+(B8)+(C2.7), (A)+(B8)+(C2.8), (A)+(B8)+(C2.9), (A)+(B8)+(C2.10), (A)+(B8)+(C2.11), (A)+(B8)+(C2.12), (A)+(B8)+(C2.13), (A)+(B8)+(C2.14), (A)+(B8)+(C2.15), (A)+(B8)+(C2.16), (A)+(B8)+(C2.17), (A)+(B8)+(C2.18), (A)+(B8)+(C2.19), (A)+(B8)+(C2.20), (A)+(B8)+(C2.21), (A)+(B8)+(C2.22), (A)+(B8)+(C2.23), (A)+(B8)+(C2.24), (A)+(B8)+(C2.25), (A)+(B8)+(C2.26), (A)+(B8)+(C2.27), (A)+(B8)+(C2.28), (A)+(B8)+(C2.29), (A)+(B8)+(C2.30), (A)+(B8)+(C2.31), (A)+(B8)+(C2.32), (A)+(B8)+(C2.33), (A)+(B8)+(C2.34), (A)+(B8)+(C2.35), (A)+(B8)+(C2.36), (A)+(B8)+(C2.37), (A)+(B8)+(C2.38), (A)+(B8)+(C2.39), (A)+(B8)+(C2.40), (A)+(B8)+(C2.41), (A)+(B8)+(C2.42), (A)+(B8)+(C2.43), (A)+(B8)+(C2.44), (A)+(B8)+(C2.45), (A)+(B8)+(C2.46), (A)+(B8)+(C2.47), (A)+(B8)+(C2.48), (A)+(B8)+(C2.49), (A)+(B8)+(C2.50), (A)+(B8)+(C2.51), (A)+(B8)+(C2.52), (A)+(B8)+(C2.53), (A)+(B8)+(C2.54), (A)+(B8)+(C2.55), (A)+(B8)+(C2.56), (A)+(B8)+(C2.57), (A)+(B8)+(C2.58), (A)+(B8)+(C2.59), (A)+(B8)+(C2.60), (A)+

(B8)+(C2.61), (A)+(B8)+(C2.62), (A)+(B8)+(C2.63), (A)+(B8)+(C2.64), (A)+(B8)+(C2.65), (A)+(B8)+(C2.66), (A)+(B8)+(C2.67), (A)+(B8)+(C2.68), (A)+(B8)+(C2.69), (A)+(B8)+(C2.70), (A)+(B8)+(C2.71), (A)+(B8)+(C2.72), (A)+(B8)+(C2.73), (A)+(B8)+(C2.74), (A)+(B8)+(C2.75), (A)+(B8)+(C2.76), (A)+(B8)+(C2.77), (A)+(B8)+(C2.78), (A)+(B8)+(C2.79), (A)+(B8)+(C2.80), (A)+(B8)+(C2.81), (A)+(B8)+(C2.82), (A)+(B8)+(C2.83), (A)+(B8)+(C2.84), (A)+(B8)+(C2.85), (A)+(B8)+(C2.86), (A)+(B8)+(C2.87), (A)+(B8)+(C2.88), (A)+(B8)+(C2.89), (A)+(B8)+(C2.90), (A)+(B8)+(C2.91), (A)+(B8)+(C2.92), (A)+(B8)+(C2.93), (A)+(B8)+(C2.94), (A)+(B8)+(C2.95), (A)+(B8)+(C2.96), (A)+(B8)+(C2.97), (A)+(B8)+(C2.98), (A)+(B8)+(C2.99), (A)+(B8)+(C2.100), (A)+(B8)+(C2.101), (A)+(B8)+(C2.102), (A)+(B8)+(C2.103), (A)+(B8)+(C2.104), (A)+(B8)+(C2.105), (A)+(B8)+(C2.106), (A)+(B8)+(C2.107), (A)+(B8)+(C2.108), (A)+(B8)+(C2.109), (A)+(B8)+(C2.110), (A)+(B8)+(C2.111), (A)+(B8)+(C2.112), (A)+(B8)+(C2.113), (A)+(B8)+(C2.114), (A)+(B8)+(C3.1), (A)+(B8)+(C3.2), (A)+(B8)+(C3.3), (A)+(B8)+(C4.1), (A)+(B8)+(C4.2), (A)+(B8)+(C4.3), (A)+(B8)+(C4.4), (A)+(B8)+(C4.5), (A)+(B8)+(C4.6), (A)+(B8)+(C4.7), (A)+(B8)+(C4.8), (A)+(B8)+(C4.9), (A)+(B8)+(C4.10), (A)+(B8)+(C4.11), (A)+(B8)+(C4.12), (A)+(B8)+(C4.13), (A)+(B8)+(C4.14), (A)+(B8)+(C4.15), (A)+(B8)+(C5.1), (A)+(B8)+(C5.2), (A)+(B8)+(C5.3), (A)+(B8)+(C5.4), (A)+(B8)+(C5.5), (A)+(B8)+(C5.6), (A)+(B8)+(C5.7), (A)+(B8)+(C5.8), (A)+(B8)+(C5.9), (A)+(B8)+(C5.10), (A)+(B8)+(C5.11), (A)+(B8)+(C5.12), (A)+(B8)+(C5.13), (A)+(B8)+(C5.14), (A)+(B8)+(C5.15), (A)+(B8)+(C5.16), (A)+(B8)+(C5.17), (A)+(B8)+(C5.18), (A)+(B8)+(C5.19), (A)+(B8)+(C5.20), (A)+(B8)+(C5.21), (A)+(B8)+(C5.22), (A)+(B8)+(C5.23), (A)+(B8)+(C5.24), (A)+(B8)+(C5.25), (A)+(B8)+(C5.26), (A)+(B8)+(C5.27), (A)+(B8)+(C5.28), (A)+(B8)+(C5.29), (A)+(B8)+(C5.30), (A)+(B8)+(C5.31), (A)+(B8)+(C5.32), (A)+(B8)+(C5.33), (A)+(B8)+(C5.34), (A)+(B8)+(C5.35), (A)+(B8)+(C5.36), (A)+(B8)+(C5.37), (A)+(B8)+(C5.38), (A)+(B8)+(C5.39), (A)+(B8)+(C5.40), (A)+(B8)+(C5.41), (A)+(B8)+(C5.42), (A)+(B8)+(C5.43), (A)+(B8)+(C5.44), (A)+(B8)+(C5.45), (A)+(B8)+(C5.46), (A)+(B8)+(C5.47), (A)+(B8)+(C5.48), (A)+(B8)+(C5.49), (A)+(B8)+(C5.50), (A)+(B8)+(C5.51), (A)+(B8)+(C5.52), (A)+(B8)+(C5.53), (A)+(B8)+(C5.54), (A)+(B8)+(C5.55), (A)+(B8)+(C5.56), (A)+(B8)+(C5.57), (A)+(B8)+(C5.58), (A)+(B8)+(C5.59), (A)+(B8)+(C5.60), (A)+(B8)+(C5.61), (A)+(B8)+(C5.62), (A)+(B8)+(C5.63), (A)+(B8)+(C5.64), (A)+(B8)+(C5.65), (A)+(B8)+(C5.66), (A)+(B8)+(C5.67), (A)+(C6.3), (A)+(B8)+(C6.4), (A)+(B8)+(C6.5), (A)+(B8)+(C6.6), (A)+(B8)+(C6.7), (A)+(B8)+(C6.8)+(A)+(B8)+(C6.9), (A)+(B8)+(C6.10), (A)+(B8)+(C6.11), (A)+(B8)+(C6.12), (A)+(B8)+(C6.13), (A)+(B8)+(C6.14), (A)+(B8)+(C6.15), (A)+(B8)+(C6.16), (A)+(B8)+(C6.17), (A)+(B8)+(C7.1), (A)+(B8)+(C7.2), (A)+(B8)+(C7.3), (A)+(B8)+(C7.4), (A)+(B8)+(C7.5), (A)+(B8)+(C7.6), (A)+(B8)+(C7.7), (A)+(B8)+(C7.8), (A)+(B8)+(C7.9), (A)+(B8)+(C7.10), (A)+(B8)+(C7.11), (A)+(B8)+(C7.12), (A)+(B8)+(C7.13), (A)+(B8)+(C7.14), (C7.12), (A)+(B8)+(C7.13), (A)+(B8)+(C7.14), (A)+(B8)+(C7.15), (A)+(B8)+(C7.16), (A)+(B8)+(C7.17), (A)+(B8)+(C7.18), (A)+(B8)+(C7.19), (A)+(B8)+(C7.20), (A)+(B8)+(C7.21), (A)+(B8)+(C7.22), (A)+(B8)+(C7.23), (A)+(B8)+(C7.24), (A)+(B8)+(C7.25), (A)+(B8)+(C7.26), (A)+(B8)+(C7.27), (A)+(B8)+(C7.28), (A)+(B8)+(C7.29), (A)+(B8)+(C7.30), (A)+(B8)+(C8.1).

The following combinations are particularly preferred:

(A)+(B1)+(C1.27), (A)+(B1)+(C1.31), (A)+(B1)+(C2.4), (A)+(B1)+(C2.5), (A)+(B1)+(C2.9), (A)+(B1)+(C2.10), (A)+(B1)+(C2.14), (A)+(B1)+(C8.1), (A)+(B1)+(C1.18), (A)+(B1)+(C2.13), (A)+(B1)+(C2.16), (A)+(B1)+(C7.19), (A)+(B1)+(C7.28), (A)+(B1)+(C1.27a), (A)+(B1)+(C1.27b), (A)+(B1)+(C1.27c), (A)+(B1)+(C1.27d), (A)+(B1)+(C1.27e), (A)+(B1)+(C1.27f).

(A)+(B2)+(C1.27), (A)+(B2)+(C1.31), (A)+(B2)+(C2.4), (A)+(B2)+(C2.5), (A)+(B2)+(C2.9), (A)+(B2)+(C2.10), (A)+(B2)+(C2.14), (A)+(B2)+(C8.1), (A)+(B2)+(C1.18), (A)+(B2)+(C2.13), (A)+(B2)+(C2.16), (A)+(B2)+(C7.19), (A)+(B2)+(C7.28), (A)+(B2)+(C1.27a), (A)+(B2)+(C1.27b), (A)+(B2)+(C1.27c), (A)+(B2)+(C1.27d), (A)+(B2)+(C1.27e), (A)+(B2)+(C1.27f), (A)+(B3)+(C1.27), (A)+(B3)+(C1.31), (A)+(B3)+(C2.4), (A)+(B3)+(C2.5), (A)+(B3)+(C2.9), (A)+(B3)+(C2.10), (A)+(B3)+(C2.14), (A)+(B3)+(C8.1), (A)+(B3)+(C1.18), (A)+(B3)+(C2.13), (A)+(B3)+(C2.16), (A)+(B3)+(C7.19), (A)+(B3)+(C7.28), (A)+(B3)+(C1.27a), (A)+(B3)+(C1.27b), (A)+(B3)+(C1.27c), (A)+(B3)+(C1.27d), (A)+(B3)+(C1.27e), (A)+(B3)+(C1.27f)

(A)+(B4)+(C1.27), (A)+(B4)+(C1.31), (A)+(B4)+(C2.4), (A)+(B4)+(C2.5), (A)+(B4)+(C2.9), (A)+(B4)+(C2.10), (A)+(B4)+(C2.14), (A)+(B4)+(C8.1), (A)+(B4)+(C1.18), (A)+(B4)+(C2.13), (A)+(B4)+(C2.16), (A)+(B4)+(C7.19), (A)+(B4)+(C7.28), (A)+(B4)+(C1.27a), (A)+(B4)+(C1.27b), (A)+(B4)+(C1.27c), (A)+(B4)+(C1.27d), (A)+(B4)+(C1.27e), (A)+(B4)+(C1.27f);

(A)+(B5)+(C1.27), (A)+(B5)+(C1.31), (A)+(B5)+(C2.4), (A)+(B5)+(C2.5), (A)+(B5)+(C2.9), (A)+(B5)+(C2.10), (A)+(B5)+(C2.14), (A)+(B5)+(C8.1), (A)+(B5)+(C1.18), (A)+(B5)+(C2.13), (A)+(B5)+(C2.16), (A)+(B5)+(C7.19), (A)+(B5)+(C7.28), (A)+(B5)+(C1.27a), (A)+(B5)+(C1.27b), (A)+(B5)+(C1.27c), (A)+(B5)+(C1.27d), (A)+(B5)+(C1.27e), (A)+(B5)+(C1.27f);

(A)+(B6)+(C1.27), (A)+(B6)+(C1.31), (A)+(B6)+(C2.4), (A)+(B6)+(C2.5), (A)+(B6)+(C2.9), (A)+(B6)+(C1.18), (A)+(B6)+(C2.13), (A)+(B6)+(C2.16), (A)+(B6)+(C7.19), (A)+(B6)+(C7.28), (A)+(B6)+(C2.10), (A)+(B6)+(C2.14), (A)+(B6)+(C8.1), (A)+(B6)+(C1.27a), (A)+(B6)+(C1.27b), (A)+(B6)+(C1.27c), (A)+(B6)+(C1.27d), (A)+(B6)+(C1.27e), (A)+(B6)+(C1.27f);

(A)+(B7)+(C1.27), (A)+(B7)+(C1.31), (A)+(B7)+(C2.4), (A)+(B7)+(C2.5), (A)+(B7)+(C2.9), (A)+(B7)+(C2.10), (A)+(B7)+(C2.14), (A)+(B7)+(C8.1), (A)+(B7)+(C1.18), (A)+(B7)+(C2.13), (A)+(B7)+(C2.16), (A)+(B7)+(C7.19), (A)+(B7)+(C7.28), (A)+(B7)+(C1.27a), (A)+(B7)+(C1.27b), (A)+(B7)+(C1.27c), (A)+(B7)+(C1.27d), (A)+(B7)+(C1.27e), (A)+(B7)+(C1.27f);

(A)+(B8)+(C1.27), (A)+(B8)+(C1.31), (A)+(B8)+(C2.4), (A)+(B8)+(C2.5), (A)+(B8)+(C2.9), (A)+(B8)+(C2.10), (A)+(B8)+(C2.14), (A)+(B8)+(C8.1), (A)+(B8)+(C1.18), (A)+(B8)+(C2.13), (A)+(B8)+(C2.16), (A)+(B8)+(C7.19), (A)+(B8)+(C7.28), (A)+(B8)+(C1.27a), (A)+(B8)+(C1.27b), (A)+(B8)+(C1.27c), (A)+(B8)+(C1.27d), (A)+(B8)+(C1.27e), (A)+(B8)+(C1.27f).

The invention is further directed to the preparation of a composition containing compound (A), spore-forming bacteria (B) and at least one biological control agent (C) selected from bacteria, in particular sporeforming bacteria, fungi or yeasts, protozoas, viruses, and entomopathogenic nematodes, inoculants, botanicals, and products produced by microorganisms including proteins or secondary metabolites particularly (C8.1) Harpin, for reducing overall damage of plants and plant parts as well as losses in harvested fruits or vegetables caused by insects, nematodes or phytopathogens.

The invention is also directed to a method for reducing overall damage of plants and plant parts as well as losses in harvested fruits or vegetables caused by insects, nematodes or phytopathogens comprising the step of simultaneously or sequentially applying compound (A), spore-forming bacteria (B) and at least one biological control agent (C) selected from bacteria, in particular spore-forming bacteria, fungi or yeasts, protozoas, viruses, and entomopathogenic nematodes, inoculants botanicals, and products produced by microorganisms including proteins or secondary metabolites, particularly (C8.1) Harpin, on the plant, plant parts, harvested fruits or vegetables.

As already mentioned before, using compound (A), spore-forming bacteria (B) and at least one biological control agent (C) selected from bacteria, in particular spore-forming bacteria, fungi or yeasts, protozoas, viruses, and entomopathogenic nematodes, inoculants, botanicals, and products produced by microorganisms including proteins or secondary metabolites, particularly (C8.1) Harpin as a combination is advantageous. The broadening of the activity spectrum to other agricultural pests (i.e. insects, acari, nematodes, and phytopathogens) and, for example to resistant strains of such agricultural pests or plant diseases can be achieved.

Also according to the invention, the compound (A) Fluopyram, (B) a spore-forming bacterium of the genera *Bacillus*, selected from *Bacillus firmus*, *Bacillus firmus* CNCM I-1582, *Bacillus cereus*, *Bacillus pumilis*, *Bacillus amyloliquefaciens*, *Bacillus subtilis* strain GB03, *Bacillus subtilis* strain QST713, and (C) a biological control agent, in particular bacteria, fungi or yeasts, protozoa, viruses, entomopathogenic nematodes, inoculants, botanicals and products produced by microorganisms including proteins or secondary metabolites, particularly (C8.1) Harpin can be used in a lower application rate and still achieve the sufficient control of the agricultural pests or plant diseases. This is particularly visible if application rates for the before mentioned compounds or biological control agents are used where the individual compounds or biological control agents show no or virtually no activity. Moreover, even an enhanced systemic action of compound (A) Fluopyram, (B) a spore-forming bacterium of the genera *Bacillus*, selected from *Bacillus firmus*, *Bacillus firma* CNCM I-1582, *Bacillus cereus*, *Bacillus pumilis*, *Bacillus amyloliquefaciens*, *Bacillus subtilis* strain GB03, *Bacillus subtilis* strain QST713, and (C) a biological control agent, in particular bacteria, fungi or yeasts, protozoa, viruses, entomopathogenic nematodes, inoculants, botanicals and products produced by microorganisms including proteins or secondary metabolites, particularly (C8.1) Harpin is higher or a persistency of the fungicidal, insecticidal, acaricidal or nematicidal action is expected.

Plant Physiology Effects

Also according to the invention, the compound (A) Fluopyram, (B) a spore-forming bacterium of the genera *Bacillus*, selected from *Bacillus firmus*, *Bacillus firma* CNCM I-1582, *Bacillus cereus*, *Bacillus pumilis*, *Bacillus amyloliquefaciens*, *Bacillus subtilis* strain GB03, *Bacillus subtilis* strain QST713, and (C) a biological control agent, in particular bacteria, fungi or yeasts, protozoa, viruses, entomopathogenic nematodes, inoculants, botanicals and products produced by microorganisms including proteins or secondary metabolites, particularly (C8.1) Harpin can be used for improving plant physiology effects.

In context with the present invention plant physiology effects comprise the following:

Abiotic stress tolerance, comprising temperature tolerance, drought tolerance and recovery after drought stress, water use efficiency (correlating to reduced water consumption), flood tolerance, ozone stress and UV tolerance, tolerance towards chemicals like heavy metals, salts, pesticides (safener) etc.

Biotic stress tolerance, comprising increased fungal resistance and increased resistance against nematodes, viruses and bacteria. In context with the present invention, biotic stress tolerance preferably comprises increased fungal resistance and increased resistance against nematodes Increased plant vigor, comprising plant health/plant quality and seed vigor, reduced stand failure, improved appearance, increased recovery, improved greening effect and improved photosynthetic efficiency.

Effects on plant hormones or functional enzymes.

Effects on growth regulators (promoters), comprising earlier germination, better emergence, more developed root system or improved root growth, increased ability of tillering, more productive tillers, earlier flowering, increased plant height or biomass, shorting of stems, improvements in shoot growth, number of kernels/ear, number of ears/m$^2$, number of stolons or number of flowers, enhanced harvest index, bigger leaves, less dead basal leaves, improved phyllotaxy, earlier maturation/earlier fruit fmish, homogenous riping, increased duration of grain filling, better fruit fmish, bigger fruit/vegetable size, sprouting resistance and reduced lodging.

Increased yield, referring to total biomass per hectare, yield per hectare, kernel/fruit weight, seed size or hectolitre weight as well as to increased product quality, comprising:

improved processability relating to size distribution (kernel, fruit, etc.), homogenous riping, grain moisture, better milling, better vinification, better brewing, increased juice yield, harvestability, digestibility, sedimentation value, falling number, pod stability, storage stability, improved fiber length/strength/uniformity, increase of milk or meet quality of silage fed animals, adaption to cooking and frying;

further comprising improved marketability relating to improved fruit/grain quality, size distribution (kernel, fruit, etc.), increased storage/shelf-life, firmness/softness, taste (aroma, texture, etc.), grade (size, shape, number of berries, etc.), number of berries/fruits per bunch, crispness, freshness, coverage with wax, frequency of physiological disorders, colour, etc.;

further comprising increased desired ingredients such as e.g. protein content, fatty acids, oil content, oil quality, aminoacid composition, sugar content, acid content (pH), sugar/acid ratio (Brix), polyphenols, starch content, nutritional quality, gluten content/index, energy content, taste, etc.;

and further comprising decreased undesired ingredients such as e.g. less mycotoxines, less aflatoxines, geosmin level, phenolic aromas, lacchase, polyphenol oxidases and peroxidases, nitrate content etc.

Sustainable agriculture, comprising nutrient use efficiency, especially nitrogen (N)-use efficiency, phosphours (P)-use efficiency, water use efficiency, improved transpiration, respiration or $CO_2$ assimilation rate, better nodulation, improved Ca-metabolism etc.

Delayed senescence, comprising improvement of plant physiology which is manifested, for example, in a longer grain filling phase, leading to higher yield, a longer duration of green leaf colouration of the plant and thus comprising colour (greening), water content, dryness etc. Accordingly, in the context of the present invention, it has been found that the specific inventive application of the active compound combination makes it possible to prolong the green leaf area duration, which delays the maturation (senescence) of the plant. The main advantage to the farmer is a longer grain filling phase leading to higher yield. There is also an advantage to the farmer on the basis of greater flexibility in the harvesting time.

Therein "sedimentation value" is a measure for protein quality and describes according to Zeleny (Zeleny value) the degree of sedimentation of flour suspended in a lactic acid solution during a standard time interval. This is taken as a measure of the baking quality. Swelling of the gluten fraction of flour in lactic acid solution affects the rate of sedimentation of a flour suspension. Both a higher gluten content and a better gluten quality give rise to slower sedimentation and higher Zeleny test values. The sedimentation value of flour depends on the wheat protein composition and is mostly correlated to the protein content, the wheat hardness, and the volume of pan and hearth loaves. A stronger correlation between loaf volume and Zeleny sedimentation volume compared to SDS sedimentation volume could be due to the protein content influencing both the volume and Zeleny value (*Czech J. Food Sci. Vol.* 21, No. 3: 91-96, 2000).

Further the "falling number" as mentioned herein is a measure for the baking quality of cereals, especially of wheat. The falling number test indicates that sprout damage may have occurred. It means that changes to the physical properties of the starch portion of the wheat kernel has already happened. Therein, the falling number instrument analyzes viscosity by measuring the resistance of a flour and water paste to a falling plunger. The time (in seconds) for this to happen is known as the falling number. The falling number results are recorded as an index of enzyme activity in a wheat or flour sample and results are expressed in time as seconds. A high falling number (for example, above 300 seconds) indicates minimal enzyme activity and sound quality wheat or flour. A low falling number (for example, below 250 seconds) indicates substantial enzyme activity and sprout-damaged wheat or flour.

The term "more developed root system" /"improved root growth" refers to longer root system, deeper root growth, faster root growth, higher root dry/fresh weight, higher root volume, larger root surface area, bigger root diameter, higher root stability, more root branching, higher number of root hairs, or more root tips and can be measured by analyzing the root architecture with suitable methodologies and Image analysis programmes (e.g. WinRhizo).

The term "crop water use efficiency" refers technically to the mass of agriculture produce per unit water consumed and economically to the value of product(s) produced per unit water volume consumed and can e.g. be measured in terms of yield per ha, biomass of the plants, thousand-kernel mass, and the number of ears per m2.

The term "nitrogen-use efficiency" refers technically to the mass of agriculture produce per unit nitrogen consumed and economically to the value of product(s) produced per unit nitrogen consumed, reflecting uptake and utilization efficiency.

Improvement in greening/improved colour and improved photosynthetic efficiency as well as the delay of senescence can be measured with well-known techniques such as a HandyPea system (Hansatech). Fv/Fm is a parameter widely used to indicate the maximum quantum efficiency of photosy stem II (P SIT). This parameter is widely considered to be a selective indication of plant photosynthetic performance with healthy samples typically achieving a maximum Fv/Fm value of approx. 0.85. Values lower than this will be observed if a sample has been exposed to some type of biotic or abiotic stress factor which has reduced the capacity for photochemical quenching of energy within PSII. Fv/Fm is presented as a ratio of variable fluorescence (Fv) over the maximum fluorescence value (Fm). The Performance Index is essentially an indicator of sample vitality. (See e.g. *Advanced Techniques in Soil Microbiology*, 2007, 11, 319-341; *Applied Soil Ecology*, 2000, 15, 169-182.)

The improvement in greening/improved colour and improved photosynthetic efficiency as well as the delay of senescence can also be assessed by measurement of the net photosynthetic rate (Pn), measurement of the chlorophyll content, e.g. by the pigment extraction method of Ziegler and Ehle, measurement of the photochemical efficiency (Fv/Fm ratio), determination of shoot growth and final root or canopy biomass, determination of tiller density as well as of root mortality.

Within the context of the present invention preference is given to improving plant physiology effects which are selected from the group comprising: enhanced root growth/more developed root system, improved to greening, improved water use efficiency (correlating to reduced water consumption), improved nutrient use efficiency, comprising especially improved nitrogen (N)-use efficiency, delayed senescence and enhanced yield.

Within the enhancement of yield preference is given as to an improvement in the sedimentation value and the falling number as well as to the improvement of the protein and sugar content—especially with plants selected from the group of cereals (preferably wheat).

Preferably the novel use of the fungicidal or nematicidal or pestidical compositions of the present invention relates to a combined use of a) preventively or curatively controlling insects, nematodes or phytopathogens, and b) at least one of enhanced root growth, improved greening, improved water use efficiency, delayed senescence and enhanced yield. From group b) enhancement of root system, water use efficiency and N-use efficiency is particularly preferred.

The compound (A) Fluopyram, (B) a spore-forming bacterium of the genera *Bacillus*, selected from *Bacillus firmus*, *Bacillus firmus* CNCM I-1582, *Bacillus cereus*, *Bacillus pumilis*, *Bacillus amyloliquefaciens*, *Bacillus subtilis* strain GB03, *Bacillus subtilis* strain QST713, and (C) a biological control agent, in particular bacteria, fungi or yeasts, protozoa, viruses, entomopathogenic nematodes, inoculants, botanicals and products produced by microorganisms including proteins or secondary metabolites, particularly (C8.1) Harpin may be applied in any desired manner, such as in the form of a seed coating, soil drench, or directly in-furrow or as a foliar spray and applied either pre-emergence, post-emergence or both. In other words, the composition can be applied to the seed, the plant or to harvested fruits and vegetables or to the soil wherein the plant is growing or wherein it is desired to grow.

The term "controlling" stands for a reduction of the damage on the plant or plant parts as well as losses in harvested fruits or vegetables caused by insects, nematodes or phytopathogens of at least 30%, preferably 50%, more preferably 60%, more preferably 75%, more preferably 80%, more preferably 90%, when compared to the untreated control.

If not mentioned otherwise, the expression "combination" stands for the various combinations of the compound (A) Fluopyram, (B) a spore-forming bacterium of the genera *Bacillus*, selected from *Bacillus firmus*, *Bacillus firmus* CNCM I-1582, *Bacillus cereus*, *Bacillus pumilis*, *Bacillus amyloliquefaciens*, *Bacillus subtilis* strain GB03, *Bacillus subtilis* strain QST713, and (C) a biological control agent, in particular bacteria, fungi or yeasts, protozoa, viruses, entomopathogenic nematodes, inoculants, botanicals and products produced by microorganisms including proteins or secondary metabolites, particularly (C8.1) Harpin in a solo-formulation, in a single "ready-mix" form, in a combined spray mixture composed from soloformulations, such as a "tank-mix", and especially in a combined use of the single active ingredients when applied in a sequential manner, i.e. one after the other within a reasonably short period, such as a few hours or days, e.g. 2 hours to 7 days. The order of applying compound (A), spore-forming bacteria (B) and at least one biological control agent (C) selected from bacteria, in particular spore-forming bacteria, fungi or yeasts, protozoas, viruses, and entomopathogenic nematodes, inoculants, botanicals, and products produced by microorganisms including proteins or secondary metabolites, particularly (C8.1) Harpin is not essential for working the present invention.

Accordingly, the term "combination" also encompasses the presence of the compound (A) Fluopyram, (B) a spore-forming bacterium of the genera *Bacillus,* selected from *Bacillus firmus, Bacillus firmus* CNCM I-1582, *Bacillus cereus, Bacillus pumilis, Bacillus amyloliquefaciens, Bacillus subtilis* strain GB03, *Bacillus subtilis* strain QST713, and (C) a biological control agent, in particular bacteria, fungi or yeasts, protozoa, viruses, entomopathogenic nematodes, inoculants, botanicals and products produced by microorganisms including proteins or secondary metabolites, particularly (C8.1) Harpin on or in a plant to be treated or its surrounding, habitat or storage space, e.g. after simultaneously or consecutively applying compound (A) Fluopyram, (B) a spore-forming bacterium of the genera *Bacillus,* selected from *Bacillus firmus, Bacillus firmus* CNCM I-1582, *Bacillus cereus, Bacillus pumilis, Bacillus amyloliquefaciens, Bacillus subtilis* strain GB03, *Bacillus subtilis* strain QST713, and (C) a biological control agent, in particular bacteria, fungi or yeasts, protozoa, viruses, entomopathogenic nematodes, inoculants, botanicals and products produced by microorganisms including proteins or secondary metabolites, particularly (C8.1) Harpin to a plant its surrounding, habitat or storage space.

A solo- or combined-formulation is the formulation which is applied to the plants to be treated (e.g., in a greenhouse, on a field, in a wood), e.g., a tank formulation comprising the biological control agent in accordance with the present invention and a compound (A) or a liquid or solid formulation comprising component (B) and the biological control agent (C) which is applied prior, after or in parallel with a compound (A) to a plant to be treated.

If the compound (A) Fluopyram, (B) a spore-forming bacterium of the genera Bacillus, selected from *Bacillus firmus, Bacillus firmus* CNCM I-1582, *Bacillus cereus, Bacillus pumilis, Bacillus amyloliquefaciens, Bacillus subtilis* strain GB03, *Bacillus subtilis* strain QST713, and (C) a biological control agent, in particular bacteria, fungi or yeasts, protozoa, viruses, entomopathogenic nematodes, inoculants, botanicals and products produced by microorganisms including proteins or secondary metabolites, particularly (C8.1) Harpin are employed or used in a sequential manner, it is preferred to treat the plants or plant parts (which includes seeds and plants emerging from the seed), harvested fruits and vegetables according to the following method: Firstly applying the compound (A) on the plant or plant parts, and secondly applying (B) the spore-forming bacteria and (C) the biological control agent selected from bacteria, in particular spore-forming bacteria, fungi or yeasts, protozoas, viruses, and entomopathogenic nematodes, inoculant, botanicals and products produced by microorganisms including proteins or secondary metabolites, particularly (C8.1) Harpin to the same plant or plant parts. The time periods between the first and the second application within a (crop) growing cycle may vary and depend on the effect to be achieved. For example, the first application is done to prevent an infestation of the plant or plant parts with insects, nematodes or phytopathogens (this is particularly the case when treating seeds) or to combat the infestation with insects, nematodes or phytopathogens (this is parparticularly the case when treating plants and plant parts) and the second application is done to prevent or control the infestation with insects, nematodes or phytopathogens. Control in this context means that the biological control agent is not able to fully exterminate the pests or phytopathogenic fungi but is able to keep the infestation on an acceptable level.

By following the before mentioned steps, a very low level of residues of the compound (A) on the treated plant, plant parts, and the harvested fruits and vegetables can be achieved.

In general, the terms "spore-forming bacteria", "fungi" or "yeasts" comprise all stages of bacteria, fungi and yeast including resting spores, conidia, blastospores, filamentous stages and other inactive forms of said organisms which can yield in active organisms. Thus, in one embodiment, said organisms are comprised in form of spores in a formulation, e.g., a solo- or combined-formulation.

In general, the term "nematode" comprises eggs, larvae, juvenile and mature forms of said organism. Thus, in one embodiment, said organisms are comprised in form of eggs, larvae, juvenile or mature form in a formulation, e.g., a solo- or combined-formulation.

Nematodes are microscopic unsegmented worms known to reside in virtually every type of environment (terrestrial, freshwater, marine). Of the over 80,000 known species many are agriculturally significant, particularly those classified as pests. One such species is the root knot nematode which attacks a broad range of plants, shrubs and crops. These soil-born nematodes attack newly formed roots causing stunted growth, swelling or gall formation. The roots may then crack open thus exposing the roots to other microorganisms such as bacteria or fungi. With environmentally friendly practices such as reduced or no tillage farming, and various nematode species acquiring resistance to transgenic seed, nematode related crop losses appear to be on the rise.

Chemical nematicides such as soil fumigants or non-fumigants have been in use for many years to combat nematode infestations. Such nematicides may require repeated applications of synthetic chemicals to the ground prior to planting. Due to their toxicity, chemical nematicides have come under scrutiny from the Environmental Protection Agency (EPA) and in some cases their use has been limited or restricted by the EPA. As the use of traditional chemical nematicides such as methyl-bromide and organophosphates continue to be phased out, a need for the development of alternative treatment options has arisen.

The term "plant to be treated" encompasses every part of a plant including its root system and the material —e.g., soil or nutrition medium—which is in a radius of at least 10 cm, 20 cm, 30 cm around the bole of a plant to be treated or which is at least 10 cm, 20 cm, 30 cm around the root system of said plant to be treated, respectively.

As already mentioned, the compound (A) Fluopyram, (B) a spore-forming bacterium of the genera *Bacillus,* selected from *Bacillus firmus, Bacillus firmus* CNCM I-1582, *Bacillus cereus, Bacillus pumilis, Bacillus amyloliquefaciens, Bacillus subtilis* strain GB03, *Bacillus subtilis* strain QST713, and (C) a biological control agent, in particular bacteria, fungi or yeasts, protozoa, viruses, entomopathogenic nematodes, inoculants, botanicals and products produced by microorganisms including proteins or secondary metabolites, particularly (C8.1) Harpin can be employed or used according to the invention as a solo- or a combined-formulation. Such formulations may include agriculturally suitable auxiliaries, solvents, carriers, surfactants or extenders.

If the active compounds in the active compound combinations according to the invention are present in certain weight ratios, the synergistic effect is particularly pronounced. However, the weight ratios of the active compounds in the active compound combinations can be varied within a relatively wide range.

In general, from 0.01 to 100 parts by weight, preferably from 0.05 to 20 parts by weight, particularly preferably from 0.1 to 10 parts by weight, of active compound of group (B) and from 0.01 to 100 parts by weight, preferably from 0.05 to 20 parts by weight, particularly preferably from 0.1 to 10 parts by weight, of active compound of group (C) are present per part by weight of active compound (A) Fluopyram. The mixing ratio is preferably to be chosen such that a synergistic active compound combination is obtained.

The weight ratio (A), (B) and (C) is selected as to give the desired, for example synergistic, action. In general, the weight ratio would vary depending on the specific active compound. Generally the weight ratio between any of (A), (B) and (C), independently of each other, is from 500 000:1 to 1:500 000, preferably 200 000:1 to 1:200 000, more preferably, 100 000:1 to 1:100 000, and most preferably 50 000:1 to 1:50 000.

Further weight ratio between any of (A), (B) and (C), independently of each other, which can be used according to the present invention with increasing preference in the order given are 75 000:1 to 1:75 000, 25 000:1 to 1:25 000. 20 000:1 to 1:20 000, 10 000:1 to 1:10 000, 5000:1 to 1:5000, 2500:1 to 1:2500, 2000:1 to 1:2000, 1000:1 to 1:1000, 750:1 to 1:750, 500: 1 to 1:500, 250: 1 to 1:250, 200:1 to 1:200, 100:1 to 1:100, 95:1 to 1:95, 90:1 to 1:90, 85:1 to 1:85, 80:1 to 1:80, 75:1 to 1:75, 70:1 to 1:70, 65:1 to 1:65, 60:1 to 1:60, 55:1 to 1:55, 45:1 to 1:45, 40:1 to 1:40, 35:1 to 1:35, 30:1 to 1:30, 25:1 to 1:25, 15:1 to 1:15, 10:1 to 1:10, 5:1 to 1:5, 4: 1 to 1:4, 3:1 to 1:3, 2:1 to 1:2.

Further weight ratio between any of (A), (B) and (C) are 1:200 000:20 000, 1:200 000:10 000.

It has to be noted that before mentioned ratios ranges are based on a the spore preparation of the bacteria, fungi or yeasts which contains $10^9$-$10^{10}$ spores (fungi or bacteria) or cells (yeast or bacteria) per gram. If spore preparations vary in density, the ratios have to be adapted accordingly to match the above listed ratio ranges. A ratio of 1:100 means 100 weight parts of the spore or cell preparation of the fungi or yeast to 1 weight part of the compound (A).

The amount of the biological control agent (C) selected from bacteria, in particular spore-forming bacteria, fungi or yeasts, protozoas, viruses, and entomopathogenic which is used or employed in combination with compound (A) Fluopyram, (B) a spore-forming bacterium of the genera *Bacillus*, selected from *Bacillus firmus*, *Bacillus firmus* CNCM I-1582, *Bacillus cereus*, *Bacillus pumilis*, *Bacillus amyloliquefaciens*, *Bacillus subtilis* strain GB03, *Bacillus subtilis* strain QST713, and (C) a biological control agent, in particular bacteria, fungi or yeasts, protozoa, viruses, entomopathogenic nematodes, inoculants, botanicals and products produced by microorganisms including proteins or secondary metabolites, particularly (C8.1) Harpin, depends on the final formulation as well as size or type of the plant, plant parts, seeds, harvested fruits and vegetables to be treated. Usually, the biological control agent to be employed or used according to the invention is present in about 2% to about 80% (w/w), preferably in about 5% to about 75% (w/w), more preferably about 10% to about 70% (w/w) of its solo-formulation or combined-formulation with the compound of formula (I), and optionally the inoculant.

If bacteria, fungi or yeasts are selected as biological control agent, in particular those who are named as being preferred, it is preferred that they are present in a solo-formulation or the combined-formulation in a concentration in excess of $10^5$-$10^{12}$ cfu/g (colony forming units per gram), preferably in excess of $10^6$-$10^{11}$ cfu/g, more preferably $10^7$-$10^{10}$ lcfu cfu/g and most preferably about $10^9$ cfu/g.

It is preferred to employ or use compound (A) Fluopyram, (B) a spore-forming bacterium of the genera *Bacillus*, selected from *Bacillus firmus*, *Bacillus firmus* CNCM I-1582, *Bacillus cereus*, *Bacillus pumilis*, *Bacillus amyloliquefaciens*, *Bacillus subtilis* strain GB03, *Bacillus subtilis* strain QST713, and (C) a biological control agent, in particular bacteria, fungi or yeasts, protozoa, viruses, entomopathogenic nematodes, inoculants, botanicals and products produced by microorganisms including proteins or secondary metabolites, particularly (C8.1) Harpin in a synergistic weight ratio. The skilled person is able to find out the synergistic weight ratios for the present invention by routine methods. The skilled person understands that these ratios refer to the ratio within a combined-formulation as well as to the calculative ratio of compound (A) Fluopyram and the biological control agent described herein when both components are applied as mono-formulations to a plant to be treated. The skilled person can calculate this ratio by simple mathematics since the volume and the amount of compound (A), compound (B) and the biological control agent (C), respectively, in a mono-formulation is known to the skilled person. In one embodiment, the said ratio refer to the ratio of the three components after all three components, i.e compound (A), compound (B) and the biological control agent (C), respectively, were applied to a plant to be treated independently whether the components were applied to a plant to be treated in form of solo-applications or in form of a combined-formulation.

It is preferred to employ or use the compound (A), compound (B) and the biological control agent (C), and in a synergistic weight ratio. The skilled person is able to find out the synergistic weight ratios for the present invention by routine methods. The skilled person understands that these ratios refer to the ratio within a combined-formulation as well as to the calculative ratio of compound (A), compound (B) and the biological control agent (C) described herein when both components are applied as mono-formulations to a plant to be treated. The skilled person can calculate this ratio by simple mathematics since the volume and the amount of compound (A), compound (B) and the biological control agent (C), respectively, in a mono-formulation is known to the skilled person. In one embodiment, the said ratio refer to the ratio of the both components after all three components, i.e. compound (A), compound (B) and the biological control agent (C), respectively, were applied to a plant to be treated independently whether the components were applied to a plant to be treated in form of solo-applications or in form of a combined-formulation.

In one embodiment of the present invention, a biological control agent (C) is a bacterium and the concentration of the bacteria after dispersal is at least 50 g/ha, at least 100 g/ha or at least 150 g/ha.

In one embodiment of the present invention, a biological control agent (C) is a bacterium, and the concentration of the bacteria after dispersal is at least 2.5 g/ha (hectare), such as 2.5-7500 g/ha, 5-2500 g/ha, 5-1500 g/ha; at least 250 g/ha; at least 100 g/ha, such as 100-5000 g/ha, 100-2500 g/ha, 100-1500 g/ha or 100-250 g/ha; or at least 800 g/ha, such as 800-5000 g/ha or 800-2500 g/ha.

In another embodiment of the present invention, a biological control agent (C) is a bacterium, such as *B. firmus* e.g., strain CNCM I-1582, and the concentration of the bacteria after dispersal is at least 50 g/ha such as 50-5000 g/ha, 50-2500 g/ha, 50-200 g/ha; at least 100 g/ha, at least 500 g/ha, at least 800 g/ha, such as 800-5000 g/ha or 800-2500 g/ha.

In another embodiment of the present invention, a biological control agent (C) is a bacterium, such as *B. subtilis*, e.g., strain GB 03, and the concentration of the bacteria after dispersal is at least 50 g/ha such as 50-5000 g/ha, 50-2500 g/ha, 50-200 g/ha; at least 100 g/ha, at least 500 g/ha, at least 800 g/ha, such as 800-5000 g/ha or 800-2500 g/ha.

In another embodiment of the present invention, a biological control agent (C) is a bacterium, such as *B. subtilis*, e.g., strain QST713, and the concentration of the bacteria after dispersal is at least 50 g/ha such as 50-5000 g/ha, 50-2500 g/ha, 50-200 g/ha; at least 100 g/ha, at least 500 g/ha, at least 800 g/ha, such as 800-5000 g/ha or 800-2500 g/ha.

In another embodiment of the present invention, a biological control agent (C) is a bacterium, such as *B. amyloliquefaciens* and the concentration of the bacteria after dispersal is at least 500 g/ha, such as 500-5000 g/ha, 500-2500 g/ha.

In one embodiment of the present invention, a biological control agent (C) is a fungus and the concentration of the fungus after dispersal is at least 1 g/ha, such as 1-7500 g/ha, 1-2500 g/ha, 1-1500 g/ha; at least 250 g/ha (hectare), at least 500 g/ha or at least 800 g/ha.

In one embodiment of the present invention, a biological control agent (C) is a fungus, such as *Paecilomyces lilacinus*, e.g., strain 251, and the concentration of the fungus after dispersal is at least 50 g/ha; at least 100 g/ha; at least 1000 g/ha; at least 2500 g/ha, such as 2500-7500 g/ha, 2500-6000 g/ha; or at least 4000 g/ha, such as 4000-6000 g/ha.

In one embodiment of the present invention, a biological control agent (C) is a fungus, such as *Metarhizium anisopliae*, e.g., strain F52 and the concentration of the fungus after dispersal is at least 1 g/ha, such as 1-7500 g/ha, 1-2500 g/ha, 1-250 g/ha; or at least 100 g/ha, such as 100 g/ha 1000 g/ha or 100-250 g/ha.

In one embodiment of the present invention, a biological control agent (C) is yeast, such as Metschnikowia fructicola, and the concentration of the yeast after dispersal is at least 50 g/ha, such as 50-5000 g/ha, 50-2000 g/ha; at least 1000 g/ha; at least 1500 g/ha, such as 500-5000 g/ha, 500-2500 g/ha, 500-2000 g/ha.

In one embodiment of the present invention, a biological control agent (C) is a virus and the concentration of the virus after dispersal is at least 50 g/ha such as 50-7500 g/ha, 50-2500 g/ha, 50-1500 g/ha; at least 100 g/ha or at least 150 g/ha.

In one embodiment of the present invention, a biological control agent (C) is a virus, such as Codling moth (Cydia pomonella) granulosis virus and the concentration of the virus after dispersal is at least 50 g/ha (hectare) such as 50-5000 g/ha, 50-2500 g/ha, 50-1500 g/ha or 50-250 g/ha; or at least 100g/ha, such as 100-500 g/ha or 100-250 g/ha.

In one embodiment of the present invention, a biological control agent (C) is an entomopathogenic nematode and the concentration of the nematodes is at least $10^6$ nematodes/ha, e.g., larval stage nematodes/ha, such as $10^6$-$10^{15}$ nematodes/ha, e.g., larval stage nematodes/ha, $10^6$-$10^{12}$ nematodes/ha, e.g., larval stage nematodes/ha, at least $10^8$ nematodes/ha, e.g., larval stage nematodes/ha such as $10^8$-$10^{15}$ nematodes/ha, e.g., larval stage nematodes/ha, $10^8$-$10^{12}$ nematodes/ha, e.g., larval stage nematodes/ha; or at least $10^9$ nematodes/ha, e.g., larval stage nematodes/ha, such as $10^9$-$10^{15}$ nematodes/ha, e.g., larval stage nematodes/ha or $10^9$-$10^{12}$ nematodes/ha, e.g., larval stage nematodes/ha.

In one embodiment of the present invention, the ratios between (B) a spore-forming bacterium of the genera *Bacillus*, selected from *Bacillus firmus, Bacillus firma* CNCM I-1582, *Bacillus cereus, Bacillus pumilis, Bacillus amyloliquefaciens, Bacillus subtilis* strain GB03, *Bacillus subtilis* strain QST713 and compound (A) in a solo- or combined-formulation or on or in a plant to be treated or its surrounding, habitat or storage space is between 500 000:1 to 1:500 000, preferably 200 000:1 to 1:200 000, more preferably, 100 000:1 to 1:100 000, and most preferably 50 000:1 to 1:50 000.

In one embodiment of the present invention, the ratios between fungi (such as *Metarhizium anisopliae, Paecilomyces lilacinus, Beauveria bassiana, Nomuraea rileyi*) and compound (A) in a solo- or combined-formulation or on or in a plant to be treated or its surrounding, habitat or storage space is between 50000:1 to 1:125, between 25000:1 to 1:25 or even 500:1 to 1:5.

In one embodiment of the present invention, the ratios between yeast (such as *Metschnikowia fructicola*) and compound (A) in a solo- or combined-formulation or on or in a plant to be treated or its surrounding, habitat or storage space is between 2500:1 to 1:125, between 1250:1 and 1:125 between 125:1 to 1:50, between 100:1 to 1:25 or even 50:1 to 1:5.

In one embodiment of the present invention, the ratios between nematodes (such as *Steinernema feltiae* and *Steinernema carpocapsae*) and compound (A) in a solo- or combined-formulation or on or in a plant to be treated or its surrounding, habitat or storage space is between 125:1 to 1:125, between 100:1 to 1:25 or even 50:1 to 1:5.

The application rate of the biological control agent selected from bacteria, in particular spore-forming bacteria, fungi or yeasts, protozoas, viruses, entomopathogenic nematodes, botanicals and products produced by microorganisms including proteins or secondary metabolites, particularly (C8.1) Harpin to be employed or used according to the present invention may vary. The skilled person is able to find the appropriate application rate by way of routine experiments.

Microorganisms such as fungi or bacteria can be obtained by conventional fermentation processes. The fermentation can be carried out using solid, semi-solid or liquid nutrient media. If spores such as conidia are used, preference is given to solid or semi-solid nutrient media. The nutrient media contain the nutrients suitable and known for the cultivation of the respective microorganisms, in particular one or more metabolizable carbon sources or nitrogen sources and mineral salts. The fermentation is generally carried out at temperatures between about 320 and about 40° C., preferably between 20° and 35° C. For example, a representative fermentation is described in U.S. Pat. No. 5,804,208.

A fermentation process comprises in general the steps of a) incubating spores such as conidia of a microorganism in or on a nutrition medium (such as agar with further additives such as oatmeal); b) separating spores such as conidia from the nutrition medium after the incubation time, (e.g., by shake off the conidia from the medium, centrifuging, filtrating); and optionally c) preparing an emulsion of said isolated conidia.

The skilled person is well aware how to adapt fermentation to a given microorganism such as fungi or bacteria. In the following, several fermentations are exemplified in more detail. These examples are not meant to limit the scope of the present invention.

Bacteria

*Bacillus thuringiensis* were cultured using media and fermentation techniques known in the art (see, for example, Rogoff et al., 1969, J. invertebrate Path. 14: 122-129; Dulmage et al., 1971, J. Invertebrate Path. 18: 353-358; Dulmage et al., in Microbial Control of Pests and Plant Diseases, H. D. Burges, ed., Academic Press, N.Y., 1980). Upon completion of the fermentation cycle, the supernatant can be recovered by separating *Bacillus thuringiensis* spores and crystals from the fermentation broth by means well known in the art, e.g., centrifugation ultrafiltration, evaporation, or spray-drying (see also WO 1996001563 which is herewith incorpotated by refernce its entirety).

The following culturing of *Bacillus thuringiensis* is e.g. exemplified in U.S. Pat. No. 5,508,032A, 1996:

A subculture of *Bacillus thuringiensis* isolates can be used to inoculate the following medium, a peptone, glucose, salts medium: Bacto Peptone 7.5 g/l Glucose, 1.0 g/l $KH_2 PO_4$, 3.4 g/l $K_2 HPO_4$, 4.35 g/l salt solution, 5.0 ml/l $CaCl_2$ solution, 5.0 ml/l salts solution (100 ml) $MgSO_4$-$7H_2O$, 2.46 g $MnSO_4$-$H_2O$, 0.04 g $ZnSO4$-$7H_2O$, 0.28 g $FeSO_4$-$7H_2O$, 0.40 g $CaCl_2$ solution (100 ml), $CaCl_2H_2O$, 3.66 g pH 7.2.

The salts solution and $CaCl_2$ solution were sterilized (e.g., filter-sterilized) and added to the sterilized (e.g., autoclaved and cooked) broth at the time of inoculation. Flasks were incubated at around 30° C. on a rotary shaker at 200 rpm for 64 hours. The procedure can be readily scaled up to large fermentors by procedures well known in the art. The *Bacillus thuringiensis* spores and crystals, obtained in the fermentation, can be isolated by procedures well known in the art. A frequently-used procedure is to subject the harvested fermentation broth to separation techniques, e.g., centrifugation.

The bacterium *Bacillus firmus*

The bacteria *Bacillus subtilis* is a naturally occurring bacteria found in soils all over the world. *Bacillus subtilis* strain QST713 was isolated in 1995 by AgraQuest Inc. from soil in a California peach orchard. This product is applied to foliage (NYDEC 2001). In contrast, *Bacillus subtilis* strain GB03 (Kodiak®) was discovered in Australia in the 1930's and is applied either as a seed treatment or directly to soil. Neither strain is considered a genetically modified organism (Cornell University: Organic Resource Guide, Material fact sheet—*Bacillus subtilis*)

Isolation of *Bacillus subtilis* and related strains from soil: To isolate wild *Bacillus subtilis* strains, e.g., 2 g soil samples were dissolved in 2 ml of 10 mM Tris/HCl (pH 7.2) and then boiled at 95° C. for 5 min From these samples, 0.1 ml of each sample was then spread onto LB plates and incubated at 37° C.

Sporulation assay: *Bacillus subtilis* strains were grown in 26 SG medium at 37° C. and sporulation was assayed at 24 hours after the end of the exponential phase. The number of spores per ml culture was determined by identifying the number of heat-resistant colony forming units (80° C. for 10 min) on LB plates.

*Bacillus subtilis*, strain Marburg, was grown aerobically in heart infusion broth (Difco Laboratories, Detroit, Mich.) on shaker at about 37° C. From an overnight culture 4 drops were inoculated into 70 ml of pre warmed broth. Growth was measured as optical density at 620 nm. Cells were collected after 3.5-4.5 hours in the exponential phase of growth. Centrifugation was carried out at room temperature for 15 min at 7000 g (The Journal of Cell Biology. Volume 48, 1971 • pages 219-224).

Bacillus subtilis is active in temperatures between 7° C. and 45° C.

*Bacillus amyloliquefaciens* strain FZB42, was originally isolated from infested soil in Germany (*Krebs et al.*, 1998, Chen et al., 2007). *Bacillus amyloliquefaciens* strain FZB42 was cultivated in Luria broth (LB -1% w/v peptone, 0.5% w/v yeast extract, 0.5% w/v NaCL) at 30° C. (Journal of Biotechnology 151 (2011) 303-311). The bacteria was grown in Landy medium as described in Koumoutsi et al., 2004. To prepare surface cultures, the strains were grown in petri dishes containing 1.5% Landy agar for 24 h at 37° C. and stored at room temperature prior to MALDI-TOF-MS analysis. Fermentation in liquid media was carried out in flasks at 30° C. and 180 rpm in a shaker (Journal of Bacteriology, February. 2004, p. 1084-1096).

Fungi

The fungus *Metarhizium anisopliae,* strain DSM 3884, is known from EP-A-0268177. The production of conidia of *Metarhizium anisopliae* is exemplified in EP 0794704 B1 (U.S. Pat. No. 5,804,208).

A nutrition medium such as oatmeal agar (e.g., composition: 30 g of oat flakes and 20g of agar) in a Petri dish was inoculated with, e.g., 3 week old conidia of the *Metarhizium anisopliae* strain DSM 3884. The incubation time to multiply the conidia is, e.g., 3, 4, 5, or 6 days. The incubation temperature can be around 7° C. to around 40° C., e.g. 22° to 25° C. The formed conidia was isolated by, e.g., shaking off the conidia. The conidia can be stirred with 50ml of water containing 1% of a non-ionic emulsifier such as an emulsifier based on polyoxy-ethylene (20) sorbitan monolaurate (Tween 20®) until a suspension was obtained in which the conidia was present as isolated particles. The conidia titer was and can be determined using, e.g., a Neubauer chamber. The conidia can be stored in closed cases under dry conditions, preferably at temperatures between 0° and 25° C.

*Paecilomyces lilacinus* strain 251 was isolated from infected nematode eggs in the Philippines, and correctly described taxonomically in 1974. Optimal laboratory growth of *Paecilomyces lilacinus* strain 251 occurs at 21-27° C., and does not grow or survive above 36° C. (U.S. Environmental Protection Agency, *P. lilacinus* strain 251 Fact sheet). The following cultivation of *Paecilomyces lilacinus* is exemplified in Patent Application WO/1994/025579 (1994):

*Paecilomyces lilacinus* (Thorn) Samson (CBS 143.75), obtained e.g. from the CBS (Central Bureau of Fungal Cultures) in Baarn (The Netherlands), can be maintained on Potato Dextrose Agar (PDA; Difco laboratories) at 25° C. A conidial suspension was obtained by adding sterilized water (e.g., 5 ml) to a Petri dish containing sporulating mycelium and scraping the surface with a glass rod. Liquid cultures were obtained by inoculating conidia of the fungus to minimal salt medium or corn flour medium supplemented with the substrate. The minimal salt medium (MM) consists of 4.56 g H2PO4, 2.77 g KH2 HPO4, 0.5 g MgS04. 7H20 and 0.5 g KCl/l, pH 6.0. Mycelium can be obtained by centrifuging a, e.g., 6 day old culture of conidia of *Paecilomyces lilacinus*. For example, cultures can be grown in a shaking water bath for several days at 30° C. and 125 strokes per minute. Culture filtrates were obtained by centrifuging cultures for, e.g., 45 min at 9000 g.

The preparation of *Metschnikowia fructicola* is exemplified in U.S. Pat. No. 6,994,849:

The yeast species *Metschnikowia fructicola* was isolated from the surface of grape berries (cv. Superior) grown in the central part of Israel. At various stages, individual berries were submersed in sterile distilled water in 100 ml beakers and shaken vigorously for 2 hours on rotary shaker at 120 rpm. Aliquots of 100 ml were removed from the wash liquid and plated on PDA (Potato Dextrose Agar; DIFCO Laboratories, U.S.A.) medium. Following 4-5 days of incubation, yeast colonies were picked randomly according to colony characteristics (color and morphology) and streaked individually on fresh medium to obtain biologically pure cultures. Cultures were further purified by repeated streaking on PDA. Identification and characterization of the new species was done at the Microbial Genomics and Bioprocessing center, USDA-ARS, Peoria, Ill., USA. *Metschnikowia fructicola* was deposited at the NRRL under the number Y-30752. This deposit has been made in compliance with the terms of the Budapest Treaty.

*Metschnikowia fructicola* was propagated under aerobic conditions at temperatures ranging from 5° C. to 37° C. Optimal growth temperature is between 20° C. and 27° C. The yeast grows in liquid medium (nutrient broth; Droby et al., 1989) with a neutral pH. The cell density of the yeast generally reached its maximum (stationary stage) growth in 24-48 hours. For laboratory and small scale tests growth in Erlenmeyer flasks containing the medium and shaken on a rotary shaker was suitable. For large scale and commercial tests, fermentation tanks and industrial growth media were preferred. The yeast cells were harvested by centrifugation using conventional laboratory or industrial centrifuges.

Viruses

*Cydia pomonella* granulosis viruses (CpGV) which are used in the products MADEX (Andermatt Biocontrol) and Granupom (Probis GmbH) are deposited since 2005 at the German Collection of Microorganisms and Cell Cultures (DSMZ). Isolates used for the production of MADEX (Andermatt Biocontrol), Granupom (Probis GmbH), VIRGO (SipcamS.p.A.) and CARPOVIRUSINE (Arysta LifeScience S.A.S) were all derived from the Mexican isolate originally isolated in 1963 and are not genetically modified. (Virus accession number: GV-0001)

The identity of the virus produce can be bioanalytically checked against the parent strain by SDS-polyacryla-midegel electrophoresis of the virus protein sand by Restriction endonuclease analysis of viral DNA.

Prior to DNA isolation the test item has to be purified. The purified CpGV OB pellet is resuspended in 1 ml sterile water and the CpGV OB concentration is enumerated in the Petroff-Hausser counting chamber. The concentration of active *Cydia pomonella* Granulosis virus (CpGV) is determined by means of a quantitative bioassay. The granules (occlusion bodies) of CpGV are counted under the light microscope. The virus titer in the end-use product is adjusted to the requested granules/l (Assessment Report: *Cydia pomonella* Granulovirus (CpGV)—Mexican Isolate (2007).

CpGV derives from the Mexican isolate of CpGV (Tanada, 1964) and is propagated in larvae of *Cydia pomonella*. Infected larvae are homogenized and centrifuged in 50% sucrose (w/w). The pellet is resuspended and the granules are purified by, e.g., centrifugation through a linear 50% to 60% (w/w) sucrose gradient, generating a virus band which is then repeatedly washed in Tris buffer and pelleted to remove residual sucrose. (Journal of general virology (1992), 73, 1621-1626).

Entomopathogenic Nematodes

Nematodes can be reared in liquid culture techniques (see, e.g., U.S. Pat. No. 5,023,183 which is herewith incorporated by reference in its entirety) and stored, for example, as eggs, larvae in suspension cultures or in clay powder or adult nematodes, e.g., in clay powder. Nematodes can be held in the refrigerator (2-6° C.) until use for up to 4 weeks and can be reactivated by suspension in warm water (>12° C.).

One method to isolate entomopathogenic nematodes from soil is described by Cairns, 1960, *Folia parasitica* 47: 315-318, 2000. For soil samples, a sieving-decanting method was employed with fmal isolation of the nematodes from the sieving debris using a Baermann funnel with cotton filter. For this method, which is commonly applied for the extraction of plant-parasitic and soil nematodes (Southey 1986), 250 ml soil was used. The nematode suspension was fixed, checked for the presence of entomopathogenic nematodes using an inverted light microscope, and the number of Steinemema specimens was determined. Species identification was mostly done at high microscopical magnification using morphological characters of the infective-stage juveniles (Sturhan in Hominick et al. 1997, and unpublished).

Entomopathogenic nematodes can be mass-produced by in-vivo or in-vitro methods. Larvae of *Galleria mellonella* are most commonly used to rear nematodes because of their commercial availability. Several researchers (Dutky et al. 1964, Howell 1979, Lindegren et al. 1993, Flanders et al. 1996) have described the methods of nematode infection, inoculation, and harvesting Using the in-vivo process, yields between $0.5 \times 10^5$-$4 \times 10^5$ infective juveniles, depending on the nematode species, have been obtained. During the past few years a distinct cottage industry has emerged in the USA which utilizes the in-vivo process for nematode mass-production for sale, especially in the home lawn and garden markets. The in-vivo process, however, lacks any economy of scale; the labor, equipment, and material (insect) costs increase as a linear function of production capacity. Perhaps even more important is the lack of improved quality while increasing scale. The in-vivo nematode production is increasingly sensitive to biological variations and catastrophes as scale increases (Friedman 1990). Several formulations have been developed for the storage and application of entomopathogenic nematodes. The shelf life of different nematode-based products varies depending on the formulation, nematode species and temperature. In the simplest type of formulation, the nematodes are impregnated onto moist carrier substrates providing substantial interstitial spaces leading to increased gas exchange. Such carriers include polyether polyurethane sponge, cedar shavings, peat, vermiculite, etc. Nematodes held on the sponge need to be hand-squeezed into water before application, whereas from the other carriers they may be applied directly to the soil as mulch (*Neotropical Entomology*, vol.30, no.2, Londrina, June 2001, ISSN 1519-566X).

A bioassay to determine nematode viability is described, e.g., in Simser (*J. of Nematology* 24(3):374-378; 1992). The Nematode viability was verified by host bioassay. Late instar larvae of the greater wax moth, Galleria mellone, were buried 2.5 cm deep between plants before nematode application (four larvae per replicate), collected after 7 days, placed in petri dishes (9 cm diameter) and held in darkness at ca. 25 C. Insect mortality (>90%) and subsequent nematode propagation with cadavers demonstrated infectivity of the nematodes. The skilled person is well aware how to adopt this kind of bioassay to different nematode species.

The preferred application rate of bacteria as biological control agent, in particular of spores of the bacteria (1.26a), namely *B. subtilis* strain GBO3, lies in the range of 0,1 to 3 kg/ha.

The preferred application rate of fungi as biological control agent, in particular the fungi *Metarhizium anisopliae* strain F 52 lies in the range of 0,1 to 3 kg/ha The preferred application rate of yeasts as biological control agent, in particular the yeast *Metschnikowia fructicola* strain NRRL Y-30752 lies in the range of 0,05 to 8 kg/ha.

The preferred application rate of protozoa, viruses, and entomopathogenic nematodes as biological control agents lies in the range of 0,5 to 10 kg/ha.

It is generally preferred to use or employ the compound (A), compound (B) and the biological control agent (C) selected from bacteria, in particular spore-forming bacteria, fungi or yeasts, protozoas, viruses, and entomopathogenic nematodes inoculants, botanicals and products produced by microorganisms including proteins or secondary metabolites, particularly (C8.1) Harpin on horticultural crops, such as cotton, flax, grapevines, fruit, vegetable, such as Rosaceae sp. (for example pomaceous fruit, such as apples and pears, but also stone fruit, such as apricots, cherries, almonds and peaches and soft fruit such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit), *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumbers), *Alliaceae* sp. (for example leek, onions), *Papilionaceae* sp. (for example peas); major crop plants, such *Gramineae* sp. (for example maize, lawn, cereals such as wheat, rye, rice, barley, oats, millet and triticale), *Poaceae* sp. (for example sugarcane), *Asteraceae* sp. (for example sunflowers), *Brassicaceae* sp. (for example white cabbage, red cabbage, broccoli, cauliflowers, Brussels sprouts, pak choi, turnip cabbage, garden radish, and also oilseed rape, mustard, horseradish and cress), *Fabacae* sp. (for example beans, peas, peanuts), *Papilionaceae* sp. (for example soya beans), *Solanaceae* sp. (for example potatoes), *Chenopodiaceae* sp. (for example sugar beet, fodder beet, Swiss chard, beetroot); crop plants and ornamental plants in garden and forest; and also in each case genetically modified varieties of these plants.

Horticultural crops particularly includes carrots, pumpkin, squash, zucchini, potato, sweet corn, onions, ornamentals, medicinal herbs, culinary herbs, tomatoes, spinach, pepper, melon, lettuce, cucumber, celery, beets, cabbage, cauliflower, broccoli, Brussels sprouts, turnip cabbage, kale, radish, rutabaga, turnip, asparagus, bean, pea, apples, raspberry, strawberry, banana, mango, grapes, peaches, pears, guava, pineapple, pomegranate, garlic, capsicum, chili, radish, star fruit, tapioca, walnuts, lemon, mandarin, mangold, mushroom, olive, orange, papaya, paprika, passion fruit, peanuts, pecan nuts, prune, pistachio nuts, persimmon, pamplemouse (grape-fruit), eggplant, endive, cranberry, gooseberry, hazel nuts, kiwifruit, almonds, amaranth, apricot, artichoke, avocado, blackberry, cashew nut, cherry, clementine, coconut, cantaloupes and includes their harvested goods, such as fruits and vegetables.

It is further generally preferred to use or employ the compound (A), compound (B) and the biological control agent (C) selected from bacteria, in particular spore-forming bacteria, fungi or yeasts, protozoas, viruses, and entomopathogenic nematodes, inoculants, botanicals and products produced by microorganisms including proteins or secondary metabolites, particularly (C8.1) Harpin on horticultural crops as well as broad acre crops such as cotton, corn, soybean, cereals, canola, oil seed rape, sugar cane and rice.

Furthermore the invention relates to a method of controlling insects, nematodes or phytopathogens, characterized in that the active compound combinations according to the invention are applied to the insects, nematodes or phytopathogens or their habitat.

If not mentioned otherwise the treatment of plants or plant parts (which includes seeds and plants emerging from the seed), harvested fruits and vegetables with the compound (A) Fluopyram, (B) a spore-forming bacterium of the genera *Bacillus*, selected from *Bacillus firmus*, *Bacillus firmus* CNCM I-1582, *Bacillus cereus*, *Bacillus pumilis*, *Bacillus amyloliquefaciens*, *Bacillus subtilis* strain GB03, *Bacillus subtilis* strain QST713, and (C) a biological control agent, in particular bacteria, fungi or yeasts, protozoa, viruses, entomopathogenic nematodes, inoculants, botanicals and products produced by microorganisms including proteins or secondary metabolites, particularly (C8.1) Harpin is carried out directly or by action on their surroundings, habitat or storage space using customary treatment methods, for example dipping, spraying, atomizing, irrigating, evaporating, dusting, fogging, broadcasting, foaming, painting, spreading-on, watering (drenching), drip irrigating. It is furthermore possible to apply compound (A) Fluopyram, (B) a spore-forming bacterium of the genera *Bacillus*, selected from *Bacillus firmus*, *Bacillus firmus* CNCM I-1582, *Bacillus cereus*, *Bacillus pumilis*, *Bacillus amyloliquefaciens*, *Bacillus subtilis* strain GB03, *Bacillus subtilis* strain QST713, and (C) a biological control agent, in particular bacteria, fungi or yeasts, protozoa, viruses, entomopathogenic nematodes, inoculants, botanicals and products produced by microorganisms including proteins or secondary metabolites, particularly (C8.1) Harpin as solo-formulation or combined-formulations by the ultra-low volume method, or to inject the compound (A) Fluopyram, (B) a spore-forming bacterium of the genera *Bacillus*, selected from *Bacillus firmus*, *Bacillus firmus* CNCM I-1582, *Bacillus cereus*, *Bacillus pumilis*, *Bacillus amyloliquefaciens*, *Bacillus subtilis* strain GB03, *Bacillus subtilis* strain QST713, and (C) a biological control agent, in particular bacteria, fungi or yeasts, protozoa, viruses, entomopathogenic nematodes, inoculants, botanicals and products produced by microorganisms including proteins or secondary metabolites, particularly (C8.1) Harpin as a composition or as sole-formulations into the soil (in-furrow).

Compositions

The present invention furthermore relates to compositions for reducing overall damage of plants and plant parts as well as losses in harvested fruits or vegetables caused by insects, nematodes or phytopathogens and which have fungicidal or nematicidal or insecticidal activity including any combination of the three activities comprising the active compound combinations according to the invention. Preferably, the compositions are fungicidal or nematicidal or insecticidal (including any combination of the three) compositions comprising agriculturally suitable auxiliaries, solvents, carriers, surfactants or extenders.

For the sake of clearness, a combination means a physical combination of (A) Fluopyram, (B) a spore-forming bacterium of the genera *Bacillus*, selected from *Bacillus firmus*,

*Bacillus firmus* CNCM I-1582, *Bacillus cereus, Bacillus pumilis, Bacillus amyloliquefaciens, Bacillus subtilis* strain GB03, *Bacillus subtilis* strain QST713, and (C) at least one biological control agent, in particular bacteria, fungi or yeasts, protozoa, viruses, entomopathogenic nematodes, botanicals and products produced by microorganisms including proteins or secondary metabolites, particularly (C8.1) Halpin, whereas a composition means a composition of the combination together with the above mentioned agriculturally suitable auxiliaries, solvents, carriers, surfactants or extenders, in a form as suitable for agrochemical application.

According to the invention, carrier is to be understood as meaning a natural or synthetic, organic or inorganic substance which is mixed or combined with the active compounds for better applicability, in particular for application to plants or plant parts or seeds. The carrier, which may be solid or liquid, is generally inert and should be suitable for use in agriculture.

Suitable solid or liquid carriers are: for example ammonium salts and natural ground minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilizers, water, alcohols, especially butanol, organic solvents, mineral oils and vegetable oils, and also derivatives thereof. It is also possible to use mixtures of such carriers. Solid carriers suitable for granules are: for example crushed and fractionated natural minerals, such as calcite, marble, pumice, sepiolite, dolomite, and also synthetic granules of inorganic and organic meals and also granules of organic material, such as sawdust, coconut shells, maize cobs and tobacco stalks.

Suitable liquefied gaseous extenders or carriers are liquids which are gaseous at ambient temperature and under atmospheric pressure, for example aerosol propellants, such as butane, propane, nitrogen and carbon dioxide.

Tackifiers, such as carboxymethylcellulose and natural and synthetic polymers in the form of powders, granules and latices, such as gum arabic, polyvinyl alcohol, polyvinyl acetate, or else natural phospholipids, such as cephalins and lecithins and synthetic phospholipids can be used in the formulations. Other possible additives are mineral and vegetable oils and waxes, optionally modified.

If the extender used is water, it is also possible for example, to use organic solvents as auxiliary solvents. Suitable liquid solvents are essentially: aromatic compounds, such as xylene, toluene or alkylnaphthalenes, chlorinated aromatic compounds or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol, and also ethers and esters thereof, ketones, such as acetone, methyl ethyl ketone, methyl isobutyl ketone or cyclohexanone, strongly polar solvents, such as dimethylformamide and dimethyl sulphoxide, and also water.

The compositions according to the invention may comprise additional further components, such as, for example, surfactants. Suitable surfactants are emulsifiers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates. The presence of a surfactant is required if one of the active compounds or one of the inert carriers is insoluble in water and when the application takes place in water. The proportion of surfactants is between 5 and 40% by weight of the composition according to the invention.

It is possible to use colorants such as inorganic pigments, for example iron oxide, titanium oxide, Prussian blue, and organic dyes, such as alizarin dyes, azo dyes and metal phthalocyanine dyes, and trace nutrients, such as salts of iron, manganese, boron, copper, cobalt, molybdenum and zinc.

If appropriate, other additional components may also be present, for example protective colloids, binders, adhesives, thickeners, thixotropic substances, penetrants, stabilizers, sequestering agents, complex formers. In general, the active compounds can be combined with any solid or liquid additive customarily used for formulation purposes.

In general, the compositions according to the invention comprise between 0.01 and 99% by weight, 0.05 and 98% by weight, preferable between 0.1 and 95% by weight, particularly preferred between 0.5 and 90% by weight of the active compound combination according to the invention, very particularly preferable between 10 and 70% by weight.

The active compound combinations or compositions according to the invention can be used as such or, depending on their respective physical or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide-coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active compound, and also microencapsulations in polymeric substances and in coating materials for seed, and also ULV cold-fogging and warm-fogging formulations.

The formulations mentioned can be prepared in a manner known per se, for example by mixing the active compounds or the active compound combinations with at least one additive. Suitable additives are all customary formulation auxiliaries, such as, for example, organic solvents, extenders, solvents or diluents, solid carriers and fillers, surfactants (such as adjuvants, emulsifiers, dispersants, protective colloids, wetting agents and tackifiers), dispersants or binders or fixatives, preservatives, dyes and pigments, defoamers, inorganic and organic thickeners, water repellents, if appropriate siccatives and UV stabilizers, gibberellins and also water and further processing auxiliaries. Depending on the formulation type to be prepared in each case, further processing steps such as, for example, wet grinding, dry grinding or granulation may be required.

The compositions according to the invention do not only comprise ready-to-use compositions which can be applied with suitable apparatus to the plant or the seed, but also commercial concentrates which have to be diluted with water prior to use.

The active compound combinations according to the invention can be present in (commercial) formulations and in the use forms prepared from these formulations as a mixture with other (known) active compounds, such as insecticides, attractants, sterilants, bactericides, acaricides, nematicides, fungicides, growth regulators, herbicides, fertilizers, safeners and Semiochemicals.

The treatment according to the invention of the plants and plant parts with the active compounds or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more layers, etc. It is furthermore possible to apply the active compound combination by the ultra-low volume method, or to inject the active compound combination or the active compound combination itself into the soil.

Seed Treatment

Moreover the invention is directed to a method for protecting seeds comprising the step of simultaneously or sequentially applying a compound (A) Fluopyram, (B) a spore-forming bacterium of the genera *Bacillus*, selected from *Bacillus firmus, Bacillus firmus* CNCM I-1582, *Bacillus cereus, Bacillus pumilis, Bacillus amyloliquefaciens, Bacillus subtilis* strain GB03, *Bacillus subtilis* strain QST713, and (C) a biological control agent, in particular bacteria, fungi or yeasts, protozoa, viruses, entomopathogenic nematodes, inoculants, botanicals and products produced by microorganisms including proteins or secondary metabolites, particularly (C8.1) Harpin on a seed or a plant emerging from the seed. The method is further called "seed treatment".

Using compound (A) Fluopyram, (B) a spore-forming bacterium of the genera *Bacillus*, selected from *Bacillus firmus, Bacillus firmus* CNCM I-1582, *Bacillus cereus, Bacillus pumilis, Bacillus amyloliquefaciens, Bacillus subtilis* strain GB03, *Bacillus subtilis* strain QST713, and (C) a biological control agent, in particular bacteria, fungi or yeasts, protozoa, viruses, entomopathogenic nematodes, inoculants, botanicals and products produced by microorganisms including proteins or secondary metabolites, particularly (C8.1) Harpin as a combination is particularly suitable for treating seed. A large part of the damage to crop plants caused by harmful agricultural insects, nematodes or phytopathogens is triggered by an infection of the seed during storage or after sowing as well as during and after germination of the plant. This phase is particularly critical since the roots and shoots of the growing plant are particularly sensitive, and even small damage may result in a weak plant (unhealthy plant), reduced yield and even in the death of the plant.

The control of insects, nematodes or phytopathogens by treating the seed of plants has been known for a long time and is the subject of continuous improvements. However, the treatment of seed entails a series of problems which cannot always be solved in a satisfactory manner Thus, it is desirable to develop methods for protecting the seed and the germinating plant which dispense with the additional application of crop protection agents after sowing or after the emergence of the plants or which at least considerably reduce additional application. It is furthermore desirable to optimize the amount of agrochemicals employed in such a way as to provide maximum protection for the seed and the germinating plant from attack by agricultural pests, but without damaging the plant itself by the active compound employed. In particular, methods for the treatment of seed should also take into consideration the intrinsic insecticidal or fungicidal or nematicidal properties of plants in order to achieve optimum protection of the seed and the germinating plant with a minimum of agrochemicals being employed.

The use or the method to use a compound (A) Fluopyram, (B) a spore-forming bacterium of the genera *Bacillus*, selected from *Bacillus firmus, Bacillus firmus* CNCM I-1582, *Bacillus cereus, Bacillus pumilis, Bacillus amyloliquefaciens, Bacillus subtilis* strain GB03, *Bacillus subtilis* strain QST713, and (C) a biological control agent, in particular bacteria, fungi or yeasts, protozoa, viruses, entomopathogenic nematodes, inoculants, botanicals and products produced by microorganisms including proteins or secondary metabolites, particularly (C8.1) Harpin simultaneously or sequentially includes the following application methods, namely both before mentioned components may be formulated into a single, stable composition with an agriculturally acceptable shelf life (so called "solo-formulation"), or being combined before or at the time of use (so called "combined-formulations"), The invention furthermore comprises a method for treating seed. The invention furthermore relates to seed treated according to one of the methods described in the preceding paragraphs. In the case of seed treatment, the treatment can be carried out by applying the compound (A) Fluopyram, (B) a spore-forming bacterium of the genera *Bacillus*, selected from *Bacillus firmus, Bacillus firmus* CNCM I-1582, *Bacillus cereus, Bacillus pumilis, Bacillus amyloliquefaciens, Bacillus subtilis* strain GB03, *Bacillus subtilis* strain QST713, and (C) a biological control agent, in particular bacteria, fungi or yeasts, protozoa, viruses, entomopathogenic nematodes, inoculants, botanicals and products produced by microorganisms including proteins or secondary metabolites, particularly (C8.1) Harpin as a solution, a powder (for dry seed treatment), a water-soluble powder (for slurry seed treatment), or by incrusting, by coating with one or more layers containing the compound (A) Fluopyram, (B) a spore-forming bacterium of the genera *Bacillus*, selected from *Bacillus firmus, Bacillus firmus* CNCM I-1582, *Bacillus cereus, Bacillus pumilis, Bacillus amyloliquefaciens, Bacillus subtilis* strain GB03, *Bacillus subtilis* strain QST713, and (C) a biological control agent, in particular bacteria, fungi or yeasts, protozoa, viruses, entomopathogenic nematodes, inoculants, botanicals and products produced by microorganisms including proteins or secondary metabolites, particularly (C8.1) Harpin.

The active compound combinations or compositions according to the invention are especially suitable for treating seed. A large part of the damage to crop plants caused by harmful organisms is triggered by an infection of the seed during storage or after sowing as well as during and after germination of the plant. This phase is particularly critical since the roots and shoots of the growing plant are particularly sensitive, and even small damage may result in the death of the plant. Accordingly, there is great interest in protecting the seed and the germinating plant by using appropriate compositions.

The control of phytopathogenic fungi by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection agents after sowing or after the emergence of the plants or which at least considerably reduce additional application. It is furthermore desirable to optimize the amount of active compound combination employed in such a way as to provide maximum protection for the seed and the germinating plant from attack by insects, nematodes or phytopathogens, but without damaging the plant itself by the active compound combination employed. In particular, methods for the treatment of seed should also take into consideration the intrinsic fungicidal or insecticidal or nematicidal properties of transgenic plants in order to achieve optimum protection of the seed and the germinating plant with a minimum of crop protection agents being employed.

Accordingly, the present invention also relates in particular to a method for protecting seed and germinating plants against attack by insects, nematodes or phytopathogens by treating the seed with a composition according to the invention. The invention also relates to the use of the compositions according to the invention for treating seed for protecting the seed and the germinating plant against insects, nematodes or phytopathogens. Furthermore, the invention relates to seed treated with a composition according to the invention for protection against insects, nematodes or phytopathogens.

The control of insects, nematodes or phytopathogens which damage plants post-emergence is carried out primarily by treating the soil and the above-ground parts of plants with crop protection compositions. Owing to the concerns regarding a possible impact of the crop protection composition on the environment and the health of humans and animals, there are efforts to reduce the amount of active compound combination applied.

One of the advantages of the present invention is that, because of the particular systemic properties of the compositions according to the invention, treatment of the seed with these compositions not only protects the seed itself, but also the resulting plants after emergence, from insects, nematodes or phytopathogens. In this manner, the immediate treatment of the crop at the time of sowing or shortly thereafter can be dispensed with.

It is also considered to be advantageous that the active compound combinations or compositions according to the invention can be used in particular also for transgenic seed where the plant growing from this seed is capable of expressing a protein which acts against insects, nematodes or phytopathogens. By treating such seed with the active compound combinations or compositions according to the invention, even by the expression of the, for example, insecticidal protein, certain insects, nematodes or phytopathogens may be controlled. Surprisingly, a further synergistic effect may be observed here, which additionally increases the effectiveness of the protection against attack by insects, nematodes or phytopathogens.

The compositions according to the invention are suitable for protecting seed of any plant variety employed in agriculture, in the greenhouse, in forests or in horticulture or viticulture. In particular, this takes the form of seed of cereals (such as wheat, barley, rye, triticale, millet, oats), maize (corn), cotton, soya bean, rice, potatoes, sunflowers, beans, coffee, beets (e.g. sugar beets and fodder beets), peanuts, oilseed rape, poppies, olives, coconuts, cacao, sugar cane, sorghum, tobacco, vegetables (such as tomatoes, cucumbers, onions and lettuce), lawn and ornamental plants (also see below).

As also described further below, the treatment of transgenic seed with the active compound combinations or compositions according to the invention is of particular importance. This refers to the seed of plants containing at least one heterologous gene which allows the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. Preferably, this heterologous gene is from *Bacillus* sp., the gene product having activity against the European corn borer or the Western corn rootworm. Particularly preferably, the heterologous gene originates from *Bacillus thuringiensis*.

In the context of the present invention, the active compound combinations or compositions according to the invention are applied on their own or in a suitable formulation to the seed. Preferably, the seed is treated in a state in which it is sufficiently stable so that the treatment does not cause any damage. In general, treatment of the seed may take place at any point in time between harvesting and sowing. Usually, the seed used is separated from the plant and freed from cobs, shells, stalks, coats, hairs or the flesh of the fruits. Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of the composition according to the invention applied to the seed or the amount of further additives is chosen in such a way that the germination of the seed is not adversely affected, or that the resulting plant is not damaged. This must be borne in mind in particular in the case of active compounds which may have phytotoxic effects at certain application rates.

The compositions according to the invention can be applied directly, that is to say without comprising further components and without having been diluted. In general, it is preferable to apply the compositions to the seed in the form of a suitable formulation. Suitable formulations and methods for the treatment of seed are known to the person skilled in the art and are described, for example, in the following documents: U.S. Pat. Nos. 4,272,417, 4,245,432, 4,808,430, 5,876,739, US 2003/0176428 A1, WO 2002/080675, WO 2002/028186.

The active compound combinations which can be used according to the invention can be converted into customary seed dressing formulations, such as solutions, emulsions, suspensions, powders, foams, slurries or other coating materials for seed, and also ULV formulations.

These formulations are prepared in a known manner by mixing the active compounds or active compound combinations with customary additives, such as, for example, customary extenders and also solvents or diluents, colorants, wetting agents, dispersants, emulsifiers, defoamers, preservatives, secondary thickeners, adhesives, gibberellins and water as well.

Suitable colorants that may be present in the seed dressing formulations which can be used according to the invention include all colorants customary for such purposes. Use may be made both of pigments, of sparing solubility in water, and of dyes, which are soluble in water. Examples that may be mentioned include the colorants known under the designations Rhodamine B, C. I. Pigment Red 112, and C. I. Solvent Red 1.

Suitable wetting agents that may be present in the seed dressing formulations which can be used according to the invention include all substances which promote wetting and are customary in the formulation of active agrochemical substances. With preference it is possible to use alkylnaphthalene-sulphonates, such as diisopropyl- or diisobutylnaphthalene-sulphonates.

Suitable dispersants or emulsifiers that may be present in the seed dressing formulations which can be used according to the invention include all nonionic, anionic, and cationic dispersants which are customary in the formulation of active agrochemical substances. With preference, it is possible to use nonionic or anionic dispersants or mixtures of nonionic or anionic dispersants. Particularly suitable nonionic dispersants are ethylene oxide-propylene oxide block polymers, alkylphenol polyglycol ethers, and tristyrylphenol polyglycol ethers, and their phosphated or sulphated derivatives. Particularly suitable anionic dispersants are lignosulphonates, polyacrylic salts, and arylsulphonate-formaldehyde condensates.

Defoamers that may be present in the seed dressing formulations to be used according to the invention include all foam-inhibiting compounds which are customary in the formulation of agrochemically active compounds. Preference is given to using silicone defoamers, magnesium stearate, silicone emulsions, long-chain alcohols, fatty acids and their salts and also organofluorine compounds and mixtures thereof.

Preservatives that may be present in the seed dressing formulations to be used according to the invention include all compounds which can be used for such purposes in agrochemical compositions. By way of example, mention may be made of dichlorophen and benzyl alcohol hemiformal.

Secondary thickeners that may be present in the seed dressing formulations to be used according to the invention include all compounds which can be used for such purposes in agrochemical compositions. Preference is given to cellulose derivatives, acrylic acid derivatives, polysaccharides, such as xanthan gum or Veegum, modified clays, phyllosilicates, such as attapulgite and bentonite, and also finely divided silicic acids.

Suitable adhesives that may be present in the seed dressing formulations to be used according to the invention include all customary binders which can be used in seed dressings. Polyvinylpyrrolidone, polyvinyl acetate, polyvinyl alcohol and tylose may be mentioned as being preferred.

Suitable gibberellins that may be present in the seed dressing formulations to be used according to the invention are preferably the gibberellins A1, A3 (=gibberellic acid), A4 and A7; particular preference is given to using gibberellic acid. The gibberellins are known (cf. R. Wegler "Chemie der Pflanzenschutz- and Schädlingsbe-kämpfungsmittel" [Chemistry of Crop Protection Agents and Pesticides], Vol. 2, Springer Verlag, 1970, pp. 401-412).

The seed dressing formulations which can be used according to the invention may be used directly or after dilution with water beforehand to treat seed of any of a very wide variety of types. The seed dressing formulations which can be used according to the invention or their dilute preparations may also be used to dress seed of transgenic plants. In this context, synergistic effects may also arise in interaction with the substances formed by expression.

Suitable mixing equipment for treating seed with the seed dressing formulations which can be used according to the invention or the preparations prepared from them by adding water includes all mixing equipment which can commonly be used for dressing. The specific procedure adopted when dressing comprises introducing the seed into a mixer, adding the particular desired amount of seed dressing formulation, either as it is or following dilution with water beforehand, and carrying out mixing until the formulation is uniformly distributed on the seed. Optionally, a drying operation follows.

The active compounds or compositions according to the invention have strong bactericidal or fungicidal or insecticidal or nematicidal activity and can be used for controlling insects, nematodes or phytopathogens in crop protection and material protection.

In crop protection, fungicides can be used for controlling phytopathogens like *Plasmodiophoromycetes, Oomycetes, Chytridiomycetes, Zygomycetes, Ascomycetes, Basidiomycetes* and *Deuteromycetes.*

In crop protection, bactericides can be used for controlling phytopathogens Pseudomonadaceae, Rhizobiaceae, Enterobacteriaceae, Corynebacteriaceae and Streptomycetaceae.

The fungicidal or insecticidal or nematicidal compositions according to the invention can be used for the curative or protective control of insects, nematodes or phytopathogens. Accordingly, the invention also relates to curative and protective methods for controlling insects, nematodes or phytopathogens using the active compound combinations or compositions according to the invention, which are applied to the seed, the plant or plant parts, the fruit or the soil in which the plants grow. Preference is given to application onto the plant or the plant parts, the fruits or the soil in which the plants grow.

The compositions according to the invention for controlling insects, nematodes or phytopathogens in crop protection comprise an active, but non-phytotoxic amount of the compounds according to the invention. "Active, but non-phytotoxic amount" shall mean an amount of the composition according to the invention which is sufficient to control or to completely kill the plant disease caused by insects, nematodes or phytopathogens, which amount at the same time does not exhibit noteworthy symptoms of phytotoxicity. These application rates generally may be varied in a broader range, which rate depends on several factors, e.g. the insects, nematodes or phytopathogens, the plant or crop, the climatic conditions and the ingredients of the composition according to the invention.

The fact that the active compounds or active compound combinations, at the concentrations required for the controlling of plant diseases, are well tolerated by plants permits the treatment of aerial plant parts, of vegetative propagation material and seed, and of the soil.

According to the invention, it is possible to treat all plants and parts of plants. Plants are to be understood here as meaning all plants and plant populations, such as wanted and unwanted wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant variety protection rights. Parts of plants are to be understood as meaning all above-ground and below-ground parts and organs of the plants, such as shoot, leaf, flower and root, examples which may be mentioned being leaves, needles, stems, trunks, flowers, fruit bodies, fruits and seeds and also roots, tubers and rhizomes. Plant parts also include harvested material and vegetative and generative propagation material, for example seedlings, tubers, rhizomes, bulbs, cuttings and seeds. Preference is given to the treatment of the plants and the above-ground and below-ground parts and organs of the plants, such as shoot, leaf, flower and root, examples which may be mentioned being leaves, needles, stems, trunks, flowers, and fruits.

The active compounds or active compound combinations of the invention, in combination with good plant tolerance and favourable toxicity to warm-blooded animals and being tolerated well by the environment, are suitable for protecting plants and plant organs, for increasing the harvest yields, for improving the quality of the harvested material. They may be preferably employed as crop protection agents. They are active against normally sensitive and resistant species and against all or some stages of development.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The terms "parts", "parts of plants" and "plant parts" have been explained above. Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

The method of treatment according to the invention is used in the treatment of genetically modified organisms (GM05), e.g. plants or seeds. Genetically modified plants (or transgenic plants) are plants of which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by down regulating or silencing other gene(s) which are present in the plant (using for example, antisense technology, co-suppression technology or RNA interference RNAi -technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in super-additive ("synergistic") effects. Thus, for example, reduced application rates or a widening of the activity spectrum or an increase in the activity of the active compound combinations and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality or a higher nutritional value of the harvested products, higher sugar concentration within the fruits, better storage stability or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted phytopathogenic fungi and/or microorganisms or viruses. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi or microorganisms or viruses, the treated plants display a substantial degree of resistance to these phytopathogenic fungi or microorganisms or viruses, Thus, the substances according to the invention can be employed for protecting plants against attack by the abovementioned phytopathogens within a certain period of time after the treatment. The period of time within which protection is effected generally extends from 1 to 10 days, preferably 1 to 7 days, after the treatment of the plants with the active compounds or active compound combinations.

Plants and plant cultivars which are preferably to be treated according to the invention include all plants which have genetic material which impart particularly advantageous, useful traits to these plants (whether obtained by breeding or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozon exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in Brassica species. However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp, the genes encoding a Petunia EPSPS, a Tomato EPSPS, or an Eleusine EPSPS. It can also be a mutated EPSPS.

Glyphosate-tolerant plants can also be obtained by expressing a gene that encodes a glyphosate oxido-reductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the above-mentioned genes.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from Streptomyces species). Plants expressing an exogenous phosphinothricin acetyltransferase are also described.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme. Tolerance to HPPD-inhibitors can also be obtained by transforming plants with genes encoding certain enzymes enabling the formation of homogentisate despite the inhibition of the native HPPD enzyme by the HPPD-inhibitor. Tolerance of plants to HPPD inhibitors can also be improved by transforming plants with a gene encoding an enzyme prephenate dehydrogenase in addition to a gene encoding an HPPD-tolerant enzyme.

Still further herbicide resistant plants are plants that are made tolerant to acetolactate synthase (ALS) inhibitors. Known ALS-inhibitors include, for example, sulfonylurea, imidazolinone, triazolopyrimidines, pyrimidinyoxy(thio)benzoates, or sulfonylaminocarbonyltriazolinone herbicides. Different mutations in the ALS enzyme (also known as acetohydroxyacid synthase, AHAS) are known to confer tolerance to different herbicides and groups of herbicides. The production of sulfonylurea-tolerant plants and imidazolinone-tolerant plants is described in WO 1996/033270. Other imidazolinone-tolerant plants are also described. Further sulfonylurea- and imidazolinone-tolerant plants are also described in for example WO 2007/024782.

Other plants tolerant to imidazolinone or sulfonylurea can be obtained by induced mutagenesis, selection in cell cultures in the presence of the herbicide or mutation breeding as described for example for soybeans, for rice, for sugar beet, for lettuce, or for sunflower.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding 1) an insecticidal crystal protein from Bacillus thuringiensis or an insecticidal portion thereof, such as the insecticidal crystal proteins listed online at: http://www.lifesci.sussex.ac.uk/Home/Neil_Crickmore/Bt/, or insecticidal portions thereof, e.g., proteins of the Cry protein classes Cry1Ab, Cry1Ac, Cry1F, Cry2Ab, Cry3Aa, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins; or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry 1A.105 protein produced by corn event MON98034 (WO 2007/027777); or 4) a protein of any one of 1) to 3) above wherein some, particularly 1 to 10, amino acids have been replaced by another amino acid to obtain a higher insecticidal activity to a target insect species, or to expand the range of target insect species affected, or because of changes introduced into the encoding DNA during cloning or transformation, such as the Cry3Bb1 protein in corn events MON863 or MON88017, or the Cry3A protein in corn event MIR604;

5) an insecticidal secreted protein from *Bacillus thuringiensis* or *Bacillus cereus*, or an insecticidal portion thereof, such as the vegetative insecticidal (VIP) proteins listed at:

http://www.lifesci.sussex.ac.uk/home/Neil_Crickmore/Bt/vip.html, e.g. proteins from the VIP3Aa protein class; or 6) secreted protein from *Bacillus thuringiensis* or *Bacillus cereus* which is insecticidal in the presence of a second secreted protein from *Bacillus thuringiensis* or *B. cereus,* such as the binary toxin made up of the VIP 1A and VIP2A proteins; or 7) hybrid insecticidal protein comprising parts from different secreted proteins from *Bacillus thuringiensis* or *Bacillus cereus,* such as a hybrid of the proteins in 1) above or a hybrid of the proteins in 2) above; or 8) protein of any one of 1) to 3) above wherein some, particularly 1 to 10, amino acids have been replaced by another amino acid to obtain a higher insecticidal activity to a target insect species, or to expand the range of target insect species affected, or because of changes introduced into the encoding DNA during cloning or transformation (while still encoding an insecticidal protein), such as the VIP3Aa protein in cotton event COT102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected when using different proteins directed at different target insect species, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression or the activity of poly(ADP-ri-bose)polymerase (PARP) gene in the plant cells or plants b. plants which contain a stress tolerance enhancing transgene capable of reducing the expression or the activity of the PARG encoding genes of the plants or plants cells.

c. plants which contain a stress tolerance enhancing transgene coding for a plant-functional enzyme of the nicotinamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase.

Plants or plant cultivars (obtained by plant biotechnology methods such as genetic engineering) which may also be treated according to the invention show altered quantity, quality or storage-stability of the harvested product or altered properties of specific ingredients of the harvested product such as :

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size or the starch grain morphology, is changed in comparison with the synthesised starch in wild type plant cells or plants, so that this is better suited for special applications.

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, plants producing alpha 1,4 glucans, plants producing alpha-1,6 branched alpha-1,4-glucans, plants producing alternan, 3) transgenic plants which produce hyaluronan.

Plants or plant cultivars (that can be obtained by plant biotechnology methods such as genetic engineering) which may also be treated according to the invention are plants, such as cotton plants, with altered fiber characteristics. Such plants can be obtained by genetic transformation or by selection of plants contain a mutation imparting such altered fiber characteristics and include:

a) Plants, such as cotton plants, containing an altered form of cellulose synthase genes, b) Plants, such as cotton plants, containing an altered form of rsw2 or rsw3 homologous nucleic acids, c) Plants, such as cotton plants, with increased expression of sucrose phosphate synthase, d) Plants, such as cotton plants, with increased expression of sucrose synthase, e) Plants, such as cotton plants, wherein the timing of the plasmodesmatal gating at the basis of the fiber cell is altered, e.g. through downregulation of fiberselective β 1,3-glucanase, f) Plants, such as cotton plants, having fibers with altered reactivity, e.g. through the expression of N-acteylglucosaminetransferase gene including nodC and chitinsynthase genes.

Plants or plant cultivars (that can be obtained by plant biotechnology methods such as genetic engineering) which may also be treated according to the invention are plants, such as oilseed rape or related Brassica plants, with altered oil profile characteristics. Such plants can be obtained by genetic transformation or by selection of plants contain a mutation imparting such altered oil characteristics and include:

a) Plants, such as oilseed rape plants, producing oil having a high oleic acid content, b) Plants such as oilseed rape plants, producing oil having a low linolenic acid content, c) Plant such as oilseed rape plants, producing oil having a low level of saturated fatty acids.

Particularly useful transgenic plants which may be treated according to the invention are plants which comprise one or more genes which encode one or more toxins, such as the following which are sold under the trade names YIELD GARD® (for example maize, cotton, soya beans), KnockOutO (for example maize), BiteGard® (for example maize), Bt-Xtra® (for example maize), StarLink® (for example maize), Bollgard® (cotton), Nucotn® (cotton), Nucotn 33B®(cotton), NatureGard® (for example maize), Protecta® and NewLeaf® (potato). Examples of herbicide-tolerant plants which may be mentioned are maize varieties, cotton varieties and soya bean varieties which are sold under the trade names Roundup Ready ED (tolerance to glyphosate, for example maize, cotton, soya bean), Liberty Link® (tolerance to phosphinotricin, for example oilseed rape), IMF) (tolerance to imidazolinones) and STS ED (tolerance to sulphonylureas, for example maize) Herbicide-resistant plants (plants bred in a conventional manner for herbicide tolerance) which may be mentioned include the varieties sold under the name Clearfield® (for example maize) Particularly useful transgenic plants which may be treated according to the invention are plants containing transformation events, or a combination of transformation events, and that are listed for example in the databases for various national or regional regulatory agencies including Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US2002120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control—herbicide tolerance, deposited as PTA-6233, described in WO2005/103266 or US2005216969); Event 3006-210-23 (cotton, insect control—herbicide tolerance, deposited as PTA-6233, described in US2007143876 or WO2005/103266); Event 3272 (corn, quality trait, deposited as PTA-9972, described in WO2006098952 or US2006230473); Event 40416 (corn, insect control—herbicide tolerance, deposited as ATCC PTA-11508, described in WO2011/075593); Event 43A47 (corn, insect control—herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US2006162007 or WO2004053062); Event B16 (corn, herbicide tolerance, not deposited, described in US2003126634); Event BPS-CV127-9 (soybean, herbicide tolerance, deposited as NCIMB No. 41603, described in WO2010/080829); Event CE43-67B (cotton, insect control, deposited as DSM ACC2724, described in US2009217423 or WO2006/128573); Event CE44-69D (cotton, insect control, not deposited, described in US20100024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US2006130175 or WO2004039986); Event COT202 (cotton, insect control, not deposited, described in US2007067868 or WO2005054479); Event COT203 (cotton, insect control, not deposited, described in WO2005/054480); Event DAS40278 (corn, herbicide tolerance, deposited as ATCC PTA-10244, described in WO2011/022469); Event DAS-59122-7 (corn, insect control—herbicide tolerance, deposited as ATCC PTA 11384, described in US2006070139); Event DAS-59132 (corn, insect control—herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US2009137395 or WO2008/112019); Event DP-305423-1 (soybean, quality trait, not deposited, described in US2008312082 or WO2008/054747); Event DP-32138-1 (corn, hybridization system, deposited as ATCC PTA-9158, described in US20090210970 or WO2009/103049); Event DP-356043-5 (soybean, herbicide tolerance, deposited as ATCC PTA-8287, described in US20100184079 or WO2008/002872); Event EE-1 (brinjal, insect control, not deposited, described in WO2007/091277); Event FI117 (corn, herbicide tolerance, deposited as ATCC 209031, described in US2006059581 or WO1998/044140); Event GA21 (corn, herbicide tolerance, deposited as ATCC 209033, described in US2005086719 or WO1998/044140); Event GG25 (corn, herbicide tolerance, deposited as ATCC 209032, described in US2005188434 or WO1998/044140); Event GHB119 (cotton, insect control—herbicide tolerance, deposited as ATCC PTA-8398, described in WO2008/151780); Event GHB614 (cotton, herbicide tolerance, deposited as ATCC PTA-6878, described in US2010050282 or WO2007/017186); Event GJ11 (corn, herbicide tolerance, deposited as ATCC 209030, described in US2005188434 or WO1998/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US2004172669 or WO2004/074492); Event JOPLIN1 (wheat, disease tolerance, not deposited, described in US2008064032); Event LL27 (soybean, herbicide tolerance, deposited as NCIMB41658, described in WO2006/108674 or US2008320616); Event LL55 (soybean, herbicide tolerance, deposited as NCIMB 41660, described in WO2006/108675 or US2008196127); Event LLcotton25 (cotton, herbicide tolerance, deposited as ATCC PTA-3343, described in WO2003013224 or US2003097687); Event LLRICE06 (rice, herbicide tolerance, deposited as ATCC-23352, described in US6468747 or WO2000/026345); Event LLRICE601 (rice, herbicide tolerance, deposited as ATCC PTA-2600, described in US20082289060 or WO2000/026356); Event LY038 (corn, quality trait, deposited as ATCC PTA-5623, described in US2007028322 or WO2005061720); Event MIR162 (corn, insect control, deposited as PTA-8166, described in US2009300784 or WO2007/142840); Event MIR604 (corn, insect control, not deposited, described in US2008167456 or WO2005103301); Event MON15985 (cotton, insect control, deposited as ATCC PTA-2516, described in US2004-250317 or WO2002/100163); Event MON810 (corn, insect control, not deposited, described in US2002102582); Event MON863 (corn, insect control, deposited as ATCC PTA-2605, described in WO2004/011601 or US2006095986); Event MON87427 (corn, pollination control, deposited as ATCC PTA-7899, described in WO2011/062904); Event MON87460 (corn, stress tolerance, deposited as ATCC PTA-8910, described in WO2009/111263 or US20110138504); Event MON87701 (soybean, insect control, deposited as ATCC PTA-8194, described in US2009130071 or WO2009/064652); Event MON87705 (soybean, quality trait-herbicide tolerance, deposited as ATCC PTA-9241, described in US20100080887 or WO2010/037016); Event MON87708 (soybean, herbicide tolerance, deposited as ATCC PTA9670, described in WO2011/034704); Event MON87754 (soybean, quality trait, deposited as ATCC PTA-9385, described in WO2010/024976); Event MON87769 (soybean, quality trait, deposited as ATCC PTA-8911, described in US20110067141 or WO2009/102873); Event MON88017 (corn, insect control—herbicide tolerance, deposited as ATCC PTA-5582, described in US2008028482 or WO2005/059103); Event MON88913 (cotton, herbicide tolerance, deposited as ATCC PTA-4854, described in WO2004/072235 or US2006059590); Event MON89034 (corn, insect control, deposited as ATCC PTA-7455, described in WO2007/140256 or US2008260932); Event MON89788 (soybean, herbicide tolerance, deposited as ATCC PTA-6708, described in US2006282915 or WO2006/130436); Event MS11 (oilseed rape, pollination control—herbicide tolerance, deposited as ATCC PTA-850 or PTA-2485, described in WO2001/031042); Event MS8 (oilseed rape, pollination control—herbicide tolerance, deposited as ATCC PTA-730, described in WO2001/041558 or US2003188347); Event NK603 (corn, herbicide tolerance, deposited as ATCC PTA-2478, described in US2007-292854); Event PE-7 (rice, insect control, not deposited, described in WO2008/114282); Event RF3 (oilseed rape, pollination control—herbicide tolerance, deposited as ATCC PTA-730, described in WO2001/041558 or US2003188347); Event RT73 (oilseed rape, herbicide tolerance, not deposited, described in WO2002/036831 or US2008070260); Event T227-1 (sugar beet, herbicide tolerance, not deposited, described in WO2002/44407 or US2009265817); Event T25 (corn, herbicide tolerance, not deposited, described in US2001029014 or WO2001/051654); Event T304-40 (cotton, insect control—herbicide tolerance, deposited as ATCC PTA-8171, described in US2010077501 or WO2008/122406); Event T342-142 (cotton, insect control, not deposited, described in WO2006/128568); Event TC1507 (corn, insect control—herbicide tolerance, not deposited, described in US2005039226 or WO2004/099447); Event VIP1034 (corn, insect control—herbicide tolerance, deposited as ATCC PTA-3925., described in WO2003/052073), Event 32316 (corn,insect control—herbicide tolerance,deposited as PTA-11507, described in WO2011/084632), Event 4114 (corn, insect control—herbicide tolerance, deposited as PTA-11506, described in WO2011/084621).

Particularly useful transgenic plants which may be treated according to the invention are plants containing transformation events, or combination of transformation events, that are listed for example in the databases from various national or regional regulatory agencies (see for example http://gmoinfo.jrc.it/gmp_browse.aspx and littp://www.agbios.com.dbase.php).

Particularly useful transgenic plants which may be treated according to the invention are plants containing transformation events, or combination of transformation events, are listed in table A

TABLE A

| | Event | Company | Description | Crop | Patent Ref |
|---|---|---|---|---|---|
| A-1 | ASR368 | Scotts Seeds | Glyphosate tolerance derived by inserting a modified 5-enolpyruvylshikimate-3-phosphate synthase (EPSPS) encoding gene from *Agrobacterium tumefaciens*, parent line B99061 | *Agrostis stolonifera* Creeping Bentgrass | US 2006162007 |
| A-2 | GM RZ13 | Monsanto Company | Beet Necrotic Yellow Vein Virus (BNYVV) resistance | *Beta vulgaris* (sugar beet) | WO 10/076212 |
| A-3 | H7-1 | Monsanto Company | Glyphosate herbicide tolerant sugar beet produced by inserting a gene encoding the enzyme 5-enolpyrunvylshikimate-3-phosphate synthase (EPSPS) from the CP4 strain of *Agrobacterium tumefaciens* | *Beta vulgaris* (sugar beet) | WO 04/074492 |
| A-4 | T120-7 | Bayer CropScience (Aventis CropScience(AgrEvo)) | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. | *Beta vulgaris* (sugar beet) | |
| A-5 | GTSB77 | Novartis Seeds; Monsanto Company | Glyphosate herbicide tolerant sugar beet produced by inserting a gene encoding the enzyme 5-enolpyrunvylshikimate-3-phosphate synthase (EPSPS) from the CP4 strain of *Agrobacterium tumefaciens*. | *Beta vulgaris* (sugar beet) | |
| A-6 | T227-1 | Monsanto Company (formerly Calgene) | Glyphosate tolerance | *Beta vulgaris* (sugar beet) | US 2004117870 |
| A-7 | 23-18-17, 23-198 | Monsanto Company (formerly Calgene) | High laurate (12:0) and myristate (14:0) canola produced by inserting a thioesterase encoding gene from the California bay laurel (*Umbellularia californica*). | *Brassica napus* (Argentine Canola) | |
| A-8 | 45A37, 46A40 | Pioneer Hi-Bred International Inc. | High oleic acid and low linolenic acid canola produced through a combination of chemical mutagenesis to select for a fatty acid desaturase mutant with elevated oleic acid, and traditional back-crossing to introduce the low linolenic acid trait. | *Brassica napus* (Argentine Canola) | |
| A-9 | 46A12, 46A16 | Pioneer Hi-Bred International Inc. | Combination of chemical mutagenesis, to achieve the high oleic acid trait, and traditional breeding with registered canola varieties. | *Brassica napus* (Argentine Canola) | |
| A-10 | GT200 | Monsanto Company | Glyphosate herbicide tolerant canola produced by inserting genes encoding the enzymes 5-enolpyrunvylshikimate-3-phosphate synthase (EPSPS) from the CP4 strain of *Agrobacterium tumefaciens* and glyphosate oxidase from *Ochrobactrum anthropi*. | *Brassica napus* (Argentine Canola) | |
| A-11 | GT73, RT73 | Monsanto Company | Glyphosate herbicide tolerant canola produced by inserting genes encoding the enzymes 5-enolpyrunvylshikimate-3-phosphate synthase (EPSPS) from the CP4 strain of *Agrobacterium tumefaciens* and glyphosate oxidase from *Ochrobactrum anthropi*. | *Brassica napus* (Argentine Canola) | |
| A-12 | HCN10 | Aventis CropScience | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. | *Brassica napus* (Argentine Canola) | |

TABLE A-continued

| | Event | Company | Description | Crop | Patent Ref |
|---|---|---|---|---|---|
| A-13 | HCN92 | Bayer CropScience (Aventis CropScience(AgrEvo)) | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. | *Brassica napus* (Argentine Canola) | |
| A-14 | MS1, RF1 =>PGS1 | Aventis CropScience (formerly Plant Genetic Systems) | Male-sterility, fertility restoration, pollination control system displaying glufosinate herbicide tolerance. MS lines contained the barnase gene from *Bacillus amyloliquefaciens*, RF lines contained the barstar gene from the same bacteria, and both lines contained the phosphinothricin N-acetyltransferase (PAT) encoding gene from *Streptomyces hygroscopicus*. | *Brassica napus* (Argentine Canola) | |
| A-15 | MS1, RF2 =>PGS2 | Aventis CropScience (formerly Plant Genetic Systems) | Male-sterility, fertility restoration, pollination control system displaying glufosinate herbicide tolerance. MS lines contained the barnase gene from *Bacillus amyloliquefaciens*, RF lines contained the barstar gene from the same bacteria, and both lines contained the phosphinothricin N-acetyltransferase (PAT) encoding gene from *Streptomyces hygroscopicus*. | *Brassica napus* (Argentine Canola) | |
| A-16 | MS8 × RF3 | Bayer CropScience (Aventis CropScience(AgrEvo)) | Male-sterility, fertility restoration, pollination control system displaying glufosinate herbicide tolerance. MS lines contained the barnase gene from *Bacillus amyloliquefaciens*, RF lines contained the barstar gene from the same bacteria, and both lines contained the phosphinothricin N-acetyltransferase (PAT) encoding gene from *Streptomyces hygroscopicus*. | *Brassica napus* (Argentine Canola) | |
| A-17 | MS-B2 | | Male sterility | *Brassica napus* (Argentine Canola) | WO 01/31042 |
| A-18 | MS-BN1/RF-BN1 | | Male sterility/restoration | *Brassica napus* (Argentine Canola) | WO 01/41558 |
| A-19 | NS738, NS1471, NS1473 | Pioneer Hi-Bred International Inc. | Selection of somaclonal variants with altered acetolactate synthase (ALS) enzymes, following chemical mutagenesis. Two lines (P1, P2) were initially selected with modifications at different unlinked loci. NS738 contains the P2 mutation only. | *Brassica napus* (Argentine Canola) | |
| A-20 | OXY-235 | Aventis CropScience (formerly Rhone Poulenc Inc.) | Tolerance to the herbicides bromoxynil and ioxynil by incorporation of the nitrilase gene from *Klebsiella pneumoniae*. | *Brassica napus* (Argentine Canola) | |
| A-21 | PHY14, PHY35 | Aventis CropScience (formerly Plant Genetic Systems) | Male sterility was via insertion of the barnase ribonuclease gene from *Bacillus amyloliquefaciens*; fertility restoration by insertion of the barstar RNase inhibitor; PPT resistance was via PPT-acetyltransferase (PAT) from *Streptomyces hygroscopicus*. | *Brassica napus* (Argentine Canola) | |
| A-22 | PHY36 | Aventis CropScience (formerly Plant Genetic Systems) | Male sterility was via insertion of the barnase ribonuclease gene from *Bacillus amyloliquefaciens*; fertility restoration by insertion of the barstar RNase inhibitor; PPT resistance was via PPT-acetyltransferase (PAT) from *Streptomyces hygroscopicus*. | *Brassica napus* (Argentine Canola) | |
| A-23 | RT73 | | Glyphosate resistance | *Brassica napus* (Argentine Canola) | WO 02/6831 |
| A-24 | T45 (HCN28) | Bayer CropScience (Aventis CropScience(AgrEvo)) | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. | *Brassica napus* (Argentine Canola) | |

TABLE A-continued

| Event | Company | Description | Crop | Patent Ref |
|---|---|---|---|---|
| A-25 | HCR-1 | Bayer CropScience (Aventis CropScience(AgrEvo)) | Introduction of the glufosinate ammonium herbicide tolerance trait from transgenic *B. napus* line T45. This trait is mediated by the phosphinothricin acetyltransferase (PAT) encoding gene from *S. viridochromogenes*. | *Brassica rapa* (Polish Canola) | |
| A-26 | ZSR500/502 | Monsanto Company | Introduction of a modified 5-enol-pyruvylshikimate-3-phosphate synthase (EPSPS) and a gene from *Achromobacter* sp that degrades glyphosate by conversion to aminomethylphosphonic acid (AMPA) and glyoxylate by inter-specific crossing with GT73. | *Brassica rapa* (Polish Canola) | WO 07/091277 |
| A-27 | EE-1 | Cornell University | Insect resistance (Cry1Ac) | Brinjal | |
| A-28 | 55-1/63-1 | Cornell University | Papaya ringspot virus (PRSV) resistant papaya produced by inserting the coat protein (CP) encoding sequences from this plant poty virus. | *Carica papaya* (Papaya) | |
| A-29 | X17-2 | University of Florida | Papaya ringspot virus (PRSV) resistant papaya produced by inserting the coat protein (CP) encoding sequences from PRSV isolate H1K with a thymidine inserted after the initiation codon to yield a frameshift. Also contains nptII as a selectable marker. | *Carica papaya* (Papaya) | |
| A-30 | RM3-3, RM3-4, RM3-6 | Bejo Zaden BV | Male sterility was via insertion of the barnase ribonuclease gene from *Bacillus amyloliquefaciens*; PPT resistance was via the bar gene from *S. hygroscopicus*, which encodes the PAT enzyme. | *Cichorium intybus* (Chicory) | |
| A-32 | A, B | Agritope Inc. | Reduced accumulation of S-adenosylmethionine (SAM), and consequently reduced ethylene synthesis, by introduction of the gene encoding S-adenosylmethionine hydrolase. | *Cucumis melo* (Melon) | |
| A-33 | CZW-3 | Asgrow (USA); Seminis Vegetable Inc. (Canada) | Cucumber mosaic virus (CMV), zucchini yellows mosaic (ZYMV) and watermelon mosaic virus (WMV) 2 resistant squash (*Curcurbita pepo*) produced by inserting the coat protein (CP) encoding sequences from each of these plant viruses into the host genome. | *Cucurbita pepo* (Squash) | |
| A-34 | ZW20 | Upjohn (USA); Seminis Vegetable Inc. (Canada) | Zucchini yellows mosaic (ZYMV) and watermelon mosaic virus (WMV) 2 resistant squash (*Curcurbita pepo*) produced by inserting the coat protein (CP) encoding sequences from each of these plant potyviruses into the host genome. | *Cucurbita pepo* (Squash) | |
| A-35 | 66 | Florigene Pty Ltd. | Delayed senescence and sulfonylurea herbicide tolerant carnations produced by inserting a truncated copy of the carnation aminocyclopropane cyclase (ACC) synthase encoding gene, which is required for normal ethylene biosynthesis. Tolerance to sulfonyl urea herbicides was via the introduction of a chlorsulfuron tolerant version of the acetolactate synthase (ALS) encoding gene from tobacco. | *Dianthus caryophyllus* (Carnation) | |
| A-36 | 4, 11, 15, 16 | Florigene Pty Ltd. | Modified colour and sulfonylurea herbicide tolerant carnations produced by inserting two anthocyanin biosynthetic genes whose expression results in a violet/mauve colouration. Tolerance to sulfonyl urea herbicides was via the introduction of a chlorsulfuron tolerant version of the acetolactate synthase (ALS) encoding gene from tobacco. | *Dianthus caryophyllus* (Carnation) | |

TABLE A-continued

| | Event | Company | Description | Crop | Patent Ref |
|---|---|---|---|---|---|
| A-37 | 959A, 988A, 1226A, 1351A, 1363A, 1400A | Florigene Pty Ltd. | Introduction of two anthocyanin biosynthetic genes to result in a violet/mauve colouration; Introduction of a variant form of acetolactate synthase (ALS). | *Dianthus caryophyllus* (Carnation) | |
| A-38 | 3560.4.3.5 | | Glyphosate/ALS inhibitor-tolerance | *Glycine max* L. (Soybean) | WO 08/002872, US 2010184079 |
| A-39 | A2704-12, A2704-21 | Bayer CropScience (Aventis CropScience(AgrEvo)) | Glufosinate ammonium herbicide tolerant soybean produced by inserting a modified phosphinothricin acetyltransferase (PAT) encoding gene from the soil bacterium *Streptomyces viridochromogenes* | *Glycine max* L. (Soybean) | WO 06/108674 |
| A-40 | A5547-127 | Bayer CropScience (Aventis CropScience(AgrEvo)) | Glufosinate ammonium herbicide tolerant soybean produced by inserting a modified phosphinothricin acetyltransferase (PAT) encoding gene from the soil bacterium *Streptomyces viridochromogenes*. | *Glycine max* L. (Soybean) | |
| A-41 | A5547-35 | Bayer CropScience (Aventis CropScience(AgrEvo)) | Glufosinate tolerance | *Glycine max* L. (Soybean) | WO 06/108675 |
| A-42 | DP-305423-1 | Pioneer Hi-Bred International Inc. | High oleic acid/ALS inhibitor tolerance; | *Glycine max* L. (Soybean) | WO 08/054747 |
| A-43 | DP356043 | Pioneer Hi-Bred International Inc. | Soybean event with two herbicide tolerance genes: glyphosate N-acetyltransferase, which detoxifies glyphosate, and a modified acetolactate synthase (A | *Glycine max* L. (Soybean) | |
| A-44 | G94-1, G94-19, G168 | DuPont Canada Agricultural Products | High oleic acid soybean produced by inserting a second copy of the fatty acid desaturase (GmFad2-1) encoding gene from soybean, which resulted in "silencing" of the endogenous host gene. | *Glycine max* L. (Soybean) | |
| A-45 | GTS 40-3-2 | Monsanto Company | Glyphosate tolerant soybean variety produced by inserting a modified 5-enolpyruvylshikimate-3-phosphate synthase (EPSPS) encoding gene from the soil bacterium *Agrobacterium tumefaciens*. | *Glycine max* L. (Soybean) | |
| A-46 | GU262 | Bayer CropScience (Aventis CropScience(AgrEvo)) | Glufosinate ammonium herbicide tolerant soybean produced by inserting a modified phosphinothricin acetyltransferase (PAT) encoding gene from the soil bacterium *Streptomyces viridochromogenes*. | *Glycine max* L. (Soybean) | |
| A-47 | MON87701 | Monsanto Company | insect resistance (Cry1ac) | *Glycine max* L. (Soybean) | WO 09/064652 |
| A-48 | MON87705 | Monsanto Company | altered fatty acid levels (mid-oleic and low saturate) | *Glycine max* L. (Soybean) | WO 10/037016 |
| A-49 | MON87754 | Monsanto Company | increased oil content; | *Glycine max* L. (Soybean) | WO 10/024976 |
| A-50 | MON87769 | Monsanto Company | stearidonic acid (SDA) comprising oil; | *Glycine max* L. (Soybean) | WO 09/102873 |
| A-51 | MON89788 | Monsanto Company | Glyphosate-tolerant soybean produced by inserting a modified 5-enolpyruvylshikimate-3-phosphate synthase (EPSPS) encoding aroA (epsps) gene from *Agrobacterium tumefaciens* CP4; | *Glycine max* L. (Soybean) | WO 06/130436 |

TABLE A-continued

| | Event | Company | Description | Crop | Patent Ref |
|---|---|---|---|---|---|
| A-52 | MON19788 | Monsanto Company | Glyphosate-tolerant soybean produced by inserting a modified 5-enolpyruvylshikimate-3-phosphate synthase (EPSPS) encoding aroA (epsps) gene from *Agrobacterium tumefaciens* CP4; | *Glycine max* L. (Soybean) | WO 06/130437 |
| A-53 | OT96-15 | Agriculture & Agri-Food Canada | Low linolenic acid soybean produced through traditional cross-breeding to incorporate the novel trait from a naturally occurring fan1 gene mutant that was selected for low linolenic acid. | *Glycine max* L. (Soybean) | |
| A-54 | W62, W98 | Bayer CropScience (Aventis CropScience(AgrEvo)) | Glufosinate ammonium herbicide tolerant soybean produced by inserting a modified phosphinothricin acetyltransferase (PAT) encoding gene from the soil bacterium *Streptomyces hygroscopicus*. | *Glycine max* L. (Soybean) | |
| A-55 | 15985 | Monsanto Company | Insect resistant cotton derived by transformation of the DP50B parent variety, which contained event 531 (expressing Cry1Ac protein), with purified plasmid DNA containing the cry2Ab gene from *B. thuringiensis* subsp. *kurstaki*. |

TABLE A-continued

| | Event | Company | Description | Crop | Patent Ref |
|---|---|---|---|---|---|
| A-69 | Cot67B | Syngenta Seeds, Inc. | Insect-resistant cotton produced by inserting a full-length cry1Ab gene from *Bacillus thuringiensis*. The APH4 encoding gene from *E. coli* was introduced as a selectable marker. | *Gossypium hirsutum* L. (Cotton) | |
| A-70 | DAS-21Ø23-5 × DAS-24236-5 | DOW AgroSciences LLC | WideStrike ™, insect-resistant cotton derived from conventional cross-breeding of parental lines 3006-210-23 (OECD identifier: DAS-21Ø23-5) and 281-24-236 (OECD identifier: DAS-24236-5). | *Gossypium hirsutum* L. (Cotton) | |
| A-71 | DAS-21Ø23-5 × DAS-24236-5 × MON88913 | DOW AgroSciences LLC and Pioneer Hi-Bred International Inc. | Stacked insect-resistant and glyphosate-tolerant cotton derived from conventional cross-breeding of WideStrike cotton (OECD identifier: DAS-21Ø23-5 × DAS-24236-5) with MON88913, known as RoundupReady Flex (OECD identifier: MON-88913-8). | *Gossypium hirsutum* L. (Cotton) | |
| A-72 | DAS-21Ø23-5 × DAS-24236-5 × MON-Ø1445-2 | DOW AgroSciences LLC | WideStrike ™/Roundup Ready ® cotton, a stacked insect-resistant and glyphosate-tolerant cotton derived from conventional cross-breeding of WideStrike cotton (OECD identifier: DAS-21Ø23-5 × DAS-24236-5) with MON1445 (OECD identifier: MON-Ø1445-2). | *Gossypium hirsutum* L. (Cotton) | |
| A-73 | EE-GH3 | | Glyphosate tolerance | *Gossypium hirsutum* L. (Cotton) | WO 07/017186 |
| A-74 | EE-GH5 | | Insect resistance (Cry1Ab) | *Gossypium hirsutum* L. (Cotton) | WO 08/122406 |
| A-75 | EE-GH6 | | Insect resistance (cry2Ae) | *Gossypium hirsutum* L. (Cotton) | WO 08/151780, US 2010218281 |
| A-76 | event 281-24-236 | | Insect resistance (Cry1F) | *Gossypium hirsutum* L. (Cotton) | WO 05/103266 |
| A-77 | Event-1 | JK Agri Genetics Ltd (India) | Insect-resistant cotton produced by inserting the cry1Ac gene from *Bacillus thuringiensis* subsp. *kurstaki* HD-73 (B.t.k.). | *Gossypium hirsutum* L. (Cotton) | |
| A-78 | event3006-210-23 | | Insect resistance (Cry1Ac) | *Gossypium hirsutum* L. (Cotton) | WO 05/103266 |
| A-79 | GHB614 | Bayer CropScience (Aventis CropScience(AgrEvo)) | Glyphosate herbicide tolerant cotton produced by inserting 2mepsps gene into variety Coker312 by *Agrobacterium* under the control of Ph4a748At and TP0tpC | *Gossypium hirsutum* L. (Cotton) | |
| A-80 | LLCotton25 | Bayer CropScience (Aventis CropScience(AgrEvo)) | Glufosinate ammonium herbicide tolerant cotton produced by inserting a modified phosphinothricin acetyltransferase (PAT) encoding gene from the soil bacterium *Streptomyces hy groscopicus*; WO 2003013224, WO 2007/017186 | *Gossypium hirsutum* L. (Cotton) | |
| A-81 | LLCotton25 × MON15985 | Bayer CropScience (Aventis CropScience(AgrEvo)) | Stacked herbicide tolerant and insect resistant cotton combining tolerance to glufosinate ammonium herbicide from LLCotton25 (OECD identifier: ACS-GHØØ1-3) with resistance to insects from MON15985 (OECD identifier: MON-15985-7) | *Gossypium hirsutum* L. (Cotton) | |
| A-82 | MON 15985 | Monsanto Company | Insect resistance (Cry1A/Cry2Ab) | *Gossypium hirsutum* L. (Cotton) | US 2004250317 |
| A-83 | MON1445/1698 | | Glyphosate herbicide tolerant cotton produced by inserting a naturally glyphosate tolerant form of the enzyme 5-enolpyruvyl shikimate-3-phosphate synthase (EPSPS) from *A. tumefaciens* strain CP4. | *Gossypium hirsutum* L. (Cotton) | |

TABLE A-continued

| | Event | Company | Description | Crop | Patent Ref |
|---|---|---|---|---|---|
| A-84 | MON15985 × MON88913 | Monsanto Company | Stacked insect resistant and glyphosate tolerant cotton produced by conventional cross-breeding of the parental lines MON88913 (OECD identifier: MON-88913-8) and 15985 (OECD identifier: MON-15985-7). Glyphosate tolerance is derived from MON88913 which contains two genes encoding the enzyme 5-enolpyruvylshikimate-3-phosphate synthase (EPSPS) from the CP4 strain of *Agrobacterium tumefaciens*. Insect resistance is derived MON15985 which was produced by transformation of the DP50B parent variety, which contained event 531 (expressing Cry1Ac protein), with purified plasmid DNA containing the cry2Ab gene from *B. thuringiensis* subsp. *kurstaki*. | *Gossypium hirsutum* L. (Cotton) | |
| A-85 | MON-15985-7 × MON-01445-2 | Monsanto Company | Stacked insect resistant and herbicide tolerant cotton derived from conventional cross-breeding of the parental lines 15985 (OECD identifier: MON-15985-7) and MON1445 (OECD identifier: MON-01445-2). | *Gossypium hirsutum* L. (Cotton) | |
| A-86 | MON531/757/1076 | Monsanto Company | Insect-resistant cotton produced by inserting the cry1Ac gene from *Bacillus thuringiensis* subsp. *kurstaki* HD-73 (B.t.k.). | *Gossypium hirsutum* L. (Cotton) | |
| A-87 | LLcotton25 | | Glufosinate resistance | *Gossypium hirsutum* L. (Cotton) | WO 03/013224 |
| A-88 | MON88913 | Monsanto Company | Glyphosate herbicide tolerant cotton produced by inserting two genes encoding the enzyme 5-enolpyruvylshikimate-3-phosphate synthase (EPSPS) from the CP4 strain of *Agrobacterium tumefaciens*. | *Gossypium hirsutum* L. (Cotton) | WO 04/072235 |
| A-89 | MON-00531-6 × MON-01445-2 | Monsanto Company | Stacked insect resistant and herbicide tolerant cotton derived from conventional cross-breeding of the parental lines MON531 (OECD identifier: MON-00531-6) and MON1445 (OECD identifier: MON-01445-2). | *Gossypium hirsutum* L. (Cotton) | |
| A-90 | PV-GHGT07 (1445) | | Glyphosate tolerance | *Gossypium hirsutum* L. (Cotton) | US 2004148666 |
| A-91 | T304-40 | | Insect-resistance (Cry1Ab) | *Gossypium hirsutum* L. (Cotton) | WO 08/122406, US 2010077501 |
| A-92 | T342-142 | | Insect resistance (Cry1Ab) | *Gossypium hirsutum* L. (Cotton) | WO 06/128568 |
| A-93 | X81359 | BASF Inc. | Tolerance to imidazolinone herbicides by selection of a naturally occurring mutant. | *Helianthus annuus* (Sunflower) | |
| A-94 | RH44 | BASF Inc. | Selection for a mutagenized version of the enzyme acetohydroxyacid synthase (AHAS), also known as acetolactate synthase (ALS) or acetolactate pyruvate-lyase. | *Lens culinaris* (Lentil) | |
| A-95 | FP967 | University of Saskatchewan, Crop Dev. Centre | A variant form of acetolactate synthase (ALS) was obtained from a chlorsulfuron tolerant line of *A. thaliana* and used to transform flax. | *Linum usitatissimum* L. (Flax, Linseed) | |
| A-96 | 5345 | Monsanto Company | Resistance to lepidopteran pests through the introduction of the cry1Ac gene from *Bacillus thuringiensis* subsp. *Kurstaki*. | *Lycopersicon esculentum* (Tomato) | |
| A-97 | 8338 | Monsanto Company | Introduction of a gene sequence encoding the enzyme 1-amino-cyclopropane-1-carboxylic acid deaminase (ACCd) that metabolizes the precursor of the fruit ripening hormone ethylene. | *Lycopersicon esculentum* (Tomato) | |

TABLE A-continued

| | Event | Company | Description | Crop | Patent Ref |
|---|---|---|---|---|---|
| A-98 | 1345-4 | DNA Plant Technology Corporation | Delayed ripening tomatoes produced by inserting an additional copy of a truncated gene encoding 1-aminocyclopropane-1-carboxyllic acid (ACC) synthase, which resulted in downregulation of the endogenous ACC synthase and reduced ethylene accumulation. | *Lycopersicon esculentum* (Tomato) | |
| A-99 | 35 1 N | Agritope Inc. | Introduction of a gene sequence encoding the enzyme S-adenosylmethionine hydrolase that metabolizes the precursor of the fruit ripening hormone ethylene | *Lycopersicon esculentum* (Tomato) | |
| A-100 | B, Da, F | Zeneca Seeds | Delayed softening tomatoes produced by inserting a truncated version of the polygalacturonase (PG) encoding gene in the sense or anti-sense orientation in order to reduce expression of the endogenous PG gene, and thus reduce pectin degradation. | *Lycopersicon esculentum* (Tomato) | |
| A-101 | FLAVR SAVR | Calgene Inc. | Delayed softening tomatoes produced by inserting an additional copy of the polygalacturonase (PG) encoding gene in the anti-sense orientation in order to reduce expression of the endogenous PG gene and thus reduce pectin degradation. | *Lycopersicon esculentum* (Tomato) | |
| A-102 | J101, J163 | Monsanto Company and Forage Genetics International | Glyphosate herbicide tolerant alfalfa (lucerne) produced by inserting a gene encoding the enzyme 5-enolpyruvylshikimate-3-phosphate synthase (EPSPS) from the CP4 strain of *Agrobacterium tumefaciens*. | *Medicago sativa* (Alfalfa) | |
| A-103 | C/F/93/08-02 | Societe National d'Exploitation des Tabacs et Allumettes | Tolerance to the herbicides bromoxynil and ioxynil by incorporation of the nitrilase gene from *Klebsiella pneumoniae*. | *Nicotiana tabacum* L. (Tobacco) | |
| A-104 | Vector 21-41 | Vector Tobacco Inc. | Reduced nicotine content through introduction of a second copy of the tobacco quinolinic acid phosphoribosyltransferase (QTPase) in the antisense orientation. The NPTII encoding gene from *E. coli* was introduced as a selectable marker to identify transformants. | *Nicotiana tabacum* L. (Tobacco) | |
| A-105 | CL121, CL141, CFX51 | BASF Inc. | Tolerance to the imidazolinone herbicide, imazethapyr, induced by chemical mutagenesis of the acetolactate synthase (ALS) enzyme using ethyl methanesulfonate (EMS). | *Oryza sativa* (Rice) | |
| A-106 | GAT-OS2 | | Glufosinate tolerance | *Oryza sativa* (Rice) | WO 01/83818 |
| A-107 | GAT-OS3 | | Glufosinate tolerance | *Oryza sativa* (Rice) | US 2008289060 |
| A-108 | IMINTA-1, IMINTA-4 | BASF Inc. | Tolerance to imidazolinone herbicides induced by chemical mutagenesis of the acetolactate synthase (ALS) enzyme using sodium azide. | *Oryza sativa* (Rice) | |
| A-109 | LLRICE06, LLRICE62 | Aventis CropScience | Glufosinate ammonium herbicide tolerant rice produced by inserting a modified phosphinothricin acetyltransferase (PAT) encoding gene from the soil bacterium *Streptomyces hygroscopicus*. | *Oryza sativa* (Rice) | |
| A-110 | LLRICE601 | Bayer CropScience (Aventis CropScience(AgrEvo)) | Glufosinate ammonium herbicide tolerant rice produced by inserting a modified phosphinothricin acetyltransferase (PAT) encoding gene from the soil bacterium *Streptomyces hygroscopicus*. | *Oryza sativa* (Rice) | WO 08/114282 |
| A-111 | PE-7 | | Insect resistance (Cry1Ac) | *Oryza sativa* (Rice) | |
| A-112 | PWC16 | BASF Inc. | Tolerance to the imidazolinone herbicide, imazethapyr, induced by chemical mutagenesis of the acetolactate synthase (ALS) enzyme using ethyl methanesulfonate (EMS). | *Oryza sativa* (Rice) | |
| A-113 | TT51 | | Insect resistance (Cry1Ab/Cry1Ac) | *Oryza sativa* (Rice) | CN 1840655 |
| A-114 | C5 | United States Department of Agriculture - Agricultural Research Service | Plum pox virus (PPV) resistant plum tree produced through *Agrobacterium*-mediated transformation with a coat protein (CP) gene from the virus. | *Prunus domestica* (Plum) | |

TABLE A-continued

| | Event | Company | Description | Crop | Patent Ref |
|---|---|---|---|---|---|
| A-115 | ATBT04-6, ATBT04-27, ATBT04-30, ATBT04-31, ATBT04-36, SPBT02-5, SPBT02-7 | Monsanto Company | Colorado potato beetle resistant potatoes produced by inserting the cry3A gene from *Bacillus thuringiensis* (subsp. *Tenebrionis*). | *Solanum tuberosum* L. (Potato) | |
| A-116 | BT6, BT10, BT12, BT16, BT17, BT18, BT23 | Monsanto Company | Colorado potato beetle resistant potatoes produced by inserting the cry3A gene from *Bacillus thuringiensis* (subsp. *Tenebrionis*). | *Solanum tuberosum* L. (Potato) | |
| A-117 | RBMT15-101, SEMT15-02, SEMT15-15 | Monsanto Company | Colorado potato beetle and potato virus Y (PVY) resistant potatoes produced by inserting the cry3A gene from *Bacillus thuringiensis* (subsp. *Tenebrionis*) and the coat protein encoding gene from PVY. | *Solanum tuberosum* L. (Potato) | |
| A-118 | RBMT21-129, RBMT21-350, RBMT22-082 | Monsanto Company | Colorado potato beetle and potato leafroll virus (PLRV) resistant potatoes produced by inserting the cry3A gene from *Bacillus thuringiensis* (subsp. *Tenebrionis*) and the replicase encoding gene from PLRV. | *Solanum tuberosum* L. (Potato) | |
| A-119 | EH92-527 | BASF Plant Science | Crop composition; Amflora; Unique EU identifier: BPS-25271-9 | *Solanum tuberosum* L. (Potato) | |
| A-120 | AP205CL | BASF Inc. | Selection for a mutagenized version of the enzyme acetohydroxyacid synthase (AHAS), also known as acetolactate synthase (ALS) or acetolactate pyruvate-lyase. | *Triticum aestivum* (Wheat) | |
| A-121 | AP602CL | BASF Inc. | Selection for a mutagenized version of the enzyme acetohydroxyacid synthase (AHAS), also known as acetolactate synthase (ALS) or acetolactate pyruvate-lyase. | *Triticum aestivum* (Wheat) | |
| A-122 | BW255-2, BW238-3 | BASF Inc. | Selection for a mutagenized version of the enzyme acetohydroxyacid synthase (AHAS), also known as acetolactate synthase (ALS) or acetolactate pyruvate-lyase. | *Triticum aestivum* (Wheat) | |
| A-123 | BW7 | BASF Inc. | Tolerance to imidazolinone herbicides induced by chemical mutagenesis of the acetohydroxyacid synthase (AHAS) gene using sodium azide. | *Triticum aestivum* (Wheat) | |
| A-124 | Event 1 | | *Fusarium* resistance (trichothecene 3-O-acetyltransferase). | *Triticum aestivum* (Wheat) | CA 2561992 |
| A-125 | JOPLIN1 | | disease (fungal) resistance (trichothecene 3-O-acetyltransferase). | *Triticum aestivum* (Wheat) | US 2008064032 |

TABLE A-continued

| | Event | Company | Description | Crop | Patent Ref |
|---|---|---|---|---|---|
| A-126 | MON71800 | Monsanto Company | Glyphosate tolerant wheat variety produced by inserting a modified 5-enolpyruvylshikimate-3-phosphate synthase (EPSPS) encoding gene from the soil bacterium *Agrobacterium tumefaciens*, strain CP4. | *Triticum aestivum* (Wheat) | |
| A-127 | SWP965001 | Cyanamid Crop Protection | Selection for a mutagenized version of the enzyme acetohydroxyacid synthase (AHAS), also known as acetolactate synthase (ALS) or acetolactate pyruvate-lyase. | *Triticum aestivum* (Wheat) | |
| A-128 | Teal 11A | BASF Inc. | Selection for a mutagenized version of the enzyme acetohydroxyacid synthase (AHAS), also known as acetolactate synthase (ALS) or acetolactate pyruvate-lyase. | *Triticum aestivum* (Wheat) | |
| A-129 | 176 | Syngenta Seeds, Inc. | Insect-resistant maize produced by inserting the cry1Ab gene from *Bacillus thuringiensis* subsp. *kurstaki*. The genetic modification affords resistance to attack by the European corn borer (ECB). | *Zea mays* L. (Maize) | |
| A-130 | 3272 | Syngenta Seeds, Inc. | Self processing corn (alpha-amylase). | *Zea mays* L. (Maize) | US 2006230473, US 2010063265 |
| A-131 | 3751IR | Pioneer Hi-Bred International Inc. | Selection of somaclonal variants by culture of embryos on imidazolinone containing media. | *Zea mays* L. (Maize) | |
| A-132 | 676, 678, 680 | Pioneer Hi-Bred International Inc. | Male-sterile and glufosinate ammonium herbicide tolerant maize produced by inserting genes encoding DNA adenine methylase and phosphinothricin acetyltransferase (PAT) from *Escherichia coli* and *Streptomyces viridochromogenes*, respectively. | *Zea mays* L. (Maize) | |
| A-133 | ACS-ZMØØ3-2 × MON-ØØ81Ø-6 | Bayer CropScience (Aventis CropScience(AgrEvo)) | Stacked insect resistant and herbicide tolerant corn hybrid derived from conventional cross-breeding of the parental lines T25 (OECD identifier: ACS-ZMØØ3-2) and MON810 (OECD identifier: MON-OØ81O-6). | *Zea mays* L. (Maize) | |
| A-134 | B16 | Dekalb Genetics Corporation | Glufosinate resistance | *Zea mays* L. (Maize) | US 2003126634 |
| A-135 | B16 (DLL25) | | Glufosinate ammonium herbicide tolerant maize produced by inserting the gene encoding phosphinothricin acetyltransferase (PAT) from *Streptomyces hygroscopicus*. | *Zea mays* L. (Maize) | |
| A-136 | BT11 (X4334CBR, X4734CBR) | Syngenta Seeds, Inc. | Insect-resistant and herbicide tolerant maize produced by inserting the cry 1Ab gene from *Bacillus thuringiensis* subsp. *kurstaki*, and the phosphinothricin N-acetyltransferase (PAT) encoding gene from *S. viridochromogenes*. | *Zea mays* L. (Maize) | WO 10/148268 |
| A-137 | BT11 × GA21 | Syngenta Seeds, Inc. | Stacked insect resistant and herbicide tolerant maize produced by conventional cross breeding of parental lines BT11 (OECD unique identifier: SYN-BTØ11-1) and GA21 (OECD unique identifier: MON-ØØ021-9). | *Zea mays* L. (Maize) | |
| A-138 | BT11 × MIR162 | Syngenta Seeds, Inc. | Stacked insect resistant and herbicide tolerant maize produced by conventional cross breeding of parental lines BT11 (OECD unique identifier: SYN-BTØ11-1) and MIR162 (OECD unique identifier: SYN-IR162-4). Resistance to the European Corn Borer and tolerance to the herbicide glufosinate ammonium (Liberty) is derived from BT11, which contains the cry1Ab gene from *Bacillus thuringiensis* subsp. *kurstaki*, and the phosphinothricin N-acetyltransferase (PAT) encoding gene from *S. viridochromogenes*. Resistance to other lepidopteran pests, including *H. zea*, *S. frugiperda*, *A. ipsilon*, and *S. albicosta*, is derived from MIR162, which contains the vip3Aa gene from *Bacillus thuringiensis* strain AB88. | *Zea mays* L. (Maize) | |

TABLE A-continued

| | Event | Company | Description | Crop | Patent Ref |
|---|---|---|---|---|---|
| A-139 | BT11 × MIR162 × MIR604 | Syngenta Seeds, Inc. | *Bacillus thuringiensis* Cry1Ab delta-endotoxin protein and the genetic material necessary for its production (via elements of vector pZO1502) in Event Bt11 corn (OECD Unique Identifier: SYN-BT011-1) × *Bacillus thuringiensis* Vip3Aa20 insecticidal protein and the genetic material necessary for its production (via elements of vector pNOV1300) in Event MIR162 maize (OECD Unique Identifier: SYN-IR162-4) × modified Cry3A protein and the genetic material necessary for its production (via elements of vector pZM26) in Event MIR604 corn (OECD Unique Identifier: SYN-IR604-5). | *Zea mays* L. (Maize) | |
| A-140 | BT11 × MIR604 | Syngenta Seeds, Inc. | Stacked insect resistant and herbicide tolerant maize produced by conventional cross breeding of parental lines BT11 (OECD unique identifier: SYN-BT011-1) and MIR604 (OECD unique identifier: SYN-IR605-5). Resistance to the European Corn Borer and tolerance to the herbicide glufosinate ammonium (Liberty) is derived from BT11, which contains the cry1Ab gene from *Bacillus thuringiensis* subsp. *kurstaki*, and the phosphinothricin N-acetyltransferase (PAT) encoding gene from *S. viridochromogenes*. Corn rootworm-resistance is derived from MIR604 which contains the mcry3A gene from *Bacillus thuringiensis*. | *Zea mays* L. (Maize) | |
| A-141 | BT11 × MIR604 × GA21 | Syngenta Seeds, Inc. | Stacked insect resistant and herbicide tolerant maize produced by conventional cross breeding of parental lines BT11 (OECD unique identifier: SYN-BT011-1), MIR604 (OECD unique identifier: SYN-IR605-5) and GA21 (OECD unique identifier: MON-00021-9). Resistance to the European Corn Borer and tolerance to the herbicide glufosinate ammonium (Liberty) is derived from BT11, which contains the cry1Ab gene from *Bacillus thuringiensis* subsp. *kurstaki*, and the phosphinothricin N-acetyltransferase (PAT) encoding gene from *S. viridochromogenes*. Corn rootworm-resistance is derived from MIR604 which contains the mcry3A gene from *Bacillus thuringiensis*. Tolerance to glyphosate herbicide is derived from GA21 which contains a a modified EPSPS gene from maize. | *Zea mays* L. (Maize) | |
| A-142 | CBH-351 | Aventis CropScience | Insect-resistant and glufosinate ammonium herbicide tolerant maize developed by inserting genes encoding Cry9C protein from *Bacillus thuringiensis* subsp *tolworthi* and phosphinothricin acetyltransferase (PAT) from *Streptomyces hygroscopicus*. | *Zea mays* L. (Maize) | |
| A-143 | DAS-06275-8 | DOW AgroSciences LLC | Lepidopteran insect resistant and glufosinate ammonium herbicide-tolerant maize variety produced by inserting the cry1F gene from *Bacillus thuringiensis var aizawai* and the phosphinothricin acetyltransferase (PAT) from *Streptomyces hygroscopicus*. | *Zea mays* L. (Maize) | |
| A-144 | DAS-59122-7 | DOW AgroSciences LLC and Pioneer Hi-Bred International Inc. | Corn rootworm-resistant maize produced by inserting the cry34Ab1 and cry35Ab1 genes from *Bacillus thuringiensis* strain PS149B1. The PAT encoding gene from *Streptomyces viridochromogenes* was introduced as a selectable marker | *Zea mays* L. (Maize) | US 2006070139, US 2011030086 |

TABLE A-continued

| | Event | Company | Description | Crop | Patent Ref |
|---|---|---|---|---|---|
| A-145 | DAS-59122-7 × NK603 | DOW AgroSciences LLC and Pioneer Hi-Bred International Inc. | Stacked insect resistant and herbicide tolerant maize produced by conventional cross breeding of parental lines DAS-59122-7 (OECD unique identifier: DAS-59122-7) with NK603 (OECD unique identifier: MON-00603-6). Corn rootworm-resistance is derived from DAS-59122-7 which contains the cry34Ab1 and cry35Ab1 genes from *Bacillus thuringiensis* strain PS149B1. Tolerance to glyphosate herbicide is derived from NK603. | *Zea mays* L. (Maize) | |
| A-146 | DAS-59122-7 × TC1507 × NK603 | DOW AgroSciences LLC and Pioneer Hi-Bred International Inc. | Stacked insect resistant and herbicide tolerant maize produced by conventional cross breeding of parental lines DAS-59122-7 (OECD unique identifier: DAS-59122-7) and TC1507 (OECD unique identifier: DAS-015O7-1) with NK603 (OECD unique identifier: MON-00603-6). Corn rootworm-resistance is derived from DAS-59122-7 which contains the cry34Ab1 and cry35Ab1 genes from *Bacillus thuringiensis* strain PS149B1. Lepidopteran resistance and tolerance to glufosinate ammonium herbicide is derived from TC1507. Tolerance to glyphosate herbicide is derived from NK603. | *Zea mays* L. (Maize) | |
| A-147 | DAS-015O7-1 × MON-00603-6 | DOW AgroSciences LLC | Stacked insect resistant and herbicide tolerant corn hybrid derived from conventional cross-breeding of the parental lines 1507 (OECD identifier: DAS-015O7-1) and NK603 (OECD identifier: MON-00603-6). | *Zea mays* L. (Maize) | |
| A-148 | DBT418 | Dekalb Genetics Corporation | Insect-resistant and glufosinate ammonium herbicide tolerant maize developed by inserting genes encoding Cry1AC protein from *Bacillus thuringiensis* subsp *kurstaki* and phosphinothricin acetyltransferase (PAT) from *Streptomyces hygroscopicus* | *Zea mays* L. (Maize) | |
| A-149 | DK404SR | BASF Inc. | Somaclonal variants with a modified acetyl-CoA-carboxylase (ACCase) were selected by culture of embryos on sethoxydim enriched medium. | *Zea mays* L. (Maize) | |
| A-150 | DP-098140-6 | | Glyphosate tolerance/ALS inhibitor tolerance | *Zea mays* L. (Maize) | WO 08/112019, US 2010240059 |
| A-151 | DP-098140-6 (Event 98140) | Pioneer Hi-Bred International Inc. | Corn line 98140 was genetically engineered to express the GAT4621 (glyphosate acetyltransferase) and ZM-HRA (modified version of a maize acetolactate synthase) proteins. The GAT4621 protein, encoded by the gat4621 gene, confers tolerance to glyphosate-containing herbicides by acetylating glyphosate and thereby rendering it non-phytotoxic. The ZM-HRA protein, encoded by the zm-hra gene, confers tolerance to the ALS-inhibiting class of herbicides. | *Zea mays* L. (Maize) | |
| A-152 | Event 3272 | Syngenta Seeds, Inc. | Maize line expressing a heat stable alpha-amylase gene amy797E for use in the dry-grind ethanol process. The phosphomannose isomerase gene from *E. coli* was used as a selectable marker. | *Zea mays* L. (Maize) | |
| A-153 | Event 98140 | Pioneer Hi-Bred International Inc. | Maize event expressing tolerance to glyphosate herbicide, via expression of a modified bacterial glyphosate N-acetyltransferase, and ALS-inhibiting herbicides, via expression of a modified form of the maize acetolactate synthase enzyme. | *Zea mays* L. (Maize) | |

TABLE A-continued

| | Event | Company | Description | Crop | Patent Ref |
|---|---|---|---|---|---|
| A-154 | EXP1910IT | Syngenta Seeds, Inc. (formerly Zeneca Seeds) | Tolerance to the imidazolinone herbicide, imazethapyr, induced by chemical mutagenesis of the acetolactate synthase (ALS) enzyme using ethyl methanesulfonate (EMS). | Zea mays L. (Maize) | |
| A-155 | FI117 | | Glyphosate resistance | Zea mays L. (Maize) | U.S. Pat. No. 6,040,497 |
| A-156 | GA21 | Monsanto Company | Glyphosate resistance: Introduction, by particle bombardment, of a modified 5-enolpyruvyl shikimate-3-phosphate synthase (EPSPS), an enzyme involved in the shikimate bio-chemical pathway for the production of the aromatic amino acids; | Zea mays L. (Maize) | U.S. Pat. No. 6,040,497 |
| A-157 | GA21 × MON810 | Monsanto Company | Stacked insect resistant and herbicide tolerant corn hybrid derived from conventional cross-breeding of the parental lines GA21 (OECD identifier: MON-00021-9) and MON810 (OECD identifier: MON-00810-6). | Zea mays L. (Maize) | |
| A-158 | GAT-ZM1 | | Glufosinate tolerance | Zea mays L. (Maize) | WO 01/51654 |
| A-159 | GG25 | | Glyphosate resistance | Zea mays L. (Maize) | U.S. Pat. No. 6,040,497 |
| A-160 | GJ11 | | Glyphosate resistance; U.S. Pat. No. 6,040,497 | Zea mays L. (Maize) | |
| A-161 | IT | Pioneer Hi-Bred International Inc. | Tolerance to the imidazolinone herbicide, imazethapyr, was obtained by in vitro selection of somaclonal variants. | Zea mays L. (Maize) | |
| A-162 | LY038 | Monsanto Company | Altered amino acid composition, specifically elevated levels of lysine, through the introduction of the cordapA gene, derived from Corynebacterium glutamicum, encoding the enzyme dihydrodipicolinate synthase (cDHDPS). | Zea mays L. (Maize) | U.S. Pat. No. 7,157,281, US 2010212051; US 2007028322 |
| A-163 | MIR162 | Syngenta Seeds, Inc. | Insect resistance | Zea mays L. (Maize) | WO 07/142840 |
| A-164 | MIR604 | | Corn rootworm resistant maize produced by transformation with a modified cry3A gene. The phosphomannose isomerase gene from E. coli was used as a selectable marker; (Cry3a055) | Zea mays L. (Maize) | EP 1737290 |
| A-165 | MIR604 × GA21 | Syngenta Seeds, Inc. | Stacked insect resistant and herbicide tolerant maize produced by conventional cross breeding of parental lines MIR604 (OECD unique identifier: SYN-IR605-5) and GA21 (OECD unique identifier: MON-00021-9). Corn rootworm-resistance is derived from MIR604 which contains the mcry3A gene from Bacillus thuringiensis. Tolerance to glyphosate herbicide is derived from GA21. | Zea mays L. (Maize) | |
| A-166 | MON80100 | Monsanto Company | Insect-resistant maize produced by inserting the cry1Ab gene from Bacillus thuringiensis subsp. kurstaki. The genetic modification affords resistance to attack by the European corn borer (ECB). | Zea mays L. (Maize) | |
| A-167 | MON802 | Monsanto Company | Insect-resistant and glyphosate herbicide tolerant maize produced by inserting the genes encoding the Cry1Ab protein from Bacillus thuringiensis and the 5-enolpyruvylshikimate-3-phosphate synthase (EPSPS) from A. tumefaciens strain CP4. | Zea mays L. (Maize) | |
| A-168 | MON809 | Pioneer Hi-Bred International Inc. | Resistance to European corn borer (Ostrinia nubilalis) by introduction of a synthetic cry1Ab gene. Glyphosate resistance via introduction of the bacterial version of a plant enzyme, 5-enolpyruvyl shikimate-3-phosphate synthase (EPSPS). | Zea mays L. (Maize) | |

TABLE A-continued

| | Event | Company | Description | Crop | Patent Ref |
|---|---|---|---|---|---|
| A-169 | MON810 | Monsanto Company | Insect-resistant maize produced by inserting a truncated form of the cry1Ab gene from *Bacillus thuringiensis* subsp. *kurstaki* HD-1. The genetic modification affords resistance to attack by the European corn borer (ECB); | *Zea mays* L. (Maize) | US 2004180373 |
| A-170 | MON810 × MON88017 | Monsanto Company | Stacked insect resistant and glyphosate tolerant maize derived from conventional cross-breeding of the parental lines MON88017 (OECD identifier: MON-Ø88Ø17-3). European corn borer (ECB) resistance is derived from a truncated form of the cry1Ab gene in MON810. Corn rootworm resistance is derived from the cry3Bb1 gene from *Bacillus thuringiensis* subspecies *kumamotoensis* strain EG4691 present in MON88017. Glyphosate tolerance is derived from a 5-enolpyruvylshikimate-3-phosphate synthase (EPSPS) encoding gene from *Agrobacterium tumefaciens* strain CP4 present in MON88017. | *Zea mays* L. (Maize) | |
| A-171 | MON832 | Monsanto Company | Introduction, by particle bombardment, of glyphosate oxidase (GOX) and a modified 5-enolpyruvyl shikimate-3-phosphate synthase (EPSPS), an enzyme involved in the shikimate biochemical pathway for the production of the aromatic amino acids. | *Zea mays* L. (Maize) | |
| A-172 | MON863 | Monsanto Company | Corn root worm resistant maize produced by inserting the cry3Bb1 gene from *Bacillus thuringiensis* subsp. *kumamotoensis*. | *Zea mays* L. (Maize) | |
| A-173 | MON863 × MON810 | Monsanto Company | Stacked insect resistant corn hybrid derived from conventional cross-breeding of the parental lines MON863 (OECD identifier: MON-Ø0863-5) and MON810 (OECD identifier: MON-Ø0810-6) | *Zea mays* L. (Maize) | |
| A-174 | MON863 × MON810 × NK603 | Monsanto Company | Stacked insect resistant and herbicide tolerant corn hybrid derived from conventional cross-breeding of the stacked hybrid MON-Ø0863-5 × MON-Ø0810-6 and NK603 (OECD identifier: MON-Ø0603-6). | *Zea mays* L. (Maize) | |
| A-175 | MON863 × NK603 | Monsanto Company | Stacked insect resistant and herbicide tolerant corn hybrid derived from conventional cross-breeding of the parental lines MON863 (OECD identifier: MON-Ø0863-5) and NK603 (OECD identifier: MON-Ø0603-6). | *Zea mays* L. (Maize) | |
| A-176 | MON87460 | Monsanto Company | Drought tolerance; Water deficit tolerance; | *Zea mays* L. (Maize) | WO 09/111263 |
| A-177 | MON88017 | Monsanto Company | Corn rootworm resistant maize produced by inserting the cry3Bb1 gene from *Bacillus thuringiensis* subspecies *kumamotoensis* strain EG4691. Glyphosate tolerance derived by inserting a 5-enolpyruvylshikimate-3-phosphate synthase (EPSPS) encoding gene from *Agrobacterium tumefaciens* strain CP4 (Glyphosate tolerance); | *Zea mays* L. (Maize) | WO 05/059103 |
| A-178 | MON89034 | Monsanto Company | Maize event expressing two different insecticidal proteins from *Bacillus thuringiensis* providing resistance to number of lepidopteran pests; nsect resistance (*Lepidoptera* - Cry1A.105-Cry2Ab); | *Zea mays* L. (Maize) | WO 07/140256 |

TABLE A-continued

| | Event | Company | Description | Crop | Patent Ref |
|---|---|---|---|---|---|
| A-179 | MON89034 × MON88017 | Monsanto Company | Stacked insect resistant and glyphosate tolerant maize derived from conventional cross-breeding of the parental lines MON89034 (OECD identifier: MON-89034-3) and MON88017 (OECD identifier: MON-88017-3). Resistance to Lepiopteran insects is derived from two crygenes present in MON89043. Corn rootworm resistance is derived from a single cry genes and glyphosate tolerance is derived from the 5-enolpyruvylshikimate-3-phosphate synthase (EPSPS) encoding gene from *Agrobacterium tumefaciens* present in MON88017. | *Zea mays* L. (Maize) | |
| A-180 | MON89034 × NK603 | Monsanto Company | Stacked insect resistant and herbicide tolerant maize produced by conventional cross breeding of parental lines MON89034 (OECD identifier: MON-89034-3) with NK603 (OECD unique identifier: MON-00603-6). Resistance to Lepiopteran insects is derived from two crygenes present in MON89043. Tolerance to glyphosate herbicide is derived from NK603. | *Zea mays* L. (Maize) | |
| A-181 | MON89034 × TC1507 × MON88017 × DAS-59122-7 | Monsanto Company | Stacked insect resistant and herbicide tolerant maize produced by conventional cross breeding of parental lines: MON89034, TC1507, MON88017, and DAS-59122. Resistance to the above-ground and below-ground insect pests and tolerance to glyphosate and glufosinate-ammonium containing herbicides. | *Zea mays* L. (Maize) | |
| A-182 | MON-00603-6 × MON-00810-6 | Monsanto Company | Stacked insect resistant and herbicide tolerant corn hybrid derived from conventional cross-breeding of the parental lines NK603 (OECD identifier: MON-00603-6) and MON810 (OECD identifier: MON-00810-6). | *Zea mays* L. (Maize) | |
| A-183 | MON-00810-6 × LY038 | Monsanto Company | Stacked insect resistant and enhanced lysine content maize derived from conventional cross-breeding of the parental lines MON810 (OECD identifier: MON-00810-6) and LY038 (OECD identifier: REN-00038-3). | *Zea mays* L. (Maize) | |
| A-184 | MON-00863-5 × MON-00603-6 | Monsanto Company | Stacked insect resistant and herbicide tolerant corn hybrid derived from conventional cross-breeding of the parental lines MON863 (OECD identifier: MON-00863-5) and NK603 (OECD identifier: MON-00603-6). | *Zea mays* L. (Maize) | |
| A-185 | MON-00863-5 × MON-00810-6 | Monsanto Company | Stacked insect resistant corn hybrid derived from conventional cross-breeding of the parental lines MON863 (OECD identifier: MON-00863-5) and MON810 (OECD identifier: MON-00810-6) | *Zea mays* L. (Maize) | |
| A-186 | MON-00863-5 × MON-00810-6 × MON-00603-6 | Monsanto Company | Stacked insect resistant and herbicide tolerant corn hybrid derived from conventional cross-breeding of the stacked hybrid MON-00863-5 × MON-00810-6 and NK603 (OECD identifier: MON-00603-6). | *Zea mays* L. (Maize) | |
| A-187 | MON-00021-9 × MON-00810-6 | Monsanto Company | Stacked insect resistant and herbicide tolerant corn hybrid derived from conventional cross-breeding of the parental lines GA21 (OECD identifier: MON-00021-9) and MON810 (OECD identifier: MON-00810-6). | *Zea mays* L. (Maize) | |

TABLE A-continued

| | Event | Company | Description | Crop | Patent Ref |
|---|---|---|---|---|---|
| A-188 | MS3 | Bayer CropScience (Aventis CropScience(AgrEvo)) | Male sterility caused by expression of the barnase ribonuclease gene from *Bacillus amyloliquefaciens*; PPT resistance was via PPT-acetyltransferase (PAT). | *Zea mays* L. (Maize) | |
| A-189 | MS6 | Bayer CropScience (Aventis CropScience(AgrEvo)) | Male sterility caused by expression of the barnase ribonuclease gene from *Bacillus amyloliquefaciens*; PPT resistance was via PPT-acetyltransferase (PAT). | *Zea mays* L. (Maize) | |
| A-190 | NK603 | Monsanto Company | Introduction, by particle bombardment, of a modified 5-enolpyruvyl shikimate-3-phosphate synthase (EPSPS), an enzyme involved in the shikimate biochemical pathway for the production of the aromatic amino acids. | *Zea mays* L. (Maize) | |
| A-191 | NK603 × MON810 | Monsanto Company | Stacked insect resistant and herbicide tolerant corn hybrid derived from conventional cross-breeding of the parental lines NK603 (OECD identifier: MON-00603-6) and MON810 (OECD identifier: MON-00810-6). | *Zea mays* L. (Maize) | |
| A-192 | NK603 × T25 | Monsanto Company | Stacked glufosinate ammonium and glyphosate herbicide tolerant maize hybrid derived from conventional cross-breeding of the parental lines NK603 (OECD identifier: MON-00603-6) and T25 (OECD identifier: ACS-ZM003-2). | *Zea mays* L. (Maize) | |
| A-193 | PV-ZMGT32 (NK603) | | Glyphosate tolerance | *zea mays* L. (Maize) | US 200705605 |
| A-194 | E6611.32.1.38/DP-32138-1/32138 | Pioneer Hi-Bred International Inc. | 1) MS45: anther-specific 5126 (*Zea mays*) promoter > fertility restoration Ms45 (*Zea mays*) coding sequence > fertility restoration Ms45 (*Zea mays*) 3'-untranslated region 2) ZM-AA1: polygalacturonase 47 (*Zea mays*) promoter > brittle-1 (*Zea mays*) chloroplast transit peptide > alpha-amylase-1 (*Zea mays*) truncated coding sequence > >In2-1 (*Zea mays*) 3'-untranslated region 3) DSRED2: 35S (Cauliflower Mosaic Virus) enhancer > lipid transfer protein-2 (*Hordeum vulgare*) promoter > red fluorescent protein (*Dicosoma* sp.) variant coding sequence > protein inhibitor II (*Solanum tuberosum*) 3'-untranslated region | *zea mays* L. (Maize) | WO 09/103049, MX 2010008977 |
| A-195 | PV-ZMIR13 (MON863) | | Insect resistance (Cry3Bb); | *Zea mays* L. (Maize) | US 200609598 |
| A-196 | SYN-BT011-1 × MON-00021-9 | Syngenta Seeds, Inc. | Stacked insect resistant and herbicide tolerant maize produced by conventional cross breeding of parental lines BT11 (OECD unique identifier: SYN-BT011-1) and GA21 (OECD unique identifier: MON-00021-9). | *Zea mays* L. (Maize) | |
| A-197 | T14 | Bayer CropScience (Aventis CropScience(AgrEvo)) | Glufosinate herbicide tolerant maize produced by inserting the phosphinothricin N-acetyltransferase (PAT) encoding gene from the aerobic actinomycete *Streptomyces viridochromogenes*. | *Zea mays* L. (Maize) | |
| A-198 | T14, T25 | Bayer CropScience (Aventis Crop Science(AgrEvo)) | Glufosinate herbicide tolerant maize produced by inserting the phosphinothricin N-acetyltransferase (PAT) encoding gene from the aerobic actinomycete *Streptomyces viridochromogenes*. | *Zea mays* L. (Maize) | |

TABLE A-continued

| Event | Company | Description | Crop | Patent Ref |
|---|---|---|---|---|
| A-199 | T25 × MON810 | Bayer CropScience (Aventis CropScience(AgrEvo)) | Stacked insect resistant and herbicide tolerant corn hybrid derived from conventional cross-breeding of the parental lines T25 (OECD identifier: ACS-ZMØØ3-2) and MON810 (OECD identifier:MON-ØØ810-6). | Zea mays L. (Maize) | |
| A-200 | TC1507 | Mycogen (c/o Dow Agro Sciences); Pioneer (c/o Dupont) | Insect-resistant and glufosinate ammonium herbicide tolerant maize produced by inserting the cry1F gene from Bacillus thuringiensis var. aizawai and the phosphinothricin N-acetyl-transferase encoding gene from Streptomyces viridochromogenes; Insect resistance (Cry1F); | Zea mays L. (Maize) | U.S. Pat. No. 7,435,807 |
| A-201 | TC1507 × DAS-59122-7 | DOW AgroSciences LLC and Pioneer Hi-Bred International Inc. | Stacked insect resistant and herbicide tolerant maize produced by conventional cross breeding of parental lines TC1507 (OECD unique identifier: DAS-Ø15Ø7-1) with DAS-59122-7 (OECD unique identifier: DAS-59122-7). Resistance to lepidopteran insects is derived from TC1507 due the presence of the cry1F gene from Bacillus thuringiensis var. aizawai. Corn rootworm-resistance is derived from DAS-59122-7 which contains the cry34Ab1 and cry35Ab1 genes from Bacillus thuringiensis strain PS149B1. Tolerance to glufosinate ammonium herbicide is derived from TC1507 from the phosphinothricin N-acetyltransferase encoding gene from Streptomyces viridochromogenes. | Zea mays L. (Maize) | |
| A-202 | VIP1034 | | Insect resistance; | Zea mays L. (Maize) | WO 03/052073 |
| A-203 | MS-B2 | | Male sterility | Brassica ssp | WO 01/31042 |
| A-204 | MS-BN1/RF-BN1 | | Male sterility/restoration | Brassica ssp | WO 01/41558 |
| A-205 | RT73 | | Glyphosate resistance | Brassica ssp | WO 02/36831 |
| A-206 | MON 87708 | MONSANTO TECHNOLOGY LLC | Dicamba herbicide tolerance, transformation vector PV-GMHT4355 1) DMO: full length transcript (Peanut Chlorotic Streak Virus) promoter > tobacco Etch Virus leader > ribulose 1,5-biphosphate carboxylase small subunit (Pisum sativum) chloroplast transit peptide > dicamba mono-oxygenase (Stenotrophomonas maltophilia) coding sequence > ribulose-1,5-bisphosphate carboxylase small subunit E9 (Pisum sativum) 3'-untranslated region. A CP4 epsps chimeric gene contained within a second T-DNA on the transformation vector used was segregated away. | Glycine max L. (Soybean) | WO 11/034704 |

TABLE A-continued

| Event | Company | Description | Crop | Patent Ref |
|---|---|---|---|---|
| A-207 | EE-GM3/ FG72 | BAYER BIOSCIENCE NV [BE]; MS TECHNOLOGIES LLC [US] | 1) Ph4a748 ABBC: sequence including the promoter region of the histone H4 gene of *Arabidopsis thaliana*, containing an internal duplication>5'tev: sequence including the leader sequence of the tobacco etch virus>TPotp Y: coding sequence of an optimized transit peptide derivative (position 55 changed into Tyrosine), containing sequence of the RuBisCO small subunit genes of *Zea mays* (corn) and *Helianthus annuus* (sunflower) >hppdPf W336: the coding sequence of the 4-hydroxyphenylpyruvate dioxygenase of *Pseudomonas fluorescens* strain A32 modified by the replacement of the amino acid Glycine 336 with a Tryptophane>3'nos: sequence including the 3' untranslated region of the nopaline synthase gene from the T-DNA of pTIT37 of *Agrobacterium tumefaciens*. 2) Ph4a748: sequence including the promoter region of the histone H4 gene of *Arabidopsis thaliana*>intron1 h3At: first intron of gene II of the histone H3.III variant of *Arabidopsis thaliana* >TPotp C: coding sequence of the optimized transit peptide, containing sequence of the RuBisCO small subunit genes of *Zea mays* (corn) and *Helianthus annuus* (sunflower) >2mepsps: the coding sequence of the double-mutant 5-enol-pyruvylshikimate-3-phosphate synthase gene of *Zea mays*>3'histonAt: sequence including the 3' untranslated region of the histone H4 gene of *Arabidopsis thaliana* | *Glycine max* L. (Soybean) | WO 11/063411 |
| A-208 | 416/ pDAB4468-0416 | DOW AGROSCIENCES LLC | A novel aad-12 transformation event for herbicide tolerance in soybean plants - referred to herein as pDAB4468-0416. The aad-12 gene (originally from *Delftia acidovorans*) encodes the aryloxyalkanoate dioxygenase (AAD-12) protein. The trait confers tolerance to 2,4-dichlorophenoxyacetic acid, for example, and to pyridyloxyacetate herbicides. The aad-12 gene, itself, for herbicide tolerance in plants was first disclosed in WO 07/053482. | *Glycine max* L. (Soybean) | WO 11/066384 |
| A-209 | 127 | | ALS/AHAS inhibitor-tolerance | *Glycine max* L. (Soybean) | WO 10/080829 |
| A-210 | A5547-35 | | Glufosinate tolerance | *Glycine max* L. (Soybean) | WO 06/108675 |
| A-211 | A2704-12 | | Glufosinate tolerance | *Glycine max* L. (Soybean) | WO 06/108674 |
| A-212 | Kefeng No. 6 | CHINA NAT RICE RES INST | Transgenic rice Kefeng 6 is a transformation event containing two insect-resistant genes, cry1Ac and SCK (modified CpTI gene) in China. | *Oryza sativa* (Rice) | CN 101824411 |
| A-213 | 17053 | | Glyphosate tolerance | *Oryza sativa* (Rice) | WO 10/117737 |
| A-214 | 17314 | | Glyphosate tolerance | *Oryza sativa* (Rice) | WO 10/117735 |
| A-215 | Event 1 | | Fusarium resistance (trichothecene 3-O-acetyltransferase) disease (fungal) resistance (trichothecene 3-O-acetyltransferase) | Wheat | CA 2561992 |
| A-216 | JOPLIN1 | | RB7 MARv3>zmUbiquitin 1 promoter>aad1>zmPER5 3'UTR>RB 7 MARv4. | Wheat | US 2008064032 |
| A-217 | DAS-40278-9 | DOW AgroSciences LLC | The aad-1 gene confers tolerance to 2,4-dichlorophenoxyacetic acid and aryloxyphenoxypropionate (commonly referred to as "fop") herbicides such as quizalofop) herbicides | *Zea mays* L. (Maize) | WO 11/022469 |

TABLE A-continued

| | Event | Company | Description | Crop | Patent Ref |
|---|---|---|---|---|---|
| A-218 | MIR604 | Syngenta Participations AG | 1) CRY3A: metallotionin-like gene (Zea mays) promoter > delta-endotoxin cry3a (Bacillus thuringiensis subsp. tenebrionis) coding sequence, modified to include a cathepsin-G protease recognition site and maize codon optimized > nopaline synthase (Agrobacterium tumefaciens) 3'-untranslated region 2) PMI: polyubiquitin (Zea mays) promoter (incl. first intron) > mannose-6-phosphate isomerase (Escherichia coli) coding sequence > nopaline synthase (Agrobacterium tumefaciens) 3'-untranslated region | Zea mays L. (Maize) | US 2005216970, US 2008167456, US 2011111420 |
| A-219 | MON 87427 | MONSANTO TECHNOLOGY LLC | The transgene insert and expression cassette of MON 87427 comprises the promoter and leader from the cauliflower mosaic virus (CaMV) 35 S containing a duplicated enhancer region (P-e35S); operably linked to a DNA leader derived from the first intron from the maize heat shock protein 70 gene (I-HSP70); operably linked to a DNA molecule encoding an N-terminal chloroplast transit peptide from the shkG gene from Arabidopsis thaliana EPSPS (Ts-CTP2); operably linked to a DNA molecule derived from the aroA gene from the Agrobacterium sp. strain CP4 and encoding the CP4 EPSPS protein; operably linked to a 3'UTR DNA molecule derived from the nopaline synthase (T-NOS) gene from Agrobacterium tumefaciens. | Zea mays L. (Maize) | WO 11/062904 |
| A-220 | DP-004114-3 | Pioneer Hi-Bred International Inc. | cry1F, cry34Ab1, cry35Ab1, and pat: resistance to certain lepidopteran and coleopteran pests, as well as tolerance to phosphinothricin. | Zea mays L. (Maize) | US 2011154523 |
| A-221 | DP-032316-8 | Pioneer Hi-Bred International Inc. | Cry1F, cry34Ab1, cry35Ab1, pat: resistance to certain lepidopteran and coleopteran pests, as well as tolerance to phosphinothricin | Zea mays L. (Maize) | US 2011154524 |
| A-222 | DP-040416-8 a | Pioneer Hi-Bred International Inc. | Cry1F, cry34Ab1, cry35Ab1, pat: resistance to certain lepidopteran and coleopteran pests, as well as tolerance to phosphinothricin | Zea mays L. (Maize) | US 20110154525 |
| A-223 | DP-043A47-3 | Pioneer Hi-Bred International Inc. | Cry1F, cry34Ab1, cry35Ab1, pat: resistance to certain lepidopteran and coleopteran pests, as well as tolerance to phosphinothricin | Zea mays L. (Maize) | US 20110154526 |
| A-224 | 5307 | | Insect (corn rootworm) resistance (FR8a) | Zea mays L. (Maize) | WO 10/077816 |

In material protection the active compounds or the active compound combinations of the invention may be used for the protection of technical materials against infestation and destruction by insects, nematodes or phytopathogens.

Technical materials are understood to be in the present context non-living materials that have been prepared for use in engineering. For example, technical materials that are to be protected against micro-biological change or destruction by the active materials of the invention can be adhesives, glues, paper and cardboard, textiles, carpets, leather, wood, paint and plastic articles, cooling lubricants and other materials that can be infested or destroyed by micro-organisms Within the context of materials to be protected are also parts of production plants and buildings, for example cooling circuits, cooling and heating systems, air conditioning and ventilation systems, which can be adversely affected by the propagation of fungi or microorganisms Within the context of the present invention, preferably mentioned as technical materials are adhesives, glues, paper and cardboard, leather, wood, paints, cooling lubricants and heat exchanger liquids, particularly preferred is wood. The combinations according to the invention can prevent disadvantageous effects like decaying, dis- and decoloring, or molding. The active compound combinations and compositions according to the invention can likewise be employed for protecting against colonization of objects, in particular ship hulls, sieves, nets, buildings, quays and signalling installations, which are in contact with sea water or brackish water.

The method of treatment according to the invention can also be used in the field of protecting storage goods against attack of insects, nematodes or phytopathogens. According to the present invention, the term "storage goods" is understood to denote natural substances of vegetable or animal origin and their processed forms, which have been taken from the natural life cycle and for which long-term protection is desired. Storage goods of vegetable origin, such as plants or parts thereof, for example stalks, leafs, tubers, seeds, fruits or grains, can be protected in the freshly harvested state or in processed form, such as pre-dried, moistened, comminuted, ground, pressed or roasted. Also falling under the defmition of storage goods is timber, whether in the form of crude timber, such as construction timber, electricity pylons and barriers, or in the form of fmished articles, such as furniture or objects made from wood. Storage goods of animal origin are hides, leather, furs, hairs and the like. The combinations according the present invention can prevent disadvantageous effects such as decay, discoloration or mold. Preferably "storage goods" is understood to denote natural substances of vegetable origin and their processed forms, more preferably fruits and their processed forms, such as pomes, stone fruits, soft fruits and citrus fruits and their processed forms.

Insects, nematodes or phytopathogens to be controlled when the compound (A), the spore-forming bacteria (B) and the biological control agents (C) are used or employed according to the invention are given hereafter:

Insects and Nematodes:

Insects are from the phylum Arthropoda, especially from the class Arachnida, for example, *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia graminum*, *Bryobia praetiosa*, *Centruroides* spp., *Chorioptes* spp., *Dermanyssus gallinae*, *Dermatophagoides pteronyssinus*, *Dermatophagoides farina*, *Dermacentor* spp., *Eotetranychus spp., Epitrimerus pyri*, *Eutetranychus* spp., *Eriophyes* spp., *Glycyphagus domesticus*, *Halotydeus destructor*, *Hemitarsonemus* spp., *Hyalomma* spp., *Ixodes* spp., *Latrodectus* spp., *Loxosceles* spp., *Metatetranychus* spp., *Neutrombicula autumnalis*, *Nuphersa* spp., *Oligonychus* spp., *Ornithodorus* spp., *Ornithonyssus* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Steneotarsonemus* spp., *Steneotarsonemus spinki*, *Tarsonemus* spp., *Tetranychus* spp., *Trombicula alfredduges* , *Vaejovis* spp., *Vasates lycopersici*;

from the class Chilopoda, for example, *Geophilus* spp., *Scutigera* spp.;

from the order or the class Collembola, for example, *Onychiurus armatus*;

from the class Diplopoda, for example, *Blaniulus guttulatus*;

from the class Insecta, e.g. from the order *Blattodea*, for example, *Blattella asahinai*, *Blattella germanica*, *Blatta orientalis*, *Leucophaea maderae*, *Panchlora* spp., *Parcoblatta* spp., *Periplaneta* spp., *Supella longipalpa*;

from the order Coleoptera, for example, *Acalymma vittatum*, *Acanthoscelides obtectus*, *Adoretus* spp., *Agelastica alni*, *Agriotes* spp., *Alphitobius diaperinus*, *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema spp.*, *Cleonus mendicus*, *Conoderus* spp., *Cosmopolites* spp., *Costelytra zealandica*, *Ctenicera* spp., *Curculio* spp., *Cryptolestes ferrugineus*, *Cryptorhynchus lapathi*, *Cylindrocopturus* spp., *Dermestes* spp., *Diabrotica* spp., *Dichocrocis* spp., *Dicladispa armigera*, *Diloboderus* spp., *Epilachna* spp., *Epitrix* spp., *Faustinus* spp., *Gibbium psylloides*, *Gnathocerus cornutus* , *Hellula undalis*, *Heteronychus arator*, *Heteronyx* spp., *Hylamorpha elegans*, *Hylotrupes bajulus*, *Hypera postica*, *Hypomeces squamosus*, *Hypothenemus* spp., *Lachnosterna consanguinea*, *Lasioderma serricorne*, *Latheticus oryzae*, *Lathridius* spp., *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Necrobia* spp., *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllophaga helleri*, *Phyllotreta* spp., *Popillia japonica*, *Premnotrypes* spp., *Prostephanus truncatus*, *Psylliodes* spp., *Ptinus* spp., *Rhizobius ventralis*, *Rhizopertha dominica*, *Sitophilus* spp., *Sitophilus oryzae*, *Sphenophorus* spp., spp., *Stegobium paniceum*, *Sternechus* spp., *Symphyletes* spp., *Tanymecus* spp., *Tenebrio molitor*, *Tenebrioides mauretanicus*, *Tribolium* spp., *Trogoderma* spp., *Tychius* spp., *Xylotrechus* spp., *Zabrus* spp.; from the order Diptera, for example, *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Calliphora vicina*, *Ceratitis capitata*, *Chironomus* spp., *Chrysomyia* spp., *Chrysops* spp., *Chrysozona pluvialis*, *Cochliomyia* spp., *Contarinia* spp., *Cordylobia anthropophaga*, *Cricotopus sylvestris*, *Culex* spp., *Culicoides* spp., *Culiseta* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gasterophilus* spp., *Glossina* spp., *Haematopota* spp., *Hydrellia* spp., *Hydrellia griseola*, *Hylelmya* spp., spp., *Hippobosca* spp., *Hypoderma* spp., *Liriomyza* spp., *Lucilia* spp., *Lutzomyia* spp, *Mansonia* spp., *Musca* spp., *Oestrus* spp., *Oscinella frit*, *Paratanytarsus* spp., *Paralauterborniella*

*subcincta, Pegomyia* spp., *Phlebotomus* spp., *Phorbia* spp., *Phormia* spp., *Piophila casei, Prodiplosis* spp., *Psila rosae, Rhagoletis* spp., *Sarcophaga* spp., *Simulium* spp., *Stomoxys* spp., *Tabanus* spp., *Tetanops* spp., *Tipula* spp.; from the order Heteroptera, for example, *Anasa tristis, Antestiopsis* spp., *Boisea* spp., *Blissus* spp., *Calocoris* spp., *Campylomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptocorisa varicornis, Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order Homoptera, for example, *Acizzia acaciaebaileyanae, Acizzia dodonaeae, Acizzia uncatoides, Acrida turrita, Acyrthosipon* spp., *Acrogonia* spp., *Aeneolamia* spp., *Agonoscena* spp., *Aleyrodes proletella, Aleurolobus barodensis, Aleurothrixus floccosus, Allocaridara malayensis, Amrasca* spp., *Anuraphis cardui, Aonidiella* spp., *Aphanostigma pini, Aphis* spp., *Arboridia apicalis, Arytainilla* spp., *Aspidiella* spp., *Aspidiotus* spp., *Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., *Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus ficus, Cicadulina mbila, Coccomytilus halli, Coccus* spp., *Cryptomyzus ribis, Cryptoneossa* spp., *Ctenarytaina* spp., *Dalbulus* spp., *Dialeurodes citri, Diaphorina citri, Diaspis* spp., *Drosicha* spp., *Dysaphis* spp., *Dysmicoccus* spp., *Empoasca* spp., *Eriosoma* spp., *Erythroneura* spp., *Eucalyptolyma* spp., *Euphyllura* spp., *Euscelis bilobatus, Ferrisia* spp., *Geococcus coffeae, Glycaspis* spp., *Heteropsylla cubana, Heteropsylla spinulosa, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Macrosteles facifrons, Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nettigoniclla spectra, Nilaparvata lugens, Oncometopia* spp., *Orthezia praelonga, Oxya chinensis, Pachypsylla* spp., *Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Prosopidopsylla flava, Protopulvinaria pyriformis, Pseudaulacaspis pentagona, Pseudococcus* spp., *Psyllopsis* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoideus titanus, Schizaphis graminum, Selenaspidus articulatus, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii, Zygina* spp.;

from the order Hymenoptera, for example, *Acromyrmex* spp., *Athalia* spp., *Atta* spp., *Diprion* spp., *Hoplocampa* spp., *Lasius* spp., *Monomorium pharaonis, Sirex* spp., *Solenopsis invicta, Tapinoma* spp., *Urocerus* spp., *Vespa* spp., *Xeris* spp.;

from the order Isopoda, for example, *Armadillidium vulgare, Oniscus asellus, Porcellio scaber;* from the order Isoptera, for example, *Coptotermes* spp., *Cornitermes cumulans, Cryptotermes* spp., *Incisitermes* spp., *Microtermes obesi, Odontotermes* spp., *Reticulitermes* spp.;

from the order Lepidoptera, for example, *Achroia grisella, Acronicta major, Adoxophyes* spp., *Aedia leucomelas, Agrotis* spp., *Alabama spp., Amyelois transitella, Anarsia* spp., *Anticarsia* spp., *Argyroploce* spp., *Baratbra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., *Choristoneura* spp., *Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia* spp., *Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamstra brassicae, Melanitis leda, Mocis* spp., *Monopis obviella, Mythimna separata, Nemapogon cloacellus, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plodia interpunctella, Plusia* spp., *Plutella xylostella, Prays* spp., *Prodenia* spp., *Protoparce* spp., *Pseudaletia* spp., *Pseudaletia unipuncta, Pseudoplusia includens, Pyrausta nubilalis, Rachiplusia nu, Schoenobius* spp., *Scirpophaga* spp., *Scirpophaga innotata, Scotia segetum, Sesamia* spp., *Sesamia inferens, Sparganothis* spp., *Spodoptera* spp., *Spodoptera praefica, Stathmopoda* spp., *Stomopteryx subsecivella, Synanthedon* spp., *Tecia solanivora, Thermesia gemmatalis, Tinea cloacella, Tinea pellionella, Tineola bisselliella, Tortrix* spp., *Trichophaga tapetzella, Trichoplusia* spp., *Tryporyza incertulas, Tuta absoluta, Virachola* spp.;

from the order Orthoptera or Saltatoria, for example, *Acheta domesticus, Dichroplus* spp., *Gryllotalpa* spp., *Hieroglyphus* spp., *Locusta* spp., *Melanoplus* spp., *Schistocerca gregaria;* from the order Phthiraptera, for example, *Damalinia* spp., *Haematopinus* spp., *Linognathus* spp., *Pediculus* spp., *Ptirus pubis, Trichodectes* spp.;

from the order Psocoptera for example *Lepinatus* spp., *Liposcelis* spp.;

from the order Siphonaptera, for example, *Ceratophyllus* spp., *Ctenocephalides* spp., *Pulex irritans, Tunga penetrans, Xenopsylla cheopsis;* from the order Thysanoptera, for example, *Anaphothrips obscurus, Baliothrips biformis, Drepanothrips reuten, Enneothrips flavens, Frankliniella* spp., *Heliothrips* spp., *Hercinothrips femoralis, Rhipiphorothrips cmentatus, Scirtothrips* spp., *Taeniothrips cardamomi, Thrips* spp.;

from the order Zygentoma (=Thysanura), for example, *Ctenolepisma* spp., *Lepisma saccharina, Lepismodes inquilinus, Thermobia domestica;* from the class Symphyla, for example, *Scutigerella* spp.;

pests from the phylum Mollusca, especially from the class Bivalvia, for example, *Dreissena* spp., and from the class Gastropoda, for example, *Anion* spp., *Biomphalaria* spp., *Bulinus* spp., *Deroceras* spp., *Galba* spp., *Lymnaea* spp., *Oncomelania* spp., *Pomacea* spp., *Succinea* spp.;

animal pests being nematodes from the phylums Plathelminthes and Nematoda, for example, *Ancylostoma duodenale, Ancylostoma ceylanicum, Acylostoma braziliensis, Ancylostoma* spp., *Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuellebomi, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti;* phytoparasitic pests being nematodes from the phylum Nematoda, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus* spp., *Trichodorus* spp., *Tylenchulus* spp., *Xiphinema* spp., *Helicotylenchus* spp., *Tylenchorhynchus* spp., *Scutellonema* spp., *Paratrichodorus* spp., *Meloinema* spp., *Paraphelenchus* spp., *Aglenchus* spp., *Belonolaimus* spp., *Nacobbus* spp., *Rotylenchulus* spp., *Rotylenchus* spp., *Neotylenchus* spp., *Paraphelenchus* spp., *Dolichodorus* spp., *Hoplolaimus* spp., *Punctodera* spp., *Criconemella* spp., *Quinisulcius* spp., *Hemicycliophora* spp., *Hirschmaniella* spp., *Anguina* spp., *Subanguina* spp., *Hemicriconemoides* spp., *Psilenchus* spp., *Pseudohalenchus* spp., *Criconemoides* spp., *Cacopaurus* spp.

The compositions according to the invention are particularly useful in controlling nematodes.

Ein Nematizid im Pflanzenschutz, wie hier beschrieben, bedeutet die Fähigkeit des Wirkstoffes, Nematoden zu kontrollieren.

"Controlling nematodes" according to the invention shall mean to kill nematodes or to prevent their development or growth. The efficacy of the compositions or combinations according to the invention is assessed by comparing the mortality of nematodes, the development of galls, the formation of cysts, the concentration of nematodes per volume of soil, of cysts, the concentration of nematodes per root, the number of nematode eggs per volume of soil, the motility of the nematodes between a plant, a plant part or the soil treated with a composition or combination according to the invention and the untreated plant, plant part or soil (100%). Preferred is a reduction by 25-50% in comparison with the untreated plant, plant part or soil, very preferred a reduction by 40-79%, and particularly preferred the complete killing and the complete prevention of the development or growth by a reduction from 70% to 100% in comparison with the untreated plant, plant part or soil.

"Controlling nematodes" according to the invention shall mean the control of the reproduction of the nematodes (e.g. development of cysts or eggs). The compositions according to the invention can used for keeping the plants healthy and can be used curatively, preventively or systemically for controlling nematodes.

The skilled person knows methods for determining the mortality of nematodes, the development of galls, the formation of cysts, the concentration of nematodes per volume of soil, of cysts, the concentration of nematodes per root, the number of nematode eggs per volume of soil, the motility of the nematodes between a plant, a plant part or the soil. The treatment according to the invention reduces the damages caused by nematodes to the plant and leads to an increase in yield.

"Nematodes" as used herein encompass all species of the order Nematoda and in particular species that are parasitic or cause health problems to plant or to fungi (for example species of the orders *Aphelenchida*, Meloidogyne, *Tylenchida* and others) or to humans and animals (for example species of the orders *Trichinellida, Tylenchida, Rhabditina,* and *Spirurida*) as well as other parasitic helminths.

"Nematodes" as used herein, refer to plant nematodes meaning plant parasitic nematodes that cause damage to plants. Plant nematodes encompass plant parasitic nematodes and nematodes living in the soil. Plant parasitic nematodes include, but are not limited to, ectoparasites such as *Xiphinema* spp., *Longidorus* spp., and *Trichodorus* spp.; semiparasites such as *Tylenchulus* spp.; migratory endoparasites such as *Pratylenchus* spp., *Radopholus* spp., and *Scutellonerna* spp.; sedentary parasites such as *Heterodera* spp., *Globoderal* spp., and *Meloidogyne* spp., and stem and leaf endoparasites such as *Ditylenchus* spp., *Aphelenchoides* spp., and *Hirshmaniella* spp. Especially harmful root parasitic soil nematodes are such as cystforming nematodes of the genera Heterodera or Globodera, and/or root knot nematodes of the genus *Meloidogyne*. Harmful species of these genera are for example *Meloidogyne incognita, Heterodera glycines* (soybean cyst nematode), *Globodera pallida* and *Globodera rostochiensis* (potato cyst nematode), which species are effectively controlled with the compounds described herein. However, the use of the compounds described herein is in no way restricted to these genera or species, but also extends in the same manner to other nematodes.

Plant nematodes include but are not limited to e.g. *Aglenchus agricola, Anguina tritici, Aphelenchoides arachidis, Aphelenchoides fragaria* and the stem and leaf endoparasites *Aphelenchoides* spp. in general, *Belonolaimus gracilis, Belonolaimus longicaudatus, Belonolaimus nortoni, Bursaphelenchus eremus, Bursaphelenchus xylophilus* and *Bursaphelenchus* spp. in general, *Cacopaurus pestis, Criconemella curvata, Criconemella onoensis, Criconemella ornata, Criconemella rusium, Criconemella xenoplax Mesocriconema xenoplax)* and *Criconemella* spp. in general, *Criconemoides ferniae, Criconemoides onoense, Criconemoides ornatum* and *Criconemoides* spp. in general, *Ditylenchus destructor, Ditylenchus dipsaci, Ditylenchus myceliophagus* and the stem and leaf endoparasites *Ditylenchus* spp. in general, *Dolichodorus heterocephalus, Globodera pallida (=Heterodera pallida), Globodera rostochiensis* (potato cyst nematode), *Globodera solanacearum, Globodera tabacum, Globodera virginia* and the sedentary, cyst forming parasites *Globodera* spp. in general *Helicotylenchus digonicus, Helicotylenchus dihystera, Helicotylenchus erythrine, Helicotylenchus multicinctus, Helicotylenchus nannus, Helicotylenchus pseudorobustus* and *Helicotylenchus* spp. in general, *Hemicriconemoides, Hemicycliophora arenaria, Hemicycliophora nudata, Hemicycliophora parvana, Heterodera avenae, Heterodera cruci-*

*ferae, Heterodera glycines* (soybean cyst nematode), *Heterodera oryzae, Heterodera schachtii, Heterodera zeae* and the sedentary, cyst forming parasites *Heterodera* spp. in general, *Hirschmaniella gracilis, Hirschmaniella oryzae Hirschmaniella spinicaudata* and the stem and leaf endoparasites *Hirschmaniella* spp. in general, *Hoplolaimus aegyptii, Hoplolaimus californicus, Hoplolaimus columbus, Hoplolaimus galeatus, Hoplolaimus indicus, Hoplolaimus magnistylus, Hoplolaimus pararobustus, Longidorus africanus, Longidorus breviannulatus, Longidorus elongatus, Longidorus laevicapitatus, Longidorus vineacola and the ectoparasites Longidorus* spp. in general, *Meloidogyne acronea, Meloidogyne africana, Meloidogyne arenaria, Meloidogyne arenaria thamesi, Meloidogyne artiella, Meloidogyne chitwoodi, Meloidogyne coffeicola, Meloidogyne ethiopica, Meloidogyne exigua, Meloidogyne graminicola, Meloidogyne graminis, Meloidogyne hapla, Meloidogyne incognita, Meloidogyne incognita acrita, Meloidogyne javanica, Meloidogyne kikuyensis, Meloidogyne naasi, Meloidogyne paranaensis, Meloidogyne thamesi* and the sedentary parasites *Meloidogyne* spp. in general, *Meloinema* spp., *Nacobbus aberrans, Neotylenchus vigissi, Paraphelenchus pseudoparietinus, Paratrichodorus allius, Paratrichodorus lobatus, Paratrichodorus minor, Paratrichodorus nanus, Paratrichodorus porosus, Paratrichodorus teres* and *Paratrichodorus* spp. in general, *Paratylenchus hamatus, Paratylenchus minutus, Paratylenchus projectus* and *Paratylenchus* spp. in general, *Pratylenchus agilis, Pratylenchus alleni, Pratylenchus andinus, Pratylenchus brachyurus, Pratylenchus cerealis, Pratylenchus coffeae, Pratylenchus crenatus, Pratylenchus delattrei, Pratylenchus giibbicaudatus, Pratylenchus goodeyi, Pratylenchus hamatus, Pratylenchus hexincisus, Pratylenchus loosi, Pratylenchus neglectus, Pratylenchus penetrans, Pratylenchus pratensis, Pratylenchus scribneri, Pratylenchus teres, Pratylenchus thornei, Pratylenchus vulnus, Pratylenchus zeae* and the migratory endoparasites *Pratylenchus* spp. in general, *Pseudohalenchus minutus, Psilenchus magnidens, Psilenchus tumidus, Punctodera chalcoensis, Quinisulcius acutus, Radopholus citrophilus, Radopholus similis,* the migratory endoparasites *Radopholus* spp. in general, *Rotylenchulus borealis, Rotylenchulus parvus, Rotylenchulus reniformis* and *Rotylenchulus* spp. in general, *Rotylenchus laurentinus, Rotylenchus macrodoratus, Rotylenchus robustus, Rotylenchus uniformis* and *Rotylenchus* spp. in general, *Scutellonema brachyurum, Scutellonema bradys, Scutellonema clathricaudatum* and the migratory endoparasites *Scutellonema* spp. in general, *Subanguina radiciola, Tetylenchus nicotianae, Trichodorus cylindricus, Trichodorus minor, Trichodorus primitivus, Trichodorus proximus, Trichodorus similis, Trichodorus sparsus* and the ectoparasites *Trichodorus* spp. in general, *Tylenchorhynchus agri, Tylenchorhynchus brassicae, Tylenchorhynchus clarus, Tylenchorhynchus claytoni, Tylenchorhynchus digitatus, Tylenchorhynchus ebriensis, Tylenchorhynchus maximus, Tylenchorhynchus nudus, Tylenchorhynchus vulgaris* and *Tylenchorhynchus* spp. in general, *Tylenchulus semipenetrans* and the semiparasites *Tylenchulus* spp. in general, *Xiphinema americanum, Xiphinema brevicolle, Xiphinema dimorphicaudatum, Xiphinema index* and the ectoparasites *Xiphinema* spp. in general.

Examples of nematodes to which a nematicide of the present invention is applicable include, but are not limited to, nematodes of the genus *Meloidogyne* such as the southern root-knot nematode (*Meloidogyne incognita*), Javanese root-knot nematode (*Meloidogyne javanica*), northern root-knot nematode (*Meloidogyne hapla*), and peanut root-knot nematode (*Meloidogyne arenaria*); nematodes of the genus *Ditylenchus* such as the potato rot nematode (*Ditylenchus destructor*) and bulb and stem nematode (*Ditylenchus dipsaci*); nematodes of the genus *Pratylenchus* such as the cob root-lesion nematode (*Pratylenchus penetrans*), chrysanthemum root-lesion nematode (*Pratylenchus fallax*), coffee root-lesion nematode (*Pratylenchus coffeae*), tea root-lesion nematode (*Pratylenchus loosi*), and walnut root-lesion nematode (*Pratylenchus vulnus*); nematodes of the genus *Globodera* such as the golden nematode (*Globodera rostochiensis*) and potato cyst nematode (*Globodera pallida*); nematodes of the genus *Heterodera* such as the soybean cyst nematode (*Heterodera glycines*) and sugar beet cyst nematode (*Heterodera schachtii*); nematodes of the genus *Aphelenchoides* such as the rice white-tip nematode (*Aphelenchoides besseyi*), chrysanthemum foliar nematode (*Aphelenchoides ritzemabosi*), and strawberry nematode (*Aphelenchoides fragariae*); nematodes of the genus *Aphelenchus* such as the mycophagous nematode (*Aphelenchus avenae*); nematodes of the genus *Radopholus* such as the burrowing nematode (*Radopholus similis*); nematodes of the genus *Tylenchulus* such as the citrus nematode (*Tylenchulus semipenetrans*); nematodes of the genus *Rotylenchulus* such as the reniform nematode (*Rotylenchulus reniformis*); nematodes that occur in trees, such as the pine wood nematode (*Bursaphelenchus xylophilus*), and the like.

Plants for which a nematicide of the present invention can be used are not particularly limited; for example, plants such as cereals (for example, rice, barley, wheat, rye, oat, corn, kaoliang 5 and the like), beans (soy-bean, azuki, bean, broad bean, peas, peanuts and the like), fruit trees/fruits (apples, citruses, pears, grapes, peaches, Japanese apricots, cherries, walnuts, almonds, bananas, strawberries and the like), vegetables (cabbage, tomato, spinach, broccoli, lettuce, onion, Welsh onion, pepper and the like), root crops (carrot, potato, sweet potato, radish, lotus root, turnip and the like), industrial crops (cotton, hemp, paper mulberry, mitsumata, rape, beet, hop, sugarcane, sugar beet, olive, rubber, coffee, tobacco, tea and the like), pepos (pumpkin, cucumber, watermelon, melon and the like), pasture plants (orchard grass, sorghum, thimosy, clover, alfalfa and the like), lawn grasses (mascarene grass, bent grass and the like), crops for flavorings etc. (lavender, rosemary, thyme, parsley, pepper, ginger and the like), and flower plants (chrysanthemum, rose, orchids and the like) can be mentioned.

The compound(s) and compositions comprising the compound(s) of the present invention is/are particularly useful in controlling nematodes in coffee belonging to at least one species selected from the group of the phytoparasitic nematodes consisting of *Pratylenchus brachyurus, Pratylenchus coffeae, Meloidogyne exigua, Meloidogyne incognita, Meloidogyne coffeicola, Helicotylenchus* spp. and also consisting of *Meloidogyne paranaensis, Rotylenchus* spp., *Xiphinema* spp., *Tylenchorhynchus* spp., *Scutellonema* spp.

Compound(s) and compositions comprising compound(s) of the present invention is/are particularly useful in controlling nematodes in potato belonging to at least one species selected from the group of the phytoparasitic nematodes consisting of *Pratylenchus brachyurus, Pratylenchus pratensis, Pratylenchus scribneri, Pratylenchus penetrans, Pratylenchus coffeae, Ditylenchus dipsaci* and also consisting of *Pratylenchus alleni, Pratylenchus andinus, Pratylenchus cerealis, Pratylenchus crenatus, Pratylenchus hexincisus, Pratylenchus loosi, Pratylenchus neglectus, Pratylenchus teres, Pratylenchus thornei, Pratylenchus vulnus, Belonolaimus longicaudatus, Trichodorus cylindricus, Trichodorus primitivus, Trichodorus proximus, Trichodorus similis,*

*Trichodorus sparsus, Paratrichodorus minor, Paratrichodorus allius, Paratrichodorus nanus, Paratrichodorus teres, Meloidogyne arenaria, Meloidogyne hapla, Meloidogyne thamesi, Meloidogyne incognita, Meloidogyne chitwoodi, Meloidogyne javanica, Nacobbus aberrans, Globodera rostochiensis, Globodera pallida, Ditylenchus destructor, Radopholus similis, Rotylenchulus reniformis, Neotylenchus vigissi, Paraphelenchus pseudoparietinus, Aphelenchoides fragariae, Meloinema* spp.

The compound(s) and compositions comprising the compound(s) of the present invention is/are particularly useful in controlling nematodes in tomato belonging to at least one species selected from the group of the phytoparasitic nematodes consisting of *Meloidogyne arenaria, Meloidogyne hapla, Meloidogyne javanica, Meloidogyne incognita, Pratylenchus penetrans* and also consisting of *Pratylenchus brachyurus, Pratylenchus coffeae, Pratylenchus scribneri, Pratylenchus vulnus, Paratrichodorus minor, Meloidogyne exigua, Nacobbus aberrans, Globodera solanacearum, Dolichodorus heterocephalus, Rotylenchulus reniformis*.

The compound(s) and compositions comprising the compound(s) of the present invention is/are particularly useful in controlling nematodes in cucurbits belonging to at least one species selected from the group of the phytoparasitic nematodes consisting of *Meloidogyne arenaria, Meloidogyne hapla, Meloidogyne javanica, Meloidogyne incognita, Rotylenchulus reniformis* and also consisting of *Pratylenchus thornei*.

The compound(s) and compositions comprising the compound(s) of the present invention is/are particularly useful in controlling nematodes in cotton belonging to at least one species selected from the group of the phytoparasitic nematodes consisting of *Belonolaimus longicaudatus, Meloidogyne incognita, Hoplolaimus columbus, Hoplolaimus galeatus, Rotylenchulus reniformis*.

The compound(s) and compositions comprising the compound(s) of the present invention is/are particularly useful in controlling nematodes in corn belonging to at least one species selected from the group of the phytoparasitic nematodes, especially consisting of *Belonolaimus longicaudatus, Paratrichodorus minor* and also consisting of *Pratylenchus brachyurus, Pratylenchus delattrei, Pratylenchus hexincisus, Pratylenchus penetrans, Pratylenchus zeae, (Belonolaimus gracilis), Belonolaimus nortoni, Longidorus breviannulatus, Meloidogyne arenaria, Meloidogyne arenaria thamesi, Meloidogyne graminis, Meloidogyne incognita, Meloidogyne incognita acrita, Meloidogyne javanica, Meloidogyne naasi, Heterodera avenae, Heterodera oryzae, Heterodera zeae, Punctodera chalcoensis, Ditylenchus dipsaci, Hoplolaimus aegyptii, Hoplolaimus magnistylus, Hoplolaimus galeatus, Hoplolaimus indicus, Helicotylenchus digonicus, Helicotylenchus dihystera, Helicotylenchus pseudorobustus, Xiphinema americanum, Dolichodorus heterocephalus, Criconemella ornata, Criconemella onoensis, Radopholus similis, Rotylenchulus borealis, Rotylenchulus parvus, Tylenchorhynchus agri, Tylenchorhynchus clarus, Tylenchorhynchus claytoni, Tylenchorhynchus maximus, Tylenchorhynchus nudus, Tylenchorhynchus vulgaris, Quinisulcius acutus, Paratylenchus minutus, Hemicycliophora parvana, Aglenchus agricola, Anguina tritici, Aphelenchoides arachidis, Scutellonema brachyurum, Subanguina radiciola*.

The compound(s) and compositions comprising the compound(s) of the present invention is/are particularly useful in controlling nematodes in soybean belonging to at least one species selected from the group of the phytoparasitic nematodes, especially consisting of *Pratylenchus brachyurus, Pratylenchus pratensis, Pratylenchus penetrans, Pratylenchus scribneri, Belonolaimus longicaudatus, Heterodera glycines, Hoplolaimus columbus* and also consisting of *Pratylenchus coffeae, Pratylenchus hexincisus, Pratylenchus neglectus, Pratylenchus crenatus, Pratylenchus alleni, Pratylenchus agilis, Pratylenchus zeae, Pratylenchus vulnus, (Belonolaimus gracilis), Meloidogyne arenaria, Meloidogyne incognita, Meloidogyne javanica, Meloidogyne hapla, Hoplolaimus columbus, Hoplolaimus galeatus, Rotylenchulus reniformis*.

The compound(s) and compositions comprising the compound(s) of the present invention is/are very particularly useful in controlling nematodes in soybean belonging to at least one species selected from the group of the phytoparasitic nematodes, especially consisting of *Pratylenchus brachyurus, Pratylenchus pratensis, Pratylenchus penetrans, Pratylenchus scribneri, Belonolaimus longicaudatus, Hoplolaimus columbus* and also consisting of *Pratylenchus coffeae, Pratylenchus hexincisus, Pratylenchus neglectus, Pratylenchus crenatus, Pratylenchus alleni, Pratylenchus agilis, Pratylenchus zeae, Pratylenchus vulnus, (Belonolaimus gracilis), Meloidogyne arenaria, Meloidogyne incognita, Meloidogyne javanica, Meloidogyne hapla, Hoplolaimus columbus, Hoplolaimus galeatus, Rotylenchulus reniformis*.

The compound(s) and compositions comprising the compound(s) of the present invention is/are particularly useful in controlling nematodes in tobacco belonging to at least one species selected from the group of the phytoparasitic nematodes, especially consisting of *Meloidogyne incognita, Meloidogyne javanica* and also consisting of *Pratylenchus brachyurus, Pratylenchus pratensis, Pratylenchus hexincisus, Pratylenchus penetrans, Pratylenchus neglectus, Pratylenchus crenatus, Pratylenchus thornei, Pratylenchus vulnus, Pratylenchus zeae, Longidorus elongatu, Paratrichodorus lobatus, Trichodorus* spp., *Meloidogyne arenaria, Meloidogyne hapla, Globodera tabacum, Globodera solanacearum, Globodera virginiae, Ditylenchus dipsaci, Rotylenchus* spp., *Helicotylenchus* spp., *Xiphinema americanum, Criconemella* spp., *Rotylenchulus reniformis, Tylenchorhynchus claytoni, Paratylenchus* spp., *Tetylenchus nicotianae*.

The compound(s) and compositions comprising the compound(s) of the present invention is/are particularly useful in controlling nematodes in citrus belonging to at least one species selected from the group of the phytoparasitic nematodes, especially consisting of *Pratylenchus coffeae* and also consisting of *Pratylenchus brachyurus, Pratylenchus vulnus, Belonolaimus longicaudatus, Paratrichodorus minor, Paratrichodorus porosus, Trichodorus, Meloidogyne incognita, Meloidogyne incognita acrita, Meloidogyne javanica, Rotylenchus macrodoratus, Xiphinema americanum, Xiphinema brevicolle, Xiphinema index, Criconemella* spp., *Hemicriconemoides, (Radopholus similis), Radopholus citrophilus, Hemicycliophora arenaria, Hemicycliophora nudata, Tylenchulus semipenetrans*.

The compound(s) and compositions comprising the compound(s) of the present invention is/are particularly useful in controlling nematodes in banana belonging to at least one species selected from the group of the phytoparasitic nematodes, especially consisting of *Pratylenchus coffeae, Radopholus similis* and also consisting of *Pratylenchus giibbicaudatus, Pratylenchus loosi, Meloidogyne* spp., *Helicotylenchus multicinctus, Helicotylenchus dihystera, Rotylenchulus* spp.

The compound(s) and compositions comprising the compound(s) of the present invention is/are particularly useful in controlling nematodes in pine apple belonging to at least one species selected from the group of the phytoparasitic nematodes, especially consisting of *Pratylenchus zeae, Pratylenchus pratensis, Pratylenchus brachyurus, Pratylenchus goodeyi., Meloidogyne* spp., *Rotylenchulus reniformis* and also consisting of *Longidorus elongatus, Longidorus laevicapitatus, Trichodorus primitivus, Trichodorus minor, Heterodera* spp., *Ditylenchus myceliophagus, Hoplolaimus californicus, Hoplolaimus pararobustus, Hoplolaimus indicus, Helicotylenchus dihystera, Helicotylenchus nannus, Helicotylenchus multicinctus, Helicotylenchus erythrine, Xiphinema dimorphicaudatum, Radopholus similis, Tylenchorhynchus digitatus, Tylenchorhynchus ebriensis, Paratylenchus minutus, Scutellonema clathricaudatum, Scutellonema bradys, Psilenchus tumidus, Psilenchus magnidens, Pseudohalenchus minutus, Criconemoides femiae, Criconemoides onoense, Criconemoides ornatum.*

The compound(s) and compositions comprising the compound(s) of the present invention is/are particularly useful in controlling nematodes in grapes belonging to at least one species selected from the group of the phytoparasitic nematodes, especially consisting of *Pratylenchus vulnus, Meloidogyne arenaria, Meloidogyne incognita, Meloidogyne javanica, Xiphinema americanum, Xiphinema* index and also consisting of *Pratylenchus pratensis, Pratylenchus scribneri, Pratylenchus neglectus, Pratylenchus brachyurus, Pratylenchus thornei, Tylenchulus semipenetrans.*

The compound(s) and compositions comprising the compound(s) of the present invention is/are particularly useful in controlling nematodes in tree crops pome fruits, belonging to at least one species selected from the group of the phytoparasitic nematodes, especially consisting of *Pratylenchus penetrans* and also consisting of *Pratylenchus vulnus, Longidorus elongatus, Meloidogyne incognita, Meloidogyne hapla.*

The compound(s) and compositions comprising the compound(s) of the present invention is/are particularly useful in controlling nematodes in tree crops stone fruits, belonging to at least one species selected from the group of the phytoparasitic nematodes, especially consisting of *Pratylenchus penetrans, Pratylenchus vulnus, Meloidogyne arenaria, Meloidogyne hapla, Meloidogyne javanica, Meloidogyne incognita, Criconemella xenoplax* and also consisting of *Pratylenchus brachyurus, Pratylenchus coffeae, Pratylenchus scribneri, Pratylenchus zeae, Belonolaimus longicaudatus, Helicotylenchus dihystera, Xiphinema americanum, Criconemella curvata, Tylenchorhynchus claytoni, Paratylenchus hamatus, Paratylenchus projectus, Scutellonema brachyurum, Hoplolaimus galeatus.*

The compound(s) and compositions comprising the compound(s) of the present invention is/are particularly useful in controlling nematodes in tree crops nuts, belonging to at least one species selected from the group of the phytoparasitic nematodes, especially consisting of *Trichodorus* spp., *Criconemella rusium* and also consisting of *Pratylenchus vulnus, Paratrichodorus* spp., *Meloidogyne incognita, Helicotylenchus* spp., *Tylenchorhynchus* spp., *Cacopaurus pestis.*

In a like manner, "nematodes" as used herein, refer to nematodes which cause damage to humans or animals Specific nematode species harmful to humans or animals are:

Trichinellida for example: *Trichuris* spp., *Capillaria* spp., *Trichomosoides* spp., *Trichinella* spp.

From the order of the Tylenchida for example: *Micronema* spp., *Strongyloides* spp.

From the order of the Rhabditina for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp. *Parelaphostrongylus* spp., *Crenosoma* spp., *Paracrenosoma* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Marshallagia* spp., *Cooperia* spp., *Nematodirus* spp., *Hyostrongylus* spp., *Obeliscoides* spp., *Amidostomum* spp., *Ollulanus* spp.

From the order of the Spirurida for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp.

Many known nematicides are equally active against other parasitic helminths and are therefore used to control human and animal parasitic worms, which do not necessarily belong to the group of nematoda. Therefore, it is envisaged by the present invention that the compounds described herein may also be used as anthelmintic drugs in a more general meaning. Pathogenic endoparasitic helminths include platyhelmintha (e g monogenea, cestodes and trematodes), acanthocephala, and pentastoma. The following helminths may be mentioned by way of example and by way of preference—but without any limitation:

Monogenea: e.g.: *Gyrodactylus* spp., *Dactylogyrus* spp., *Polystoma* spp.

Cestodes: From the order of the Pseudophyllidea for example: *Diphyllobothrium* spp., *Spirometra* spp., *Schistocephalus* spp., *Ligula* spp., *Bothridium* spp., *Diplogonoporus* spp.

From the order of the Cyclophyllida for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.

Trematodes: From the class of the Digenea for example: *Diplostomum* spp., *Posthodiplostomum* spp., *Schitosoma* spp., *Trichobilharzia* spp., *Ornithobilharzia* spp., *Austrobilharzia* spp., *Gigantobilharzia* spp., *Lencochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.

Acantocephala: From the order of the Oligacanthorhynchida z.B: *Macracanthorhynchus* spp., *Prosthenorchis* spp.; from the order of the Polymorphida for example: *Filicollis* spp.; from the order of the Moniliformida for example: *Moniliformis* spp., From the order of the Echinorhynchida for example *Acanthocephalus* spp., *Echinorhynchus* spp., *Leptorhynchoides* spp.

Pentastoma: From the order of the Porocephalida for example *Linguatula* spp.

In the veterinary field and in animal keeping, the administration of the active compounds according to the invention is carried out in the known manner directly or enterally, parenterally, dermally or nasally in the form of suitable preparations. Administration can be carried out prophylactically or therapeutically.

Some phytopathogens of fungal diseases which can be treated by the combination according to the invention comprising compound (A), the spore-forming bacteria (B) and the biological control agents (C) may be mentioned by way of example, but not by way of limitation:

Powdery Mildew Diseases such as Blumeria diseases caused for example by Blumeria graminis; Podosphaera diseases caused for example by Podosphaera leucotricha; Sphaerotheca diseases caused for example by Sphaerotheca fuliginea; Uncinula diseases caused for example by Uncinula necator;

Rust Diseases such as Gymnosporangium diseases caused for example by *Gymnosporangium sabinae;* *Hemileia* diseases caused for example by *Hemileia vastatrix;* *Phakopsora* diseases caused for example by *Phakopsora pachyrhizi* and *Phakopsora meibomiae;* *Puccinia* diseases caused for example by *Puccinia recondita, Puccinia graminis* or *Puccinia striiformis;* *Uromyces* diseases caused for example by *Uromyces appendiculatus;*

Oomycete Diseases such as Albugo diseases caused for example by *Albugo candida;* Bremia diseases caused for example by *Bremia lactucae;* Peronospora diseases caused for example by *Peronospora pisi* and *Peronospora brassicae;* Phytophthora diseases caused for example by *Phytophthora infestans;*

*Plasmopara* diseases caused for example by *Plasmopara viticola;* *Pseudoperonospora* diseases caused for example by *Pseudoperonospora humuli* and *Pseudoperonospora cubensis;* *Pythium* diseases caused for example by *Pythium ultimum;*

Leaf spot, Leaf blotch and Leaf Blight Diseases such as *Alternaria* diseases caused for example by *Alternaria solani;* *Cercospora* diseases caused for example by *Cercospora beticola;* *Cladosporium* diseases caused for example by *Cladosporium cucumerinum;* *Cochliobolus* diseases caused for example by *Cochliobolus sativus* (*Conidiaform: Drechslera, Syn: Helminthosporium*) or *Cochliobolus miyabeanus;* *Colletotrichum* diseases caused for example by *Colletotrichum lindemuthianum;* *Cycloconium* diseases caused for example by *Cycloconium oleaginum;* *Diaporthe* diseases caused for example by *Diaporthe citri;* *Elsinoe* diseases caused for example by *Elsinoe fawcettii;* *Gloeosporium* diseases caused for example by *Gloeosporium laeticolor;* *Glomerella* diseases caused for example by *Glomerella cingulata;* *Guignardia* diseases caused for example by *Guignardia bidwellii;* *Leptosphaeria* diseases caused for example by *Leptosphaeria maculans* and *Leptosphaeria nodorum;* *Magnaporthe* diseases caused for example by *Magnaporthe grisea;* *Mycosphaerella* diseases caused for example by *Mycosphaerella graminicola, Mycosphaerella arachidicola* and *Mycosphaerella fijiensis;*

*Phaeosphaeria* diseases caused for example by *Phaeosphaeria nodorum;* *Pyrenophora* diseases caused for example by *Pyrenophora teres* or *Pyrenophora tritici repentis;* *Ramularia*-diseases caused for example by *Ramularia collo-cygni* or *Ramularia areola;* *Rhynchosporium* diseases caused for example by *Rhynchosporium secalis;* *Septoria* diseases caused for example by *Septoria apii* and *Septoria lycopersici;* *Typhula* diseases caused for example by *Thyphula incarnata;* *Venturia* diseases caused for example by *Venturia inaequalis;*

Root-, Sheath and Stem Diseases such as *Corticium* diseases caused for example by *Corticium graminearum;* *Fusarium* diseases caused for example by *Fusarium oxysporum;* *Gaeumannomyces* diseases caused for example by *Gaeumannomyces graminis;* *Rhizoctonia* diseases caused for example by *Rhizoctonia solani;* *Sarocladium* diseases caused for example by *Sarocladium oryzae;* *Sclerotium* diseases caused for example by *Sclerotium oryzae;* *Tapesia* diseases caused for example by *Tapesia acuformis;* *Thielaviopsis* diseases caused for example by *Thielaviopsis basicola;*

Ear and Panicle Diseases including Maize cob such as *Alternaria* diseases caused for example by *Alternaria* spp.; *Aspergillus* diseases caused for example by *Aspergillus flavus;* *Cladosporium* diseases caused for example by *Cladosporium cladosporioides;* *Claviceps* diseases caused for example by *Claviceps purpurea;* *Fusarium* diseases caused for example by *Fusarium culmorum;* *Gibberella* diseases caused for example by *Gibberella zeae;* *Monographella* diseases caused for example by *Monographella nivalis;* Smut- and Bunt Diseases such as *Sphacelotheca* diseases caused for example by *Sphacelotheca reiliana;* *Tilletia* diseases caused for example by *Tilletia caries;* *Urocystis* diseases caused for example by *Urocystis occulta;* *Ustilago* diseases caused for example by *Ustilago nuda;*

Fruit Rot and Mould Diseases such as *Aspergillus* diseases caused for example by *Aspergillus flavus;* *Botrytis* diseases caused for example by *Botrytis cinerea;* *Penicillium* diseases caused for example by *Penicillium expansum* and *Penicillium purpurogenum;* *Rhizopus* diseases caused by example by *Rhizopus stolonifer* *Sclerotinia* diseases caused for example by *Sclerotinia sclerotiorum;* *Verticillium* diseases caused for example by *Verticillium alboatrum;*

Seed- and Soilborne Decay, Mould, Wilt, Rot and Damping-off diseases caused for example by *Alternaria* diseases caused for example by *Alternaria brassicicola;* *Aphanomyces* diseases caused for example by *Aphanomyces euteiches;* *Ascochyta* diseases caused for example by *Ascochyta lentis;* *Aspergillus* diseases caused for example by *Aspergillus flavus;* *Cladosporium* diseases caused for example by *Cladosporium herbarum;* *Cochliobolus* diseases caused for example by *Cochliobolus sativus;* (*Conidiaform: Drechslera, Bipolaris Syn: Helminthosporium*); *Colletotrichum* diseases caused for example by *Colletotrichum coccodes;* *Fusarium* diseases caused for example by *Fusarium culmorum;* *Gibberella* diseases caused for example by *Gibberella zeae;* *Macrophomina* diseases caused for example by *Macrophomina phaseolina;* *Microdochium* diseases caused for example by *Microdochium nivale;* *Monographella* diseases caused for example by *Monographella nivalis;* *Penicillium* diseases caused for example by *Penicillium expansum;* *Phoma* diseases caused for example by *Phoma lingam;* *Phomopsis* diseases caused for example by *Phomopsis sojae;* *Phytophthora* diseases caused for example by *Phytophthora cactorum;* *Pyrenophora* diseases caused for example by *Pyrenophora graminea;* *Pyricularia* diseases caused for example by *Pyricularia oryzae;* *Pythium* diseases caused for example by *Pythium ultimum;* Rhizoctonia diseases caused for example by *Rhizoctonia solani;* Rhizopus diseases caused for example by *Rhizopus oryzae;* Sclerotium diseases caused for example by *Sclerotium rolfsii;* Septoria diseases caused for example by *Septoria nodorum;* Typhula diseases caused for example by *Typhula incarnata;* Verticillium diseases caused for example by *Verticillium dahliae;*

Canker, Broom and Dieback Diseases such as Nectria diseases caused for example by *Nectria galligena;* Blight Diseases such as Monilinia diseases caused for example by *Monilinia laxa;* Leaf Blister or Leaf Curl Diseases including deformation of blooms and fruits such as Exobasidium diseases caused for example by *Exobasidium vexans.*

Taphrina diseases caused for example by *Taphrina deformans;*

Decline Diseases of Wooden Plants such as Esca disease caused for example by *Phaeomoniella clamydospora, Phaeoacremonium aleophilum* and *Fomitiporia mediterranea;* Ganoderma diseases caused for example by *Ganoderma boninense;* Rigidoporus diseases caused for example by *Rigidoporus lignosus*

Diseases of Flowers and Seeds such as Botrytis diseases caused for example by *Botrytis cinerea;*

Diseases of Tubers such as Rhizoctonia diseases caused for example by *Rhizoctonia solani;* Helminthosporium diseases caused for example by *Helminthosporium solani;*

Club root diseases such as Plasmodiophora diseases, cause for example by *Plamodiophora brassicae.*

Diseases caused by Bacterial Organisms such as Xanthomonas species for example *Xanthomonas campestris* pv. *oryzae;* Pseudomonas species for example *Pseudomonas syringae* pv *lachrymans;* Erwinia species for example *Erwinia amylovora.*

Preference is given to controlling the following diseases of soya beans:

Fungal diseases on leaves, stems, pods and seeds caused, for example, by alternaria leaf spot (*Alternaria spec. atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmopspora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia Southern blight (*Sclerotinia rolfsii*), thielaviopsis root rot (*Thielaviopsis basicola*).

It is also possible to control resistant strains of the organisms mentioned above.

Phytopathogens capable of degrading or changing the industrial materials which may be mentioned are, for example, bacteria, fungi, yeasts, algae and slime organisms. The active compound combinations and compositions according to the invention preferably act against phytopathogens, in particular moulds, wood-discolouring and wood-destroying fungi (*Basidiomycetes*) and against slime organisms and algae. Phytopathogens of the following genera may be mentioned as examples: Alternaria, such as *Alternaria tennis*, Aspergillus, such as *Aspergillus niger*, Chaetomium, such as *Chaetomium globosum*, Coniophora, such as *Coniophora puetana*, Lentinus, such as *Lentinus tigrinus*, Penicillium, such as *Penicillium glaucum*, Polyporus, such as *Polyporus versicolor*, Aureobasidium, such as *Aureobasidium pullulans*, Sclerophoma, such as *Sclerophoma pityophila*, Trichoderma, such as *Trichoderma viride*, Escherichia, such as *Escherichia coli*, Pseudomonas, such as *Pseudomonas aeruginosa*, and Staphylococcus, such as *Staphylococcus aureus.*

In addition, the combination comprising (A) *Fluopyram*, (B) a spore-forming bacterium of the genera *Bacillus*, and (C) a biological control agent, in particular bacteria, fungi or yeasts, protozoa, viruses, entomopathogenic nematodes, inoculants, botanicals and products produced by microorganisms including proteins or secondary metabolites, particularly (C8.1) Harpin according to the invention also have very good antimycotic activity. They have a very broad antimycotic activity spectrum in particular against dermatophytes and yeasts, moulds and diphasic fungi (for example against Candida species such as *Candida albicans, Candida glabrata*) and *Epidermophyton floccosum*, Aspergillus species such as *Aspergillus niger* and *Aspergillus fumigatus*, Trichophyton species such as *Trichophyton mentagrophytes*, Microsporon species such as *Microsporon canis* and *audouinii* The list of these fungi by no means limits the mycotic spectrum which can be covered, but is only for illustration.

When applying the compounds or the active compound combination according to the invention the application rates can be varied within a broad range. The dose of active compound combination/application rate usually applied in the method of treatment according to the invention is generally and advantageously for treatment of part of plants, e.g. leaves (foliar treatment): from 0.01 to 10,000 g/ha, preferably from 50 to 1,000 g/ha, more preferably from 100 to 750 g/ha; in case of drench or drip application, the dose can even be reduced, especially while using inert substrates like rockwool or perlite;

for seed treatment: from 2 to 250 g per 100 kg of seed, preferably from 3 to 200 g per 100 kg of seed, more preferably from 2.5 to 50 g per 100 kg of seed, even more preferably from 2.5 to 25 g per 100 kg of seed;

for soil treatment: from 0.01 to 10,000 g/ha, preferably from 1 to 5,000 g/ha.

The doses herein indicated are given as illustrative examples of the method according to the invention. A person skilled in the art will know how to adapt the application doses, notably according to the nature of the plant or crop to be treated.

The active compound combination or composition according to the invention can be used in order to protect plants within a certain time range after the treatment against pests or phytopathogenic fungi or microorganisms The time range, in which protection is effected, spans in general 1 to 28 days, preferably 1 to 14 days, more preferably 1 to 10 days, even more preferably 1 to 7 days after the treatment of the plants with the combinations or up to 200 days after the treatment of plant propagation material.

The application of the active copmpound combination or compositions according to the invention on growing plants or plant parts can also be used to protect plants or plant parts after harvesting.

According to the invention, post-harvest and storage diseases may be caused for example by the following fungi: *Colletotrichum* spp., e.g. *Colletotrichum musae, Colletotrichum gloeosporioides, Colletotrichum coccodes; Fusarium* spp., e.g. *Fusarium semitectum, Fusarium moniliforme, Fusarium solani, Fusarium oxysporum; Verticillium* spp., e.g. *Verticillium theobromae; Nigrospora* spp.; *Botrytis* spp., e.g. *Botrytis cinerea; Geotrichum* spp., e.g. *Geotrichum candidum; Phomopsis* spp., *Phomopsis natalensis; Diplodia* spp., e.g. *Diplodia citri; Alternaria* spp., e.g. *Alternaria citri, Alternaria alternata; Phytophthora* spp., e.g. *Phytophthora citrophthora, Phytophthora fragariae, Phytophthora cactorum, Phytophthora parasitica; Septoria* spp., e.g. *Septoria depressa; Mucor* spp., e.g. *Mucor piriformis; Monilinia* spp., e.g. *Monilinia fructigena, Monilinia laxa; Venturia* spp., e.g. *Venturia inaequalis, Venturia pyrina; Rhizopus* spp., e.g. *Rhizopus stolonifer, Rhizopus oryzae; Glomerella* spp., e.g. *Glomerella cingulata; Sclerotinia* spp., e.g. *Sclerotinia fruiticola; Ceratocystis* spp., e.g. *Ceratocystis paradoxa; Penicillium*spp., e.g. *Penicillium funiculosum, Penicillium expansum, Penicillium digitatum, Penicillium italicum; Gloeosporium* spp., e.g. *Gloeosporium album, Gloeosporium perennans, Gloeosporium fructigenum, Gloeosporium singulata; Phlyctaena* spp., e.g. *Phlyctaena vagabunda; Cylindrocarpon* spp., e.g. *Cylindrocarpon mali; Stemphyllium* spp., e.g. *Stemphyllium vesicarium; Phacydiopycnis* spp., e.g. *Phacydiopycnis malirum; Thielaviopsis* spp., e.g. *Thielaviopsis paradoxy; Aspergillus* spp., e.g. *Aspergillus niger, Aspergillus carbonarius; Nectria* spp., e.g. *Nectria galligena; Pezicula* spp.

According to the invention, post-harvest storage disorders are for example scald, scorch, softening, senescent breakdown, lenticel spots, bitter pit, browning, water core, vascular breakdown, $CO_2$ injury, $CO_2$ deficiency and $O_2$ deficiency.

Furthermore combinations and compositions according to the invention may also be used to reduce the contents of mycotoxins in plants and the harvested plant material and therefore in foods and animal feed stuff made therefrom. Especially but not exclusively the following mycotoxins can be specified: Deoxynivalenole (DON), Nivalenole, 15-Ac-DON, 3-Ac-DON, T2-und HT2-Toxins, *Fumonisines, Zearalenone Moniliformine, Fusarine, Diaceotoxyscirpenole* (DAS), *Beauvericine, Enniatine, Fusaroproliferine, Fusarenole, Ochratoxines, Patuline, Ergotalkaloides und Aflatoxins,* which are caused for example by the following fungal diseases: *Fusarium* spec., like *Fusarium acuminatum, F. avenaceum, E crookwellense, F. culmorum, F. graminearum (Gibberella zeae), F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* and others but also by *Aspergillus* spec., *Penicillium* spec., *Claviceps purpurea, Stachybotrys* spec. and others.

The good fungicidal or insecticidal or nematicidal activity of the active compound combinations according to the invention is evident from the example below. While the individual active compounds exhibit weaknesses with regard to the fungicidal or insecticidal or nematicidal activity, the combinations have an activity which exceeds a simple addition of activities.

A synergistic effect of the combinations according to the invention is always present when the fungicidal or nematicidal or nematicidal activity of the active compound combinations exceeds the total of the activities of the active compounds when applied individually.

The expected activity for a given combination of two active compounds can be calculated as follows (cf. Colby, S. R., "Calculating Synergistic and Antagonistic Responses of Herbicide Combinations", Weeds 1967, 15, 20-22):

If

X is the efficacy when active compound A is applied at an application rate of m ppm (or g/ha), Y is the efficacy when active compound B is applied at an application rate of n ppm (or g/ha), Z is the efficacy when employing active compound C at an application rate of r ppm (or g/ha), $E^1$ is the efficacy when the active compounds A and B (or A and C, or B and C) are applied at application rates of m and n (or m and r, or n and r) ppm (or g/ha), respectively, and E2 is the efficacy when employing active compounds A and B and C at application rates of m and n and r ppm (or g/ha), then $$E_1 = X + Y - \frac{X \cdot Y}{100}$$

and for a combination of 3 active compounds:

$$E_2 = X + Y + Z - \left(\frac{X \cdot Y + X \cdot Z + Y \cdot Z}{100}\right) + \frac{X \cdot Y \cdot Z}{10000}$$

The degree of efficacy, expressed in % is denoted. 0% means an efficacy which corresponds to that of the control while an efficacy of 100% means that no disease is observed.

If the actual fungicidal or nematicidal activity exceeds the calculated value, then the activity of the combination is superadditive, i.e. a synergistic effect exists. In this case, the efficacy which was actually observed must be greater than the value for the expected efficacy (E) calculated from the abovementioned formula. A further way of demonstrating a synergistic effect is the method of Tammes (cf. "Isoboles, a graphic representation of synergism in pesticides" in *Neth. Plant Path.,* 1964, 70, 73-80).

EXAMPLE 1

Meloidogyne incognita—test (MELGIN)

Solvent: 125.0 parts by weight of acetone

To produce a suitable preparation of active compound, 1 part by weight of active compound is mixed with the stated amount of solvent, and the concentrate is diluted with water to the desired concentration. The preparation of the bacteria, fungi or yeast products contains $10^9$-$10^{10}$ spores/g or cells/g. To produce a suitable preparation of a biological suspension the cells or spores are diluted with emulsifier-containing water to the desired concentration.

Vessels are filled with sand, a solution of the active ingredient, a suspension containing eggs and larvae of

*Meloidogyne incognita* and salad seeds. The salad seeds germinate and the seedlings grow. Galls develop in the roots.

After the specified period of time the nematicidal activity is determined on the basis of the percentage of gall formation. When *Meloidogyne incognita* attacks roots of plants, it deforms the normal root cells and establishes giant cells and consequently the attacked roots form galls. 100% means that no galls were found; 0% means that the number of galls found on the roots of the treated plants was equal to that in untreated control plants.

The following combinations of *Bacillus firmus* CNCM I-1582, *Fluopyram* and an additional compound showed a synergistic effect according to the invention:

| Active ingredient | Concentration ppm | Mortality in % after $21^d$ |
|---|---|---|
| *Bacillus firmus* CNCM I-1582 | 100 | 0 |
| Fluopyram | 0.0005 | 0 |
| *Bacillus thuringiensis* subsp. *tenebrionis* | 10 | 0 |
| *Bacillus firmus* CNCM I-1582 + | | obs.*  cal.** |
| Fluopyram + *B. thuringiensis tenebrionis* | 100 + 0.0005 + 10 | 90  0 |
| *Metarhizium anisopliae* strain F52 | 5 | 0 |
| *Bacillus firmus* CNCM I-1582 + | | obs.*  cal.** |
| Fluopyram + *M. anisopliae* strain F52 | 100 + 0.0005 + 5 | 70  0 |

*obs. = observed insecticidal efficacy,
**cal. = efficacy calculated with Colby-formula

The invention claimed is:

1. An active compound combination comprising:
   (A) Fluopyram,
   (B) a spore-forming bacterium of the genera *Bacillus*, selected from the group consisting of *Bacillus firmus*, and
   (C) at least one biological control agent selected from the group consisting of (C2.14) *Paecilomyces lilacinus*,
   wherein the only active components in the combination are actives (A), (B), and (C).

2. The active compound combination according to claim 1, wherein the combination has fungicidal and nematicidal and optionally insecticidal activity.

3. A composition comprising the active compound combination according to claim 1 and further comprising at least one of an auxiliary, solvent, carrier, surfactant and/or extender.

4. The active compound combination according to claim 1, wherein (B) is (B1) *Bacillus firmus* strain CNCM I-1582.

5. The active compound combination according to claim 1, wherein (C) is spores of *P. lilacinus* strain 251(AGAL 89/030550).

6. The active compound combination according to claim 5, wherein (B) is (B1) *Bacillus firmus* strain CNCM I-1582.

7. Seed treated with the active compound combination according to claim 1.

8. A method for controlling insects, nematodes or phytopathogens comprising applying an active compound combination according to claim 1 to seed, a plant, to fruit of a plant and/or to soil on which a plant grows and/or is supposed to grow.

9. The method according to claim 8, wherein the plant, the fruit of the plant and/or the soil on which the plant grows and/or is intended to grow is treated.

10. The method according to claim 8, wherein, in treatment of leaves of the plant, from 0.01 to 10 000 g/ha is employed and in the treatment of seed, from 2 to 200 g per 100 kg of seed is employed.

11. A method for treating seed, seed of a transgenic plant, and/or a transgenic plant comprising applying the active compound combination according to claim 1 to the seed, the seed of the transgenic plant and/or the transgenic plant.

12. A method of treating a plant comprising applying the active compound combination according to claim 1 to a plant or part of a plant for improvement of plant properties comprising one or more of better growth or increased harvest yields or a better developed root system or a larger leaf area or greener leaves or stronger shoots.

* * * * *